(12) United States Patent
Chen et al.

(10) Patent No.: US 10,959,984 B2
(45) Date of Patent: Mar. 30, 2021

(54) METHODS FOR TREATING CANCER WITH RORγ INHIBITORS

(71) Applicant: THE REGENTS OF THE UNIVERSITY OF CALIFORNIA, Oakland, CA (US)

(72) Inventors: Hongwu Chen, Davis, CA (US); June X. Zou, Davis, CA (US); Junjian Wang, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/701,122

(22) Filed: Sep. 11, 2017

(65) Prior Publication Data

US 2018/0085348 A1 Mar. 29, 2018

Related U.S. Application Data

(63) Continuation of application No. PCT/US2016/021983, filed on Mar. 11, 2016.

(60) Provisional application No. 62/280,081, filed on Jan. 18, 2016, provisional application No. 62/132,465, filed on Mar. 12, 2015.

(51) Int. Cl.

| | |
|---|---|
| *A61K 31/496* | (2006.01) |
| *A61K 31/167* | (2006.01) |
| *A61K 31/403* | (2006.01) |
| *C07D 209/56* | (2006.01) |
| *C07D 419/12* | (2006.01) |
| *C07D 401/12* | (2006.01) |
| *C07D 403/12* | (2006.01) |
| *C07D 405/12* | (2006.01) |
| *C07K 14/705* | (2006.01) |
| *A61K 31/18* | (2006.01) |
| *A61K 31/185* | (2006.01) |
| *A61K 31/4166* | (2006.01) |
| *A61K 31/4725* | (2006.01) |
| *A61K 31/655* | (2006.01) |
| *A61K 31/713* | (2006.01) |
| *C12N 15/113* | (2010.01) |

(52) U.S. Cl.
CPC ............ *A61K 31/403* (2013.01); *A61K 31/18* (2013.01); *A61K 31/185* (2013.01); *A61K 31/4166* (2013.01); *A61K 31/4725* (2013.01); *A61K 31/496* (2013.01); *A61K 31/655* (2013.01); *A61K 31/713* (2013.01); *C07D 209/56* (2013.01); *C07D 401/12* (2013.01); *C07D 403/12* (2013.01); *C07D 405/12* (2013.01); *C07K 14/70567* (2013.01); *C12N 15/1138* (2013.01); *C12N 2310/14* (2013.01); *C12N 2320/31* (2013.01)

(58) Field of Classification Search
CPC ............................ A61K 31/496; A61K 31/167
See application file for complete search history.

(56) References Cited

U.S. PATENT DOCUMENTS

| | | | |
|---|---|---|---|
| 2007/0154487 A1 | 7/2007 | Littman et al. | |
| 2014/0187554 A1* | 7/2014 | Kamenecka | C07D 295/096 514/235.5 |
| 2014/0315881 A1 | 10/2014 | Baloglu et al. | |
| 2015/0118305 A1 | 4/2015 | Cornblatt et al. | |

FOREIGN PATENT DOCUMENTS

| | | |
|---|---|---|
| CN | 105272904 | 1/2016 |
| EP | 2738170 A1 | 6/2014 |
| WO | 2011/115892 A1 | 9/2011 |
| WO | 2012100734 A1 | 8/2012 |
| WO | 2012106995 A1 | 8/2012 |
| WO | 2012/129394 A2 | 9/2012 |
| WO | 2013019682 A1 | 2/2013 |
| WO | 2013160418 A1 | 10/2013 |
| WO | 2013171729 A2 | 11/2013 |
| WO | 2014008214 A1 | 1/2014 |
| WO | 2014028589 A2 | 2/2014 |
| WO | 2014028591 A2 | 2/2014 |
| WO | 2014028597 A2 | 2/2014 |
| WO | 2014028600 A2 | 2/2014 |
| WO | 2014089241 | 6/2014 |
| WO | 2014179564 A1 | 11/2014 |
| WO | 2015008234 A1 | 1/2015 |
| WO | 2015036411 A2 | 3/2015 |
| WO | 2015061515 A1 | 4/2015 |
| WO | 2015082533 A1 | 6/2015 |
| WO | 2015083130 A1 | 6/2015 |

(Continued)

OTHER PUBLICATIONS

Bai Qiang et al. Chinese Journal of Andrology, 2004, vol. 2, abstract.*
Li et al. Cancer Research, 2013, vol. 73, Iss. 2, pp. 483-489.*
Bielawsky et al. Biol. Pharm. Bull., 2006, vol. 29, No. 7, pp. 1493-1497.*
Lin et al. PLOS One, 2015, vol. 10, No. 5, pp. 1-14.*
Agoulnik et al., "Androgens Modulate Expression of Transcription Intermediary Factor 2, an Androgen Receptor Coactivator whose Expression Level Correlates with Early Biochemical Recurrence in Prostate Cancer," Cancer Res., 2006, vol. 66, No. 21, pp. 10594-10602.

(Continued)

*Primary Examiner* — Samira J Jean-Louis
(74) *Attorney, Agent, or Firm* — Kilpatrick Townsend & Stockton LLP

(57) ABSTRACT

The present invention provides compositions, methods, and kits comprising one or more RORγ inhibitors, alone or in combination with one or more anticancer drugs, such as an anti-androgen drug, that are useful for treating cancer, e.g., prostate cancer, such as castration-resistant prostate cancer (CRPC), and numerous other types of cancer including lung cancer, breast cancer, liver cancer, ovarian cancer, endometrial cancer, bladder cancer, colon cancer, lymphoma, and glioma.

19 Claims, 66 Drawing Sheets

Specification includes a Sequence Listing.

(56) References Cited

FOREIGN PATENT DOCUMENTS

| WO | 2015096771 A1 | 7/2015 |
|---|---|---|
| WO | 2015101928 A1 | 7/2015 |
| WO | 2015116904 A1 | 8/2015 |
| WO | 2016145298 A1 | 9/2016 |
| WO | 2017127442 A1 | 7/2017 |

OTHER PUBLICATIONS

Antonarakis et al., "AR-V7 and Resistance to Enzalutamide and Abiraterone in Prostate Cancer," N Eng J Med, Sep. 11, 2014; 371, pp. 1028-1038, DOI: 10.1056/NEJMoa1315815.

Asangani et al., "Therapeutic targeting of BET bromodomain proteins in castration-resistant prostate cancer," Nature, Jun. 12, 2014, vol. 510, pp. 278-282.

Chang et al., "Pharmacologic Repression of Retinoic Acid Receptor—Related Orphan Nuclear Receptor r is Therapeutic in the Collagen-Induced Arthritis Experimental Model," Arthritis & Rheumatology, vol. 66, No. 3, Mar. 2014, pp. 579-588.

Ciofani et al., "A Validated Regulatory Network for Th17 Cell Specification," Cell, Oct. 12, 2012, vol. 151, pp. 289-303.

Deblois et al., "Oestrogen-related receptors in breast cancer: control of cellular metabolism and beyond," Cancer, Jan. 2013, vol. 13, pp. 27-36.

European Application No. 16762587.0, Extended European Search Report dated Jul. 26, 2018, 9 pages.

Fauber et al., "Discovery of 1-{4[3-Fluoro-4((3S,6R)-3-methyl-1,1-dioxo-6-phenyl-[1,2]thiazinan-2-ylmethyl)-phenyl]-piperazin-1-yl}ethanone (GNE-3500): a Potent, Selective, and Orally Bioavailable Retinoic Acid Receptor-Related Orphan Receptor C (RORc or RORγ) Inverse Agonist," J. Med. Chem., 2015, vol. 58, pp. 5308-5322; DOI: 10.1021/acs.jmedchem.5b00597.

Fauber et al., Reduction in lipophilicity improved the solubility, plasma—protein binding, and permeability of tertiary sulfonamide RORc inverse agonists, Bioorganic & Medicinal Chemistry Letters, 2014, vol. 24, pp. 3891-3897.

Ferraldeschi et al., "Targeting the androgen receptor pathway in castration-resistant prostate cancer: progresses and prospects," Oncogene, 2015, vol. 34, pp. 1745-1757.

Flaveny et al., "Broad Anti-tumor Activity of a Small Molecule that Selectively Targets the Warburg Effect and Lipogenesis," Cancer Cell, 2015, vol. 28, pp. 42-56.

Frigo et al., "CaM Kinase Kinase b-Mediated Activation of the Growth Regulatory Kinase AMPK is Required for Androgen-Dependent Migration of Prostate Cancer Cells," Cancer Res, 2011, 71(2), pp. 528-537, DOI: 10.1158/0008-5472.CAN-10-2581.

Gege, Christian, "Retinoid-related orphan receptor gamma t (RORγt) inhibitors from Vitae Pharmaceuticals (WO2015116904) and structure proposal for their Phase I candidate VTP-43742," Expert Opin. Ther. Patents, 2016, vol. 26, No. 6, pp. 737-744, DOI: 10.1517/13543776.2016.1153066.

Gege, Christian, "Retinoid-related orphan receptor γ t modulators: comparison of Glenmark's me-too patent application (WO2015008234) with the originator application from Merck Sharp and Dohme (WO2012106995)," Expert Opin. Ther. Patents, 2015, 25(10), pp. 1215-1221, DOI: 10.1517/13543776.2015.1065816.

Giguere et al., "Isoform-specific amino-terminal domains dictate DNA-binding properties of RORa, a novel family of orphan hormone nuclear receptors," Genes Dev, 1994, vol. 8, pp. 538-553, doi:10.1101/gad.8.5.538.

Hu et al., "Distinct Transcriptional Programs Mediated by the Ligand-Dependent Full-Length Androgen Receptor and its Splice Variants in Castration-Resistant Prostate Cancer," Cancer Res, 2012, vol. 72, pp. 3457-3462, DOI: 10.1158/0008-5472.CAN-11-3892.

International Application No. PCT/US2017/013966, International Search Report dated Apr. 5, 2017, 2 pages.

Karantanos et al., "Understanding the Mechanisms of Androgen Deprivation Resistance in Prostate Cancer at the Molecular Level," European Urology, 2015, vol. 67, pp. 470-479.

Kojetin et al., "REV-ERB and ROR nuclear receptors as drug targets Nature Reviews," Mar. 2014, vol. 13, pp. 197-216.

Kumar et al., "Identification of SR2211: A Potent Synthetic RORγ-Selective Modulator" ACS Chem. Biol., 2012, vol. 7, pp. 672-677, dx.doi.org/10.1021/cb200496y.

Kumar et al., "Identification of SR3335 (ML-176): A Synthetic RORr Selective Inverse Agonist," ACS Chem. Biol., 2011, vol. 6, pp. 218-222, x.doi.org/10.1021/cb1002762.

Kumar et al., "The Benzenesulfoamide T0901317 [N-(2,2,2-Trifluoroethyl)-N-[ 4-[2, 2, 2-trifluoro-1-hydroxy-1-(trifluoromethyl)ethyl]phenyl]benzenesulfonamide] is a Novel Retinoic Acid Receptor-Receptor-Related Orphan Receptor-α/γ Inverse Agonist," Molecular Pharmacology, 2010, vol. 77, No. 2, pp. 228-236.

Lai et al., "New Therapeutic Approach to Suppress Castration-Resistant Prostate Cancer Using ASC-J9 via Targeting Androgen Receptor in Selective Prostate Cells," Am J Pathol, Feb. 2013, vol. 182, No. 2, pp. 460-473.

Lange et al., "Aberrant Presentation of HPA-Reactive Carbohydrates Implies Selectin-Independent Metastasis Formation in Human Prostate Cancer," Clin Cancer Res, vol. 20, No. 7, pp. 1791-1802, DOI: 10.1158/1078-0432.CCR-13-2308.

Li et al., "LEF1 in Androgen-Independent Prostate Cancer: Regulation of Androgen Receptor Expression, Prostate Cancer Growth, and Invasion," Caner Res, 2009, vol. 69, No. 8, pp. 3332-3338, DOI: 10.1158/0008-5472.CAN-08-3380.

Liu et al., "Niclosamide Inhibits Androgen Receptor Variants Expression and Overcomes Enzalutamide Resistance in Castration-Resistant Prostate Cancer," Clin Cancer Res, Jun. 15, 2014, vol. 20, No. 12, pp. 3198-3210, doi:10.1158/1078-0432.CCR-13-3296.

Louie et al., "ACTR/AIB1 Functions as an E2F1 Coactivator to Promote Breast Cancer Cell Proliferation and Antiestrogen Resistance," Mol. Cel. Biol., Jun. 2004, vol. 24, No. 12, pp. 5157-5171, DOI: 10.1128/MCB.24.12.5157-5171.2004.

Lu et al., "Are androgen receptor variants a substitute for the full-length receptor?" Nat. Rev. Urol., Mar. 2015, vol. 12, pp. 137-144.

Malik et al., "Targeting the MLL complex in castration-resistant prostate cancer," Nature Medicine, Apr. 2015, vol. 21, No. 4, pp. 344-352.

Mendiratta et al., Genomic Strategy for Targeting Therapy in Castration-Resistant Prostate Cancer, J Clin Oncol, Apr. 20, 2009, vol. 27, No. 12, pp. 2022-2029, DOI: 10.1200/JCO.2008.17.2882.

Meissburger et al., "Adipogenesis and insulin sensitivity in obesity are regulated by retinoid-related orphan receptor gamma," EMBO Mol. Med, 2011, vol. 3, pp. 637-651, DOI 10.1002/emmm.201100172.

Monstaghel et al., "Molecular Pathways: Targeting Resistance in the Androgen Receptor for Therapeutic Benefit," Clin. Cancer Res., Feb. 15, 2014, vol. 20, No. 4, pp. 791-798, DOI: 10.1158/1078-0432.CCR-12-3601.

Myung et al., "An androgen receptor N-terminal domain antagonist for treating prostate cancer," J Clin Invest., Jul. 2013, vol. 123, No. 7, pp. 2948-2960.

Qin et al., "Androgen deprivation—induced NCoA2 promotes metastatic and castration-resistant prostate cancer," J Clin Invest., 2014, vol. 124, No. 11, pp. 5013-5026.

Rene et al., "Minor Structural Change to Tertiary Sulfonamide RORc Ligands Led to Opposite Mechanisms of Action," ACS Med. Che. Lett., 2015, vol. 6, pp. 276-281, DOI: 10.1021/ml500420y.

Roshan-Moniri et al., "Orphan nuclear receptors as drug targets for the treatment of prostate and breast cancers," Cancer Treatment Reviews, 2014, pp. 1-16.

Sharma et al., "The Androgen Receptor Induces a Distinct Transcriptional Program in Castration-Resistant Prostate Cancer in Man," Cancer Cell, Jan. 14, 2013, vol. 23, pp. 35-47.

Sharma et al., "The retinoblastoma tumor suppressor controls androgen signaling and human prostate cancer progression," J Clin Invest., Dec. 2010, Vo. 120, No. 12, pp. 4478-4492.

Solt et al., "Identification of a Selective RORγ Ligand That Suppresses $T_H17$ Cells and Stimulates T Regulatory Cells," ACS Chemical Biology, 2012, vol. 7, pp. 1515-1519.

(56) References Cited

OTHER PUBLICATIONS

Solt et al., "Suppression of $T_H17$ Differentiation and Autoimmunity by a Synthetic Ror Ligand," Nature, Apr. 28, 2011, vol. 472, 17 pages.
Sun et al., "Requirement for RORγ in Thymocyte Survival and Lymphoid Organ Development," Science, Jun. 30, 2000, vol. 288, pp. 2369-2373, DOI: 10.1126/science.288.5475.2369.
Takeda et al., "Retinoic Acid-Related Orphan Receptor c (RORc): A Novel Participant in the Diurnal Regulation of Hepatic Gluconeogenesis and Insulin Sensitivity," PLoS Genetics, May 2014, vol. 10, Issue 5, e1004331, 16 pages, doi:10.1371/journal.pgen.1004331.
Taylor et al., "Integrative Genomic Profiling of Human Prostate Cancer," Cancer Cell, Jul. 13, 2010, vol. 18, pp. 11-22.
Tien et al., "The Steroid Receptor Coactivator-3 is Required for the Development of Castration-Resistant Prostate Cancer," Cancer Res., Jul. 1, 2013, vol. 73, No. 13, pp. 3997-4008.
Van Niel et al., A Reversed Sulfonamide Series of Selective Rorc Inverse Agonists, Bioorganic & Medicinal Chemistry Letters, 2014, vol. 24, pp. 5769-5776.
Wang et al., "Bufalin is a Potent Small-Molecule Inhibitor of the Steroid Receptor Coactivators SRC-3 and SRC-1," Cancer Res, Mar. 1, 2014, vol. 74, No. 5, pp. 1506-1517, DOI: 10.1158/0008-5472.CAN-13-2939.
Wang et al., "Discovery of novel N-(5-(aryl carbonyl) thiazol-2-yl) amides and N-(5-(aryl carbonyl)thiophen-2-yl) amides as potent RORct inhibitors," Bioorganic & Medicinal Chemistry, 2014, vol. 22, pp. 692-702.
Wang et al., Discovery of Biaryl Amides as Potent, Orally Bioavailable, and CNS Penetrant RORγt Inhibitors, ACS Medicinal Chemistry Letters, vol. 6, 2015, pp. 787-792.
Xiao et al., "Small-Molecule RORgt Antagonists Inhibit T Helper 17 Cell Transcriptional Network by Divergent Mechanisms," Immunity, vol. 40, Apr. 17, 2014, pp. 477-489.
Yamamoto et al., "Generation 2.5 Antisense Oligonucleotides Targeting the Androgen Receptor and its Splice Variants Suppress Enzalutamide-Resistant Prostate Cancer Cell Growth," Clin Cancer Res, 2015, vol. 21, pp. 1675-1687, DOI: 10.1158/1078-0432.CCR-14-1108.
Yang et al., "Induction of Androgen Receptor Expression by Phosphatidylinositol 3-Kinase/Akt Downstream Substrate, FOXO3a, and Their Roles in Apoptosis of LNCaP Prostate Cancer Cells," J. Biol. Chem., Sep. 30, 2005, vol. 280, No. 39, pp. 33558-33565.
Yang et al., "T Helper 17 Lineage Differentiation is Programmed by Orphan Nuclear Receptors Ror Alpha and Ror Gamma," Immunity, Jan. 2008, vol. 28, No. 1, pp. 29-39.
Yu et al., "Galeterone Prevents Androgen Receptor Binding to Chromatin and Enhances Degradation of Mutant Androgen Receptor," Clin Cancer Res, 2014, vol. 20, pp. 4075-4085, DOI: 10.1158/1078-0432.CCR-14-0292.
Zhang et al., "Discovery of 2-Oxo-1,2-Dihydrobenzo[cd]indole-6-Sulfonamide Derivatives as New RORγ Inhibitors Using Virtual Screening, Synthesis and Biological Evaluation," European Journal of Medicinal Chemistry, Jun. 2014, vol. 8, pp. 431-441.
Zhang et al., "Interleukin-17 Promotes Development of Castration-Resistant Prostate Cancer Potentially Through Creating an Immunotolerant and Pro-Angiogenic Tumor Microenvironment," The Prostate, vol. 74, No. 8, Apr. 2014, pp. 869-879.
Zhang et al., "NF-κB Regulates Androgen Receptor Expression and Prostate Cancer Growth," Amer. J. Pathology, Aug. 2009, vol. 175, No. 2, pp. 489-499.
Zhang et al., "ROR nuclear receptors: structures, related diseases, and drug discovery," Acta Pharmacologica Sinica, 2015, vol. 36, pp. 71-87.
Zhao et al., "Nuclear receptors rock around the clock," EMBO reports, 2014, vol. 15, No. 5, pp. 518-528, DOI 10.1002/embr.201338271.
Zhong et al., "p300 Acetyltransferase Regulates Androgen Receptor Degradation and PTEN-Deficient Prostate Tumorigenesis," Caner Res., Mar. 15, 2014, vol. 74, No. 6, pp. 1870-1880.
Zou et al., "Androgen-Induced Coactivator ANCCA Mediates Specific Androgen Receptor Signaling in Prostate Cancer," Cancer Res, 2009, vol. 69, No. 8, pp. 3339-3346, DOI: 10.1158/0008-5472.CAN-08-3440.
Shanmugam, M.K. et al.; "Ursolic acid in cancer prevention and treatment: Molecular targets, pharmacokinetics and clinical studies"; *Biochemical Pharmacology;* vol. 85; 2013; pp. 1579-1587.
Yeh, J-Y. et al.; "Inhibitory Effects of Digitalis on the Proliferation of Androgen Dependent and Independent Prostate Cancer Cells"; *The Journal of Urology;* vol. 166, No. 5; 2001; p. 1937-1942.

\* cited by examiner

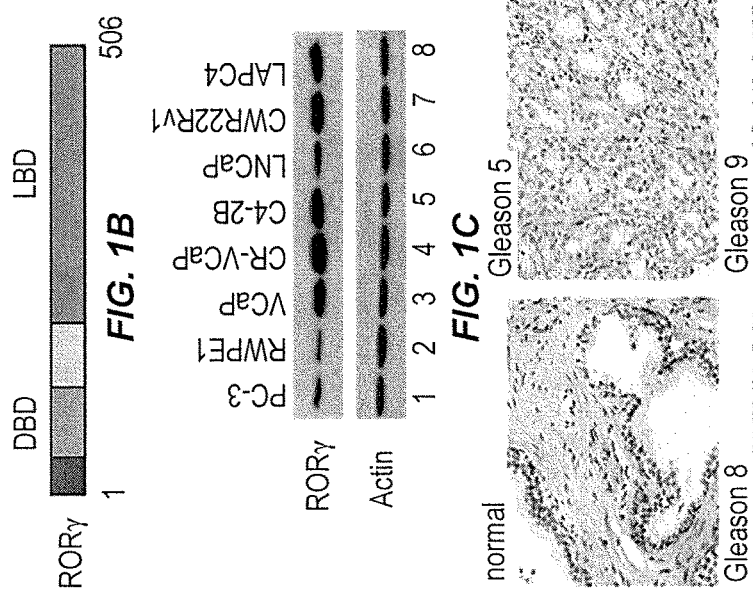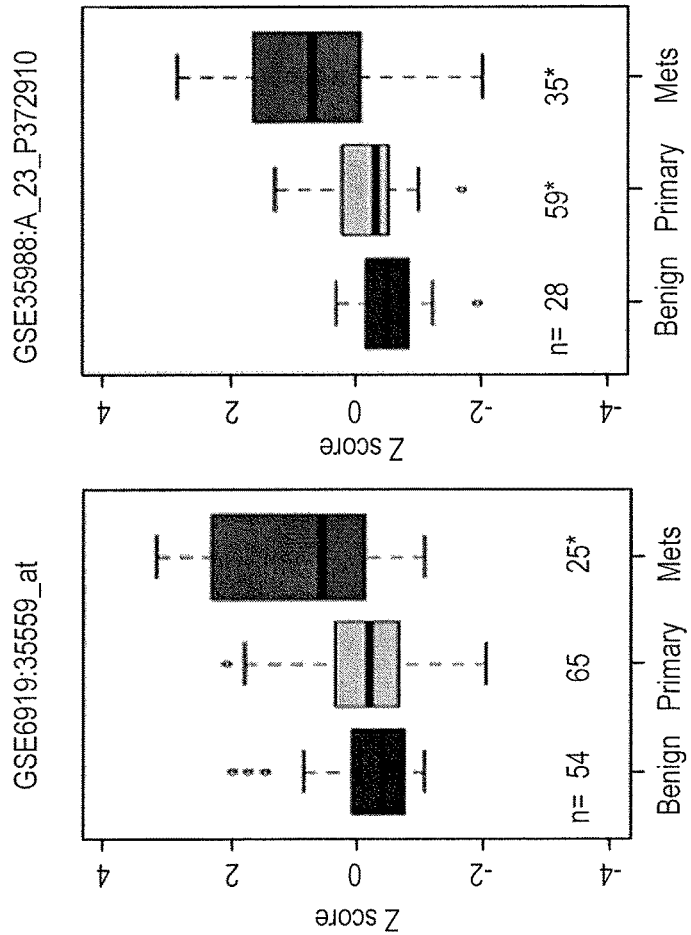
FIG. 1A  FIG. 1B  FIG. 1C  FIG. 1D

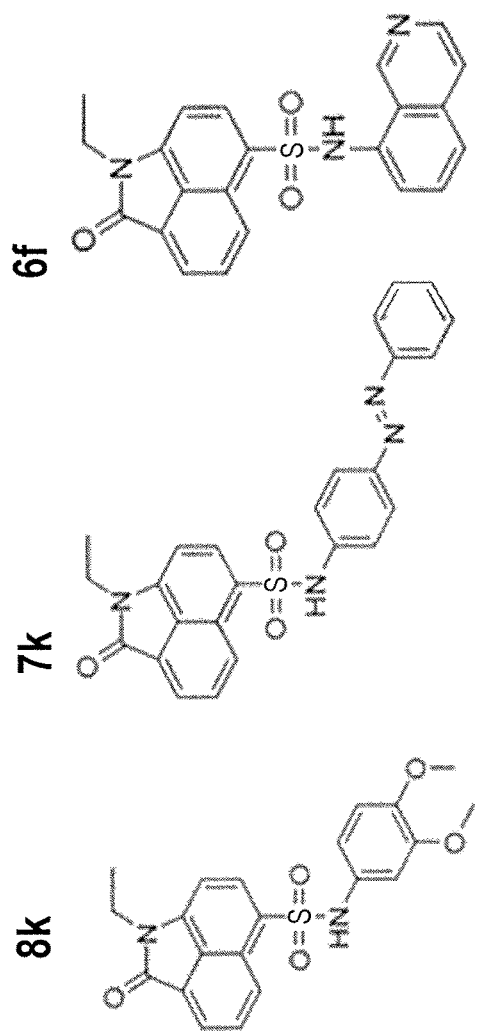
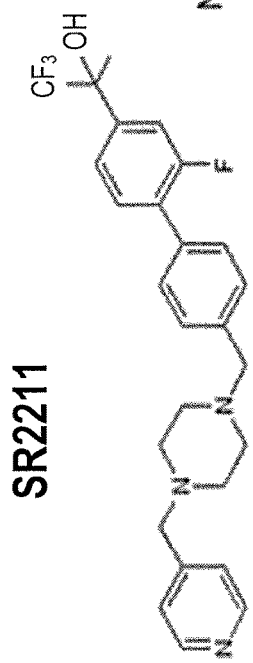
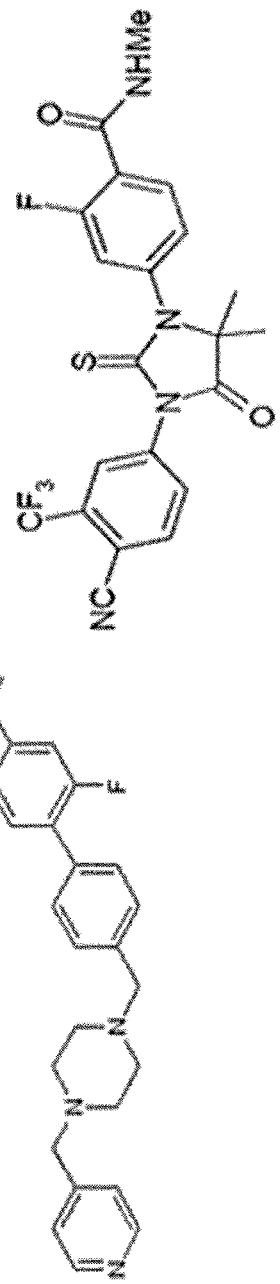
FIG. 2A

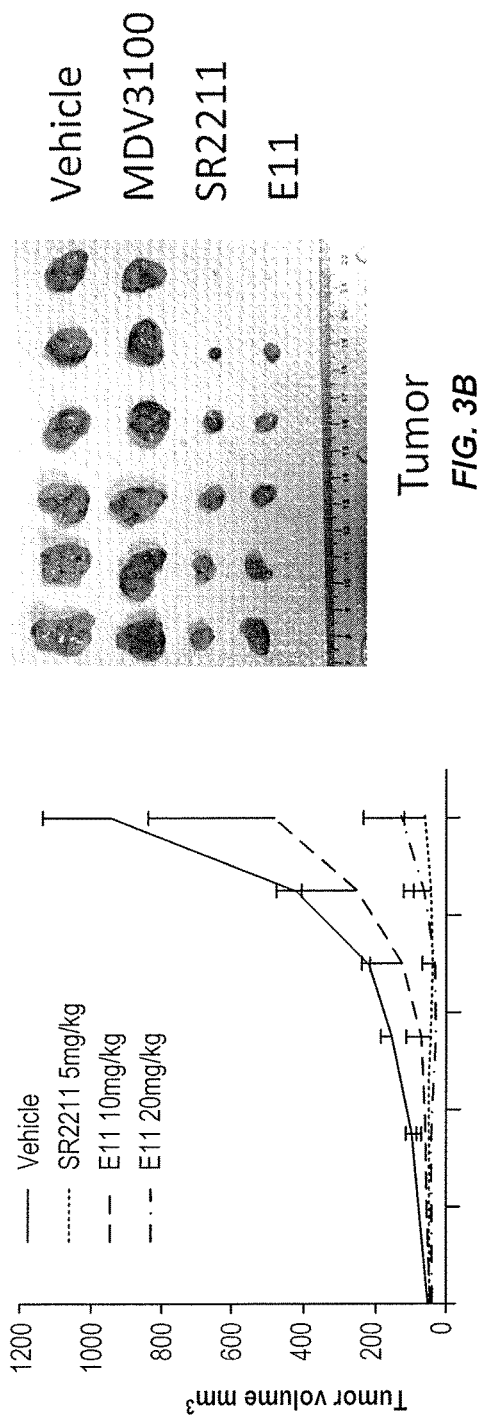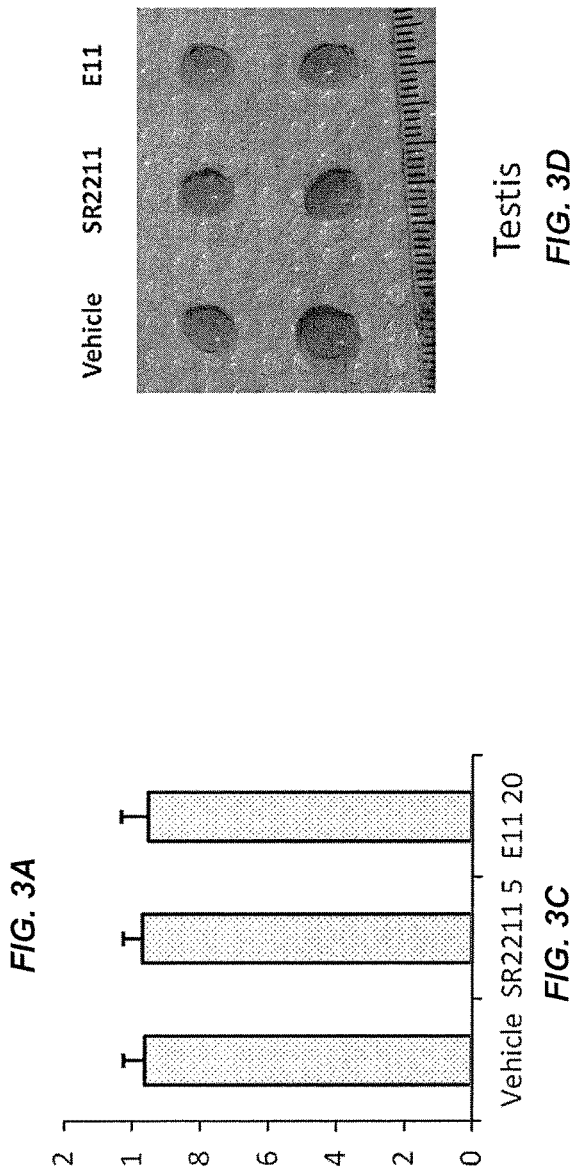
FIG. 3A
FIG. 3B Tumor
FIG. 3C
FIG. 3D Testis

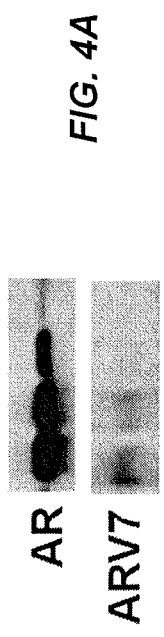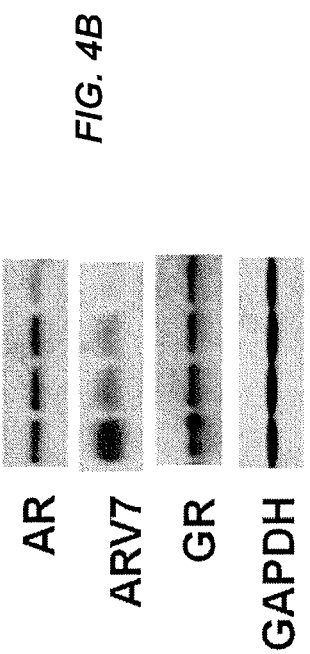

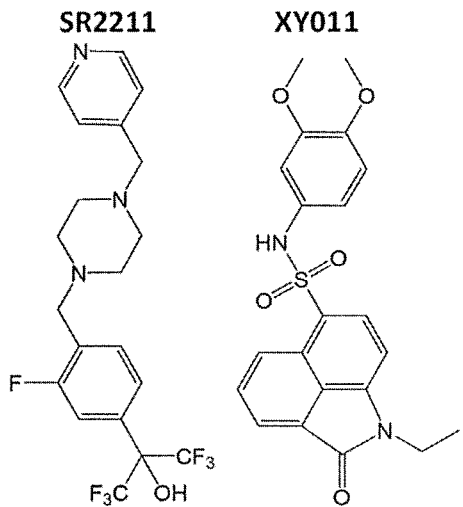
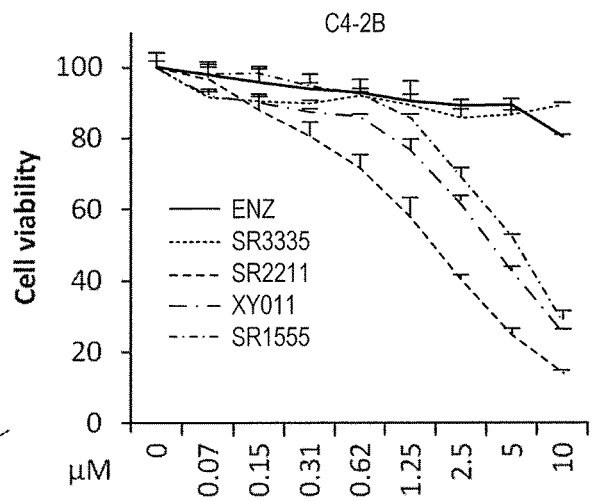
FIG. 7A
FIG. 7B
| Cell line | AR signaling | IC$_{50}$ (µM) | |
|---|---|---|---|
| | | SR2211 | ENZ |
| LNCaP | Positive | 1.5 | 32.5 |
| C4-2B | Positive | 2.1 | 45.5 |
| LAPC4 | Positive | 3.2 | 43.3 |
| VCaP | Positive | 3.7 | 29.5 |
| PC346 | Positive | 4.8 | 35.7 |
| 22RV1 | Positive | 5.4 | >50 |
| PC-3 | Negative | 36.2 | >50 |
| PNT2 | Negative | 51.5 | |
| RWPE1 | Low | 48.9 | |
| IMR90 | Negative | 40.0 | |
FIG. 7C

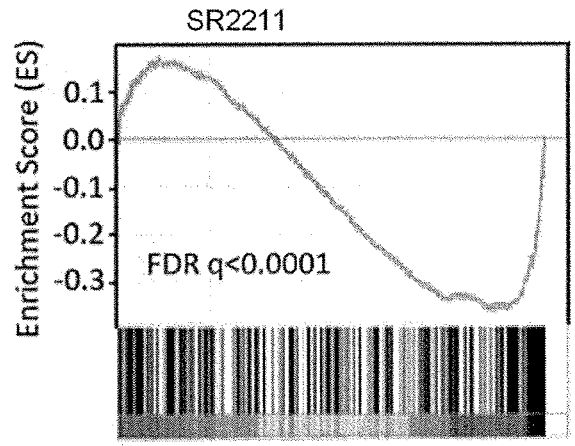
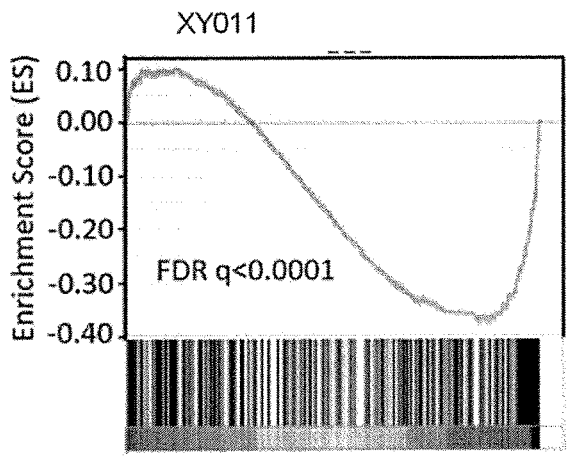
FIG. 8B
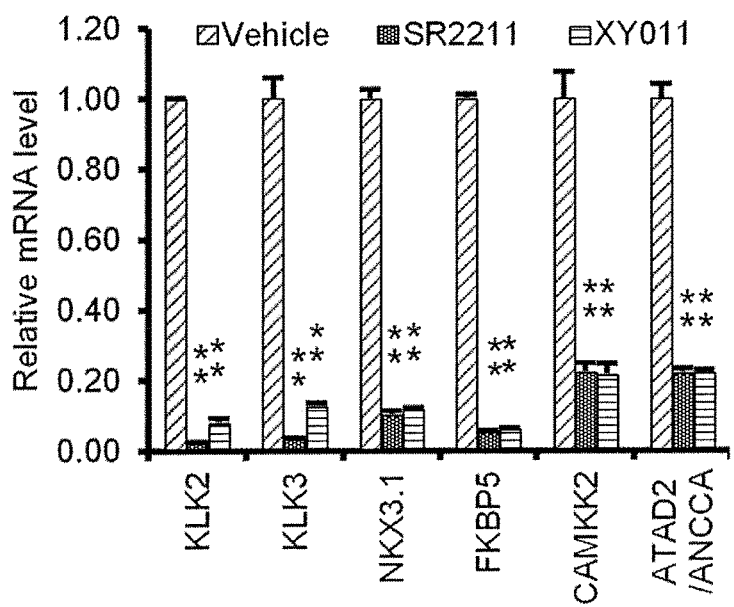
FIG. 8C

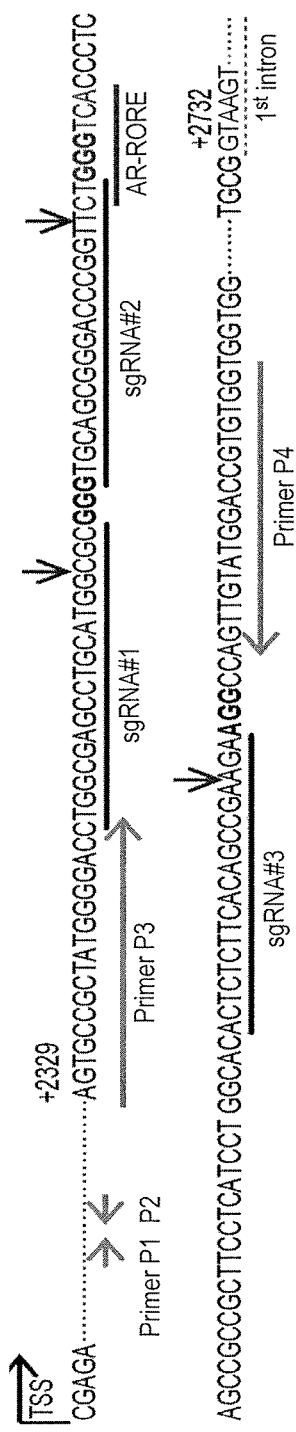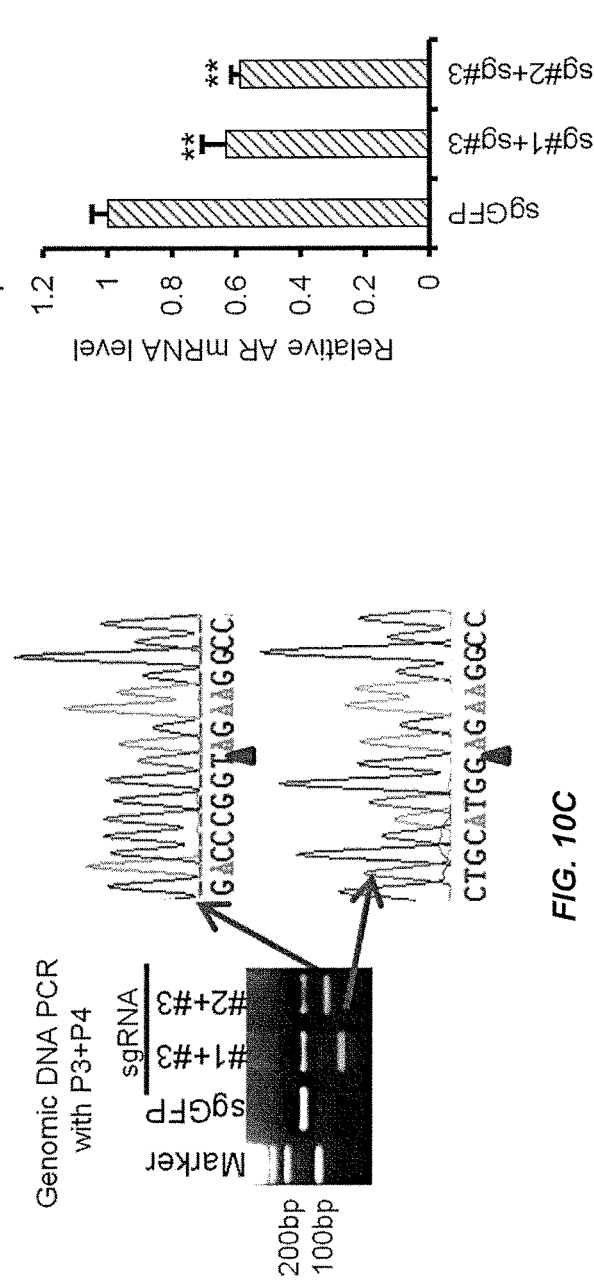
FIG. 10B
FIG. 10C
FIG. 10D

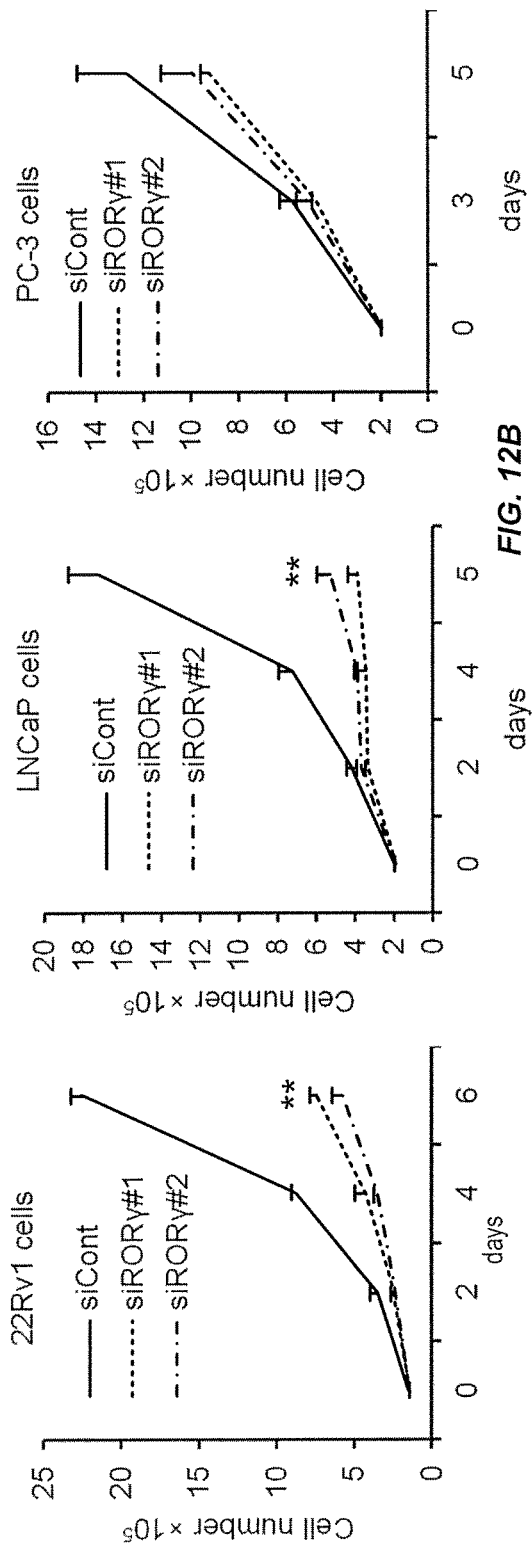
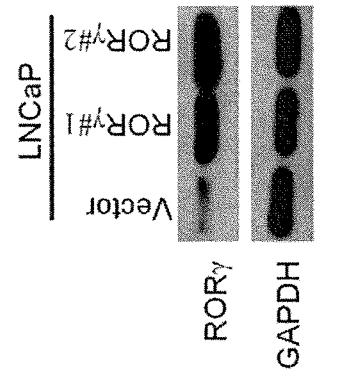
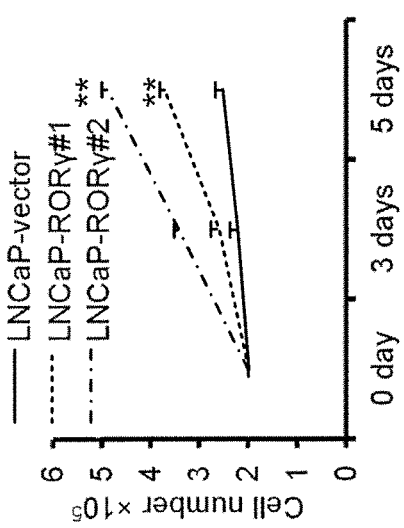
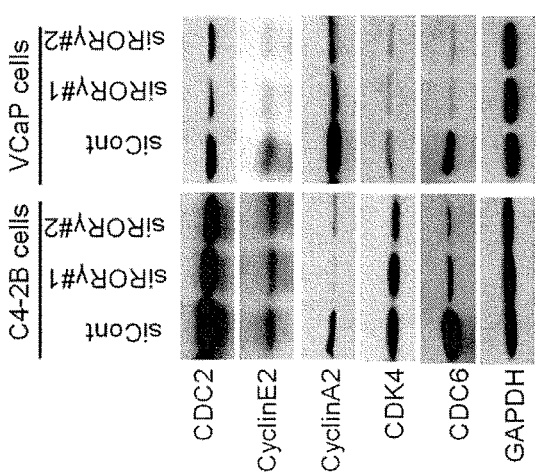
FIG. 12B
FIG. 12D
FIG. 12C

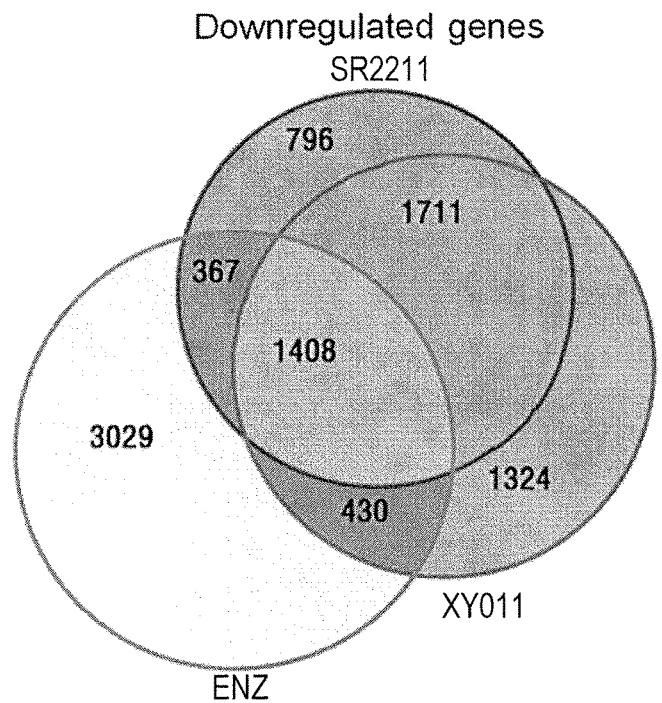
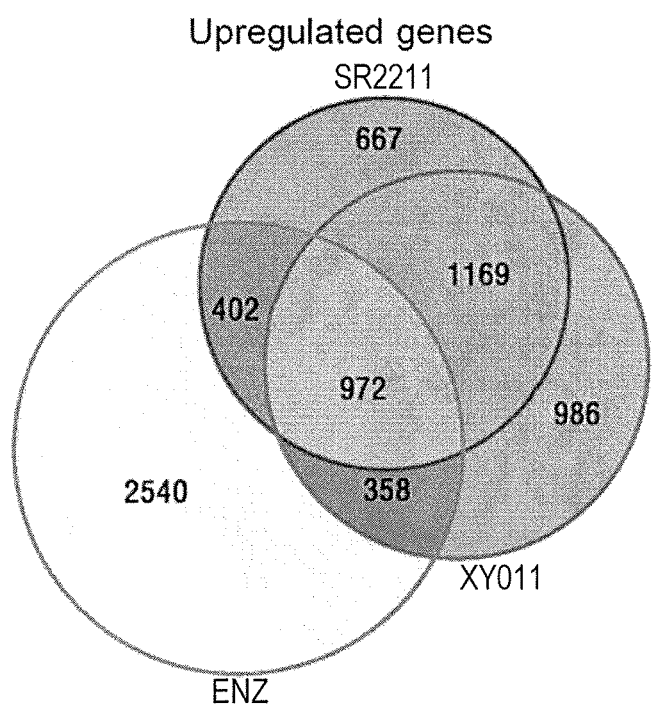
FIG. 14B

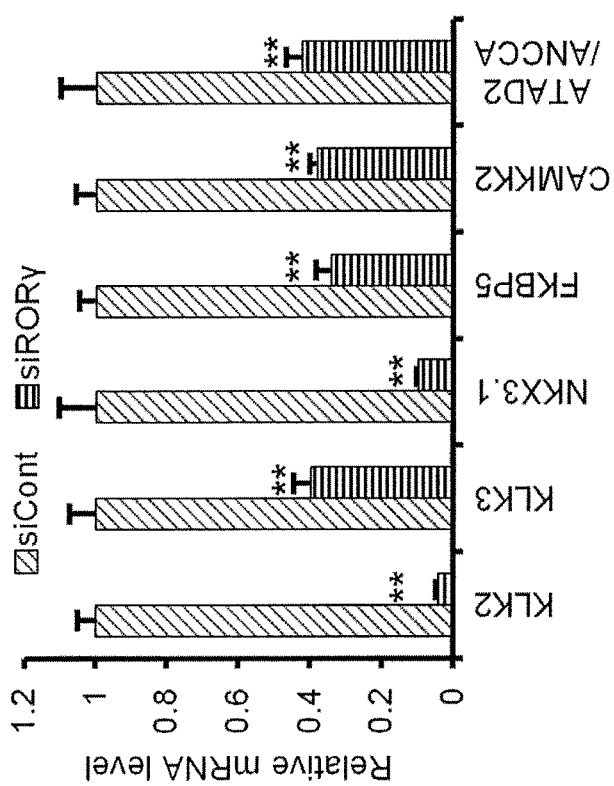
FIG. 14E

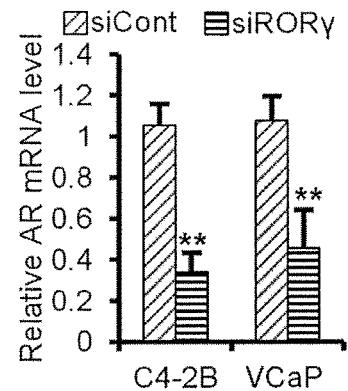
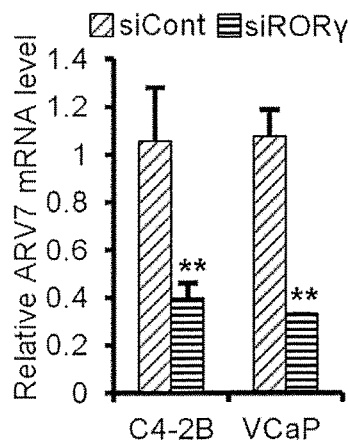
FIG. 15A
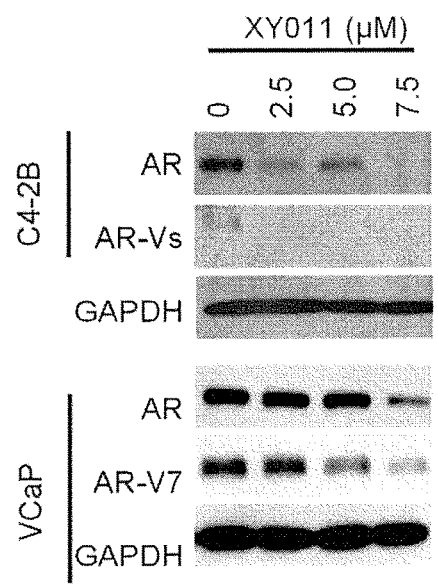
FIG. 15B
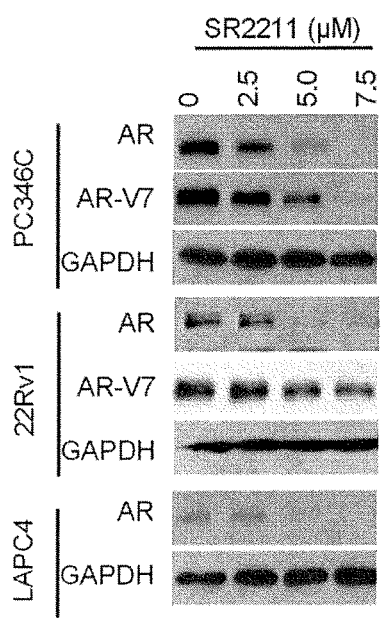
FIG. 15C
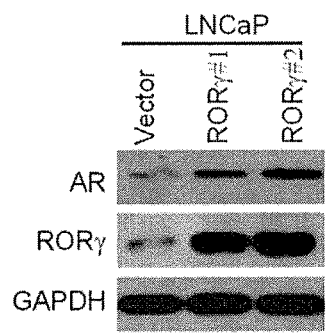
FIG. 15D

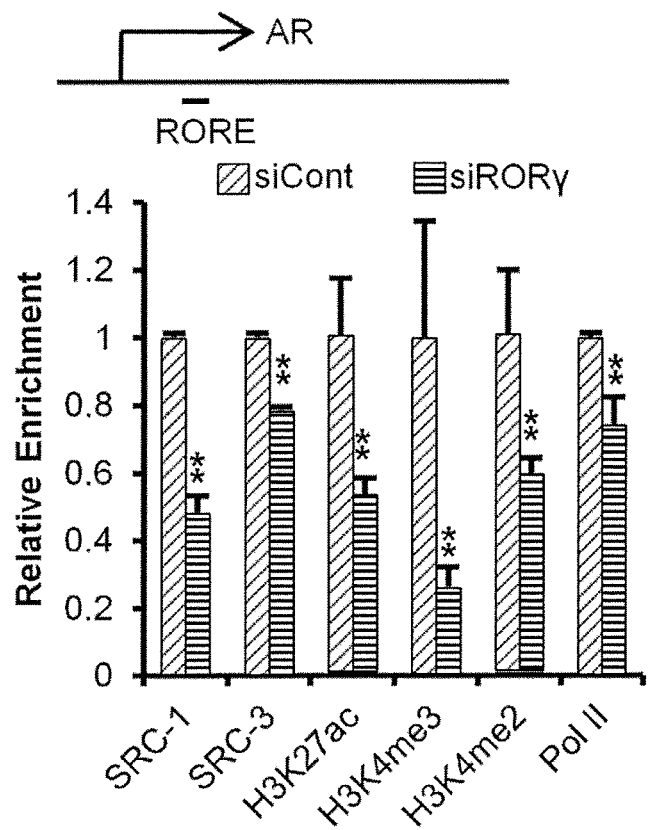
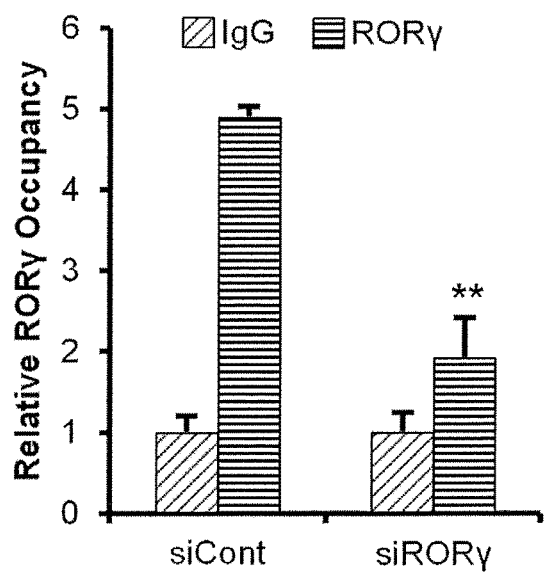
*FIG. 21*

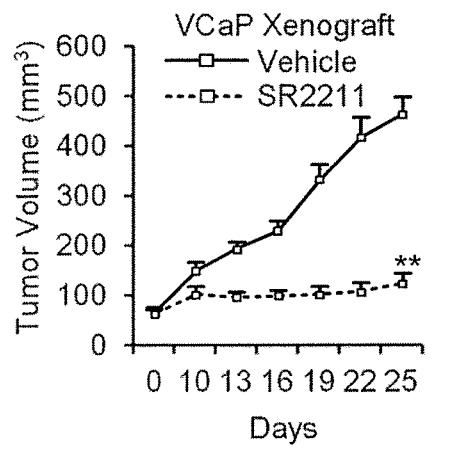
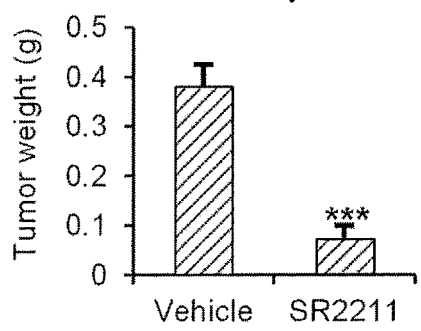
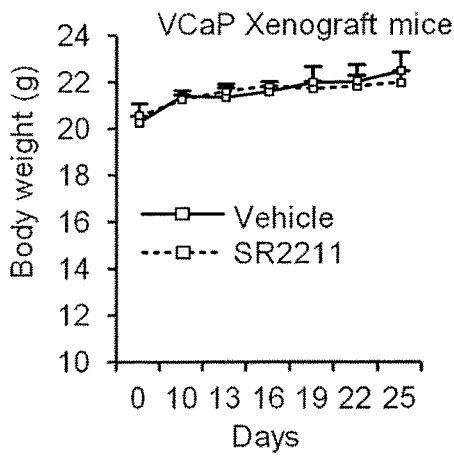
FIG. 23A
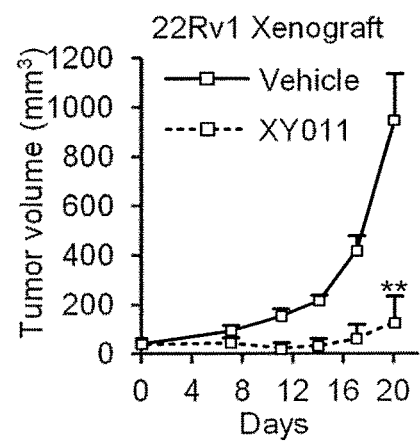
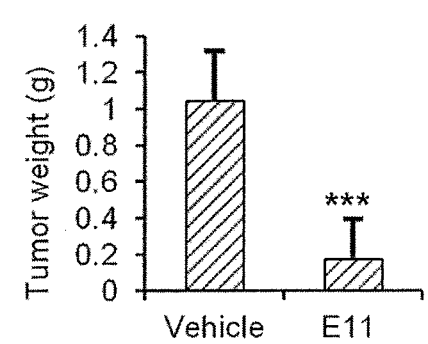
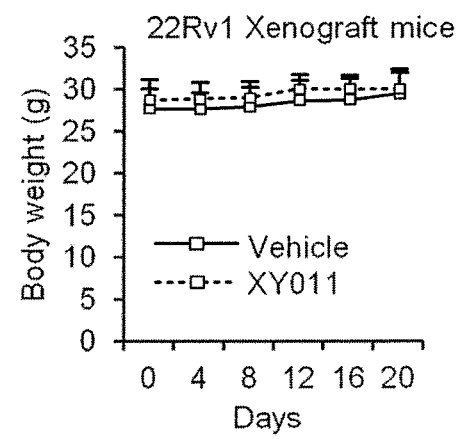
FIG. 23B

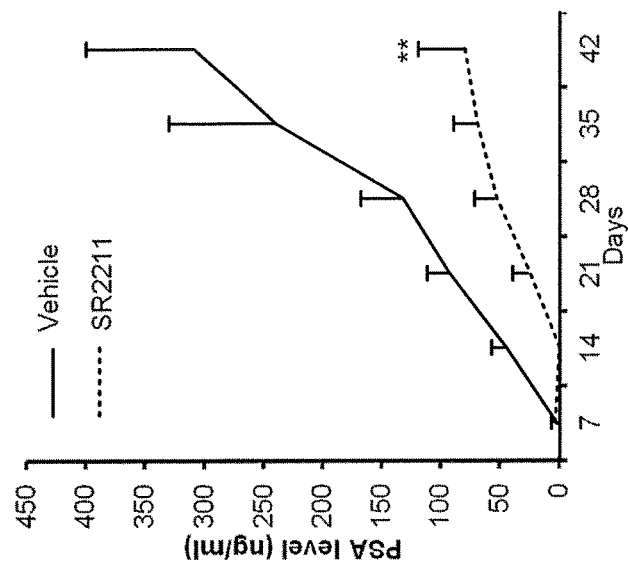
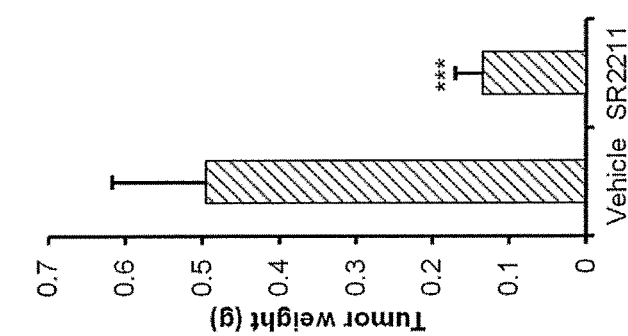
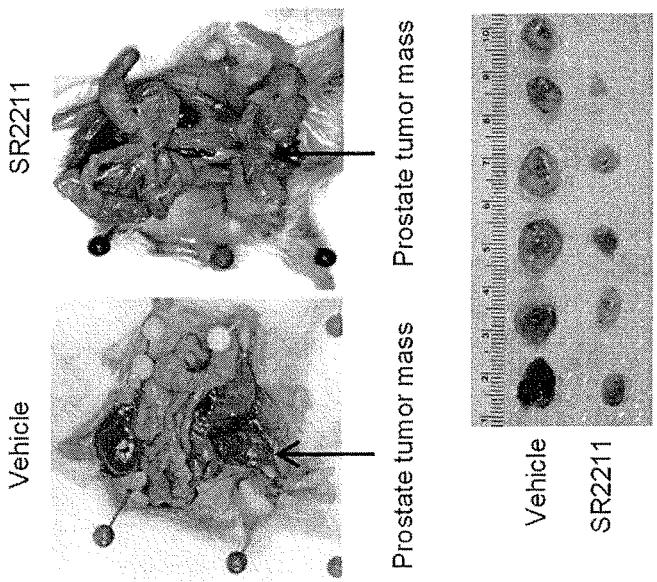
FIG. 25C
FIG. 25B
FIG. 25A

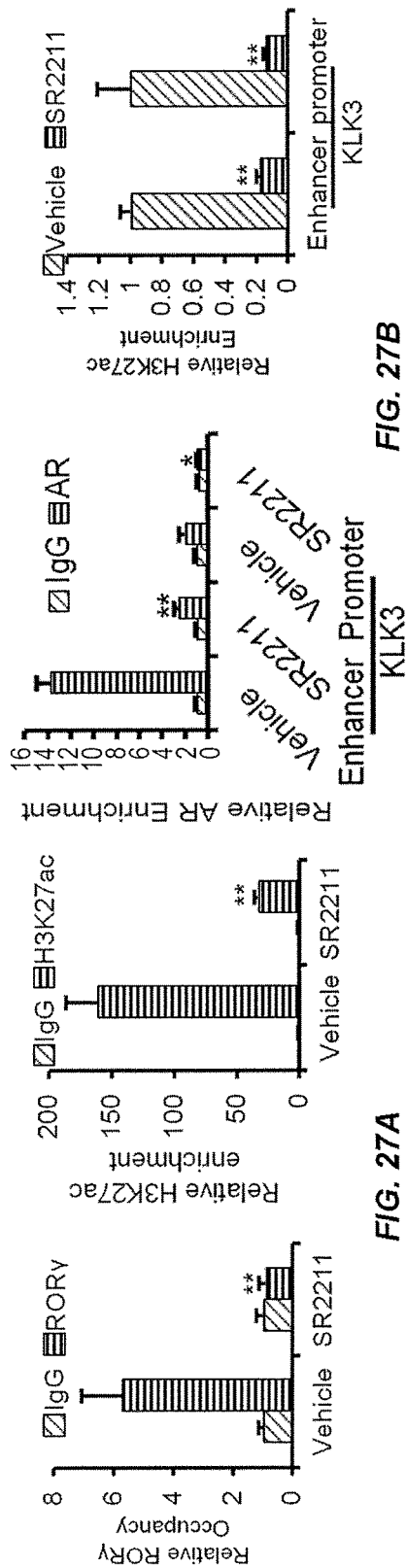
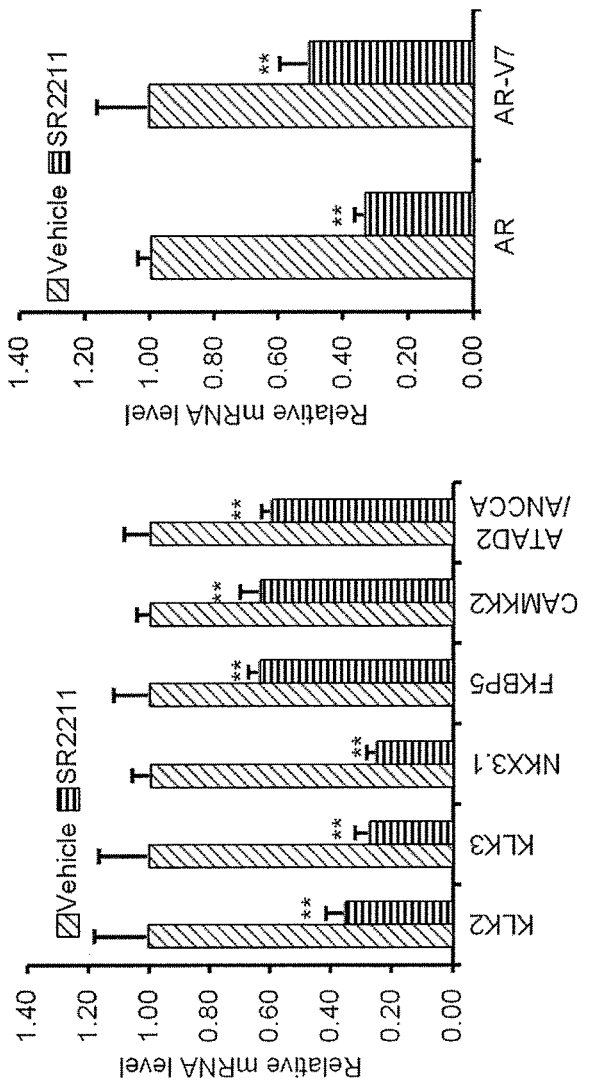
FIG. 27A
FIG. 27B
FIG. 27C

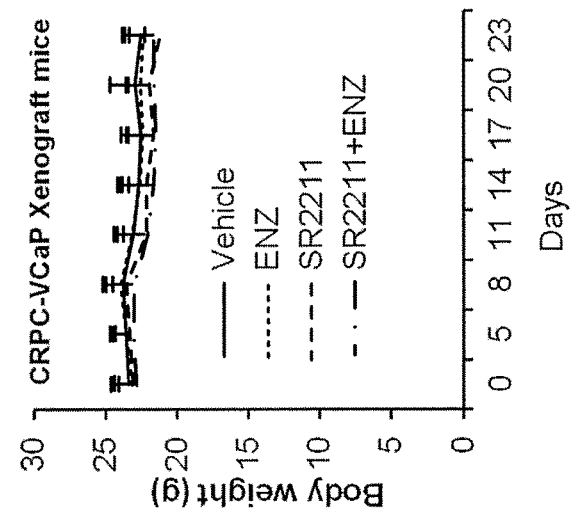
FIG. 28B
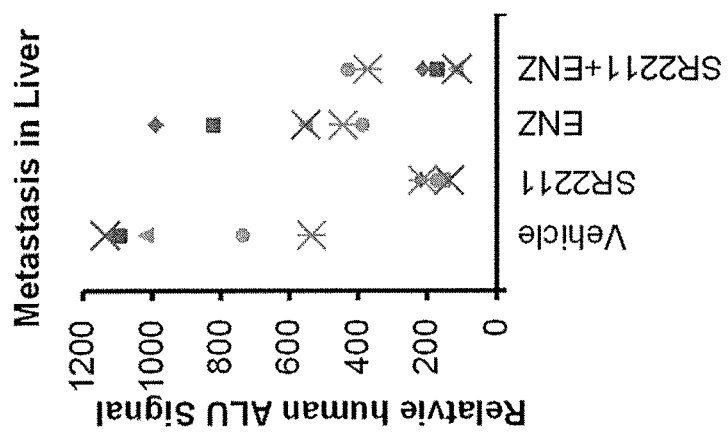
FIG. 28A
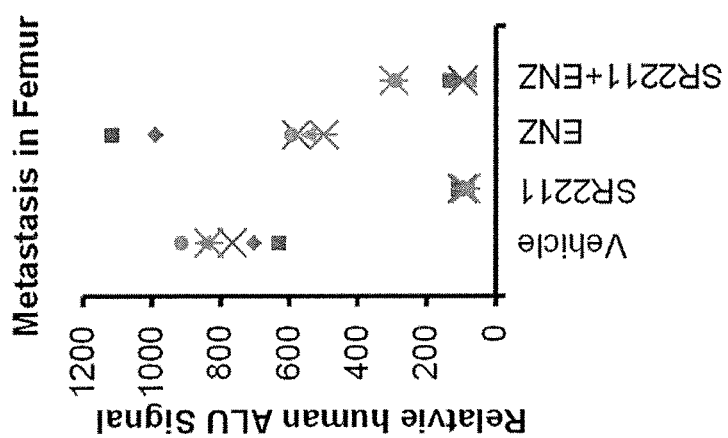

| Tissue weight (g) | Control | SR2211 (5mg/kg) | P-value |
|---|---|---|---|
| Prostate &Seminal Vescle, | 0.164 ± 0.006 | 0.159 ± 0.005 | = 0.59 |
| Testis, | 0.0983 ± 0.006 | 0.0986 ± 0.004 | =0.094 |
| Liver | 1.58 ± 0.039 | 1.61 ± 0.064 | = 0.70 |
| Kidney | 0.469 ± 0.007 | 0.458 ± 0.007 | = 0.17 |
| Heart | 0.135 ± 0.008 | 0.153 ± 0.007 | = 0.15 |
| Spleen | 0.109 ± 0.005 | 0.117 ± 0.008 | = 0.47 |
| Lung | 0.185 ± 0.008 | 0.206 ± 0.007 | = 0.12 |
| WAT*, | 0.129 ± 0.015 | 0.079 ± 0.005 | = 0.01 |

*WAT : White adipose tissue from epididymal fat pad

*FIG. 28C*

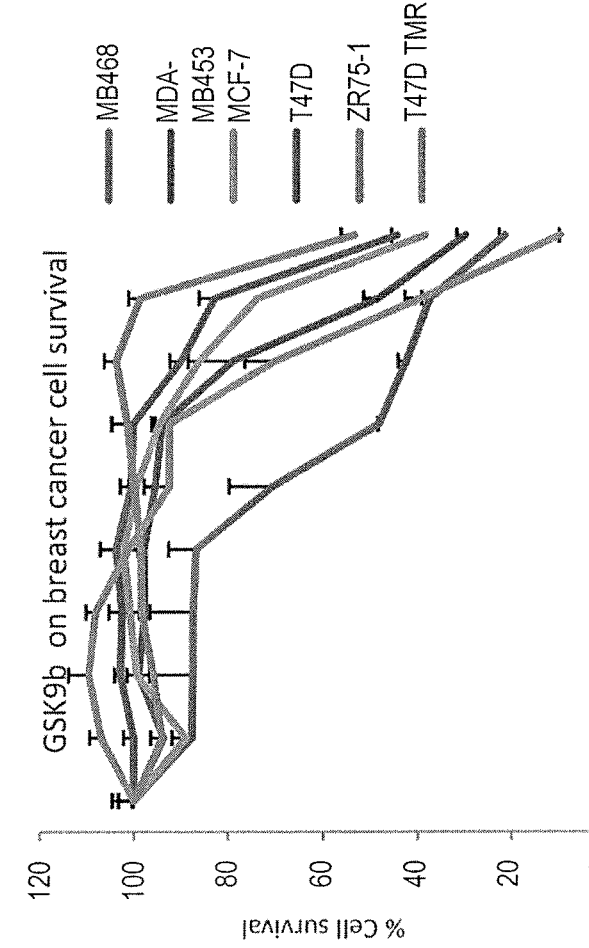
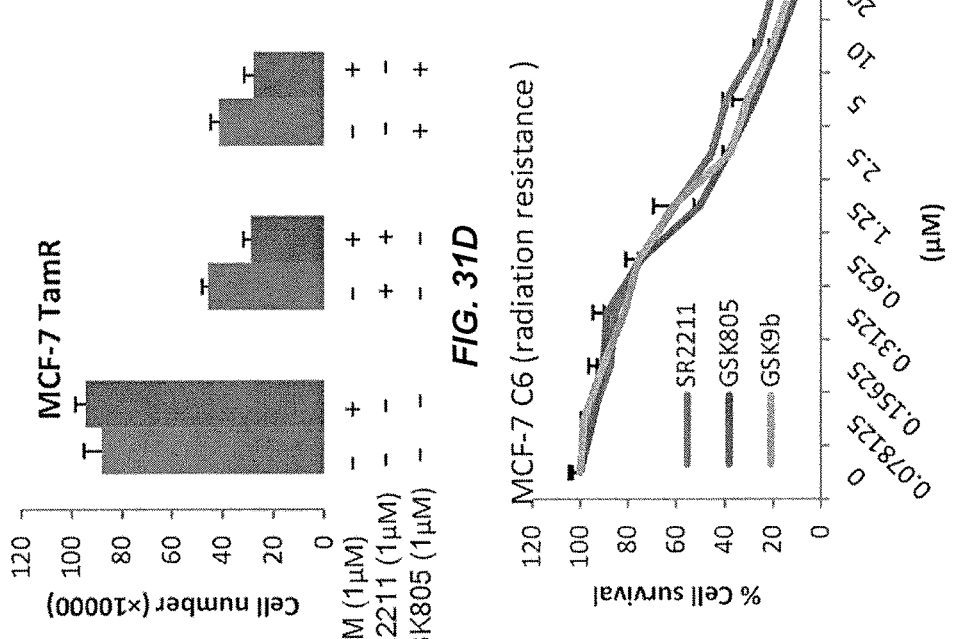
FIG. 31D
FIG. 31E
FIG. 31C

| Breast cancer cell lines | background | IC$_{50}$ (μM) for SR2211 | IC$_{50}$ (μM) for GSK805 | IC$_{50}$ (μM) for GSK9b | IC$_{50}$ (μM) for GNE3500 |
|---|---|---|---|---|---|
| HCC1954 | HER2 positive | 2.26 | 0.70 | 2.52 | 8.56 |
| MB468 | TNBC | 2.04 | 0.78 | | 7.65 |
| BT20 | TNBC | 2.41 | 1.74 | | |
| MB231 | TNBC | 4.34 | 2.10 | | 8.2 |
| sum149 | TNBC | 2.4 | 3.33 | | |
| HCC1937 | TNBC | 2.91 | 5.18 | | |
| MCF-7 | ER positive | 5.74 | 18.42 | 9.3 | 18.5 |
| T47D | ER positive | 22.65 | 10.68 | 13.53 | 21.2 |
| T47D TamR | Tamoxifen resistance | 3.62 | 3.04 | 3.8 | 11.5 |
| MCF-7 C6 | Radiation resistance | 1.87 | 1.41 | 1.62 | 8.56 |

*FIG. 31F*

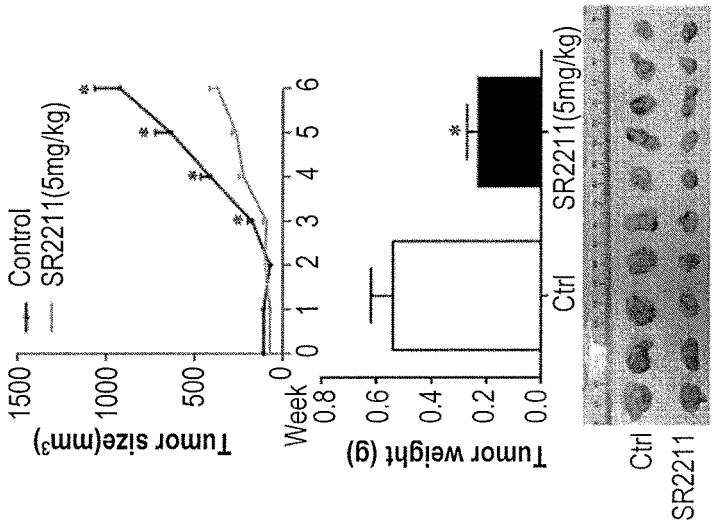

FIG. 32D

Scid Mice DOB:20141124; xenograft A549 cell lines at 20150219; compound Sr2211(5mg/kg) treatment from 20150225, total 6 weeks.

| lung cancer cell line | background | $IC_{50}$ (μM) for SR2211 | $IC_{50}$ (μM) for GSK805 |
|---|---|---|---|
| A427 | K-Ras mutant /resistance to Erlotinib | 3.904 | 8.411 |
| Calu1 | K-Ras mutant | 2.619 | 2.489 |
| H1666 | BRAF mutant | 2.533 | 2.382 |
| A549 | K-Ras mutant/EGFR wt | 4.157 | 4.455 |
| H23 | K-Ras mutant/EGFRwt | 4.816 | 8.497 |
| HCC827 | sensitive to Erlotinib | 7.738 | 7.878 |
| H358 | K-Ras mutant | 9.765 | 7.254 |
| H69 | small lung cancer | 4.360 | 4.06 |
| H209 | small lung cancer | 7.910 | 11.52 |
| PC-9 | sensitive to Erlotinib | 9.615 | 6.413 |
| H1975 | resistance to Erlotinib | 19.764 | 17.93 |

FIG. 32C

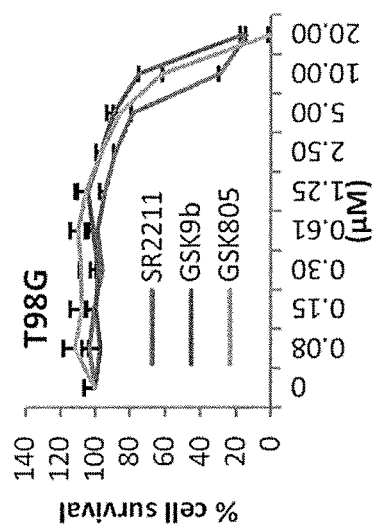
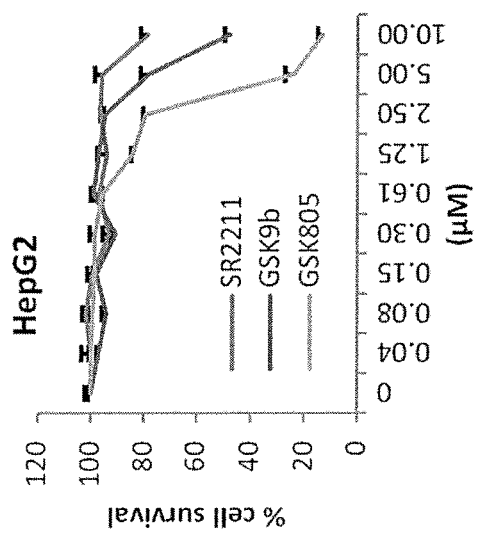
FIG. 33D
FIG. 33E

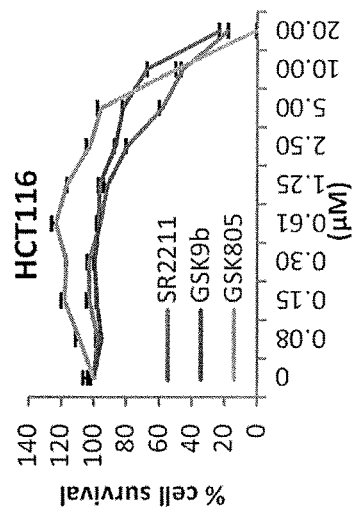
FIG. 33G
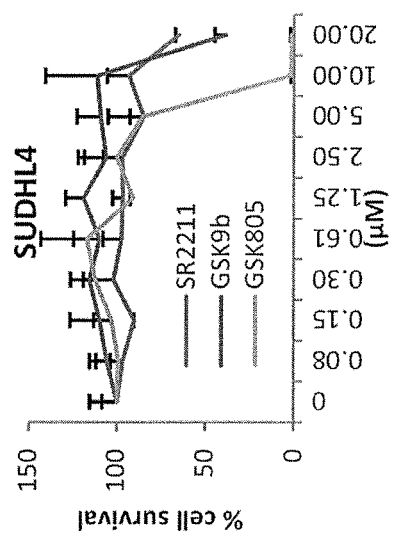
FIG. 33F
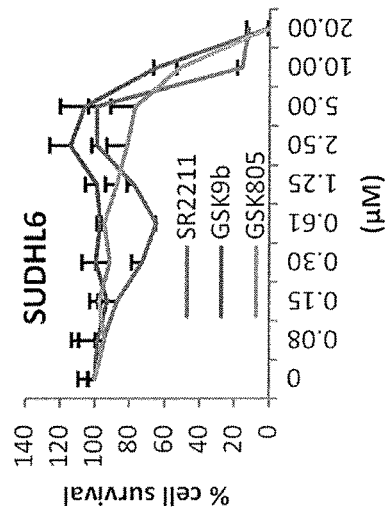

METHODS FOR TREATING CANCER WITH RORγ INHIBITORS

CROSS-REFERENCES TO RELATED APPLICATIONS

This application is a continuation of International Patent Application No. PCT/US2016/021983, filed Mar. 11, 2016, which claims priority to U.S. Provisional Application No. 62/132,465, filed Mar. 12, 2015, and U.S. Provisional Application No. 62/280,081, filed Jan. 18, 2016, the disclosures of which are hereby incorporated by reference in their entirety for all purposes.

STATEMENT AS TO RIGHTS TO INVENTIONS MADE UNDER FEDERALLY SPONSORED RESEARCH AND DEVELOPMENT

This invention was made with Government support under Grant No. CA206222, awarded by the National Institutes of Health; and Grant No. 101BX002237 awarded by the Veterans' Administration. The Government has certain rights in this invention.

REFERENCE TO A SEQUENCE LISTING

The Sequence Listing written in file_070772-1061385_Substitute_Sequence_Listing.txt created on Dec. 11, 2017, 25,606 bytes, machine format IBM-PC, MS-Windows operating system, is hereby incorporated by reference in its entirety for all purposes.

BACKGROUND OF THE INVENTION

Cancer is a leading cause of death in the United States, and despite the development of various different treatment methods such as chemotherapy, radiation therapy, and hormone deprivation therapy, there is no 100% effective cure to these diseases. One of the reasons current cancer treatment methods do not result in eradication of the cancerous tissue in afflicted individuals is through the development of drug resistance by the cancerous cells. Patients who exhibit drug resistance to a particular cancer drug will have tumors that no longer react to the drug and can continue growing despite continued treatment.

Because drug resistance can be a common outcome during the course of administering a particular cancer therapy, it is important to continue developing new drugs and to identify new targets to treat cancer. For example, advanced prostate cancers (PCa) such as metastatic castration-resistant prostate cancers (mCRPCs) are deadly diseases. The most effective therapeutics such as enzalutamide and abiraterone give only a few months of overall survival benefit in a subgroup of the PCa patients.

As such, there is currently a need in the art for new methods and compositions for treating cancer patients and patients with drug-resistant cancers. The present disclosure addresses these and other needs.

BRIEF SUMMARY OF THE INVENTION

In a first aspect, the present invention provides a method for treating cancer in a subject, the method comprising administering to the subject an effective amount of a retinoic acid receptor-related orphan receptor γ (RORγ) inhibitor.

In some embodiments, the cancer is resistant to an anticancer drug. Non-limiting examples of anticancer drugs include anti-androgen drugs, chemotherapeutic agents, radiotherapeutic agents, antigen-specific immunotherapeutic agents, endocrine therapies, tyrosine kinase inhibitors, and combinations thereof. In certain instances, the anti-androgen drug is selected from the group consisting of enzalutamide, bicalutamide, arbiraterone, nilutamide, flutamide, apalutamide, finasteride, dutasteride, alfatradiol, and combinations thereof. In other instances, the chemotherapeutic agent is tamoxifen, a taxane (e.g., paclitaxel and/or docetaxel), or combinations thereof.

In some embodiments, the cancer is selected from the group consisting of a prostate cancer, lung cancer, breast cancer, liver cancer, ovarian cancer, endometrial cancer, bladder cancer, colon cancer, lymphoma, and glioma.

In certain embodiments, the prostate cancer is a castration-resistant prostate cancer. In particular embodiments, the castration-resistant prostate cancer is resistant to an anticancer drug such as, e.g., an anti-androgen drug and/or a taxane. In some instances, the anti-androgen drug is selected from the group consisting of enzalutamide, bicalutamide, arbiraterone, nilutamide, flutamide, apalutamide, finasteride, dutasteride, alfatradiol, and combinations thereof. In other instances, the taxane is selected from the group consisting of paclitaxel, docetaxel, and combinations thereof.

In some embodiments, the lung cancer is a non-small-cell lung cancer (NSCLC), K-Ras mutant lung cancer, BRAF mutant lung cancer, EGFR mutant lung cancer, tyrosine kinase inhibitor-resistant lung cancer, or small cell lung cancer (SCLC).

In some embodiments, the breast cancer is a triple-negative breast cancer (TNBC), tamoxifen-resistant breast cancer, radiation-resistant breast cancer, HER2-positive breast cancer, or ER-positive breast cancer.

In some embodiments, the RORγ inhibitor is a small molecule compound. Non-limiting examples of small molecule RORγ inhibitors are shown in Table 1 and Formula I. In certain embodiments, the small molecule compound selectively binds to RORγ and inhibits RORγ activity. In other embodiments, the subject is a mammal (e.g., human) in need of cancer treatment.

In a second aspect, the present invention provides a method for treating a cancer in a subject, the method comprising administering to the subject an effective amount of a retinoic acid receptor-related orphan receptor γ (RORγ) inhibitor in combination with an effective amount of an anticancer drug.

In some embodiments, the cancer is resistant to the anticancer drug. In particular embodiments, the RORγ inhibitor enhances the therapeutic effect of the anticancer drug. For example, the RORγ inhibitor can reverse or reduce cancer cell resistance to the anticancer drug and/or sensitize cancer cells to the anticancer drug.

In some embodiments, the cancer is selected from the group consisting of a prostate cancer, lung cancer, breast cancer, liver cancer, ovarian cancer, endometrial cancer, bladder cancer, colon cancer, lymphoma, and glioma.

In certain embodiments, the prostate cancer is a castration-resistant prostate cancer. In particular embodiments, the castration-resistant prostate cancer is resistant to an anticancer drug such as, e.g., an anti-androgen drug and/or a taxane. In some instances, the anti-androgen drug is selected from the group consisting of enzalutamide, bicalutamide, arbiraterone, nilutamide, flutamide, apalutamide, finasteride, dutasteride, alfatradiol, and combinations thereof. In other instances, the taxane is selected from the group consisting of paclitaxel, docetaxel, and combinations thereof.

In some embodiments, the lung cancer is a non-small-cell lung cancer (NSCLC), K-Ras mutant lung cancer, BRAF mutant lung cancer, EGFR mutant lung cancer, tyrosine kinase inhibitor-resistant lung cancer, or small cell lung cancer (SCLC).

In some embodiments, the breast cancer is a triple-negative breast cancer (TNBC), tamoxifen-resistant breast cancer, radiation-resistant breast cancer, HER2-positive breast cancer, or ER-positive breast cancer.

In some embodiments, the RORγ inhibitor is a small molecule compound. Non-limiting examples of small molecule RORγ inhibitors are shown in Table 1 and Formula I. In certain embodiments, the small molecule compound selectively binds to RORγ and inhibits RORγ activity. In other embodiments, the subject is a mammal (e.g., human) in need of cancer treatment.

In some embodiments, the anticancer drug is selected from the group consisting of an anti-androgen drug, chemotherapeutic agent, radiotherapeutic agent, antigen-specific immunotherapeutic agent, endocrine therapy, tyrosine kinase inhibitor, and combinations thereof. In certain instances, the anti-androgen drug is selected from the group consisting of enzalutamide, bicalutamide, arbiraterone, nilutamide, flutamide, apalutamide, finasteride, dutasteride, alfatradiol, and combinations thereof. In other instances, the chemotherapeutic agent is tamoxifen, a taxane (e.g., paclitaxel and/or docetaxel), or combinations thereof.

As a non-limiting example, a subject with a prostate cancer that is resistant to treatment with an anti-androgen drug such as enzalutamide can be administered the anti-androgen drug with an amount of a RORγ inhibitor sufficient to reverse or reduce prostate cancer cell resistance to the anti-androgen drug and/or sensitize the prostate cancer cells to the anti-androgen drug.

As another non-limiting example, a subject with a prostate cancer that is resistant to treatment with a taxane such as docetaxel can be administered the taxane with an amount of a RORγ inhibitor sufficient to reverse or reduce prostate cancer cell resistance to the taxane and/or sensitize the prostate cancer cells to the taxane.

As yet another non-limiting example, a subject with a breast cancer that is resistant to treatment with a chemotherapeutic agent such as tamoxifen can be administered the chemotherapeutic agent with an amount of a RORγ inhibitor sufficient to reverse or reduce breast cancer cell resistance to the chemotherapeutic agent and/or sensitize the breast cancer cells to the chemotherapeutic agent.

As a further non-limiting example, a subject with a breast cancer that is resistant to radiation treatment can be administered radiotherapy with an amount of a RORγ inhibitor sufficient to reverse or reduce breast cancer cell resistance to the radiotherapy and/or sensitize the breast cancer cells to the radiotherapy.

In a third aspect, the present invention provides a composition comprising a retinoic acid receptor-related orphan receptor γ (RORγ) inhibitor and an anticancer drug.

In some embodiments, the RORγ inhibitor is a small molecule compound. Non-limiting examples of small molecule RORγ inhibitors are shown in Table 1 and Formula I. In certain embodiments, the small molecule compound selectively binds to RORγ and inhibits RORγ activity.

In some embodiments, the anticancer drug is selected from the group consisting of an anti-androgen drug, chemotherapeutic agent, radiotherapeutic agent, antigen-specific immunotherapeutic agent, endocrine therapy, tyrosine kinase inhibitor, and combinations thereof. In certain instances, the anti-androgen drug is selected from the group consisting of enzalutamide, bicalutamide, arbiraterone, nilutamide, flutamide, apalutamide, finasteride, dutasteride, alfatradiol, and combinations thereof. In other instances, the chemotherapeutic agent is tamoxifen, a taxane (e.g., paclitaxel and/or docetaxel), or combinations thereof.

In some embodiments, the composition further comprises a pharmaceutically acceptable excipient or diluent. In other embodiments, the composition is formulated for oral or parenteral (e.g., intravenous) administration.

In a fourth aspect, the present invention provides a kit comprising a retinoic acid receptor-related orphan receptor γ (RORγ) inhibitor and an anticancer drug.

In some embodiments, the RORγ inhibitor is a small molecule compound. Non-limiting examples of small molecule RORγ inhibitors are shown in Table 1 and Formula I. In certain embodiments, the small molecule compound selectively binds to RORγ and inhibits RORγ activity.

In some embodiments, the anticancer drug is selected from the group consisting of an anti-androgen drug, chemotherapeutic agent, radiotherapeutic agent, antigen-specific immunotherapeutic agent, endocrine therapy, tyrosine kinase inhibitor, and combinations thereof. In certain instances, the anti-androgen drug is selected from the group consisting of enzalutamide, bicalutamide, arbiraterone, nilutamide, flutamide, apalutamide, finasteride, dutasteride, alfatradiol, and combinations thereof. In other instances, the chemotherapeutic agent is tamoxifen, a taxane (e.g., paclitaxel and/or docetaxel), or combinations thereof.

In some embodiments, the kit further comprises a label with instructions for administering the RORγ inhibitor and/or the anticancer drug to a subject. In certain instances, the subject is a mammal (e.g., human) in need of cancer treatment.

Other objects, features, and advantages of the present invention will be apparent to one of skill in the art from the following detailed description and figures.

BRIEF DESCRIPTION OF THE DRAWINGS

FIGS. 1A-1D show that orphan nuclear receptor RORγ is overexpressed in metastatic prostate cancer. FIG. 1A: RORC transcript levels from two gene Expression Omnibus (GEO) data sets of Chandran U R, 2007 and Grasso C S, 2012 were queried for association with disease status (benign, primary and metastatic). FIG. 1B: Schematic of nuclear receptor RORγ structure and function. FIG. 1C: Immunoblotting analysis of RORγ protein in prostate cancer and noncancer cell lines. Shown are representative blots. FIG. 1D: Representative images from RORγ immunohistochemistry of normal prostate (n=8) or a cohort of PCa tumor specimens (n=70).

FIGS. 2A-2F show that a number of different RORγ antagonists display potent anticancer activities. FIG. 2A: Chemical structures of RORγ antagonists SR2211, 8k, 7k, and 6f, and anti-androgen drug enzalutamide (ENZ). FIG. 2B: Cell growth of C4-2B cells treated with the indicated concentrations of ENZ and 8k ("Cmpd8k") for different days. Note: 8k is also known as E11 (see, FIGS. 3A-3D) and XY011. FIG. 2C: Cell growth of C4-2B cells treated with the indicated concentrations of 6F, 8C and 8k for different days. FIG. 2D: Cell growth of CR-VCaP cells treated with the indicated concentrations of SR2211 and Cmpd8k for different days. CR-VCaP is a castration-resistant subline of VCaP that was derived from a VCaP xenograft tumor that grew back in the mouse after the mouse was castrated. VCaP cells were obtained initially from ATCC. FIG. 2E: Relative cell growth of 8k and vehicle on different cell lines. FIG. 2F: Relative cell apoptosis of 8k and vehicle on C4-2B and CR-VCaP cells.

FIGS. 3A-3D show that RORγ antagonists strongly inhibit growth of enzalutamide-resistant tumors. MDV3100=enzalutamide. FIG. 3A: Effects of the indicated treatments (SR2211, 5 mg/kg i.p., E11, 10 mg/kg and 20 mg/kg i.p., respectively, five times per week; or vehicle) on the growth of 22Rv1 xenografts (n=6 mice per group). Note: E11 is also known as 8k (see, FIGS. 2A-2F) and XY011. FIG. 3B: Images of xenograft tumors from mice treated with Vehicle, MDV3100, SR2211, and E11 respectively. FIG. 3C: The testis weight from mice treated with vehicle, SR2211 or E11 for 24 days. FIG. 3D: Representative images of testis from vehicle- or SR2211-treated mice.

FIGS. 4A-4B show that RORγ antagonists potently inhibit the expression of aberrant androgen receptor (AR) that drives tumor progression. FIG. 4A: Immunoblotting of AR (full length) and AR-V7 in C4-2B treated with SR2211 and vehicle at the indicated concentrations for 72 h. FIG. 4B: Immunoblotting of AR (full length), AR-V7 and GR in VCaP cells treated with SR2211 and vehicle at the indicated concentrations for 72 h.

FIG. 6A: RORC transcript levels from two Gene Expression Omnibus (GEO) data sets of Chandran U R, 2007 and Grasso C S, 2012 were queried for association with disease status (benign, primary and metastatic). P values were calculated by using two-tailed Student's t test. Box plot line (from top to bottom): maximum; Q3, third quartile; median; Q1, first quartile; and minimum. FIG. 6B: Representative images from RORγ immunohistochemistry of normal prostate (n=8) or a cohort of PCa tumor specimens (n=70). Immunohistochemistry (IHC) analysis of association of RORγ protein levels with pathological parameters in a cohort of prostate cancer tumor specimens (n=70). FIG. 6C: Immunoblotting analysis of RORγ protein in prostate cancer and noncancer cell lines. Shown are representative blots. FIG. 6D: C4-2B cells (left) in 9% charcoal-dextrand-stripped (cds) fetal bovine serum (FBS), plus 1% FBS medium, and VCaP cells (right) in regular FBS medium were transfected with siRNAs against RORC (siRORC-1 and siRORC-2) or control siRNA (si-Cont). After the indicated time points, viable cells were counted. FIG. 6E: C4-2B cells were treated as in FIG. 6D, and apoptosis was analyzed by measuring caspase3/7 activity. FIG. 6F: Immunoblotting analysis of the indicated proteins in C4-2B and VCaP cells transfected with RORC or control siRNA and incubated for 3 d.

FIGS. 7A-7G show that RORγ antagonists potently inhibit growth of CRPC cells. FIG. 7A: Chemical structures of RORγ antagonists SR221 land XY011. FIG. 7B: Cell viability, as measured by Cell-Titer GLO (Promega) of C4-2B cells treated with the indicated concentrations of ENZ, RORα agonist SR3335 and RORγ antagonists SR2211, XY011 and SR1555 for 4 d. Experiments were performed with three independent experiments and sextuplicate. FIG. 7C: Half-maximal inhibitory concentration ($IC_{50}$) for SR2211 and ENZ in indicated cell lines treated for 4 days is shown. FIG. 7D: C4-2B and 22Rv1 cells were treated with vehicle (DMSO) or the indicated concentrations of SR2211 or XY011 for 14 d, after which colony formation was assessed. *$P<0.05$, $P<0.01$; Student's t test, n=3. FIG. 7E: Caspase-3/7 (Cas3/7) activities in C4-2B and 22Rv1 cells treated with vehicle or the indicated RORγ antagonists for 3 d. $P<0.01$; Student's t test, n=3. FIG. 7F: TUNEL-positive apoptotic cells treated with vehicle or RORγ antagonists (5 μM) were counted and expressed as a percentage of total cells. Data shown are mean percentage of apoptotic cells±s.d. *$P<0.05$, **$P<0.01$; Student's t test, n=3. FIG. 7G: Immunoblotting analysis of the indicated proteins in C4-2B cells treated with vehicle or the indicated RORγ antagonists for 3 d. Representative blots; n=3.

FIGS. 8A-8C show that RORγ controls AR-dependent gene programs. FIG. 8A: Heat map displaying the fold changes of gene expression, as detected by RNA-seq in C4-2B cells treated with either SR2211 (5 μM), XY011 (5 μM) or ENZ (20 μM) for 48 h, as compared to vehicle (DMSO). Left, genes displayed were altered in their expression with $log_2>0.5$ in at least one condition. Cluster 1, genes inhibited by both antagonists; cluster 2, genes induced by SR2211 but inhibited by XY011; cluster 3, genes induced by both antagonists; cluster 4, genes inhibited by SR2211 but induced by XY011. Middle and right, androgen-responsive, AR activity-signature genes that were altered in expression are displayed, with AR target genes in light blue, as defined by AR ChIP-seq peaks. Genes that were also affected by ENZ are displayed for comparison. FIG. 8B: GSEA of the AR activity signature in C4-2B cells treated with 5 μM of SR2211 (up) or XY011 (down), as compared to vehicle. The signature was defined by genes that underwent significant expression changes as a result of androgen stimulation in PCa cells and androgen deprivation in human tumors. FIG. 8C: qRT-PCR analysis of the indicated genes in C4-2B cells treated with vehicle or with RORγ antagonists (5 μM) for 48 h. Data shown are mean±s.d. Student's t test, **$P<0.001$; in =3.

FIG. 9A: Immunoblotting of AR (full length) and AR variants, in C4-2B cells or in VCaP cells, both treated with control or RORC siRNAs, or with RORγ antagonists at the indicated concentrations for 72 h. Representative blots; n=4. FIG. 9B: qRT-PCR analysis of full-length AR expression and AR-V7 expression in VCaP cells treated with vehicle, 5 μM of SR2211 for 48 h. **$P<0.01$; Student's t test; n=3. FIG. 9C: ChIP-seq summary plot of AR enrichment (average coverage; left) across AR-binding sites (ARBS) and H3K27ac enrichment (middle) across the indicated genomic distance in different treatments. Right, genome browser display of AR-binding and H3K27ac-enrichment events on enhancers and/or promoters of the AR target genes KLK2, KLK3 and CAMAKK2. ChIP-seq was performed in C4-2B cells treated with either vehicle or SR2211 (5 μM) for 24 h. FIG. 9D: ChIP-qPCR analysis of relative AR at the indicated gene promoter and/or enhancers in C4-2B cells treated with vehicle or 5 μM of SR2211 for 24 h. *$P<0.05$, **$P<0.01$; Student's t test; n=3. Data shown above are mean±s.d. FIG. 9E: ChIP-qPCR analysis of relative p300 histone acetylase and Pol II occupancy, or histone modifications at the indicated gene promoter and/or enhancers in C4-2B cells treated with vehicle or 5 μM of SR2211 for 24 h. *$P<0.05$, **$P<0.01$; Student's t test; n=3. Data shown above are mean±s.d.

FIGS. 10A-10G show that RORγ directly controls AR gene expression through an exonic RORE and SRCs. FIG. 10A: Upper panel shows a schematic of AR gene locus with ChIP primer-pair locations indicated by horizontal short lines and their distance in kb relative to the TSS. The primer pair amplifying the RORE site is highlighted. Lower panel shows ChIP-qPCR analysis of RORγ occupancy at the locus in C4-2B cells treated with vehicle or 5 μM SR2211. n=3. Data shown are mean±s.d. FIG. 10B: Schematic diagram depicting the locations of sgRNAs targeting the AR-RORE region (SEQ ID NOS: 95 and 96); of primers used for genomic DNA PCR or RT-PCR; and of predicted Cas9 cleavage sites (arrowheads). Note that because of the lack of an additional protospacer adjacent motif (PAM) sequence at or near the RORE, sgRNA 2 is the only one that can be designed to cause indel-type alterations adjacent to the RORE sequence. FIG. 10C: PCR and sequencing analysis of genomic DNA from editing-heterogenous C4-2B cells treated with the indicated sgRNAs and Cas9 (SEQ ID NOS: 97 and 98). Genomic DNA PCR was performed by using primers P3 and P4. The top band indicates the expected full-length PCR amplicons. The two lower bands indicate the expected PCR amplicons, with deletions caused by the indicated sgRNA-guided editing. PCR products containing the deletion amplicons were cloned and sequenced. Representative sequencing chromatograms of expected deletion junctions; n=25. Arrowheads indicate expected deletion junction. FIG. 10D: qRT-PCR analysis with primers P1 and P2 of AR mRNA in C4-2B cells treated with the indicated sgRNAs. P<0.01; Student's t test; n=3. FIG. 10E: Semi-quantitative RT-PCR analysis with primers P3 and P4 of AR mRNA in C4-2B cells treated with the indicated sgRNAs and RORγ antagonists (5 μM; 48 h), as illustrated at left, for measuring the effects of the antagonists on AR mRNA expression from wild-type or deleted alleles. Representative gel images are shown; n=3. FIG. 10F: Sequences of the wild-type (SEQ ID NO: 99) and mutant form of AR-RORE (SEQ ID NO: 100) linked to reporters (top). AR-RORE reporter-gene assays, with 293T cells showing the effects of mutating the RORE sequence or RORγ (left), or showing the effects of the antagonists (right) on RORγ activation. P<0.01; Student's t test; n=3. FIG. 10G: ChIP-qPCR analysis of relative occupancy by the indicated proteins at the AR-RORE site in C4-2B cells treated with vehicle or with 5 μM SR2211 for 24 h. *P<0.05, **P<0.01; Student's t test; n=3. Data shown are mean±s.d.

FIG. 11A: Effects of the indicated treatments (SR2211, 5 mg/kg i.p. five times per week; or vehicle) on the growth of C4-2B (n=6 mice per group). Treatment started when C4-2B tumors reached approximately 100 mm³. Mean tumor volume±s.e.m. and representative tumor images are shown. Scale bar, 1 cm. Significance was calculated using Student's t test. *P=0.000293, P=6.67×10⁻⁵, *P=1.13×10⁻⁵. FIG. 11B: Effects of the indicated treatments (SR2211, 5 mg/kg i.p. five times per week; ENZ, 10 mg/kg orally, five times per week; or vehicle) on the growth of 22Rv1 xenografts (n=6 mice per group). Treatment started when 22Rv1 tumors reached approximately 50 mm³. Mean tumor volume±s.e.m. and representative tumor images are shown. Scale bar, 1 cm. Significance was calculated using Student's t test. #P=3.03× 10⁻⁸, P=1.77×10⁻⁹, *P=1.14×10⁻⁸. FIG. 11C: Immunoblotting (left) of C4-2B xenograft tumors after 24 d of treatment with vehicle or SR2211, as in FIG. 11A. Cell lysate for each lane was from homogenized tumor tissues randomly combined from three mice of vehicle or SR2211 group. Anti-cleaved caspase3 immunohistochemistry images of tumor sections are shown at right. Scale bar, 50 μm. FIG. 11D: Left, schematic illustrating CRPC-VCaP xenograft tumor establishment and treatment. Castrated mice bearing the CRPC-VCaP xenografts (n=6 mice per group) received vehicle, SR2211 (i.p., 5 mg/kg), ENZ (oral, 10 mg/kg) or a combination of SR2211 and ENZ, as indicated, five times per week. Mean tumor volume±s.e.m. is shown. Significance was calculated using Student's t test. *P=1.98×10⁻¹⁰, P=1.46×10⁻¹⁰, *P=7.21×10⁻¹³.

FIGS. 12A-12D show that overexpression of RORγ, not RORα or RORβ, associates with metastatic CRPC progression. FIG. 12A: RORA and RORB transcript expression in two prostate cancer microarray studies from the GEO database. Data sets were analyzed for the transcript levels of RORA and RORB genes, which encode RORα and RORβ proteins respectively, in benign prostate tissues, and primary or metastatic prostate tumor tissues (top). Oncoprint display from cBioPortal of the three ROR gene alterations in metastatic prostate cancer tumors from 150 patients reported in a recent study[45] (bottom). MYC and EZH2 are displayed for comparison of their alteration frequency and individual tumor relationship with the three ROR genes in the same study. FIG. 12B: VCaP, 22Rv1, LNCaP and PC-3 cells were transfected with RORC or control siRNA. After the indicated time, cells were harvested for determining cell growth by counting viable cells. n=3. FIG. 12C: C4-2B and VCaP cells were transfected with RORC or control siRNA. Three days later, cells were harvested for immunoblotting with indicated antibodies. FIG. 12D: LNCaP cells ectopically expressing RORγ and the control cells were cultured in charcoal:dextran stripped (cds) serum-supplemented medium. After the indicated times, cells were harvested for determining cell growth by counting viable cells, n=3. After three days, cells were harvested for immunoblotting with RORγ or GAPDH antibodies.

FIG. 13A: C4-2B and 22Rv1 cell proliferation after RORγ antagonist treatment. Cells were seeded in 6-well plates and counted after cells were treated with indicated concentrations of RORγ antagonists for 0, 2, 4 and 6 days by Coulter counter. Data are shown as mean±s.d. n=3. FIG. 13B: Representative images of colony formation of C4-2B and 22Rv1 cells treated with vehicle, SR2211 or XY011 for 14 days. FIG. 13C: Representative images of TUNEL positive cells treated with vehicle or the antagonists (5 μM) in 22Rv1 cells are shown. FIG. 13D: C4-2B were treated with vehicle or SR2211. Three days later, cells were harvested for immunoblotting with the indicated antibodies. FIG. 13E: 22Rv1 cells were treated with vehicle or SR2211. Three days later, cells were harvested for immunoblotting with the indicated antibodies.

FIGS. 14A-14E show that RORγ antagonists strongly inhibit AR signaling. FIG. 14A: Heat-map display of the inhibitor-altered expression of genes involved in cell proliferation and survival in C4-2B cells treated with 5 μM SR2211 or XY011 for 48 hours. Gene expression profiling was performed with RNA-sequencing. FIG. 14B: Venn diagrams display overlapping number of up- or down-regulated genes (>1.2 fold) in C4-2B cells between SR2211 (5 μM), XY011 (5 μM) and ENZ (20 μM) treatment. Gene expression profiling was performed after RNA-sequencing. FIG. 14C: Heat-map display of the altered expression of AR-V7 up-regulated genes in C4-2B cells treated as above. FIG. 14D: Heat-map display of the altered expression of the core 16-AR CRPC gene set in C4-2B cells treated as above. FIG. 14E: qRT-PCR analysis of indicated genes in C4-2B cells treated with indicated siRNA (left) or with ENZ (right)

for 48 hours. Data are shown as mean±s.d. Significance was calculated using Student's t-test. **p<0.001.

FIGS. 15A-15D show that RORγ controls AR and its variant expression in prostate cancer cells. FIG. 15A: qRT-PCR analysis of AR full-length and variant AR-V7 expression in C4-2B and VCaP cells treated with indicated siRNAs for 48 hours. Data are shown as mean±s.d. Significance was calculated using Student's t-test. **p<0.001. FIG. 15B: Immunoblotting of AR and its variants or AR-V7 in C4-2B and VCaP cells treated with vehicle or XY011 for 72 hours. FIG. 15C: Immunoblotting of AR and its variant AR-V7 in PC346C, 22Rv1 and LAPC4 cells treated with vehicle or SR2211 for 72 hours. FIG. 15D: Immunoblotting of AR and RORγ in LNCaP cells ectopically expressing RORγ and the control cells cultured in charcoal:dextran stripped (cds) serum-supplemented medium.

Figure 16A:
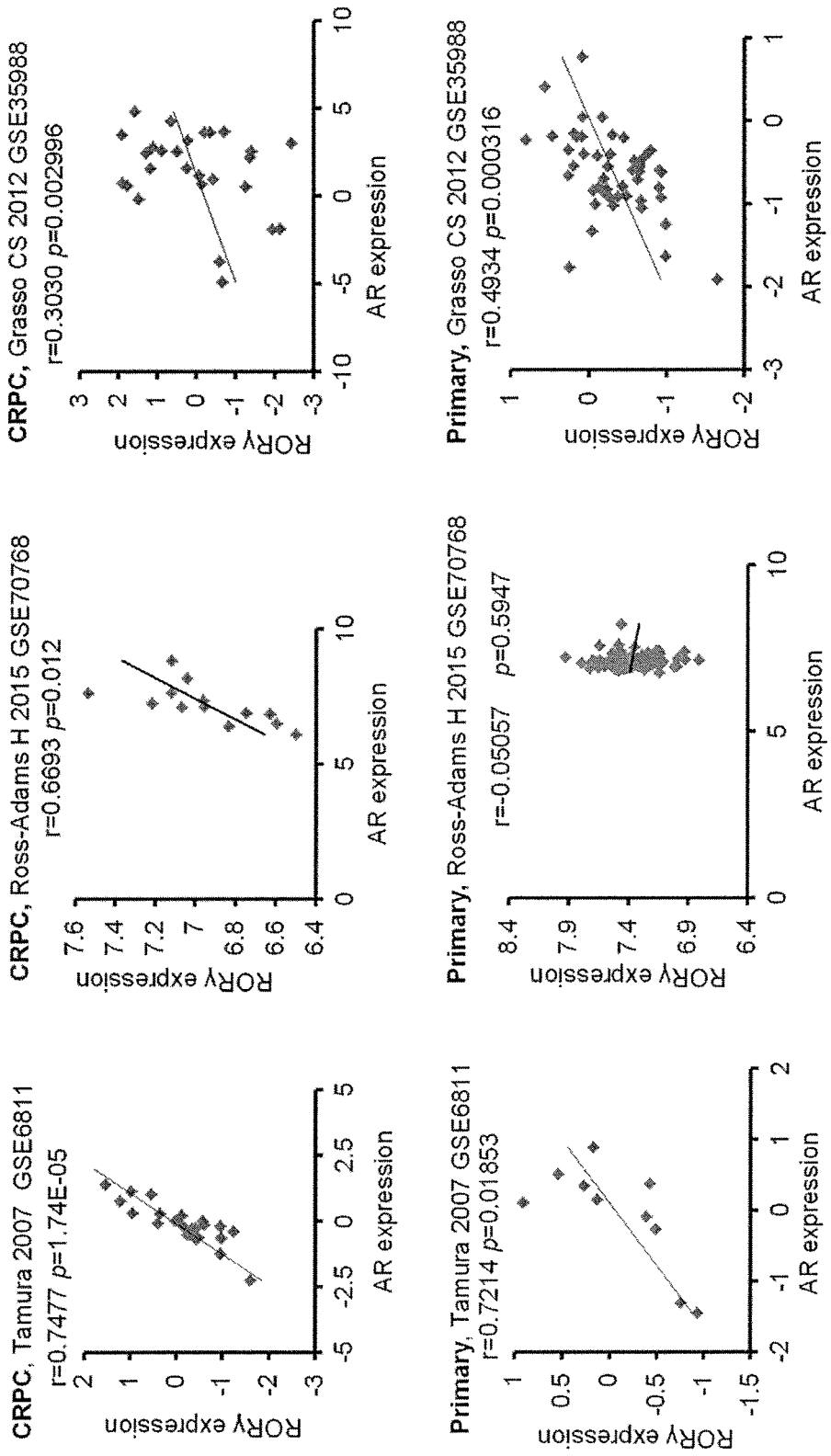
Figure 16B:
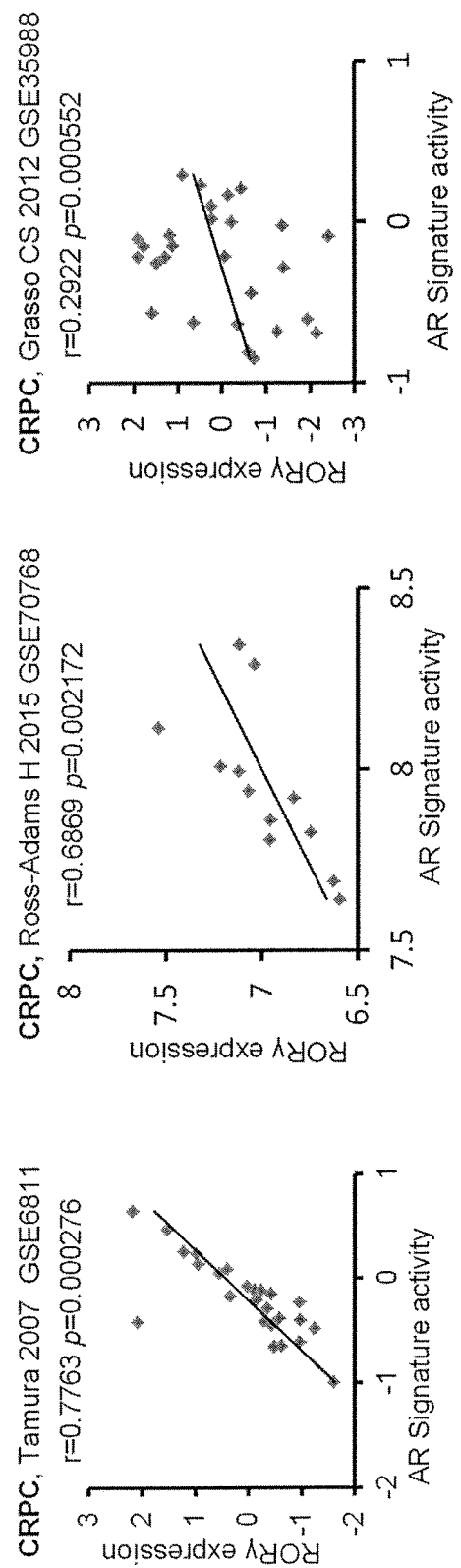

FIGS. 16A-16B show the correlation of RORγ expression with the gene expression of AR and CRPC AR signature activity in clinical tumor data sets. FIG. 16A: Scatter plots showing correlation between RORγ and AR gene expression in primary tumors or CRPC tumors. Gene expression profiles are from different clinical data sets (GSE6811, GSE70768 and GSE35988-GPL6480). Scatter plots showing correlation between RORγ expression and AR expression in CRPC tumors. FIG. 16B: Scatter plots showing correlation between RORγ and AR gene expression in primary tumors or CRPC tumors. Gene expression profiles are from different clinical data sets (GSE6811, GSE70768 and GSE35988-GPL6480). Scatter plots showing correlation between RORγ expression and CRPC AR signature activity in CRPC tumors.

Figure 17A:
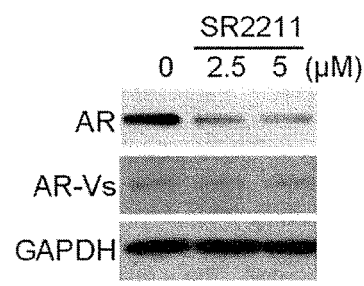
Figure 17B:
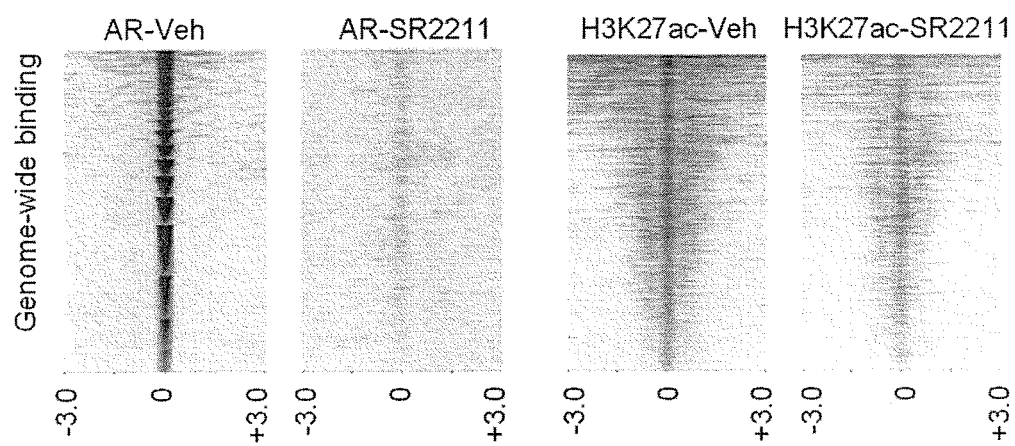
Figure 17C:
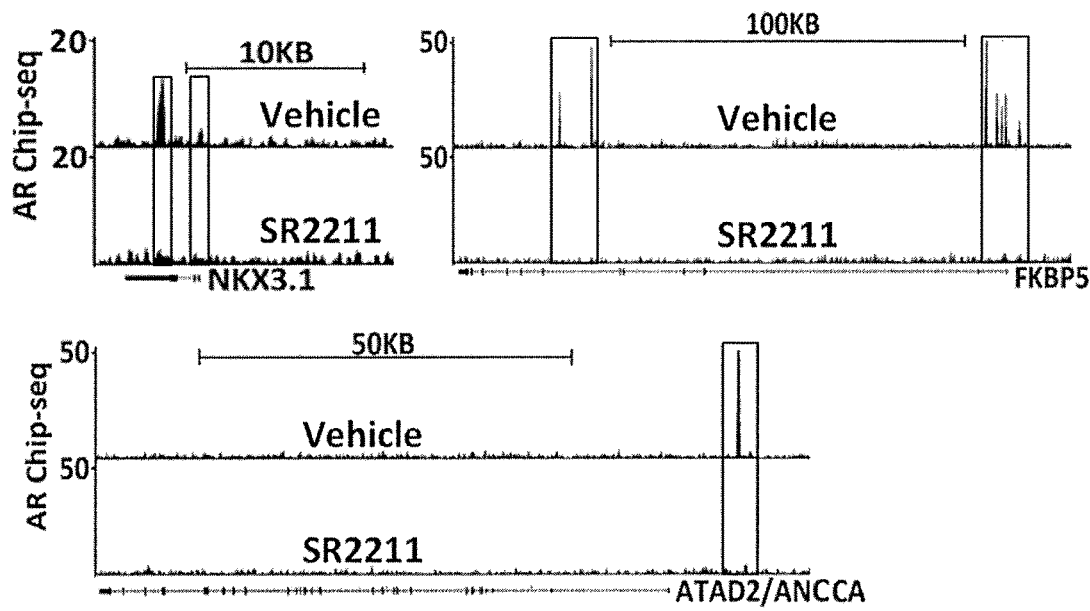
Figure 17D:
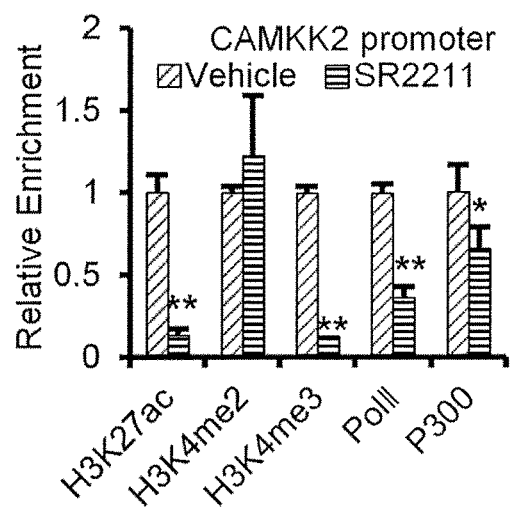
Figure 17E:
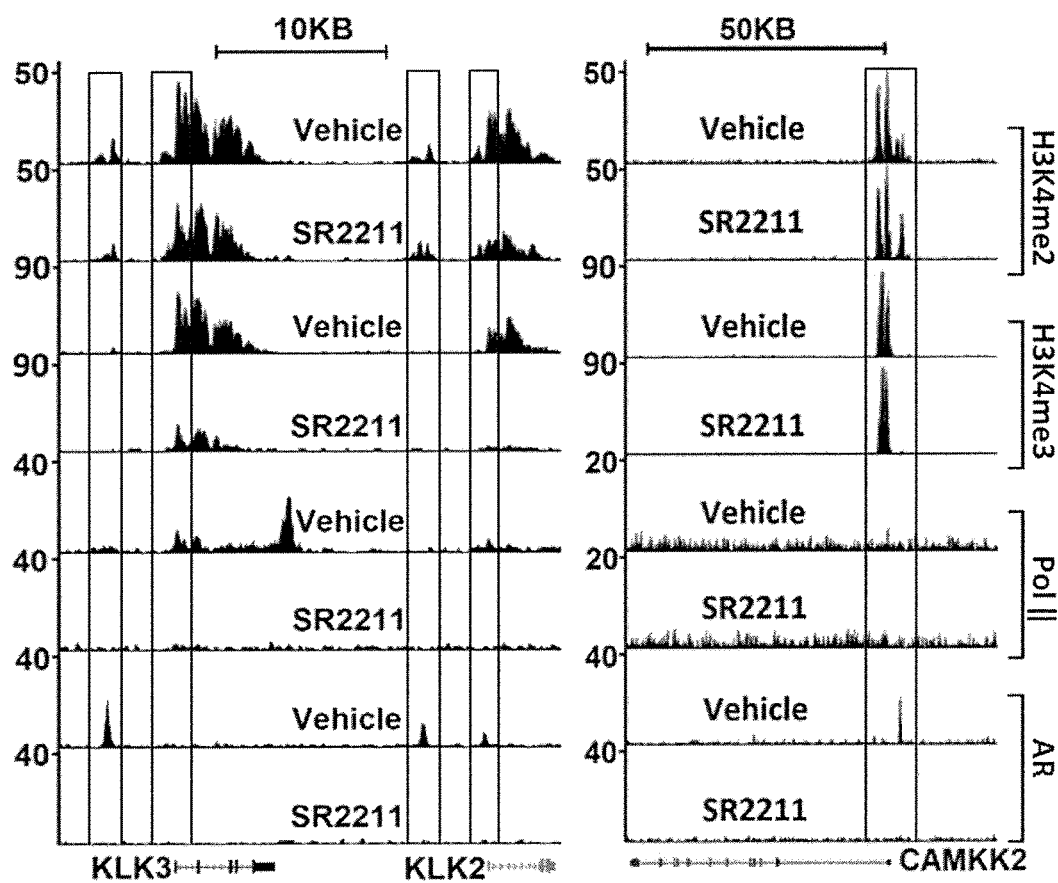
Figure 17F:
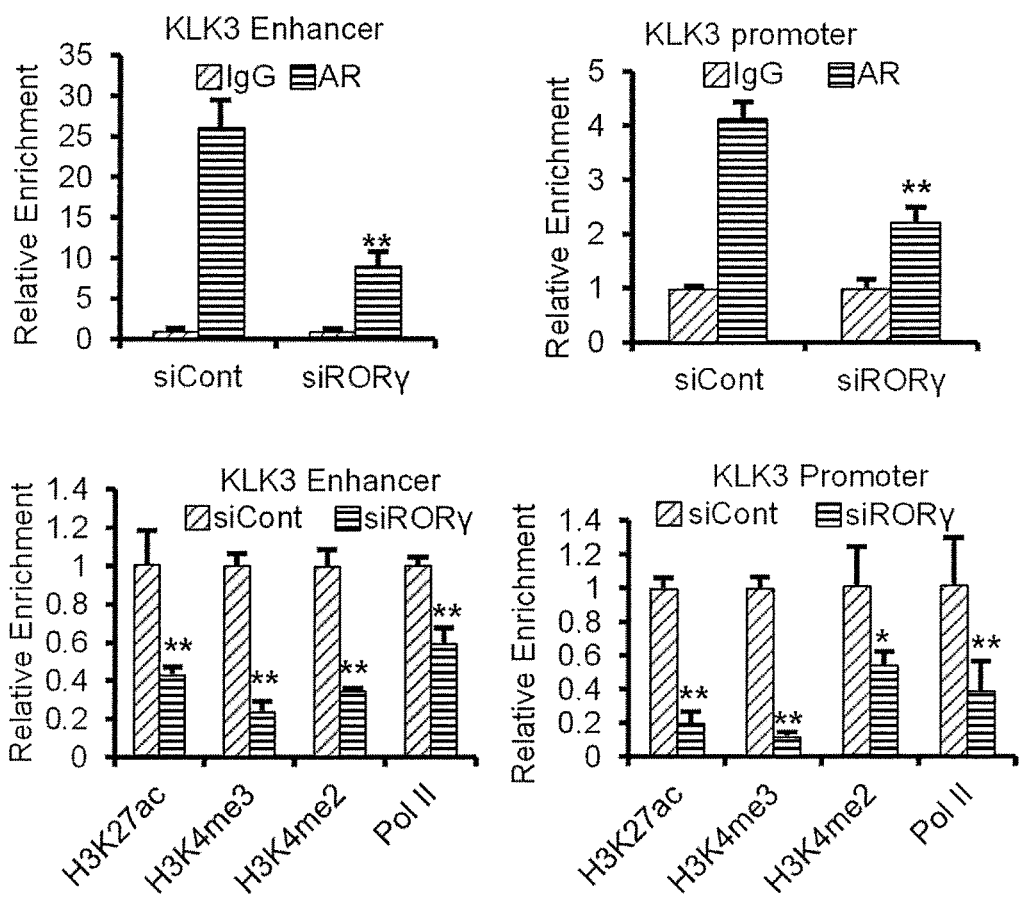
Figure 17G:
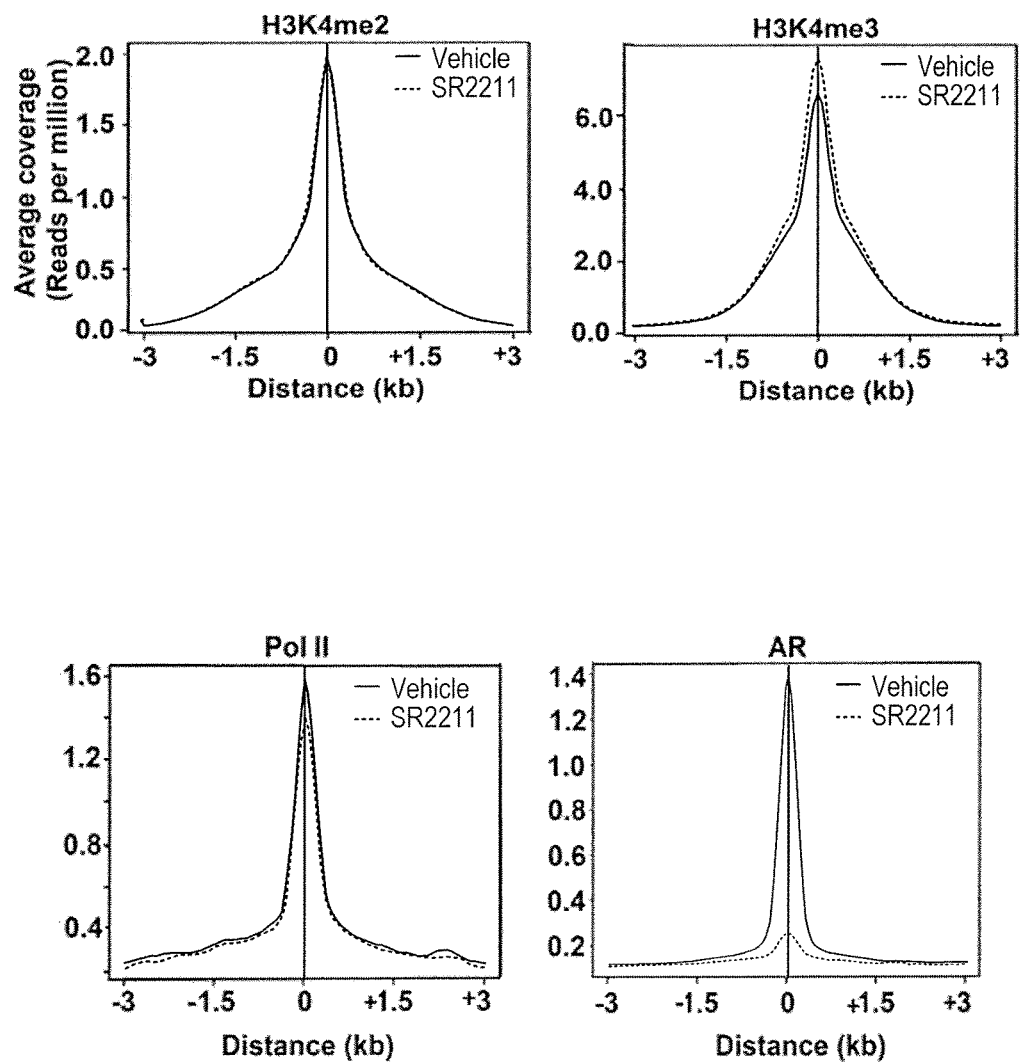

FIGS. 17A-17G show the effects of RORγ inhibition on AR genome binding, histone modifications, and Pol-II recruitment. FIG. 17A: Immuoblotting of AR and its variants in C4-2B cells treated with vehicle or SR2211 (5 µM) for 24 hours. FIG. 17B: Heat-map presentation of AR enrichment (average coverage) across AR-binding sites (ARBS) and H3K27ac enrichment across the enrichment regions in cells treated with vehicle or SR2211 (5 µM) for 24 hours in cells treated as in FIG. 17A. FIG. 17C: Genome browser display of AR binding events on the enhancers and/or promoters of AR-target NKX3.1, FKBP5 and ATAD2/ANCCA genes. AR ChIP-seq was performed in C4-2B cells treated for 24 hours with vehicle or SR2211 (5 µM). FIG. 17D: ChIP-qPCR analysis of relative enrichment of H3K4me2, H3K4me3, H3K27ac, RNA polymerase II (pol II), and acetylase p300 at the promoter of AR-target gene CAMKK2 in C4-2B cells treated with vehicle or SR2211 (5 µM) for 24 hours. Data are shown as mean±s.d. Significance was calculated using Student's t-test. p<0.001, n=3. FIG. 17E: Genome browser display of AR, H3K4me2, H3K4me3 and RNA polymerase II (Pol II) binding events on the enhancers and/or promoters of AR-target KLK2, KLK3 and CAMKK2 genes. ChIP-seq of AR, H3K3K4me2/3 and RNA polymerase II (Pol II) were performed in C4-2B cells treated for 24 hours with vehicle or SR2211 (5 µM). Note: the AR ChIP-seq data shown here were obtained from an experiment separate from the data shown in FIGS. 9A-9E. FIG. 17F: ChIP-qPCR analysis of relative enrichment of AR, H3K4me2, H3K4me3, H3K27ac, RNA polymerase II (pol II), at KLK3 promoter and enhancer in C4-2B cells treated with control or RORγ siRNA for 72 hours. Data are shown as mean±s.d. Significance was calculated using Student's t-test. p<0.001, n=3. FIG. 17G: Enrichment summary plots of AR, H3K4me2, H3K4me3 and pol II across their corresponding binding sites in different treatment groups. ChIP-seq was performed as in FIG. 17E.

Figure 18A:
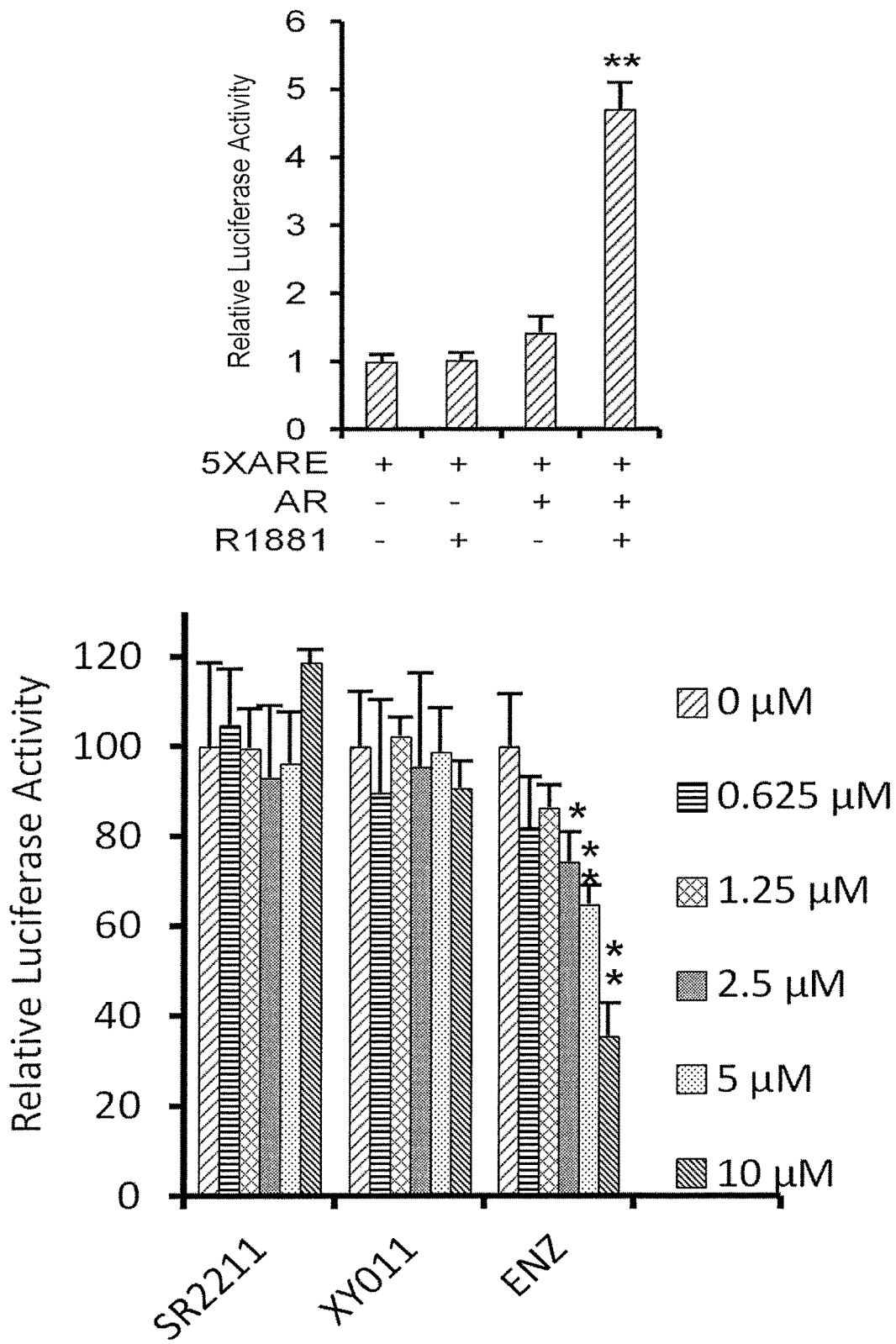
Figure 18B:
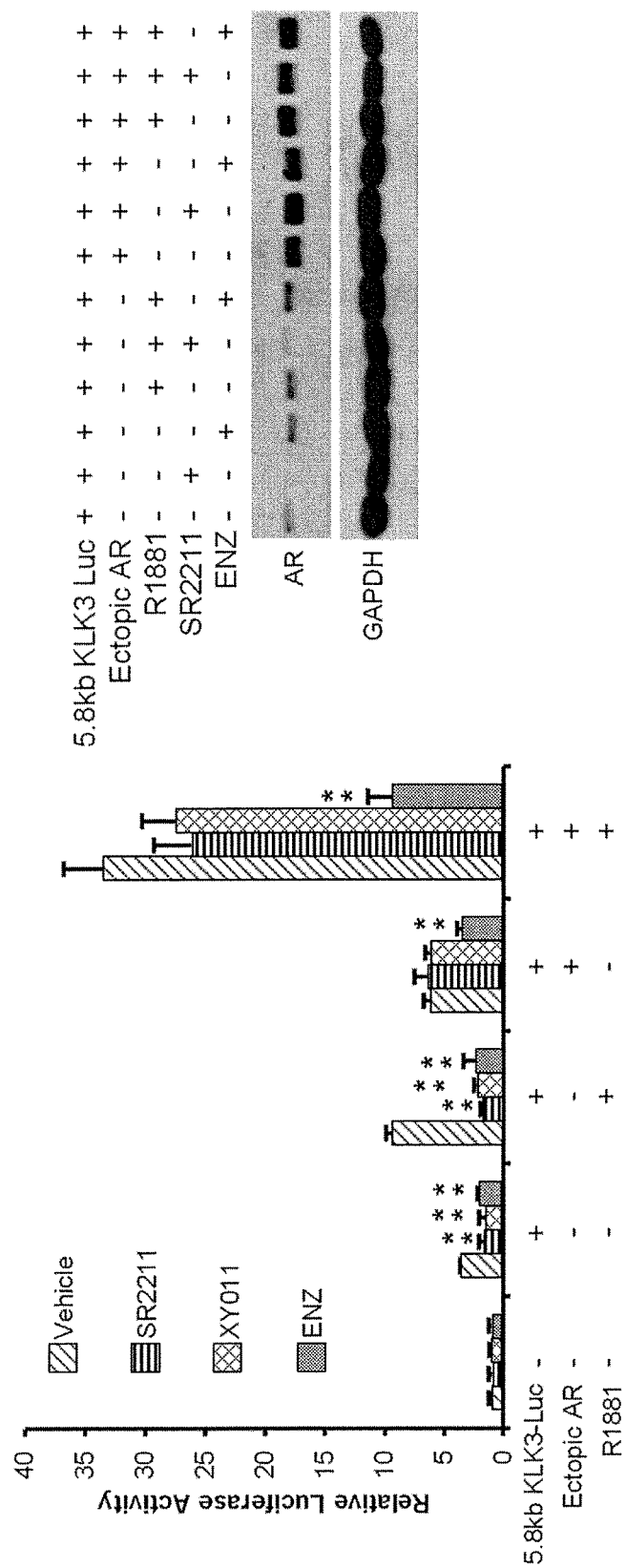

FIGS. 18A-18B show that RORγ antagonists inhibit AR function through suppression of AR expression. FIG. 18A: Left: 22Rv1 cells in charcoal-stripped medium were transfected with 5×ARE-tk-luc and AR expression construct as indicated. Sixteen hours later, cells were treated with 3 nM R1881 for 24 hours, before harvested for luciferase activity measurement. Right: 22Rv1 cells were transfected as above, and then treated with R1881 and RORγ antagonists or AR antagonist (enzalutamide, ENZ) at the indicated concentration. *p<0.05, p<0.01, n=3. FIG. 18B: Left: 22Rv1 cells in charcoal-stripped medium were transfected with 5.8 kb KLK3-luc and AR expression construct as indicated. Sixteen hours later, and then treated with R1881 (3 nM) and RORγ antagonists (5 µM) or AR antagonist (ENZ, 20 µM), before harvested for measuring luciferase activity (left) or immunoblotting with the indicated antibodies (right). p<0.01, n=3.

Figure 10A:
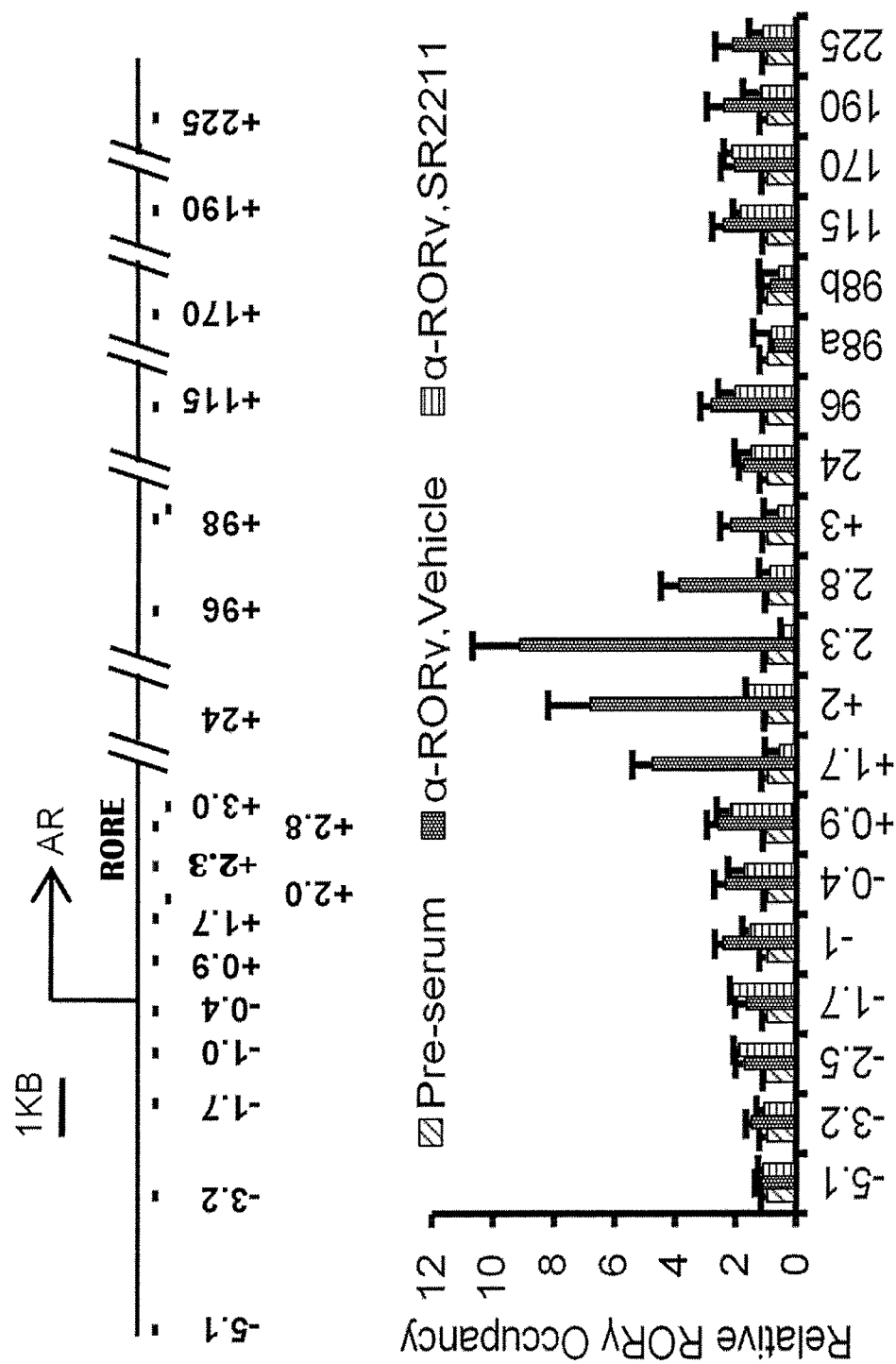
Figure 10E:
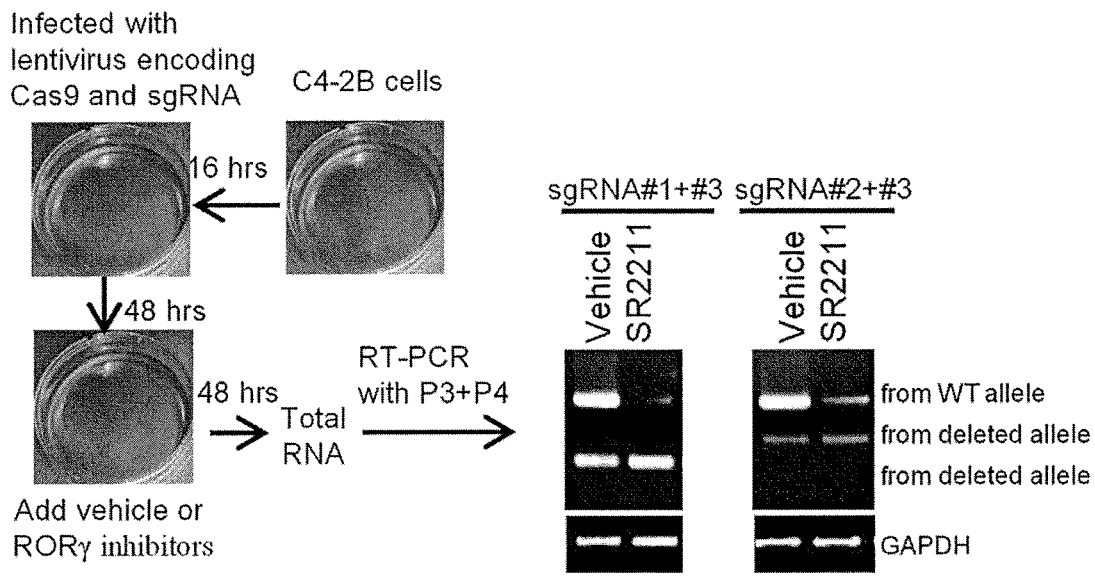
Figure 19A:
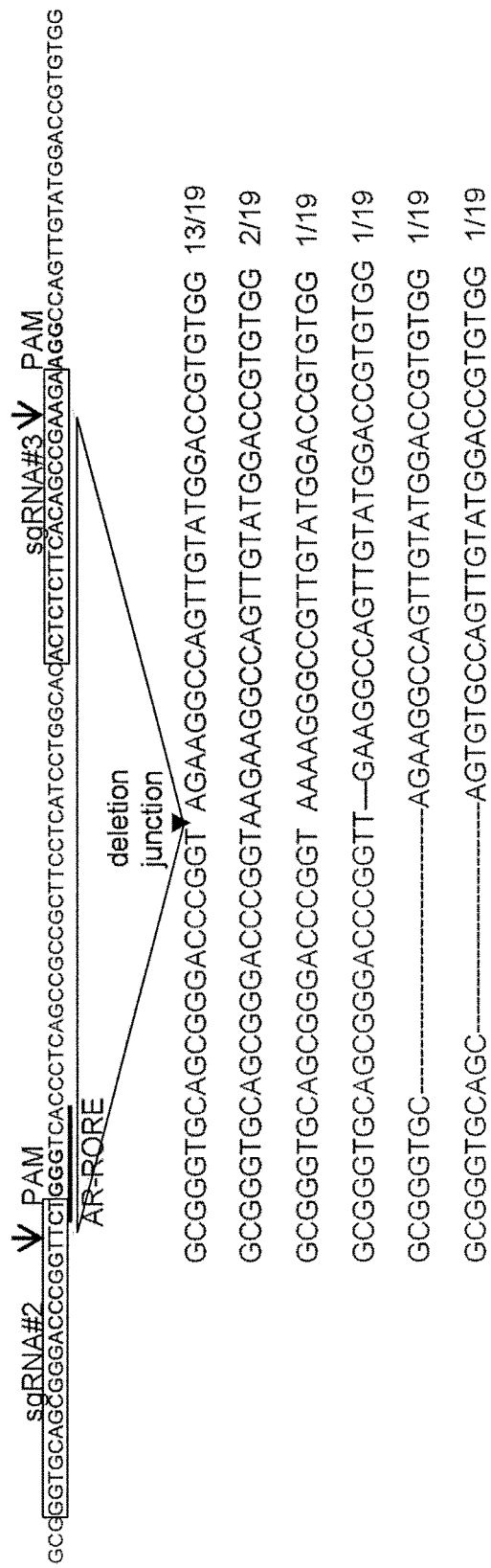
Figure 19B:
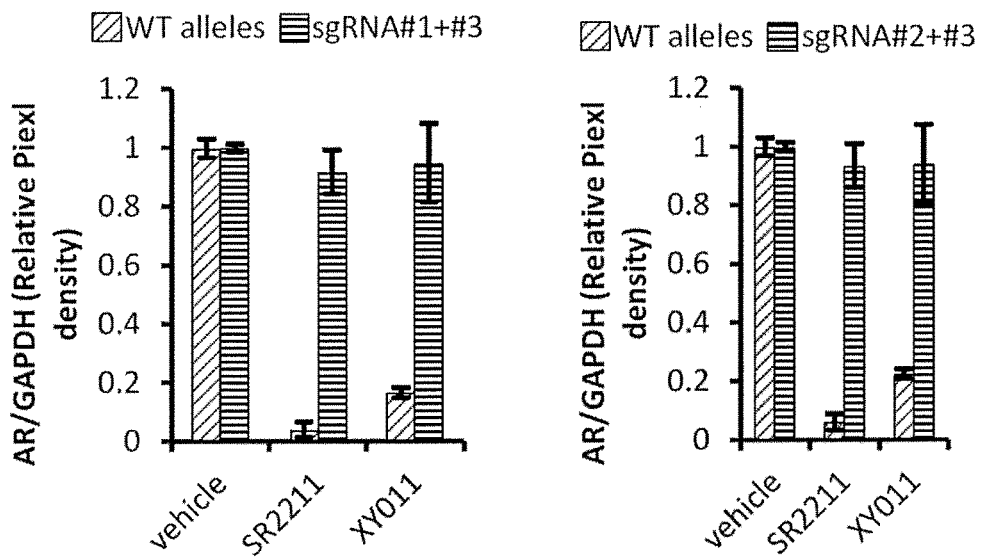
Figure 19C:
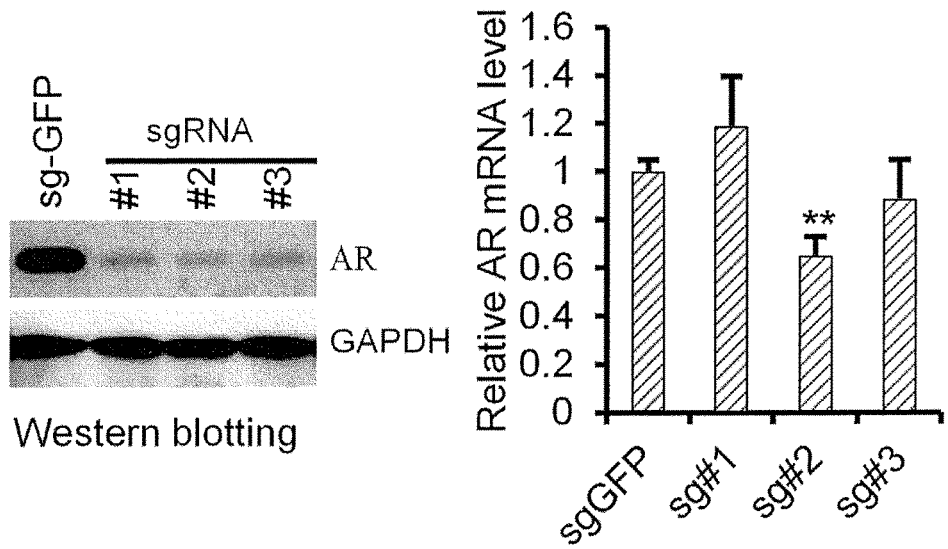

FIGS. 19A-19C show the effects of CRISPR/Cas9 editing of AR-RORE site on AR gene expression. FIG. 19A: Sequencing analysis of the deletion junction of the AR-RORE site (SEQ ID NOS: 101, 102, 103, 104, 105, 106, and 107). PCR products from sgRNA-2+sgRNA-3 deleted alleles (FIG. 10C) were cloned and 19 individual clones were sequenced to determine the sequence of deletion junctions and frequency. The top row shows the wild-type sequence and the arrows indicate expected cleavage sites of Cas9. FIG. 19B: Quantitative analysis of RT-PCR products from AR wild type (WT) and indicated sgRNA-deleted alleles in cells treated with vehicle or RORγ antagonists. C4-2B cells were infected with lentivirus encoding Cas9 and indicated sgRNAs. After two days, cells were treated with vehicle or the RORγ antagonists (5 µM) for another two days before harvested for semi-quantitative RT-PCR. PCR products were separated by agarose gel as shown in FIG. 10E. The experiments were repeated three times. The pixel density of DNA bands from each experiment was quantified and normalized to GAPDH. FIG. 19C: Effects of individual sgRNA-mediated alteration of the AR locus on AR expression. Left, immunoblotting of AR and GAPDH with C4-2B cells treated by indicated sgRNA expressing lentivirus. Right, Real-time qRT-PCR analysis of AR expression in C4-2B cells treated as above. **p<0.01, n=3.

Figure 20A:
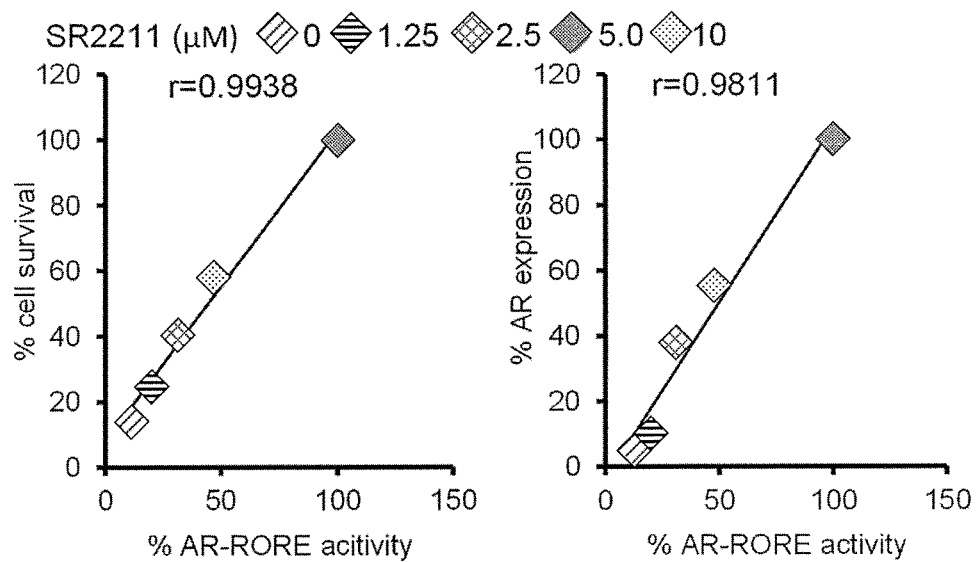
Figure 20B:
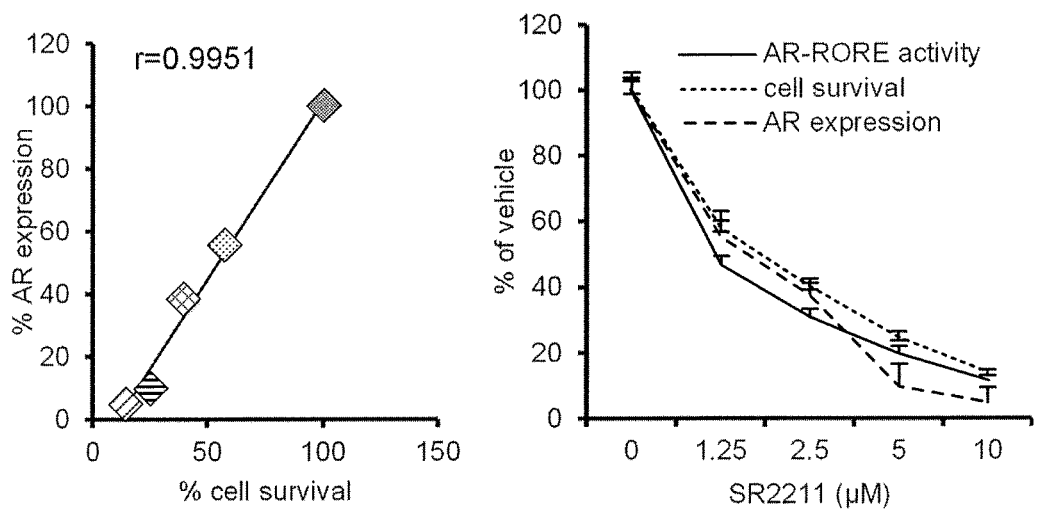

FIGS. 20A-20B show the correlation between ROR inhibition, AR expression inhibition and anti-proliferation by different concentrations of a RORγ antagonist. FIG. 20A: Scatter plot of percentage of indicated inhibitory activities of SR2211 at different concentrations. The results showed a tight correlation between RORγ inhibition, AR expression inhibition and anti-proliferation by SR2211. RORγ inhibition was measured by reporter gene assay as in FIG. 10F. Anti-proliferation/cell viability was measured by Cell-Titer GLO as in FIG. 7B. AR expression inhibition was analyzed by AR immunoblotting followed by quantification of full-length AR protein bands. FIG. 20B: Combined plotting of AR-RORE inhibition, AR expression inhibition and anti-proliferation of SR2211 at different concentrations.

FIG. 21 shows the effects of RORγ knockdown on the occupancy of SRCs and pol-II as well as histone modifications at the AR-RORE site. ChIP-qPCR analysis of relative enrichment of RORγ, H3K4me2, H3K4me3, H3K27ac, RNA polymerase II (pol II) at the AR-RORE site in C4-2B cells treated with control or RORγ siRNA for 72 hours. **p<0.01, n=3.

Figure 22A:
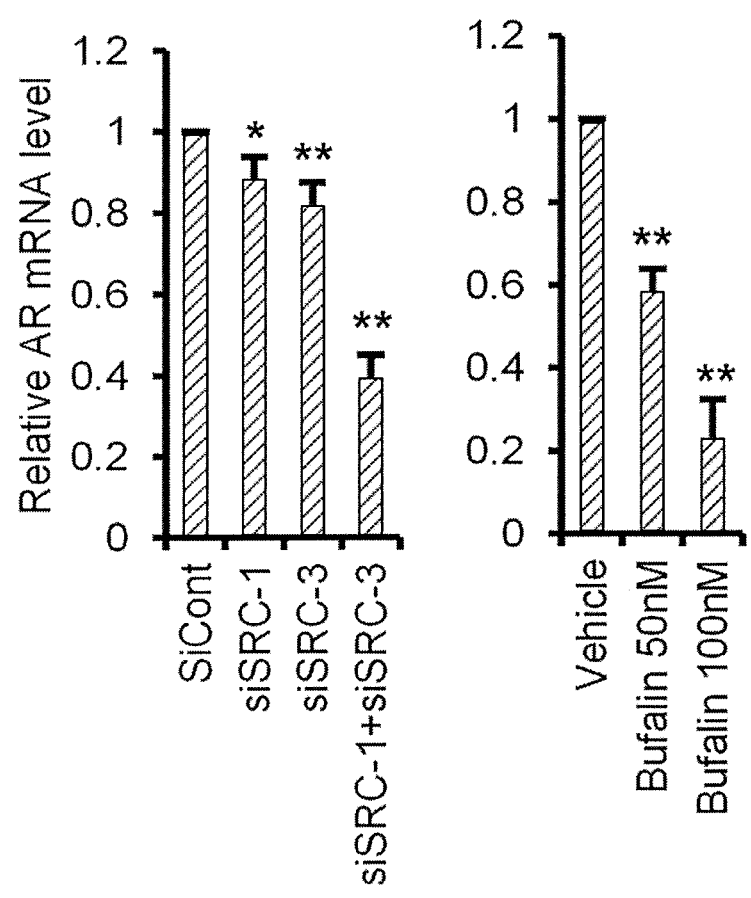
Figure 22B:
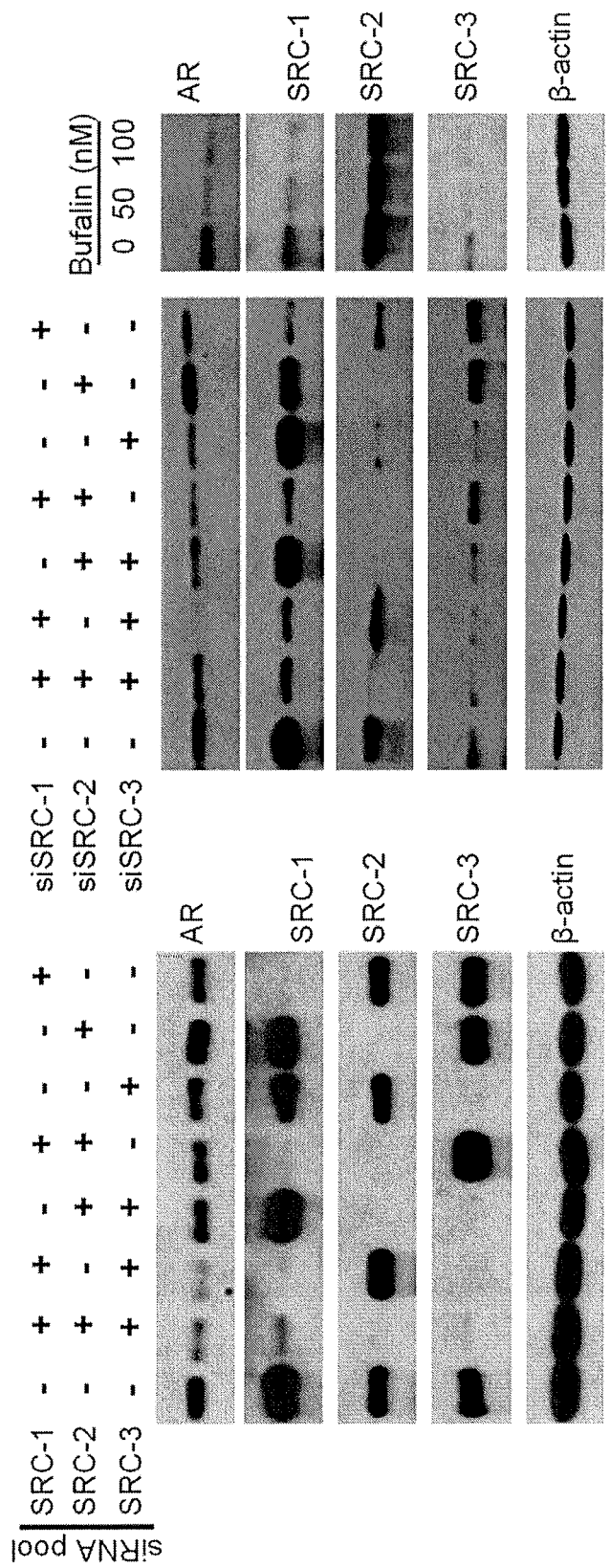
Figure 22C:
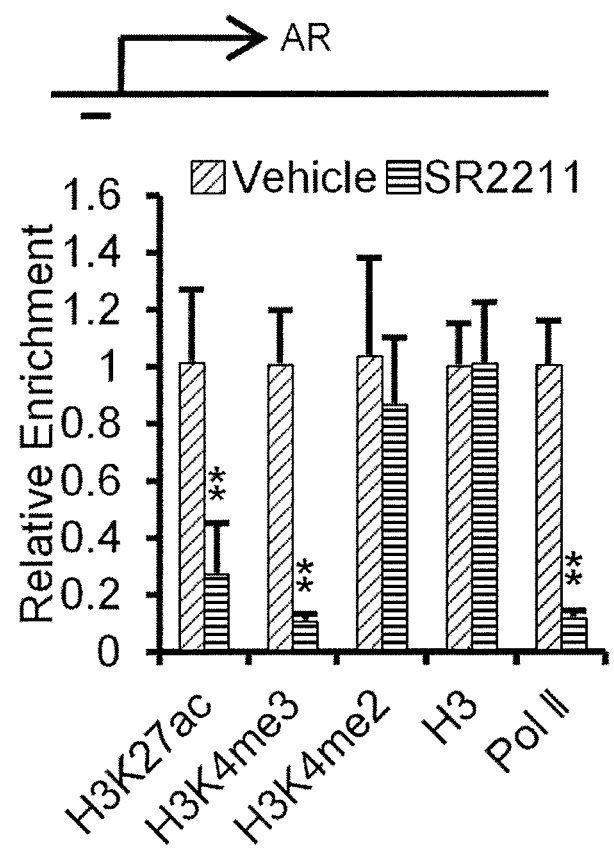

FIGS. 22A-22C show the effects of different SRC coactivator inhibition on AR expression and SR2211 effects on histone modifications and Pol II recruitment at AR promoter. FIG. 22A: qRT-PCR analysis of AR expression in C4-2B cells treated with indicated siRNAs (left) or bufalin for 48 hours or 24 hours respectively. *p<0.05, p<0.01, n=3. FIG. 22B: Left and middle: immunoblotting analysis of indicated proteins in C4-2B cells transfected with smart pool siRNA (left; see, O'Malley et al., Cancer Cell, 28:240-252 (2015)), or individual siRNA targeting different SRCs (middle) or control siRNAs, individually or in different combinations. Right: immunoblotting analysis of C4-2B cells treated with vehicle or bufalin at indicated concentrations for 2 days. FIG. 22C: ChIP-PCR analysis of relative occupancy by H3K4me2, H3K4me3, H3K27ac, Plo II and H3 at AR gene promoter in C4-2B cells treated with vehicle or SR2211 (5 µM) for 24 hours. p<0.01, n=3. Data are shown as mean±s.d. Significance was calculated using Student's t-test.

FIGS. 23A-23B show the in vivo effects of RORγ antagonists on growth of prostate cancer xenograft tumors and mouse body weight. FIG. 23A: Effects of SR2211 (5 mg/kg, i.p., 5 times a week) or vehicle treatment on growth of VCaP xenografts (n=8 mice per group). Mean tumor volume±s.e.m, mean body weight±s.e.m and mean tumor weight±s.e.m are shown. Significance was calculated using Student's t-test.p=2.89E-09, *p=3.44E-08. FIG. 23B: Effects of XY011 (20 mg/kg, i.p., 5 times a week) or vehicle treatment on growth of 22Rv1 xenografts (in =6 mice per group). Mean tumor volume±s.e.m, mean body weight±s.e.m and mean tumor weight±s.e.m are shown. Significance was calculated using Student's 1-test. p=9.99E-08, *p=4.71E-06.

Figure 24:
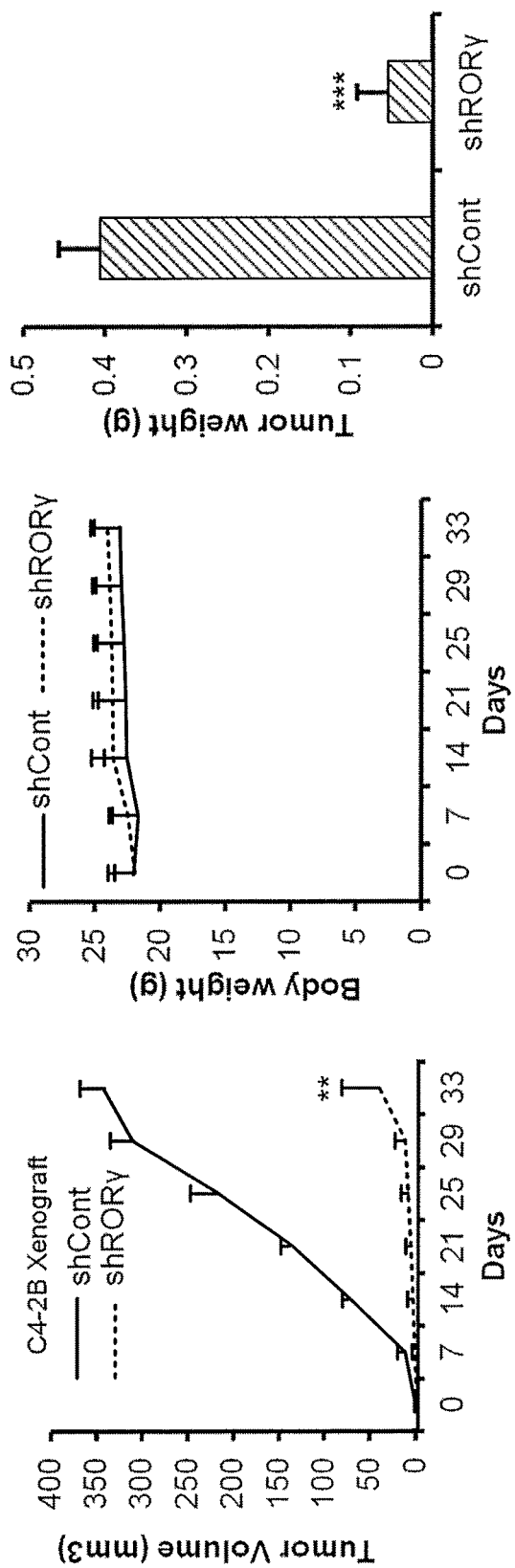

FIG. 24 shows the in vivo effects of RORγ shRNA on growth of prostate cancer C4-2B xenograft tumors and mouse body weight. Effects of control or RORγ shRNA on growth of C4-2B xenografts (n=6 mice per group). Mean tumor volume±s.e.m and mean tumor weight±s.e.m are shown. Student's t-test, p=3.14E-08, *p=3.52E-07.

FIGS. 25A-25C show the in viro effects of RORγ antagonists on growth of C4-2B prostate orthotopic tumors, mouse body weight and serum PSA level. FIG. 25A: Pictures of orthotopically implanted C4-2B tumors grown in SCID mice treated with vehicle or SR2211 (5 mg/kg, i.p., 5 times a week). FIG. 25B: The weights of C4-2B orthotopic tumors from mice treated with SR2211 (5 mg/kg, i.p., 5 times a week) or vehicle (n=6 mice per group). Mean tumor weight±s.e.m is shown. Student's t-test, *p=4.766E-05. FIG. 25C: Tumor growth was monitored by measuring serum PSA levels on the indicated days. Mean PSA level±s.e.m is shown. Student's 1-test, *p=1.2683E-05.

Figure 26C:
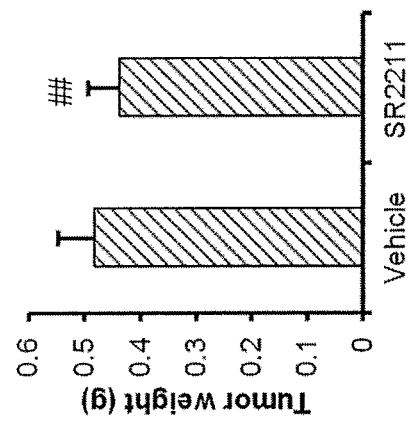
Figure 26B:
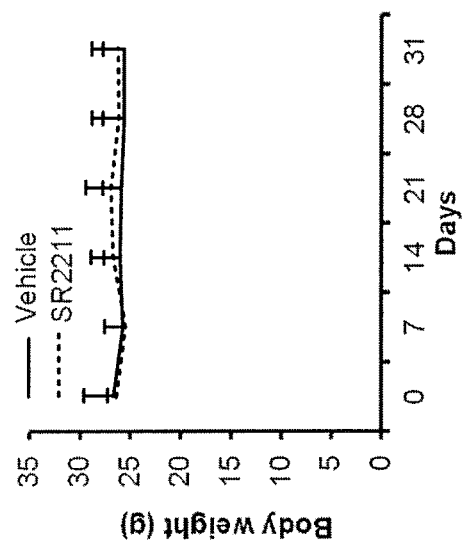
Figure 26A:
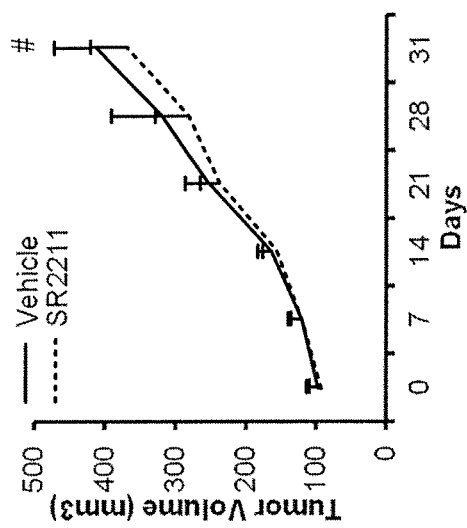

FIGS. 26A-26C show the in vivo effects of RORγ antagonist on growth of PC-3 xenograft tumors, mouse body weight and tumor weight. Effects of SR2211 (5 mg/kg, i.p., 5 times a week) or vehicle treatment on growth of PC-3 xenografts (n=6 mice per group). Mean tumor volume±s.e.m (FIG. 26A), mean body weight±s.e.m (FIG. 26B) and mean tumor weight±s.e.m (FIG. 26C) are shown. Significance was calculated using Student's 1-test, #p=0.06, ##F0.07.

Figure 11B:
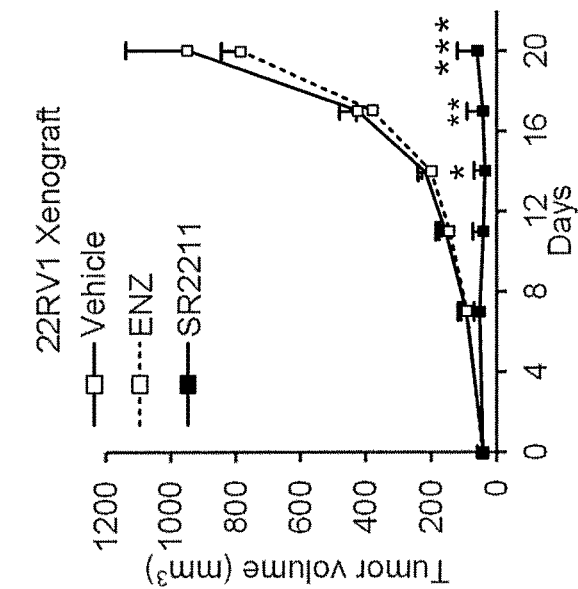
FIGS. 11A-11D show that RORγ antagonists potently inhibit tumor growth.
Figure 11A:
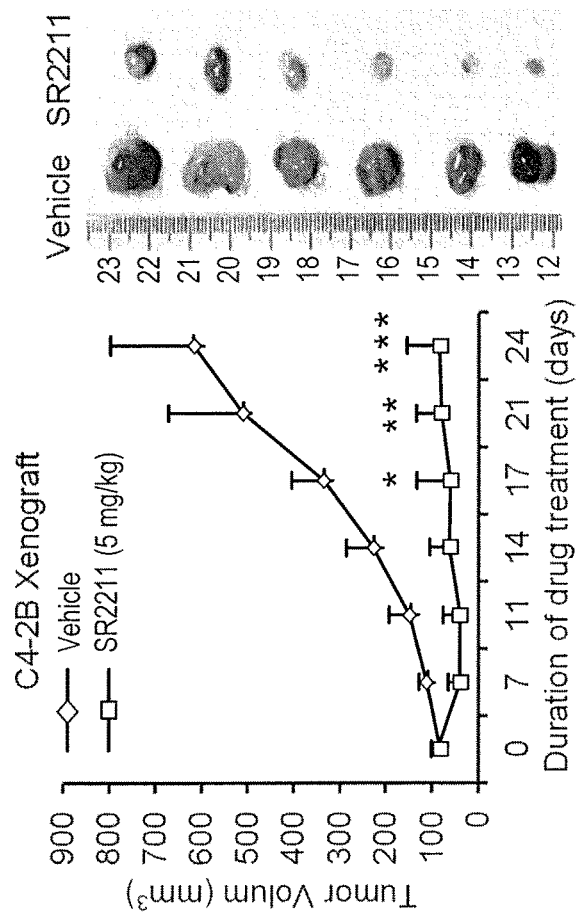

FIGS. 27A-27C show that RORγ inhibition strongly suppresses AR and its variant expression and eliminates AR binding in vivo. FIG. 27A: ChIP analysis of relative RORγ occupancy at the AR-RORE site in C4-2B xenograft tumors after treatment with vehicle or SR2211 as in FIG. 11A. Tumors were harvested after 24 days treatment. Three different tumors in each treatment were used for the ChIP assay. **p<0.01, n=3. FIG. 27B: ChIP analysis of relative AR occupancy at the promoter and enhancer ARE sites of KLK3 in C4-2B xenograft tumors after treatment with vehicle or SR2211 as in FIG. 27A. *p<0.05, p<0.01, n=3. FIG. 27C: qRT-PCR analysis of AR and AR target gene expression in C4-2B xenograft tumors after treatment with vehicle or SR2211 as in FIG. 27A. p<0.01, n=3.

FIGS. 28A-28C show the in vivo effects of RORγ inhibition on tumor metastasis, mouse body weight and organ weight in xenograft models. FIG. 28A: Mice bearing VCaP xenografts as in FIG. 11D, treated with vehicle, SR2211, ENZ or combination for 23 d, were assessed for spontaneous metastasis to the femur (bone marrow) and liver. Genomic DNA isolated from these sites was analyzed for metastasized cells by measuring human Alu sequence (by Alu-qPCR). FIG. 28B: Body weight of mice from different treatment groups. FIG. 28C: Weight of indicated tissues from mice treated with vehicle or SR2211 for 24 days as in FIG. 11A of C4-2B xenograft model. Significance was calculated using Student's t-test, *p=0.01, n=6.

Figure 29A:
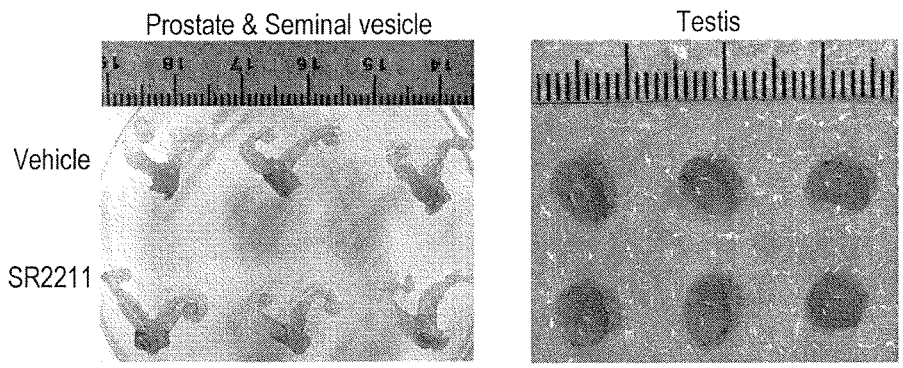
Figure 29B:
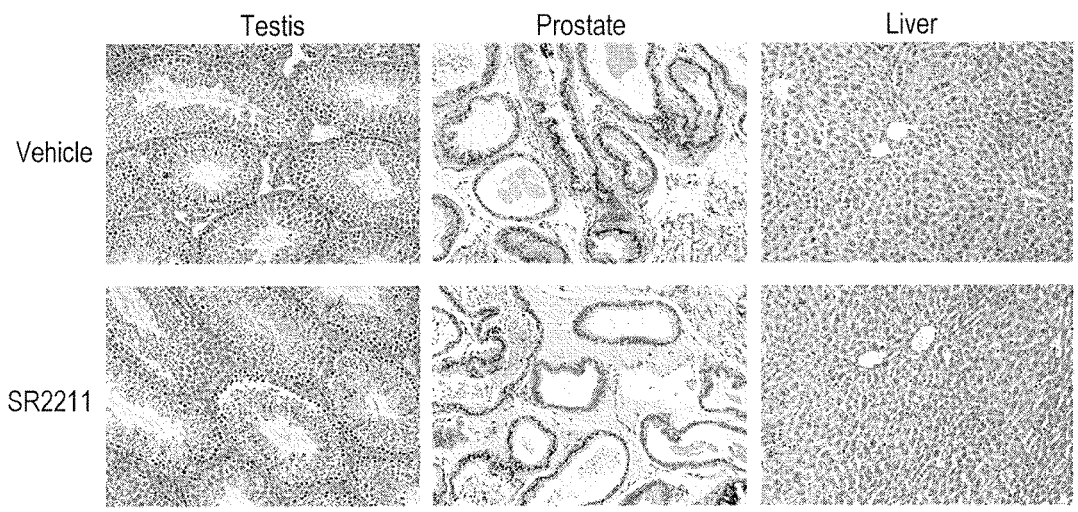
Figure 29C:
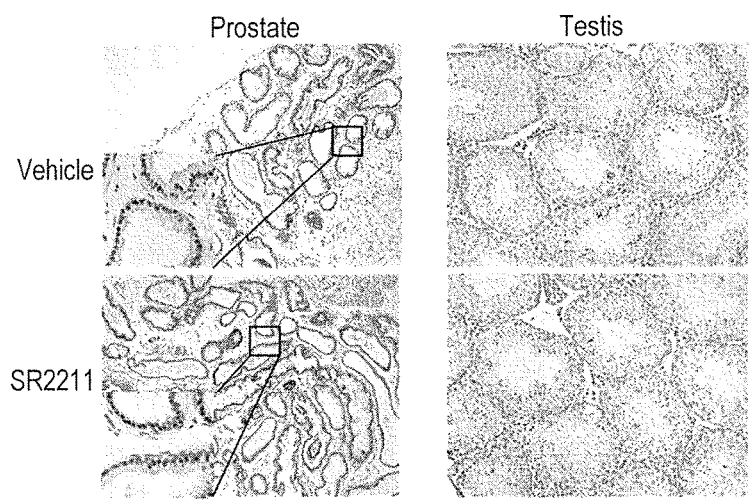

FIGS. 29A-29C show the in vivo effects of RORγ antagonists on normal mouse prostate and testis. FIG. 29A: Representative images of seminal vesicle and prostate, and testis from mice treated with vehicle or SR2211 for 24 days are shown. FIG. 29B: Representative H&E images of prostate, testis and liver from vehicle- or SR2211-treated mice. FIG. 29C: Representative anti-AR IHC images of prostate and testis sections from mice treated with vehicle or SR2211.

Figures 30A, 30B:
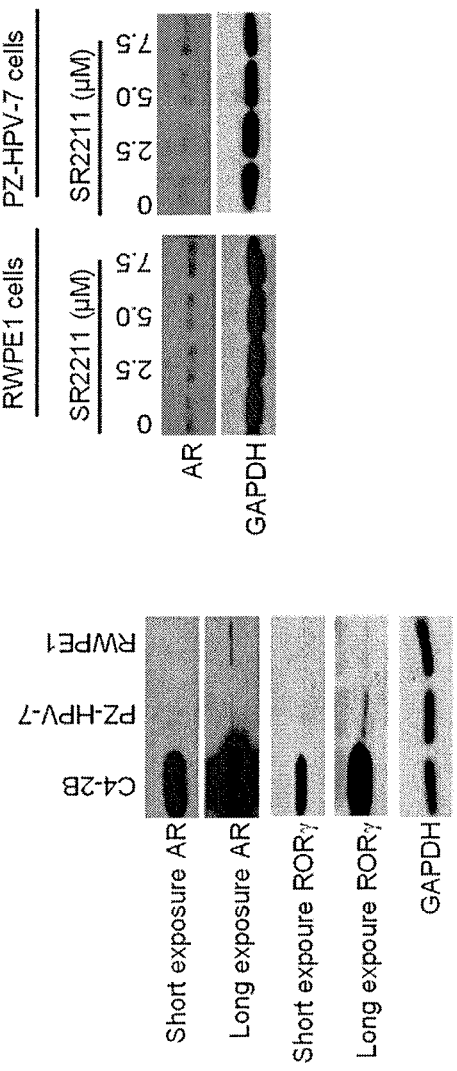

FIGS. 30A-30B show the lack of inhibitory effects by RORγ antagonists on AR expression in non-malignant, human prostate epithelial cells. FIG. 30A: Immunoblotting analysis of RORγ and AR expression in non-malignant, human prostate epithelial RWPE1 and PZ-HPV7 cells with the indicated treatments. FIG. 30B: Comparison of genomic DNA sequences at the 3' end region of AR exon 1 between different species with sequences matching the RORE motif and deviations highlighted (SEQ ID NOS: 108, 109, 110, 111, 112, 113, and 114). Note: the corresponding murine sequences (CTGGATCG) are predicted to be unfunctional as a RORE because of the two deviations (underlined) from the consensus RORE motif.

Figures 31A, 31B:
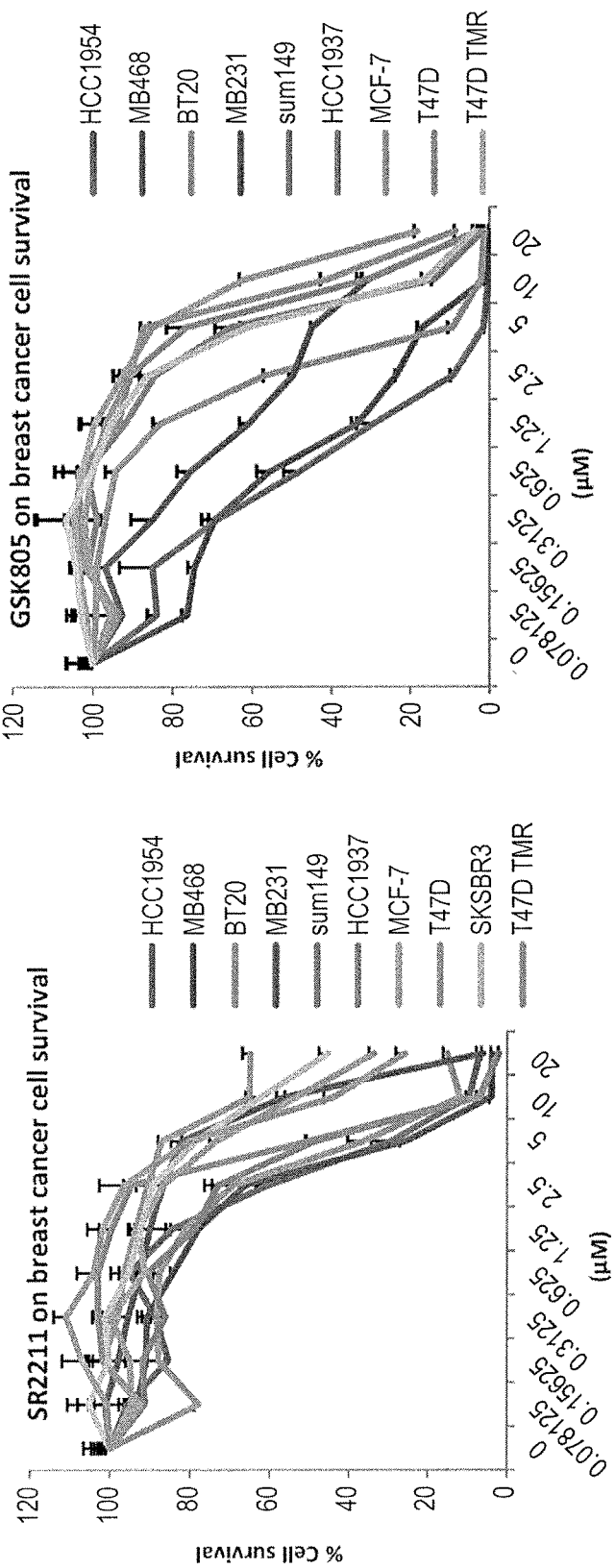

FIG. 31A: Cell viability, as measured by Cell-Titer GLO, of different breast cancer cells treated with the indicated concentrations of SR2211 for 4 days. FIG. 31B: Cell viability, as measured by Cell-Titer GLO, of different breast cancer cells treated with the indicated concentrations of GSK805 for 4 days. FIG. 31C: Cell viability, as measured by Cell-Titer GLO, of different breast cancer cells treated with the indicated concentrations of GSK9B for 4 days. FIG. 31D: SR2211 and GSK805 sensitized MCF-7 TamR cells to tamoxifen (TAM) induced cell growth inhibition. FIG. 31E: Cell viability, as measured by Cell-Titer GLO, of MCF-7 C6 radiation resistant cells treated with the indicated concentrations of SR2211, GSK805 and GSK9b for 4 days. FIG. 31F: Half-maximal inhibitory concentration ($IC_{50}$) for SR2211, GSK805, GSK9b and GNE3500 in indicated cell lines treated for 4 days.

Figures 32A, 32B:
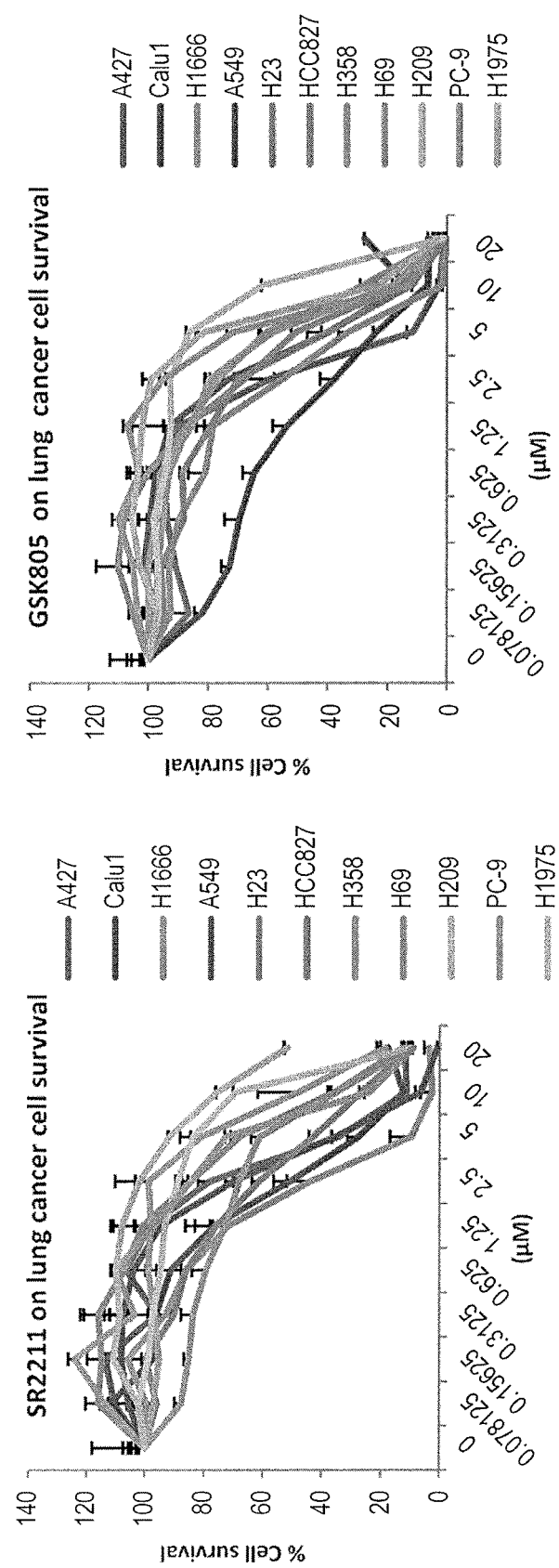

FIG. 32A: Cell viability, as measured by Cell-Titer GLO, of different lung cancer cells treated with the indicated concentrations of SR2211 for 4 days. FIG. 32B: Cell viability, as measured by Cell-Titer GLO, of different lung cancer cells treated with the indicated concentrations of GSK805 for 4 days. FIG. 32C: Half-maximal inhibitory concentration ($IC_{50}$) for SR2211 and GSK805 in indicated lung cancer cell lines treated for 4 days. FIG. 32D: Effects of the indicated treatments (SR2211, 5 mg/kg i.p. five times per week; or vehicle) on the growth of lung cancer A549 xenografts (n=6 mice per group). Treatment started when A549 tumors reached approximately 100 mm³. Mean tumor volume±s.e.m., Mean tumor weight±s.e.m. and representative tumor images are shown. P<0.01.

Figures 33A, 33B, 33C:
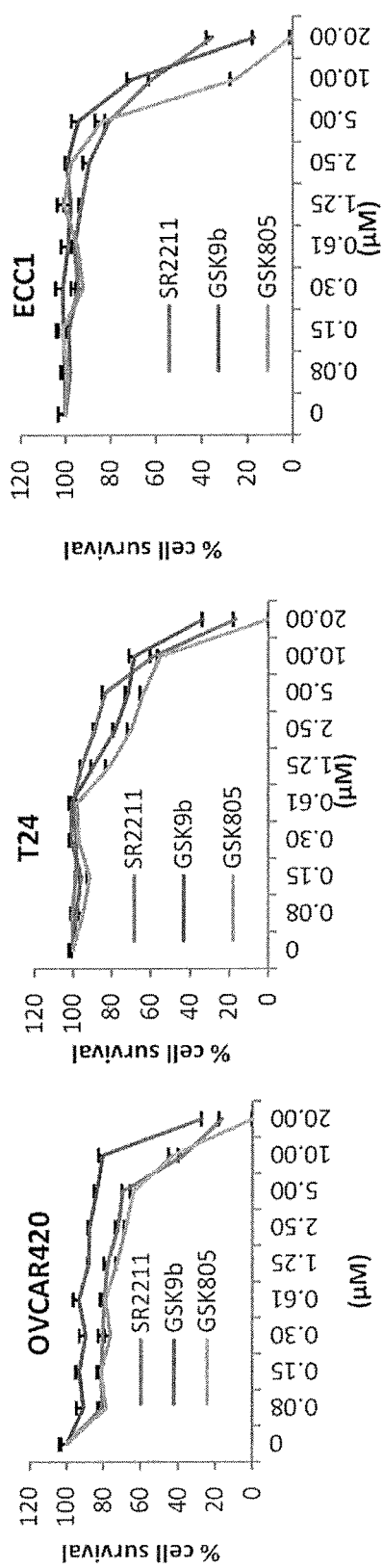
Figures 33H, 33I:
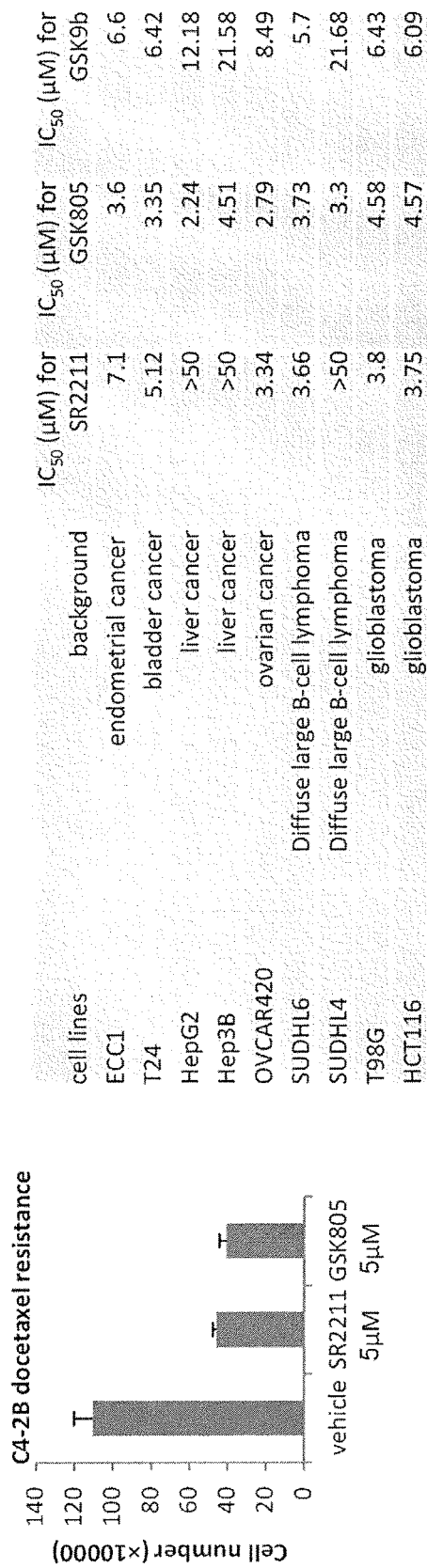

FIG. 33A: Cell viability, as measured by Cell-Titer GLO, of ovarian cancer OVCAR420 cells treated with the indicated concentrations of SR2211, GSK9b and GSK805 for 4 days. FIG. 33B: Cell viability, as measured by Cell-Titer GLO, of bladder cancer T24 cells treated with the indicated concentrations of SR2211, GSK9b and GSK805 for 4 days. FIG. 33C: Cell viability, as measured by Cell-Titer GLO, of endometrial ECC1 cells treated with the indicated concentrations of SR2211, GSK9b and GSK805 for 4 days. FIG. 33D: Cell viability, as measured by Cell-Titer GLO, of liver cancer HepG2 and Hep3B cells treated with the indicated concentrations of SR2211, GSK9b and GSK805 for 4 days. FIG. 33E: Cell viability, as measured by Cell-Titer GLO, of glioblastoma T98G cells treated with the indicated concentrations of SR2211, GSK9b and GSK805 for 4 days. FIG. 33F: Cell viability, as measured by Cell-Titer GLO, of leukemia SUDHL4 and SUDHL6 cells treated with the indicated concentrations of SR2211, GSK9b and GSK805 for 4 days. FIG. 33G: Cell viability, as measured by Cell-Titer GLO, of colon cancer HCT116 cells treated with the indicated concentrations of SR2211, GSK9b and GSK805 for 4 days. FIG. 33H: Cell viability, as measured by Cell-Titer GLO, of C4-2B docetaxel-resistant cells treated with the SR2211 and GSK805 for 4 days. FIG. 33I: Half-maximal inhibitory concentration ($IC_{50}$) for SR2211, GSK9b and GSK805 in indicated cell lines treated for 4 days.

DETAILED DESCRIPTION OF THE INVENTION

I. Introduction

The present disclosure relates to inhibitors of a nuclear receptor known as retinoic acid receptor-related orphan receptor γ (RORγ or RORgamma). In one aspect of this invention, it was suprisingly found that RORγ inhibitors are useful in the treatment of cancer. In some embodiments, it was also found that RORγ inhibitors can reverse or reduce cancer cell resistance to different classes of anticancer drugs and/or sensitize drug-resistant cancer cells to such anticancer drugs. Non-limiting examples of anticancer drugs that can be administered in combination with RORγ inhibitors to enhance the therapeutic effect of the anticancer drug include anti-androgen drugs (e.g., bicalutamide, enzalutamide, arbiraterone, etc.), chemotherapeutic agents (e.g., tamoxifen and/or taxanes such as docetaxel), and combinations thereof.

RORγ inhibitors include compounds that inhibit RORγ transcription, translation, stability, and/or activity. Inhibition of RORγ activity can include inhibition of recruitment of coactivators such as SRC-1 and/or SRC-3 to an androgen receptor (AR) ROR response element (RORE). In some embodiments, inhibition of RORγ activity can include inhibition of transcription of the AR gene and/or a variant thereof such as AR-V7.

As described herein, the present inventors have found that small molecule inhibitors or genetic silencing of RORγ strongly inhibit the growth of metastatic castration-resistant prostate cancer (mCRPC)-type prostate cancer (PCa) cells and xenograft tumors and induce marked cell death. A major proportion of human PCa tumors was also found to overexpress RORγ protein. Mechanistically, it was found that one major target of RORγ is the androgen receptor (AR), which expression and function are strongly inhibited by the RORγ-specific small molecules and siRNA silencing. AR protein is aberrantly overexpressed and plays a pivotal role in tumors of PCa including mCRPCs. The present inventors have also found that small molecule inhibitors of RORγ strongly inhibit the growth and survival of cancer cells of numerous other cancer types including lung cancer, breast cancer, liver cancer, ovarian cancer, endometrial cancer, bladder cancer, colon cancer, lymphoma, and glioblastoma multiforme.

In particular, the Examples below demonstrate the following exemplary novel features and advantages of the present invention:

1. The RORγ protein, a member of the nuclear receptor family type of transcription factor, has so far never been implicated to play a direct function in any type of human cancers. Therefore, its function and expression in human cancers are almost completely unknown.

2. The inhibitory small molecules of RORγ (not those of RORα) or the RORγ gene silencing siRNAs have a mechanism of action (MOA) in inhibition of PCa cells or tumors that is very different from current PCa therapeutics being used in the clinic (e.g., bicalutamide, enzalutamide, abiratoerone) or being developed (e.g., ARN509, EPI-001, ASC-J9, niclosamide).

3. Small molecules with potential therapeutic value demonstrated in preclinical PCa models have a direct target, namely, RORγ protein, which is defined in PCa tumor cells. In contrast, other small molecules such as ASC-J9 or niclosamide that show tumor inhibition of PCa models do not have well defined protein or other cellular targets.

4. By targeting one protein target, namely RORγ, two most important PCa tumor-driving pathways are potently inhibited. One pathway is the AR gene/protein itself. The findings described in the Examples indicate that RORγ directly activates the AR gene transcription in the same cancer cell and that the RORγ inhibitors strongly suppress the AR expression. The other pathway is the tumor androgen biosynthesis pathway where multiple key androgen synthesis enzyme genes are inhibited by the RORγ inhibitors.

5. Targeting RORγ in tumor cells actually targets the root cause of advanced PCa problems, namely the aberrant expression of AR (i.e., both full-length AR and spliced AR variants) in PCa tumor cells. Numerous clinical and preclinical studies indicate that aberrant AR is the major driver of PCa progression and therapeutic resistance.

6. Different small molecule inhibitors of RORγ are effective in strongly inhibiting the growth and survival of human cancer cells from numerous cancer types that are resistant to different therapies including chemotherapeutic agents, radiation, and targeted therapies such as tamoxifen. The RORγ inhibitors can also sensitize the resistant cancer cells to therapeutic drugs such as tamoxifen.

7. Small molecule inhibitors of RORγ strongly inhibit tumor growth of a xenograft lung tumor model.

II. Definitions

It is noted here that as used in this specification and the appended claims, the singular forms "a," "an," and "the" include plural reference unless the context clearly dictates otherwise.

The term "RORγ" refers to either or both isoforms encoded by the RORC (RAR-related orphan receptor C) gene, namely RORγ (also referred to as RORγ1 or RORC1) and RORγt (also known as RORγ2 or RORC2).

The terms "subject", "patient" or "individual" are used herein interchangeably to include a human or animal. For example, the animal subject may be a mammal, a primate (e.g., a monkey), a livestock animal (e.g., a horse, a cow, a sheep, a pig, or a goat), a companion animal (e.g., a dog, a cat), a laboratory test animal (e.g., a mouse, a rat, a guinea pig, a bird), an animal of veterinary significance, or an animal of economic significance.

As used herein, the term "effective amount" includes a dosage sufficient to produce a desired result with respect to the indicated disorder, condition, or mental state. The desired result may comprise a subjective or objective improvement in the recipient of the dosage. In one non-limiting example, an effective amount of a RORγ inhibitor includes an amount sufficient to alleviate the signs, symptoms, or causes of a cancer such as prostate cancer, e.g. CRPC. Thus, an effective amount can be an amount that slows or reverses tumor growth, increases mean time of survival, inhibits tumor progression or metastasis, or sensitizes a cancer cell to an anticancer drug to which it has become or is resistant. Also, in a second non-limiting example, an effective amount of a RORγ inhibitor includes an amount sufficient to cause a substantial improvement in a subject having cancer when administered to the subject. The amount will vary with the type of cancer being treated, the stage of advancement of the cancer, the type and concentration of composition applied, and the amount of anticancer drug (e.g., anti-androgen drug) that is also administered to the subject. In a third non-limiting example, an effective amount of a ROR inhibitor can include an amount that is effective in enhancing the therapeutic activity of anticancer drugs such as anti-androgen drugs (e.g., bicalutamide, enzalutamide, arbiraterone, etc.) and/or chemotherapeutic agents (e.g., tamoxifen and/or taxanes such as docetaxel).

As used herein, the term "treating" includes, but is not limited to, methods and manipulations to produce beneficial changes in a recipient's health status, e.g., a patient's cancer status. The changes can be either subjective or objective and can relate to features such as symptoms or signs of the cancer being treated. For example, if the patient notes decreased pain, then successful treatment of pain has occurred. For example, if a decrease in the amount of swelling has occurred, then a beneficial treatment of inflammation has occurred. Similarly, if the clinician notes objective changes, such as reducing the number of cancer cells, the growth of the cancer cells, the size of cancer tumors, or the resistance of the cancer cells to another cancer drug, then treatment of cancer has also been beneficial. Preventing the deterioration of a recipient's status is also included by the term. Treating, as used herein, also includes administering a RORγ inhibitor alone or in combination with an anticancer drug to a subject having cancer. In certain instances, the cancer is prostate cancer, lung cancer, breast cancer, liver cancer, ovarian cancer, endometrial cancer, bladder cancer, colon cancer, lymphoma, or glioblastoma multiforme.

As used herein, the term "administering" includes activities associated with providing a patient an amount of a compound described herein, e.g., one or more RORγ inhibitors. Administering includes providing unit dosages of compositions set forth herein to a patient in need thereof. Administering includes providing effective amounts of compounds, e.g., RORγ inhibitors, for a specified period of time, e.g., for about 1, 2, 3, 4, 5, 6, 7, 8, 9, 10, 12, 13, 14, 15, 16, 17, 18, 19, 20, 21, 22, 23, 24, 25, 26, 27, 28, 29, 30, 31 or more days, or in a specified sequence, e.g., administration of one or more RORγ inhibitors followed by the administration of one or more anticancer drugs, or vice versa.

As used herein, the term "co-administering" includes sequential or simultaneous administration of two or more structurally different compounds. For example, two or more structurally different pharmaceutically active compounds can be co-administered by administering a pharmaceutical composition adapted for oral administration that contains two or more structurally different active pharmaceutically active compounds. As another example, two or more structurally different compounds can be co-administered by administering one compound and then administering the other compound. In some instances, the co-administered compounds are administered by the same route. In other instances, the co-administered compounds are administered via different routes. For example, one compound can be administered orally, and the other compound can be administered, e.g., sequentially or simultaneously, via intravenous or intraperitoneal injection.

As used herein, the term "cancer" refers to conditions including solid cancers, lymphomas, and leukemias. Examples of different types of cancers include, but are not limited to, prostate cancer, lung cancer (e.g., non-small cell lung cancer or NSCLC), ovarian cancer, colorectal cancer, liver cancer (i.e., hepatocarcinoma), renal cancer (i.e., renal cell carcinoma). bladder cancer, breast cancer, thyroid cancer, pleural cancer, pancreatic cancer, uterine cancer, cervical cancer, testicular cancer, anal cancer, bile duct cancer, gastrointestinal carcinoid tumors, esophageal cancer, gall bladder cancer, appendix cancer, small intestine cancer, stomach (gastric) cancer, cancer of the central nervous system, skin cancer, choriocarcinoma, head and neck cancer, blood cancer, endometrial cancer, osteogenic sarcoma, fibrosarcoma, neuroblastoma, glioma, melanoma, B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, acute myelocytic leukemia, and multiple myeloma. In some instances, the cancer can be metastatic. In certain instances, the cancer is prostate cancer, lung cancer, breast cancer, liver cancer, ovarian cancer, endometrial cancer, bladder cancer, colon cancer, lymphoma, or a glioma such as glioblastoma multiforme. In other instances, the cancer can be resistant to an anticancer drug, e.g., an anti-androgen-resistant cancer, a taxane-resistant cancer (e.g., docetaxel-resistant cancer), a tamoxifen-resistant cancer, a radiation-resistant cancer, or a tyrosine kinase inhibitor-resistant cancer.

As used herein, the terms "prostate cancer" or "prostate cancer cell" refer to a cancer cell or cells that reside in prostate tissue. The prostate cancer can be benign, malignant, or metastatic. The prostate cancer can be androgen-insensitive, hormone-resistant, or castrate-resistant. The prostate cancer can be "advanced stage prostate cancer" or "advanced prostate cancer." Advanced stage prostate cancer includes a class of prostate cancers that has progressed beyond early stages of the disease. Typically, advanced stage prostate cancers are associated with a poor prognosis. Types of advanced stage prostate cancers include, but are not limited to, metastatic prostate cancer, drug-resistant prostate cancer such as anti-androgen-resistant prostate cancer (e.g., enzalutamide-resistant prostate cancer, abiraterone-resistant prostate cancer, bicalutamide-resistant prostate cancer, etc.), taxane-resistant prostate cancer (e.g., docetaxel-resistant prostate cancer) and the like, hormone refractory prostate cancer, castration-resistant prostate cancer (CRPC), metastatic castration-resistant prostate cancer, AR-V7-induced drug-resistant prostate cancer such as AR-V7-induced anti-androgen-resistant prostate cancer (e.g., AR-V7-induced enzalutamide-resistant prostate cancer), AKR1C3-induced drug-resistant prostate cancer such as AKR1C3-induced anti-androgen-resistant prostate cancer (e.g., AKR1C3-induced enzalutamide-resistant prostate cancer), and combinations thereof. In some instances, the advanced stage prostate cancers do not generally respond, or are resistant, to treatment with one or more of the following conventional prostate cancer therapies: enzalutamide, abiraterone, bicalutamide, and docetaxel. Compounds, compositions, and methods of the present invention are provided for treating prostate cancer, such as advanced stage prostate cancer, including any one or more (e.g., two, three, four, five, six, seven, eight, nine, ten, or more) of the types of advanced stage prostate cancers disclosed herein.

As used herein, the phrase "enhancing the therapeutic effects" includes any of a number of subjective or objective factors indicating a beneficial response or improvement of the condition being treated as discussed herein. For example, enhancing the therapeutic effects of an anticancer drug such as an anti-androgen drug (e.g., enzalutamide, abiraterone, or bicalutamide) or a chemotherapeutic agent such as tamoxifen or a taxane (e.g., docetaxel) includes reversing or reducing cancer cell resistance and/or sensitizing a drug-resistant cancer to anticancer drug therapy. Also, for example, enhancing the therapeutic effects of an anticancer drug includes altering drug-resistant cancer cells so that the cells are not resistant to the anticancer drug. Also, for example, enhancing the therapeutic effects of an anticancer drug includes additively or synergistically improving or increasing the activity of the anticancer drug. In some embodiments, the enhancement includes a one-fold, two-fold, three-fold, five-fold, ten-fold, twenty-fold, fifty-fold, hundred-fold, or thousand-fold increase in the therapeutic activity of an anticancer drug used to treat cancer.

As used herein, the phrase "reversing cancer cell resistance" includes altering or modifying a cancer cell that is resistant to anticancer drug therapy so that the cell is no longer resistant to anticancer drug therapy.

As used herein, the phrase "reducing cancer cell resistance" includes increasing the therapeutic activity of an anticancer drug towards cancer cells that are, or previously were, resistant to anticancer drug therapy.

As used herein, the phrase "sensitizing cancer cell resistance" includes inducing sensitization towards anticancer drug therapy in cancer cells which are resistant to anticancer drug therapy. Sensitization as used herein includes inducing the ability of a cancer cell to be effectively treated with an anticancer drug. Sensitization also includes reducing the dosage required to achieve a beneficial effect with an anticancer drug.

As used herein, the phrase "anti-androgen drug" includes anti-androgen compounds that alter the androgen pathway by blocking the androgen receptors, competing for binding sites on the cell's surface, or affecting or mediating androgen production. Anti-androgen drugs are useful for treating several diseases including, but not limited to, prostate cancer. Anti-androgen drugs include, but are not limited to, enzalutamide, abiraterone, bicalutamide, flutamide, nilutamide, apalutamide, finasteride, dutasteride, alfatradiol, and combinations thereof.

As used herein, the term "androgen receptor" or "AR" includes a nuclear receptor that binds androgenic hormones testosterone or dihydrotestosterone in the cytoplasm and translocates to the nucleus. AR modulates, inter alia, transcription of target genes by binding to Androgen Response Elements (AREs) in the promoters of such target genes.

As used herein, the term "AR variant" includes a splice variant of full-length AR. Various AR variants are known. See, Guo et al., *Cancer Res.*, 69(6):2305-13 (2009). Exemplary AR variants include, but are not limited to, variants lacking a functional ligand binding domain (LBD). An example of an AR variant that lacks an LBD is AR-V7. "AR-V7" includes androgen receptor splice variant 7, a contituitively active variant of an AR that lacks a functional ligand binding domain (LBD). See, e.g., Hu et al., *Cancer Research*, 69(1):16-22 (2009).

"Pharmaceutically acceptable" or "therapeutically acceptable" includes a substance which does not interfere with the effectiveness or the biological activity of the active ingredients and which is not toxic to the hosts in the amounts used, and which hosts may be either humans or animals to which it is to be administered.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of $-(CH_2)_n-$. where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups can be substituted or unsubstituted.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Heteroalkyl" refers to an alkyl group of any suitable length and having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers and alkyl-amines. The heteroatom portion of the heteroalkyl can replace a hydrogen of the alkyl group to form a hydroxy, thio or amino group. Alternatively, the heteroatom portion can be the connecting atom, or be inserted between two carbon atoms.

"Haloalkyl" refers to an alkyl group, where some or all of the hydrogen atoms are replaced with halogen atoms. As for alkyl group, haloalkyl groups can have any suitable number of carbon atoms, such as $C_{1-6}$. For example, haloalkyl includes trifluoromethyl, flouromethyl, etc. In some instances, the term "perfluoro" can be used to define a compound or radical where all the hydrogens are replaced with fluorine. For example, perfluoromethyl refers to 1,1,1-trifluoromethyl.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted.

"Heterocycloalkyl" refers to a saturated or partially unsaturated ring system having from 3 to 13 ring members and from 1 to 4 heteroatoms of N, O and S. Heterocycloalkyl groups can include fused bi- or tri-cyclic systems, and can include one or more points of unsaturation. Additional heteroatoms can also be useful, including, but not limited to, B, Al, Si and P. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, 3 to 12 or 3 to 13 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, or morpholine. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with C1.6 alkyl, oxo (=O), or aryl, among many others.

The heterocycloalkyl groups can be linked via any position on the ring. For example, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, and morpholine can be 1-, 2-, 3- or 4-morpholine.

III. Description of the Embodiments

The present invention provides compositions, methods, and kits comprising one or more ROR inhibitors, alone or in combination with one or more anticancer drugs, such as an anti-androgen drug, that are useful for treating cancer, e.g., prostate cancer, such as castration-resistant prostate cancer (CRPC), and numerous other types of cancer including lung cancer, breast cancer, liver cancer, ovarian cancer, endometrial cancer, bladder cancer, colon cancer, lymphoma, and glioma.

A. RORγ Inhibitors

RORγ inhibitors (i.e., RORγ antagonists) include compounds that inhibit retinoic acid receptor-related orphan receptor γ (RORγ) transcription, translation, stability, and/or activity. In certain embodiments, RORγ inhibitors bind to RORγ and inhibit the activity of the receptor. In other embodiments, RORγ inhibitors selectively bind to RORγ and inhibit RORγ activity relative to RORα and/or RORβ.

In some instances, inhibition of RORγ activity can include inhibition of recruitment of coactivators such as SRC-1 and/or SRC-3 to an androgen receptor (AR) ROR response element (RORE). In other instances, inhibition of RORγ activity can include inhibition of transcription of the AR gene and/or a variant thereof such as AR-V7.

In some embodiments, RORγ inhibitors include inverse agonists that bind to RORγ and decrease its activity below a constitutive (e.g., intrinsic or basal) level activity in the absence of any ligand. In some embodiments, RORγ inhibitors include pharmaceutically acceptable salts, derivatives, analogs, isomers, racemates, prodrugs, co-crystalline complexes, hydrates, and solvates thereof.

In particular embodiments, the RORγ inhibitor is a small molecule compound. In some instances, the RORγ inhibitor is a small organic molecule, either naturally occurring or synthetic, that has a molecular weight of more than about 50 Daltons and less than about 2500 Daltons, e.g., between about 100 to about 2000 Daltons, between about 100 to about 1000 Daltons, between about 200 to about 1000 Daltons, or between about 200 to about 500 Daltons.

In certain embodiments, the RORγ inhibitor has a half-maximal inhibitory concentration (IC50) value of from about 100 nM to about 100 μM, e.g., from about 100 nM to about 50 μM, from about 100 nM to about 25 μM, from about 100 nM to about 10 μM, from about 500 nM to about 100 μM, from about 500 nM to about 50 μM, from about 500 nM to about 25 μM, from about 500 nM to about 10 μM, from about 1 μM to about 100 μM, from about 1 μM to about 50 μM, from about 1 μM to about 25 μM, from about 1 μM to about 10 μM, or about 100 nM, 200 nM, 300 nM, 400 nM, 500 nM, 600 nM, 700 nM, 800 nM, 900 nM, 1 μM, 2 μM, 3 μM, 4 μM, 5 μM, 6 μM, 7 μM, 8 μM, 9 μM, or 10 μM. In some instances, the IC50 value for a specific RORγ inhibitor is measured using an in vitro assay in cancer cells that have been incubated with the RORγ inhibitor. The IC50 value can be determined based on the effect of the RORγ inhibitor in inhibiting the survival of cancer cells such as cells from a cancer cell line or primary tumor cells. In other embodiments, the RORγ inhibitor has an inhibitor constant (Ki) that is essentially the same numerical value as the IC50 value, or is about one-half the value of the IC50 value.

Non-limiting examples of RORγ inhibitors include, but are not limited to, the small molecule compounds disclosed in Table 1.

TABLE 1

Exemplary RORγ inhibitors

| Name | Chemical Structure |
|---|---|
| T0901317 N-(2,2,2-Trifluoroethyl)-N-[4-[2,2,2-trifluoro-1-hydroxy-1-(trifluoromethyl)ethyl]phenyl] benzenesulfonamide | |
| Digoxin | 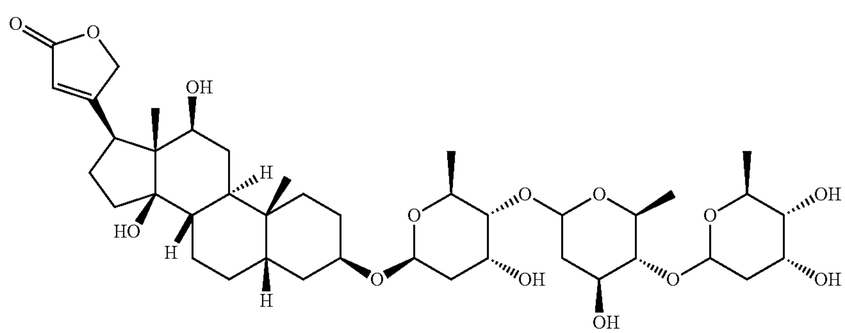 [SMILES: C[C@@H]1OC(O[C@H]2[C@H](C)OC(O[C@@H]3[C@H](O)C[C@@H](O[C@@H]4CC[C@]5(C)[C@@H](CC[C@H]6[C@H]5C[C@H](O)[C@@]5(C)[C@H](C7=CC(=O)OC7)CC[C@@]65O)C4)O[C@H]3C)C[C@@H]2O)C[C@@H](O)[C@H]1O] |
| Ursolic acid | 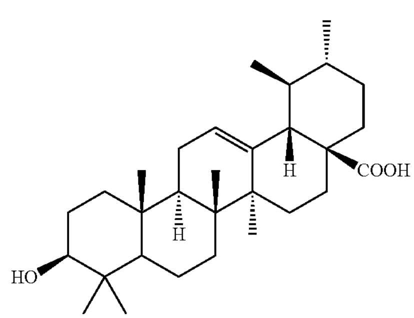 |

TABLE 1-continued

Exemplary RORγ inhibitors

| Name | Chemical Structure |
| --- | --- |
| SR1001<br>N-(5-(N-(4-(1,1,1,3,3,3-Hexafluoro-2-hydroxypropan-2-yl)phenyl)sulphamoyl)-4-methylthiazol-2-yl)acetamide | 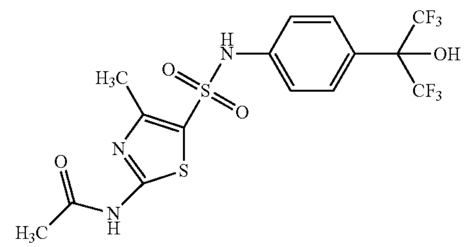 [SMILES: CC(=O)Nc1nc(C)c(S(=O)(=O)Nc2ccc(C(O)(C(F)(F)F)C(F)(F)F)cc2)s1] |
| SR2211<br>2-Fluoro-4'-[[4-(4-pyridinylmethyl)-1-piperazinyl]methyl]-α,α-bis(trifluoromethyl)-[1,1'-biphenyl]-4-methanol | |
| SR1555<br>1-(4-((4'-(1,1,1,3,3,3-hexafluoro-2-hydroxypropan-2-yl)-[1,1'-biphenyl]-4-yl)methyl)piperazin-1-yl)ethanone, monohydrochloride | 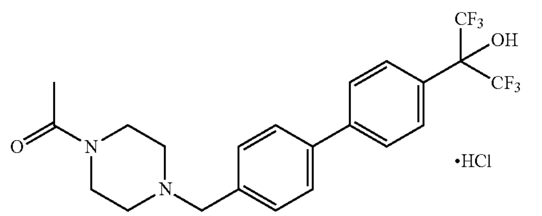 [SMILES: CC(=O)N1CCN(Cc2ccc(-c3ccc(C(O)(C(F)(F)F)C(F)(F)F)cc3)cc2)CC1 ; Cl] |
| ML209 (SR9805)<br>(Khan et al., Bioorg. Med. Chem. Lett., 23:532-6 (2013)) | 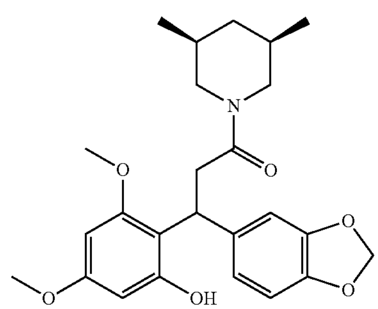 [SMILES: COc1cc(O)c(C(CC(=O)N2C[C@H](C)C[C@H](C)C2)c2ccc3c(c2)OCO3)c(OC)c1] |
| GSK805<br>N-(3,5-Dichloro-4-(2-(trifluoromethoxy)phenyl)phenyl)-2-(4-ethylsulfonylphenyl)acetamide | 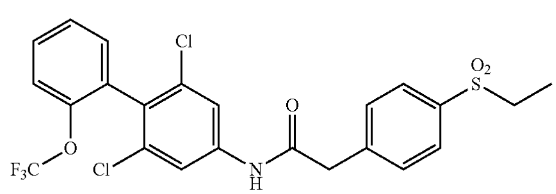 [SMILES: CCS(=O)(=O)c1ccc(CC(=O)Nc2cc(Cl)c(-c3ccccc3OC(F)(F)F)c(Cl)c2)cc1] |
| GSK9b<br>N-(2,6-dichloro-2'-trifluoromethoxy)-[1,1'-biphenyl]-4-yl-2-(4-sulfamoylphenyl)acetamide | 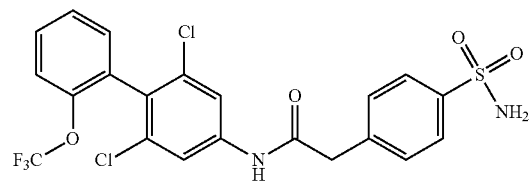 [SMILES: NS(=O)(=O)c1ccc(CC(=O)Nc2cc(Cl)c(-c3ccccc3OC(F)(F)F)c(Cl)c2)cc1] |

TABLE 1-continued

Exemplary RORγ inhibitors

| Name | Chemical Structure |
|---|---|
| TMP778 (Skepner et al., J. Immunol., 192:2564-75 (2014)) | 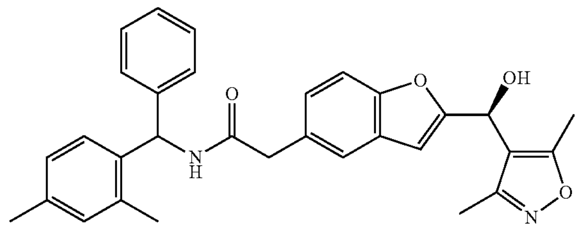 |
| GNE-3500 1-{4-[3-fluoro-4-((3S,6R)-3-methyl-1,1-dioxo-6-phenyl-[1,2]thiazinan-2-ylmethyl)-phenyl]-piperazin-1-yl}-ethanone) | 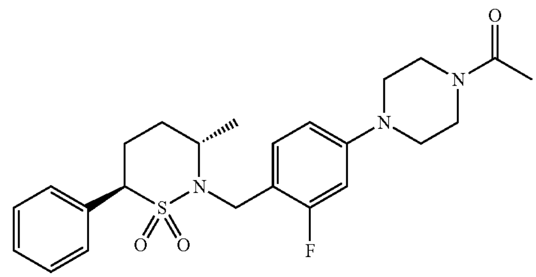 [SMILES: CC(=O)N1CCN(c2ccc(CN3[C@@H](C)CC[C@H](c4ccccc4)S3(=O)=O)c(F)c2)CC1] |
| VTP-43742 (S)-N-((5-ethylsulfonyl)pyridin-2-yl)methyl)-7-isopropyl-6-(((1r,4S)-4-(trifluoromethyl)cyclohexyl)methyl)-6,7-dihydro-5H-pyrrolo[3,4-b]pyridine-3-carboxamide | 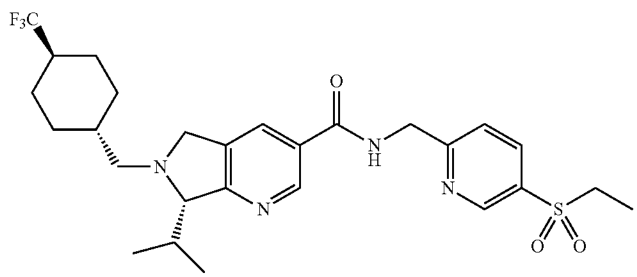 [SMILES: CCS(=O)(=O)c1ccc(CNC(=O)c2cnc3c(c2)CN(C[C@H]2CC[C@H](C(F)(F)F)CC2)[C@H]3C(C)C)nc1] |

Additional examples of ROR inhibitors include, but are not limited to, 2-oxo-1,2-dihydrobenzo[cd]indole-6-sulfonamide derivatives such as those compounds described in, e.g., Zhang et al., Eur. J. Med. Chem., 6; 78:431-41 (2014), the contents of which are herein incorporated by reference in their entirety for all purposes.

In certain embodiments, the RORγ inhibitors include compounds represented by Formula I:

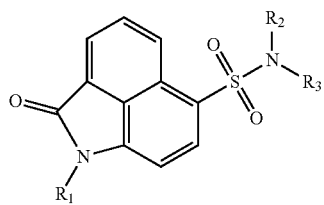

(I)

wherein:

$R_1$ is selected from the group consisting of H, $C_{1-8}$alkyl, $C_{2-8}$alkeyl, —C(O)$R^a$, —C(O)NH$R^a$, $C_{1-8}$heteroalkyl, $C_{1-8}$alkyleneC(O)$R^a$, and $C_{1-8}$alkyleneC(O)NH$R^a$;

each $R^a$ is independently selected from the group consisting of H, $C_{1-8}$alkyl, $C_{2-8}$alkeyl, alkyoxy, —OH, and —SH;

$R_2$ is selected from the group consisting of H, $C_{1-8}$alkyl, —C(O)$R^b$, —C(O)NH$R^b$, $C_{1-8}$alkyleneC(O)$R^b$, and $C_{1-8}$alkyleneC(O)NH$R^b$;

$R^b$ is selected from the group consisting of H, $C_{1-5}$alkyl, alkoxy, —OH, —SH, cycloalkyl, heterocycloalkyl, aryl, and heteroaryl, wherein the cycloalkyl, heterocycloalkyl, aryl, and heteroaryl group can be optionally substituted with 1-3 $R^c$ substituents;

each $R^c$ is independently selected from the group consisting of $C_{1-8}$alkyl, $C_{1-8}$haloalkyl, $C_{1-8}$heteroalkyl, —OH, —SH, —NH$R^a$, —C(O)$R^a$, —C(O)NH$R^a$, $C_{1-8}$heteroalkyl, $C_{1-8}$alkyleneC(O)$R^a$, and $C_{1-8}$alkyleneC(O)NH$R^a$;

$R_3$ is selected from the group consisting of cycloalkyl, heterocycloalkyl, aryl, heteroaryl, $C_{1-8}$alkylenecycloalkyl, $C_{1-8}$alkyleneheterocycloalkyl, $C_{1-8}$alkylenearyl, $C_{1-8}$alkyleneheteroaryl, wherein the cycloalkyl, heterocycloalkyl, aryl, heteroaryl group can be optionally substituted with 1-5 $R^d$ substituents;

each $R^d$ is independently selected from the group consisting of halo, $C_{1-8}$alkyl, alkoxy, $C_{1-8}$haloalkyl, $C_{1-8}$heteroalkyl, oxo, thioxo, aryl, heteroaryl, —O$R^e$, —S$R^e$, —NH$R^e$, —C(O)$R^e$, —C(O)NH$R^e$, —NHC(O)$R^e$, diazenyl-$R^e$, $C_{1-3}$alkylenearyl, $C_{1-3}$alkyleneheteroaryl; and each $R^e$ is independently selected from the group consisting of H, $C_{1-8}$alkyl, $C_{2-5}$alkeyl, alkyoxy, —OH, —SH, aryl, and heteroaryl, wherein the aryl and heteroaryl can be optionally substituted with 1-3 $R^a$ substituents.

In some embodiments, $R_1$ is selected from the group consisting of H and $C_{1-3}$ alkyl.

In some embodiments, $R_2$ is selected from the group consisting of H and C(O)$R^b$, wherein $R^b$ is an optionally substituted heteroaryl.

In some embodiments, R₃ is selected from the group consisting of the substituents shown in Table 2.
TABLE 2
Exemplary substituents for R₃
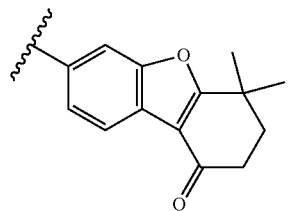 [SMILES: *c1ccc2c3c(oc2c1)C(C)(C)CCC3=O]
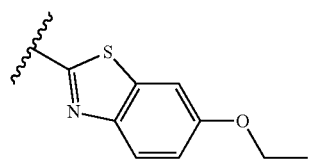 [SMILES: *c1nc2ccc(OCC)cc2s1]
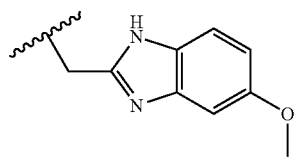 [SMILES: *Cc1nc2cc(OC)ccc2[nH]1]
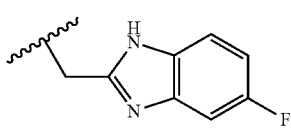 [SMILES: *Cc1nc2cc(F)ccc2[nH]1]
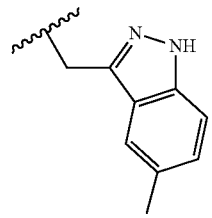 [SMILES: *Cc1n[nH]c2ccc(C)cc12]
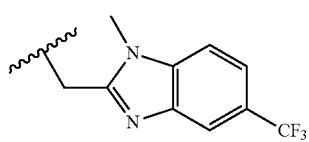 [SMILES: *Cc1nc2cc(C(F)(F)F)ccc2n1C]
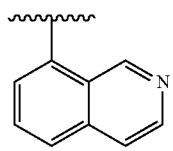 [SMILES: *c1cccc2ccncc12]
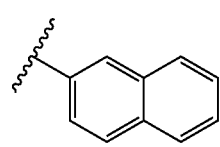 [SMILES: *c1ccc2ccccc2c1]
TABLE 2-continued
Exemplary substituents for R₃
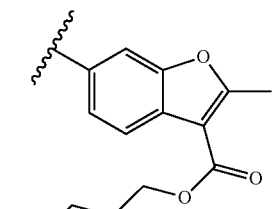
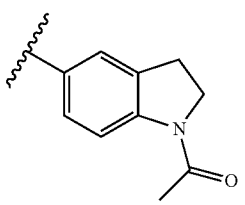 [SMILES: *c1ccc2c(c1)CCN2C(C)=O]
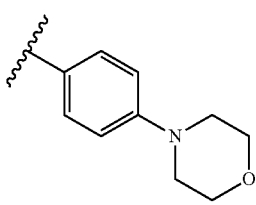 [SMILES: *c1ccc(N2CCOCC2)cc1]
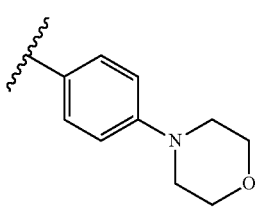 [SMILES: *c1ccc(N2CCOCC2)cc1]
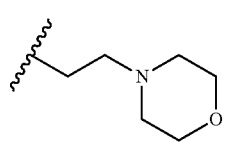 [SMILES: *CCN1CCOCC1]
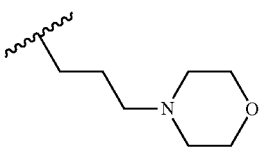 [SMILES: *CCCN1CCOCC1]
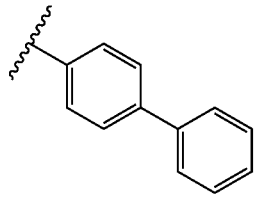 [SMILES: *c1ccc(-c2ccccc2)cc1]
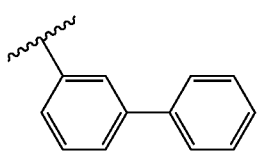 [SMILES: *c1cccc(-c2ccccc2)c1]

TABLE 2-continued
Exemplary substituents for R$_3$
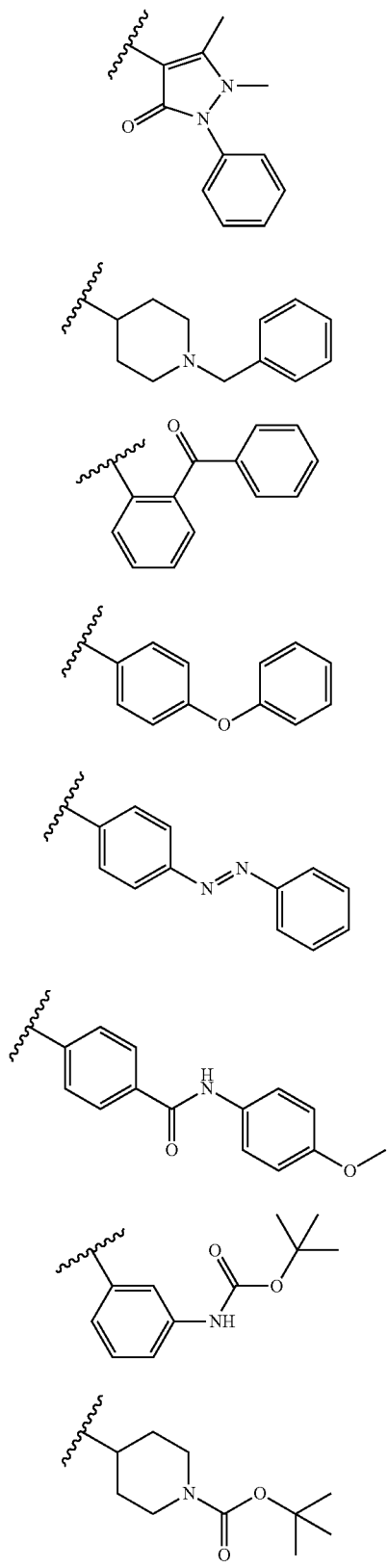
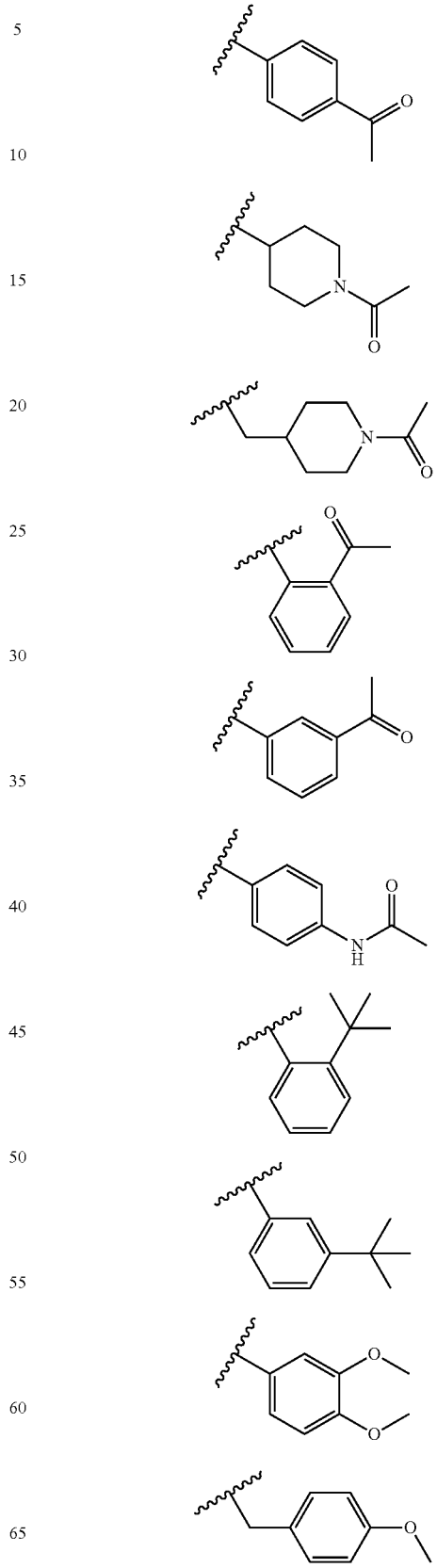

TABLE 2-continued

Exemplary substituents for R$_3$

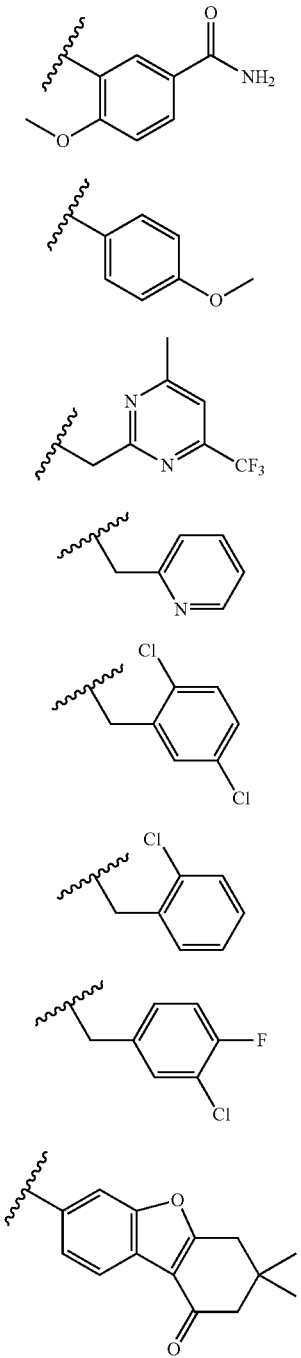

*The squiggly line represents the point of attachment to the remainder of the molecule.

In some embodiments, the variable groups R$_1$, R$_2$, and R$_3$ are as defined in International Patent Publication No. WO 2015/096771, the contents of which are herein incorporated by reference in their entirety for all purposes.

In particular embodiments, the compound of Formula I comprises N-(3',4'-dimethoxyphenyl)-1-ethyl-2-oxo-1,2-dihydrobenzo[cd]indole-6-sulfonamide (known as XY011, E11, and 8k). In other embodiments, the compound of Formula I comprises (E)-1-ethyl-2-oxo-N-(4'-(phenyldiazenyl)phenyl)-1,2-dihydrobenzo[cd]indole-6-sulfonamide (known as 7k). In other embodiments, the compound of Formula I comprises 1-Ethyl-N-(isoquinolin-7'-yl)-2-oxo-1,2-dihydrobenzo[cd]indole-6-sulfonamide (known as 6f). See. Zhang et al., *Eur. J. Med. Chem.,* 6; 78:431-41 (2014), the contents of which are herein incorporated by reference in their entirety for all purposes.

In some embodiments, the RORγ inhibitors include the thiazolopyrrolidine inhibitors (e.g., compounds comprising a 5,6-dihydro-4H-pyrrolo[3,4-d]thiazole core) described in International Patent Publication No. WO 2014/179564, the contents of which are herein incorporated by reference in their entirety for all purposes. In other embodiments, the RORγ inhibitors include the dihydropyrrolopyridine inhibitors (e.g., compounds comprising a 6,7-dihydro-5H-pyrrolo[3,4-b]pyridine core) described in International Patent Publication No. WO 2015/116904, the contents of which are herein incorporated by reference in their entirety for all purposes. In particular embodiments, the dihydropyrrolopyridine inhibitor is VTP-43742. See, Gege, *Expert Opinion on Therapeutic Patents,* DOI: 10.1517/13543776.2016.1153066 (2016), the contents of which are herein incorporated by reference in their entirety for all purposes.

In some embodiments, the RORγ inhibitors include the bicyclic heterocyclic inhibitors (e.g., compounds comprising a thieno[3,2-b]pyrrole or thieno[3,2-c]pyrazole core) described in International Patent Publication No. WO 2015/008234, the contents of which are herein incorporated by reference in their entirety for all purposes. See, Gege, *Expert Opinion on Therapeutic Patents,* 25:10, 1215-1221, DOI: 10.1517/13543776.2015.1065816 (2015), the contents of which are herein incorporated by reference in their entirety for all purposes.

Additional examples of RORγ inhibitors include, but are not limited to, the aryl and heteroaryl amide compounds described in International Patent Publication No. WO 2013/171729, the 4-heteroaryl substituted benzoic acid compounds described in International Patent Publication No. WO 2014/028589, the N-alkylated indole and indazole compounds described in International Patent Publication No. WO 2014/028591, the 3-cyclohexenyl and cyclohexyl substituted indole and indazole compounds described in International Patent Publication No. WO 2014/028597, the 3-aminocycloalkyl compounds described in International Patent Publication No. WO 2014/028600, the keto-imidazopyridine derivatives described in International Patent Publication No. WO 2015/036411, the fused pyridine and pyrimidine derivatives described in International Patent Publication No. WO 2015/083130, the fused thiophene and thiazole derivatives described in International Patent Publication No. WO 2015/101928, the compounds described in International Patent Publication Nos. WO 2012/100734, WO 2012/106995, WO 2013/160418, WO 2015/061515, WO 2015/082533, and WO 2013/019682, the 6-sultam compounds described in Fauber et al., *J. Med. Chem.,* 58(13):5308-22 (2015), and the biaryl amides described in Wang et al., *ACS Med. Chem. Lett.,* 6:787-92 (2015), the contents of which are herein incorporated by reference in their entirety for all purposes.

One of ordinary skill in the art will understand that known and candidate RORγ inhibitors can be tested for their effect on any type of cancer using in vitro assays that assess the viability, apoptosis, growth, and/or colony formation of cancer cell lines or primary cancer (e.g., tumor) cells. See, Example 1 below for exemplary protocols of cell viability, apoptosis, growth, and colony formation assays. One of ordinary skill in the art will also understand that known and candidate RORγ inhibitors can be tested for their effect on any type of cancer using in vivo animal models such as xenograft tumor models. See, Example 1 below for exemplary protocols of xenograft tumor models and treatment with RORγ inhibitors.

B. Anticancer Drugs

In certain embodiments, the RORγ inhibitors of the present invention can be used in combination with an anticancer drug to reduce or reverse cancer cell resistance to the anticancer drug by sensitizing the cancer cell to the anticancer drug.

Non-limiting examples of anticancer drugs include anti-androgen drugs, chemotherapeutic agents, radiotherapeutic agents, antigen-specific immunotherapeutic agents, endocrine therapies, tyrosine kinase inhibitors, and combinations thereof.

1. Anti-Androgen Drugs

Anti-androgen drugs are compounds that inhibit the transcription, translation, stability, and/or activity of androgen receptors (AR) or variants thereof (e.g. AR-V7). Inhibition of AR activity can include inhibition of recruitment of AR to Androgen Response Elements (AREs). In some embodiments, inhibition of AR activity can include inhibition of recruitment of AR to the PSA promoter. In some embodiments, inhibition of AR activity can include inhibition of AR-induced activation of the PSA promoter. In some embodiments, inhibition of AR activity can include inhibition of AR-induced PSA production. For example, inhibition of AR can include inhibition of production of PSA in the absence of DHT.

Anti-androgen drugs include, but are not limited to, enzalutamide, abiraterone, bicalutamide, flutamide, nilutamide, apalutamide, finasteride, dutasteride, alfatradiol, and combinations thereof.

In some embodiments, the present invention provides a composition comprising one or more RORγ inhibitors in combination with one or more anti-androgen drugs. In certain instances, the composition further comprises a pharmaceutically acceptable excipient or diluent. In other instances, the composition is formulated for oral or parenteral administration.

In other embodiments, the present invention provides a method for treating cancer in a subject comprising administering to the subject an effective amount of one or more RORγ inhibitors in combination with one or more anti-androgen drugs. In certain instances, the effective amount of one or more RORγ inhibitors is an amount sufficient to sensitize an anti-androgen drug-resistant cancer such as anti-androgen drug-resistant prostate cancer (e.g., castration-resistant prostate cancer) to anti-androgen drug treatment. The RORγ inhibitors and anti-androgen drugs can be delivered to a subject via the same route of administration (e.g., orally or parenterally) or via different routes of administration (e.g., intravenously for RORγ inhibitors and orally for anti-androgen drugs, or vice versa).

2. Chemotherapeutic Agents

Chemotherapeutic agents are well known in the art and include, but are not limited to, anthracenediones (anthraquinones) such as anthracyclines (e.g., daunorubicin (daunomycin; rubidomycin), doxorubicin, epirubicin, idarubicin, and valrubicin), mitoxantrone, and pixantrone; platinum-based agents (e.g., cisplatin, carboplatin, oxaliplatin, satraplatin, picoplatin, nedaplatin, triplatin, and lipoplatin); tamoxifen and metabolites thereof such as 4-hydroxytamoxifen (afimoxifene) and N-desmethyl-4-hydroxytamoxifen (endoxifen); taxanes such as paclitaxel (taxol), docetaxel, cabazitaxel, hongdoushan A, hongdoushan B, hongdoushan C, baccatin I. baccatin II, and 10-deacetylbaccatin; alkylating agents (e.g., nitrogen mustards such as mechlorethamine (HN2), cyclophosphamide, ifosfamide, melphalan (L-sarcolysin), and chlorambucil); ethylenimines and methylmelamines (e.g., hexamethylmelamine, thiotepa, alkyl sulphonates such as busulfan, nitrosoureas such as carmustine (BCNU), lomustine (CCNLJ), semustine (methyl-CCN-U), and streptozoein (streptozotocin), and triazenes such as decarbazine (DTIC; dimethyltriazenoimidazolecarboxamide)); antimetabolites (e.g., folic acid analogues such as methotrexate (amethopterin), pyrimidine analogues such as fluorouracil (5-fluorouracil; 5-FU), floxuridine (fluorodeoxyuridine; FUdR), and cytarabine (cytosine arabinoside), and purine analogues and related inhibitors such as mercaptopurine (6-mercaptopurine; 6-MP), thioguanine (6-thioguanine; 6-TG), and pentostatin (2'-deoxycofonnycin)); natural products (e.g., vinca alkaloids such as vinblastine (VLB) and vincristine, epipodophyllotoxins such as etoposide and teniposide, and antibiotics such as dactinomycin (actinomycin D), bleomycin, plicamycin (mithramycin), and mitomycin (mitomycin Q); enzymes such as L-asparaginase; biological response modifiers such as interferon alpha); substituted ureas such as hydroxyurea; methyl hydrazine derivatives such as procarbazine (N-methylhydrazine; MIH); adrenocortical suppressants such as mitotane (o,p'-DDD) and aminoglutethimide; analogs thereof; derivatives thereof; and combinations thereof.

In some embodiments, the present invention provides a composition comprising one or more RORγ inhibitors in combination with one or more chemotherapeutic agents. In certain instances, the composition further comprises a pharmaceutically acceptable excipient or diluent. In other instances, the composition is formulated for oral or parenteral administration.

In other embodiments, the present invention provides a method for treating cancer in a subject comprising administering to the subject an effective amount of one or more RORγ inhibitors in combination with one or more chemotherapeutic agents. In certain instances, the effective amount of one or more RORγ inhibitors is an amount sufficient to sensitize a chemotherapy drug-resistant cancer such as a tamoxifen-resistant cancer (e.g., tamoxifen-resistant breast cancer) or a taxane-resistant cancer (e.g., docetaxel-resistant prostate cancer) to chemotherapy drug treatment. The RORγ inhibitors and chemotherapeutic agents can be delivered to a subject via the same route of administration (e.g., orally or parenterally) or via different routes of administration (e.g., intravenously for RORγ inhibitors and orally for chemotherapeutic agents, or vice versa).

3. Radiotherapeutic Agents

Radiotherapeutic agents are well known in the art and can comprise external-beam radiation therapy and/or internal radiation therapy. External beam radiation therapy delivers radioactive beams of high energy X-rays and/or gamma rays to a patient's tumor, whereas internal radiation therapy delivers radioactive atoms to a patient's tumor. Both external beam radiation therapy and internal radiation therapy are used to suppress tumor growth or kill cancer cells by delivering a sufficient quantity of radioactivity to the target site. In some embodiments, the radiotherpaeutic agent comprises a radioactive atom and is complexed with a biologic or synthetic agent to increase delivery to the target site. Such biologic or synthetic agents are known in the art. Suitable radioactive atoms for use with the RORγ inhibitors of the present invention include any of the radionuclides described herein, or any other isotope which emits enough energy to destroy a targeted tissue or cell. In some embodiments, radiotherapeutic agents may be coupled to targeting moieties, such as antibodies, to improve the localization of radiotherapeutic agents to cancerous cells.

The term "radionuclide" is intended to include any nuclide that exhibits radioactivity. A "nuclide" refers to a type of atom specified by its atomic number, atomic mass, and energy state, such as carbon 14 ($^{14}C$). "Radioactivity" refers to the radiation, including alpha particles, beta particles, nucleons, electrons, positrons, neutrinos, and gamma rays, emitted by a radioactive substance. Examples of radionuclides suitable for use in the present invention include, but are not limited to, fluorine 18 ($^{18}F$), fluorine 19 ($^{19}F$), phosphorus 32 ($^{32}P$), scandium 47 ($^{47}Sc$), cobalt 55 ($^{55}Co$), copper 60 ($^{60}Cu$), copper 61 ($^{61}Cu$), copper 62 ($^{62}Cu$), copper 64 ($^{64}Cu$), gallium 66 ($^{66}Ga$), copper 67 ($^{67}Cu$), gallium 67 ($^{67}Ga$), gallium 68 ($^{68}Ga$), rubidium 82 ($^{82}Rb$), yttrium 86 ($^{86}Y$), yttrium 87 ($^{87}Y$), strontium 89 ($^{89}Sr$), yttrium 90 ($^{90}Y$), rhodium 105 ($^{105}Rh$), silver 111 ($^{111}Ag$), indium 111 ($^{111}In$), iodine 124 ($^{124}I$), iodine 125 ($^{125}I$), iodine 131 ($^{131}I$), tin 117m ($^{117}Sn$), technetium 99m ($^{99m}Tc$), promethium 149 ($^{149}Pm$), samarium 153 ($^{153}Sm$), holmium 166 ($^{166}Ho$), lutetium 177 ($^{177}Lu$), rhenium 186 ($^{186}Re$), rhenium 188 ($^{188}Re$), thallium 201 ($^{201}Tl$), astatine 211 ($^{211}At$), and bismuth 212 ($^{212}Bi$). As used herein, the "m" in $^{117m}Sn$ and $^{99m}Tc$ stands for the meta state. Additionally, naturally-occurring radioactive elements such as uranium, radium, and thorium, which typically represent mixtures of radioisotopes, are suitable examples of radionuclides. $^{67}Cu$, $^{131}I$, $^{177}Lu$, and $^{186}Re$ are beta- and gamma-emitting radionuclides. $^{212}Bi$ is an alpha- and beta-emitting radionuclide. $^{211}At$ is an alpha-emitting radionuclide. $^{32}P$, $^{47}Sc$, $^{89}Sr$, $^{90}Y$, $^{105}Rh$, $^{111}Ag$, $^{117m}Sn$, $^{149}Pm$, $^{153}Sm$, $^{166}Ho$, and $^{188}Re$ are examples of beta-emitting radionuclides. $^{67}Ga$, $^{111}In$, $^{99m}Tc$, and $^{201}Tl$ are examples of gamma-emitting radionuclides. $^{55}Co$, $^{60}Cu$, $^{61}Cu$, $^{62}Cu$, $^{66}Ga$, $^{68}Ga$, $^{82}Rb$, and $^{86}Y$ are examples of positron-emitting radionuclides. $^{64}Cu$ is a beta- and positron-emitting radionuclide.

In some embodiments, the present invention provides a composition comprising one or more RORγ inhibitors in combination with one or more radiotherapeutic agents. In certain instances, the composition further comprises a pharmaceutically acceptable excipient or diluent. In other instances, the composition is formulated for oral or parenteral administration.

In other embodiments, the present invention provides a method for treating cancer in a subject comprising administering to the subject an effective amount of one or more RORγ inhibitors in combination with one or more radiotherapeutic agents. In certain instances, the effective amount of one or more RORγ inhibitors is an amount sufficient to sensitize a radiation-resistant cancer such as a radiation-resistant breast cancer to radiation treatment. The RORγ inhibitors and radiotherapeutic agents can be delivered to a subject via the same route of administration (e.g., orally or parenterally) or via different routes of administration (e.g., intravenously for RORγ inhibitors and orally for radiotherapeutic agents, or vice versa).

4. Endocrine Therapies

Endocrine therapy is the manipulation of the endocrine system through the administration of specific hormones or drugs which inhibit or decrease the production or activity of targeted hormones or alter the gene expression pattern of targeted cells. Endocrine therapy is particularly useful in certain types of cancer, including breast cancer. Any known hormone antagonist or modulator may be used in the present invention. Endocrine therapies useful in the present invention include, but are not limited to, aromatase inhibitors (e.g. letrozole), megestrol acetate, flutamide, tamoxifen, raloxifene, lasofoxifene, bazedoxifene, bazedoxifene/conjugated estrogens, and combinations thereof.

In some embodiments, the present invention provides a composition comprising one or more RORγ inhibitors in combination with one or more endocrine therapies. In certain instances, the composition further comprises a pharmaceutically acceptable excipient or diluent. In other instances, the composition is formulated for oral or parenteral administration.

In other embodiments, the present invention provides a method for treating cancer in a subject comprising administering to the subject an effective amount of one or more RORγ inhibitors in combination with one or more endocrine therapies. In certain instances, the effective amount of one or more RORγ inhibitors is an amount sufficient to sensitize an endocrine therapy-resistant cancer such as a tamoxifen-resistant breast cancer to endocrine therapy. The RORγ inhibitors and endocrine therapies can be delivered to a subject via the same route of administration (e.g., orally or parenterally) or via different routes of administration (e.g., intravenously for RORγ inhibitors and orally for endocrine therapies, or vice versa).

5. Tyrosine Kinase Inhibitors

Tyrosine kinase inhibitors are small molecules that inhibit tyrosine kinase proteins. Tyrosine kinases are enzymes that activate many proteins in cellular signal transduction cascades by addition of a phosphate group to the protein. High expression and aberrant activation, of tyrosine kinase proteins can cause undesirable "switching on" of cellular signaling pathways that can result in uncontrolled cellular proliferation associated with cancerous cellular phenotypes. Various forms of cancer are currently treated by inhibiting or reducing the activity of poorly regulated tyrosine kinase proteins with tyrosine kinase inhibitors. Treatment regimens with tyrosine kinase inhibitors can suppress, reduce the incidence, reduce the severity, or inhibit the progression of cancer. Examples of tyrosine kinase inhibitors include, but are not limited to, gefitinib, erlotinib, sorafenib, sunitinib, dasatinib, lapatinib, nilotinib, bortezomib, salinomycin, and combinations thereof.

In some embodiments, the present invention provides a composition comprising one or more RORγ inhibitors in combination with one or more tyrosine kinase inhibitors. In certain instances, the composition further comprises a pharmaceutically acceptable excipient or diluent. In other instances, the composition is formulated for oral or parenteral administration.

In other embodiments, the present invention provides a method for treating cancer in a subject comprising administering to the subject an effective amount of one or more RORγ inhibitors in combination with one or more tyrosine kinase inhibitors. In certain instances, the effective amount of one or more RORγ inhibitors is an amount sufficient to sensitize a tyrosine kinase inhibitor-resistant cancer such as a tyrosine kinase inhibitor-resistant non-small-cell lung cancer (NSCLC) to tyrosine kinase inhibitor therapy. The RORγ inhibitors and tyrosine kinase inhibitors can be delivered to a subject via the same route of administration (e.g., orally or parenterally) or via different routes of administration (e.g., intravenously for RORγ inhibitors and orally for tyrosine kinase inhibitors, or vice versa).

6. Antigen-Specific Immunotherapeutic Agents

In some embodiments, antigen-specific immunotherapeutic agents include compounds and compositions designed to stimulate the immune system to specifically recognize antigens expressed or overexpressed by cancerous cells. In other embodiments, antigen-specific immunotherapeutic agents include compounds and compositions that will specifically recognize antigens expressed or overexpressed by cancerous cells. Non-limiting examples of antigen-specific immunotherapeutic agents include vaccines (e.g., peptide vaccines), antibodies, cytotoxic T cell lymphocytes (CTLs), chimeric antigen receptor T cells (CAR-T cells), immune checkpoints (e.g., CTLA-4, PD-1, and PD-L1), immune modulating cytokines (e.g., IL-6 and IL-17), and combinations thereof. In particular embodiments, the antigens presented by cancerous cells are highly specific to each cancer type, and the vaccines, antibodies, CTLs, and/or CAR-T cells used is dependent on the cancer type being treated.

A vaccine can stimulate the immune system to specifically recognize and attack antigens presented by cancerous cells. Vaccines can comprise one or more peptides, peptide fragments, fusion peptides, DNA, RNA, other biologic or non-biologic material, or combinations thereof.

In some embodiments, one or more peptides, peptide fragments, or fusion peptides may be used for a peptide vaccine. The peptides may be harvested from an endogenous source or chemically synthesized. The peptides chosen are specific for the type of cancer being treated. For example, when targeting cancer cells, some commonly targeted proteins include GM-CSF, IL-13Rα2, EphA2, and Survivin; however, specific cancer types will have specifically preferred peptides used for targeting afflicted cells. In some embodiments, the one or more peptides in the peptide vaccine are free soluble peptides. In other embodiments, the one or more peptides in the peptide vaccine are tethered together using any means known in the art.

In some embodiments, vaccines include cancer vaccines such as, e.g., tecemotide (L-BLP25), oncophage, sipuleucel-T, and combinations thereof. Tecemotide (L-BLP25) is a liposomal antigen-specific cancer immunotherapy that contains 25 amino acids from the immunogenic tandem-repeat region of MUC1 (see, e.g., Mehta N R et al., *Clin. Cancer Res.*, 18:2861-2871 (2012)).

Antibodies can recognize antigens expressed or overexpressed by cancerous cells. Antigens recognized by these antibodies can be proteins expressed, activated, or overexpressed on the cell surface or proteins secreted into the extracellular fluid. In some embodiments, antibodies can be used to target human effector cells (e.g., macrophages) against the cancerous cells. In some embodiments, antibodies are used to inhibit the normal function of cell surface receptors. In some embodiments, antibodies bind to the ligands of cell surface receptors to block the cellular signaling cascade. Antibodies used as antigen-specific immunotherapeutic agents can be monoclonal or polyclonal antibodies as well as chimeric, humanized, or human antibodies, and can be previously isolated from the patient or produced from another biologic source. Methods of producing antibodies are well known in the art, and may be made by any known means. For example, antibodies described herein can be produced by conventional monoclonal antibody methodology e.g., the standard somatic cell hybridization technique of Kohler and Milstein, *Nature* 256: 495 (1975), the contents of which are herein incorporated by reference for all purposes. In some embodiments, antibodies useful in the treatment of cancer include immune checkpoint inhibitors. In particular embodiments, antibodies useful in the treatment of cancer include, but are not limited to, alemtuzumab, bevacizumab, cetuximab, ipilimumab, nivolumab, ofatumumab, panitumumab, pembrolizumab, atezolizumab, rituximab, trastuzumab, and combinations thereof.

The use of CTLs and CAR-T cells as antigen-specific immunotherapeutic agents is a form of adoptive T cell transfer therapy. Adoptive T cell transfer therapy is a technique that can boost the natural immune system's ability to combat cancer by enriching for and/or designing T cells that are able to effectively recognize, bind, and kill a diseased cell. CTLs can recognize and bind cancerous cells using T-cell receptors (TCR). TCRs contain a highly variable binding region that allow them to recognize a large range of antigens. TCRs bind to the major histocompatibility complex I (MHC I) of cancerous cells presenting an appropriate antigen. TCRs binding is highly specific, so only a small number of CTLs will be able to recognize a particular antigen. Once an antigen is recognized by CTLs binding to the MHC I complex of the cancerous cell, they activate to induce cellular death. Activated CTLs proliferate to fight the detected cancer.

CTLs administered in this therapy may be derived from the subject or may be derived from other biological sources. Methods for producing CTLs directed to a particular antigen are well known in the art, and can be harvested from an individual possessing a CTL directed to a particular antigen or produced outside of the body (ex vivo). For example, when treating cancer, cytotoxic T cells from a subject's tumor are isolated, the cytotoxic T cells with the greatest antitumor activity are identified, the identified cytotoxic T cells are cultured to produce large amounts of the most effective cells, and the cultured cytotoxic T cells are reintroduced into the subject to treat the cancer. CTLs can also be produced in healthy individuals using ex vivo techniques described in U.S. Pat. No. 5,962,318, and U.S. Patent Application Publication No. 2009/0324539, the contents of which are herein incorporated by reference for all purposes. The ex vivo methods described herein can be useful for individuals both before cancer onset or after cancer onset.

CAR-T cells are modified T cells which have been engineered to possess a cellular specificity domain that has not been produced naturally. The natural specificity domain of T cells are T-cell receptors that recognize a particular antigen presented on MHC class I molecules. In some embodiments, CAR-T cells possess a T-cell receptor that has not been naturally produced in a subject's body. In some embodiments, the cellular specificity domain is a monoclonal antibody that is specific for the targeted cells or tissue. CAR-T cells can be produced using any means known in the art. In some embodiments, cytotoxic T cells are harvested from a subject's blood, the cytotoxic T cells are genetically modified by inserting a gene that encodes for a receptor that recognizes an antigen specific to the cancer affecting the subject, the CAR-T cells are cultured and can be stored for later use or reintroduced into the subject's body to treat the cancer. For more information on the details of producing CAR-T cells, see, e.g., U.S. Pat. No. 9,102,760, U.S. Pat. No. 8,399,645, U.S. Pat. No. 8,975,071, and U.S. Pat. No. 8,916,381, the contents of which are herein incorporated by reference for all purposes.

In some embodiments, the present invention provides a composition comprising one or more RORγ inhibitors in combination with one or more antigen-specific immunotherapeutic agents. In certain instances, the composition further comprises a pharmaceutically acceptable excipient or diluent. In other instances, the composition is formulated for oral or parenteral administration.

In other embodiments, the present invention provides a method for treating cancer in a subject comprising administering to the subject an effective amount of one or more RORγ inhibitors in combination with one or more antigen-specific immunotherapeutic agents. In certain instances, the effective amount of one or more RORγ inhibitors is an amount sufficient to sensitize a cancer that is resistant to treatment with antigen-specific immunotherapeutic agents to such treatment. The RORγ inhibitors and antigen-specific immunotherapeutic agents can be delivered to a subject via the same route of administration (e.g., orally or parenterally) or via different routes of administration (e.g., intravenously for RORγ inhibitors and orally for antigen-specific immunotherapeutic agents, or vice versa).

C. Diseases and Conditions

In certain aspects, a cancer can be treated or prevented by administering one or more RORγ inhibitors. In some embodiments, the one or more RORγ inhibitors are administered in combination with an anticancer drug. Cancer generally includes any of various malignant neoplasms characterized by the proliferation of anaplastic cells that tend to invade surrounding tissue and metastasize to new body sites. Non-limiting examples of different types of cancer suitable for treatment using the compositions of the present invention include prostate cancer, lung cancer, ovarian cancer, breast cancer, bladder cancer, thyroid cancer, liver cancer, pleural cancer, pancreatic cancer, cervical cancer, testicular cancer, colon cancer, anal cancer, bile duct cancer, gastrointestinal carcinoid tumors, esophageal cancer, gall bladder cancer, rectal cancer, appendix cancer, small intestine cancer, stomach (gastric) cancer, renal cancer (i.e., renal cell carcinoma), cancer of the central nervous system, skin cancer, choriocarcinomas, head and neck cancers, bone cancer, osteogenic sarcomas, fibrosarcoma, neuroblastoma, glioma, endometrial cancer, melanoma, leukemia (e.g., acute lymphocytic leukemia, chronic lymphocytic leukemia, acute myelogenous leukemia, chronic myelogenous leukemia, or hairy cell leukemia), lymphoma (e.g., non-Hodgkin's lymphoma, Hodgkin's lymphoma, B-cell lymphoma, or Burkitt's lymphoma), and multiple myeloma.

In particular embodiments, the cancer is an epithelial cancer (e.g., prostate cancer, ovarian cancer, breast cancer, and the like), or a blood cancer (e.g., leukemia, lymphoma, multiple myeloma). In some embodiments, the cancer is a prostate cancer. In certain embodiments, the prostate cancer is an advanced stage prostate cancer selected from one or more of metastatic prostate cancer, drug-resistant prostate cancer (e.g., anti-androgen-resistant prostate cancer such as enzalutamide-resistant prostate cancer, abiraterone-resistant prostate cancer, bicalutamide-resistant prostate cancer, etc.; taxane-resistant prostate cancer; docetaxel-resistant prostate cancer; and the like), hormone refractory prostate cancer, castration-resistant prostate cancer (CRPC), metastatic castration-resistant prostate cancer, AR-V7-induced drug-resistant prostate cancer such as AR-V7-induced anti-androgen-resistant prostate cancer (e.g., AR-V7-induced enzalutamide-resistant prostate cancer), AKRIC3-induced drug-resistant prostate cancer such as AKRIC3-induced anti-androgen-resistant prostate cancer (e.g., AKRIC3-induced enzalutamide-resistant prostate cancer), and combinations thereof.

In other embodiments, the cancer is a lung cancer, breast cancer, liver cancer, ovarian cancer, endometrial cancer, bladder cancer, colon cancer, lymphoma, or a glioma. In certain instances, the lung cancer is a non-small-cell lung cancer (NSCLC), K-Ras mutant lung cancer. BRAF mutant lung cancer, tyrosine kinase inhibitor-resistant lung cancer, small cell lung cancer (SCLC), adenocarcinoma (e.g., adenocarcinoma in situ), squamous cell carcinoma, large cell carcinoma, bronchial carcinoid, or combinations thereof. In certain instances, the breast cancer is triple-negative breast cancer (TNBC), tamoxifen-resistant breast cancer, radiation-resistant breast cancer, ductal carcinoma in situ, invasive ductal carcinoma, HER2-positive breast cancer, ER-positive breast cancer, inflammatory breast cancer, metastatic breast cancer, medullary carcinoma, tubular carcinoma, mucinous carcinoma (colloid), or combinations thereof. In certain instances, the liver cancer is a hepatocellular carcinoma (HCC), cholangiocarcinoma (bile duct cancer), angiosarcoma, hepatoblastoma, or combinations thereof. In certain instances, the glioma is an ependymoma, astrocytoma (e.g., glioblastoma multiforme), oligodendroglioma, brainstem glioma, optic nerve glioma, or combinations thereof (e.g., mixed glioma).

D. Pharmaceutical Compositions

The pharmaceutical compositions of the present invention encompass compositions made by admixing one or more RORγ inhibitors, such as SR2211 and/or XY011, and a pharmaceutically acceptable carrier and/or excipient or diluent. Such compositions are suitable for pharmaceutical use in an animal or human.

The pharmaceutical compositions of the present invention may be prepared by any of the methods well-known in the art of pharmacy. Pharmaceutically acceptable carriers suitable for use with the present invention include any of the standard pharmaceutical carriers, buffers and excipients, including phosphate-buffered saline solution, water, and emulsions (such as an oil/water or water/oil emulsion), and various types of wetting agents and/or adjuvants. Suitable pharmaceutical carriers and their formulations are described in Remington's Pharmaceutical Sciences (Mack Publishing Co., Easton, 19th ed. 1995). Preferred pharmaceutical carriers depend upon the intended mode of administration of the active agent(s).

The pharmaceutical compositions of the present invention can include one or more RORγ inhibitors (e.g., SR2211 and/or XY011), one or more anticancer drugs such as an anti-androgen drug (e.g., enzalutamide, abiraterone, and/or bicalutamide) and/or a chemotherapeutic agent (e.g., tamoxifen and/or a taxane such as docetaxel), or any pharmaceutically acceptable salts thereof, as an active ingredient, and a pharmaceutically acceptable carrier and/or excipient or diluent. In particular embodiments, the pharmaceutical composition can include one or more RORγ inhibitors, such as SR2211 and/or XY011., and an anti-androgen drug, such as enzalutamide. A pharmaceutical composition may optionally contain other therapeutic ingredients.

The compounds of the present invention can be combined as the active ingredient in intimate admixture with a suitable pharmaceutical carrier and/or excipient according to conventional pharmaceutical compounding techniques. Any carrier and/or excipient suitable for the form of preparation desired for administration is contemplated for use with the compounds disclosed herein.

In some embodiments, the pharmaceutical compositions comprising one or more RORγ inhibitors and the pharmaceutical compositions comprising one or more anticancer drugs are prepared as a single medicament. In other embodiments, the pharmaceutical compositions comprising one or more RORγ inhibitors and the pharmaceutical compositions comprising one or more anticancer drugs are prepared as separate medicaments.

The pharmaceutical compositions of the present invention include formulations suitable for topical, parenteral, pulmonary, nasal, rectal, or oral administration. The most suitable route of administration in any given case will depend in part on the nature and severity of the cancer condition and also optionally the stage of the cancer.

In embodiments where the RORγ inhibitor is administered in combination with an anticancer drug, the administration of the RORγ inhibitor and the anticancer drug may be administered using the same or a different administration route. For example, in some embodiments, both the RORγ inhibitor and the anticancer drug may be administered orally or parenterally (e.g., intravenously). For example, in other embodiments, the RORγ inhibitor may be administered orally, while the anticancer drug may be administered parenterally (e.g., intravenously), or vice versa.

Other preferred compositions include compositions suitable for systemic (enteral or parenteral) administration. Systemic administration includes oral, rectal, sublingual, or sublabial administration. In some embodiments, the compositions may be administered via a syringe or intravenously.

Compositions for pulmonary administration include, but are not limited to, dry powder compositions consisting of the powder of a compound described herein, or a salt thereof, and the powder of a suitable carrier and/or lubricant. The compositions for pulmonary administration can be inhaled from any suitable dry powder inhaler device known to a person skilled in the art.

Compositions for systemic administration include, but are not limited to, dry powder compositions consisting of the composition as set forth herein and the powder of a suitable carrier and/or excipient. The compositions for systemic administration can be represented by, but not limited to, tablets, capsules, pills, syrups, solutions, and suspensions.

In some embodiments, the present invention provides compositions further including a pharmaceutical surfactant. In other embodiments, the present invention provides compositions further including a cryoprotectant. In some embodiments, the cryoprotectant is selected from the group consisting of glucose, sucrose, trehalose, lactose, sodium glutamate, PVP, HPβCD, CD, glycerol, maltose, mannitol, and saccharose.

In some embodiments, the present invention provides a pharmaceutical composition including one or more RORγ inhibitors, such as SR2211 and/or XY011, and a pharmaceutically acceptable excipient. In some embodiments, the present invention provides a pharmaceutical composition including one or more RORγ inhibitors, such as SR2211 and/or XY011, and one or more anticancer drugs such as an anti-androgen drug (e.g., enzalutamide, abiraterone, and/or bicalutamide) and/or a chemotherapeutic agent (e.g., tamoxifen and/or a taxane such as docetaxel), in combination with a pharmaceutically acceptable excipient. In particular embodiments, the present invention provides a pharmaceutical composition including one or more RORγ inhibitors, such as SR2211 and/or XY011, and an anti-androgen drug, such as enzalutamide, in combination with a pharmaceutically acceptable excipient. In some of these embodiments, the pharmaceutically acceptable excipient includes a salt or a diluent.

In some embodiments, the present invention provides compositions including an effective amount of one or more RORγ inhibitors, such as SR2211 and/or XY011. In some embodiments, the composition is formulated for oral administration or parenteral (e.g., intravenous) administration and includes one or more RORγ inhibitors, such as SR2211 and/or XY011, and at least one member selected from the group consisting of an aqueous solution and a buffer solution. In some embodiments, the composition can include an effective amount of one or more RORγ inhibitors, such as SR2211 and/or XY011, and one or more anticancer drugs such as an anti-androgen drug (e.g., enzalutamide, abiraterone, and/or bicalutamide) and/or a chemotherapeutic agent (e.g., tamoxifen and/or a taxane such as docetaxel).

Pharmaceutical compositions or medicaments for use in the present invention can be formulated by standard techniques using one or more physiologically acceptable carriers or excipients. Suitable pharmaceutical carriers are described herein and in Remington: The Science and Practice of Pharmacy, 21st Ed., University of the Sciences in Philadelphia, Lippencott Williams & Wilkins (2005).

For oral administration, a pharmaceutical composition or a medicament can take the form of, e.g., a tablet or a capsule prepared by conventional means with a pharmaceutically acceptable excipient. Preferred are tablets and gelatin capsules comprising the active ingredient(s), together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, anhydrous colloidal silica, talcum, stearic acid, its magnesium or calcium salt (e.g., magnesium stearate or calcium stearate), metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulfate, and/or (f) absorbents, colorants, flavors and sweeteners. In some embodiments, the tablet contains a mixture of hydroxypropyl methylcellulose, polyethyleneglycol 6000 and titatium dioxide. Tablets may be either film coated or enteric coated according to methods known in the art.

Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

Controlled release parenteral formulations of the compositions of the present invention can be made as implants, oily injections, or as particulate systems. For a broad overview of delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles.

Polymers can be used for ion-controlled release of compositions of the present invention. Various degradable and nondegradable polymeric matrices for use in controlled drug delivery are known in the art (Langer R., Accounts Chem. Res., 26:537-542 (1993)). For example, the block copolymer, polaxamer 407 exists as a viscous yet mobile liquid at low temperatures but forms a semisolid gel at body temperature. It has shown to be an effective vehicle for formulation and sustained delivery of recombinant interleukin 2 and urease (Johnston et al., *Pharm. Res.*, 9:425-434 (1992); and Pec et al., *J. Parent. Sci. Iech.*, 44(2):58 65 (1990)). Alternatively, hydroxyapatite has been used as a microcarrier for controlled release of proteins (Ijntema et al., *Int. J. Pharm.*, 112:215-224 (1994)). In yet another aspect, liposomes are used for controlled release as well as drug targeting of the lipid-capsulated drug (Betageri et al., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

E. Methods of Administration

Pharmaceutical compositions or medicaments comprising one or more RORγ inhibitors can be administered to a subject at a therapeutically effective dose to treat the subject's cancer, as described herein. In some embodiments, pharmaceutical compositions or medicaments comprising one or more RORγ inhibitors can be co-administered to a subject in combination with an effective amount of an anticancer drug at a therapeutically effective dose to treat the subject's cancer, as described herein. In some embodiments, the pharmaceutical composition or medicament comprising one or more RORγ inhibitors is administered to a subject in an amount sufficient in to elicit an effective therapeutic response in the subject. In some embodiments, the pharmaceutical composition or medicament comprising one or more RORγ inhibitors can be co-administered to a subject at a therapeutically effective dose in combination with an effective amount of an anticancer drug to elicit an effective therapeutic response in the subject.

In certain methods of treating cancer, set forth herein, the methods comprise first administering one or more RORγ inhibitors, such as SR2211 and/or XY011, to a patient having cancer, and then administering an anticancer drug, such as an anti-androgen drug and/or a chemotherapeutic agent, to the patient. In certain methods of treating cancer, set forth herein, the methods comprise first administering an anticancer drug, such as an anti-androgen drug and/or a chemotherapeutic agent, to a patient having cancer, and then administering one or more RORγ inhibitors, such as SR2211 and/or XY011, to the patient. In certain methods of treating cancer, set forth herein, the methods comprise co-administering one or more RORγ inhibitors, such as SR2211 and/or XY011, with an anticancer drug, such as an anti-androgen drug and/or a chemotherapeutic agent, to a patient having cancer.

In some embodiments, the methods of administration comprise administering one or more RORγ inhibitors, such as SR2211 and/or XY011, alone or in combination with enzalutamide to a patient in need thereof. In other embodiments, the methods of administration comprise administering one or more RORγ inhibitors, such as SR2211 and/or XY011, alone or in combination with abiraterone to a patient in need thereof. In yet other embodiments, the methods comprise administering one or more RORγ inhibitors, such as SR2211 and/or XY011, alone or in combination with bicalutamide to a patient in need thereof. In still yet other embodiments, the methods comprise administering one or more RORγ inhibitors, such as SR2211 and/or XY011, alone or in combination with a taxane such as docetaxel to a patient in need thereof. In further embodiments, the methods comprise administering one or more RORγ inhibitors, such as SR2211 and/or XY011, alone or in combination with tamoxifen to a patient in need thereof.

In certain embodiments, the present invention provides a method of delivering an effective amount of one or more RORγ inhibitors, such as SR2211 and/or XY011, to a patient having cancer such as prostate cancer (e.g., CRPC).

The RORγ inhibitors described herein are useful in the manufacture of a pharmaceutical composition or a medicament. A pharmaceutical composition or medicament can be administered to a subject in need thereof, e.g. a patient having a cancer such as prostate cancer (e.g., CRPC), lung cancer, breast cancer, liver cancer, ovarian cancer, endometrial cancer, bladder cancer, colon cancer, lymphoma, or a glioma.

Pharmaceutical compositions or medicaments for use in the present invention can be formulated by standard techniques using one or more physiologically acceptable carriers or excipients. Suitable pharmaceutical carriers are described herein and in "Remington's Pharmaceutical Sciences" by E. W. Martin. Compounds and agents of the present invention and their physiologically acceptable salts and solvates can be formulated for administration by any suitable route, including via inhalation, topically, nasally, orally, intravenously, parenterally, or rectally.

1. Routes of Administration

Typical formulations for topical administration include creams, ointments, sprays, lotions, and patches. The pharmaceutical composition can, however, be formulated for any type of administration, e.g., intradermal, subdermal, intravenous, intramuscular, intranasal, intracerebral, intratracheal, intraarterial, intraperitoneal, intravesical, intrapleural, intracoronary or intratumoral injection, with a syringe or other devices. Formulation for administration by inhalation (e.g., aerosol), or for oral or rectal administration is also contemplated.

Suitable formulations for transdermal application include an effective amount of one or more compounds described herein, optionally with a carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

For oral administration, a pharmaceutical composition or a medicament can take the form of, for example, a tablet or a capsule prepared by conventional means with a pharmaceutically acceptable excipient. The present invention provides tablets and gelatin capsules comprising one or more RORγ inhibitors, such as SR2211 and/or XY011, alone or in combination with other compounds such as anticancer drugs, or a dried solid powder of these drugs, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, talcum, stearic acid, magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound(s).

The compositions and formulations set forth herein can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient(s) can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient(s).

For administration by inhalation, the compositions of the present invention may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound(s) and a suitable powder base, for example, lactose or starch.

The compositions set forth herein can also be formulated in rectal compositions, for example, suppositories or retention enemas, for example, containing conventional suppository bases, for example, cocoa butter or other glycerides.

Furthermore, the active ingredient(s) can be formulated as a depot preparation. Such long-acting formulations can be administered by implantation (for example, subcutaneously or intramuscularly) or by intramuscular injection. Thus, for example, one or more of the compounds described herein can be formulated with suitable polymeric or hydrophobic materials (for example as an emulsion in an acceptable oil) or ion exchange resins, or as sparingly soluble derivatives, for example, as a sparingly soluble salt.

In particular embodiments, a pharmaceutical composition or medicament of the present invention can comprise (i) an effective amount of one or more RORγ inhibitors, such as SR2211 and/or XY011, and (ii) optionally an anticancer drug such as an anti-androgen drug (e.g., enzalutamide, abiraterone, bicalutamide), a chemotherapeutic agent such as a taxane (e.g., docetaxel) or tamoxifen, and combinations thereof. The therapeutic agent(s) may be used individually, sequentially, or in combination with one or more other such therapeutic agents (e.g., a first therapeutic agent, a second therapeutic agent, a compound of the present invention, etc.). Administration may be by the same or different route of administration or together in the same pharmaceutical formulation.

2. Dosage

Pharmaceutical compositions or medicaments can be administered to a subject at a therapeutically effective dose to prevent, treat, sensitize, or control a cancer such as prostate cancer (e.g., CRPC), lung cancer, breast cancer, liver cancer, ovarian cancer, endometrial cancer, bladder cancer, colon cancer, lymphoma, or a glioma as described herein. The pharmaceutical composition or medicament is administered to a subject in an amount sufficient to elicit an effective therapeutic response in the subject. An effective therapeutic response includes a response that at least partially arrests or slows the symptoms or complications of the cancer. An amount adequate to accomplish this is defined as a "therapeutically effective dose."

The dosage of active agents administered is dependent on the subject's body weight, age, individual condition, surface area or volume of the area to be treated and on the form of administration. The size of the dose also will be determined by the existence, nature, and extent of any adverse effects that accompany the administration of a particular formulation in a particular subject. A unit dosage for oral administration to a mammal of about 50 to about 70 kg may contain between about 5 and about 500 mg, about 25-200 mg, about 100 and about 1000 mg, about 200 and about 2000 mg, about 500 and about 5000 mg, or between about 1000 and about 2000 mg of the active ingredient. A unit dosage for oral administration to a mammal of about 50 to about 70 kg may contain about 10 mg, 20 mg, 25 mg, 50 mg, 75 mg, 100 mg, 200 mg, 300 mg, 400 mg, 500 mg, 600 mg, 700 mg, 800 mg, 900 mg, 1,000 mg, 1,250 mg, 1,500 mg, 2,000 mg, 2,500 mg, 3,000 mg, or more of the active ingredient. Typically, a dosage of the active compound(s) of the present invention is a dosage that is sufficient to achieve the desired effect. Optimal dosing schedules can be calculated from measurements of active agent accumulation in the body of a subject. In general, dosage may be given once or more of daily, weekly, or monthly. Persons of ordinary skill in the art can easily determine optimum dosages, dosing methodologies and repetition rates.

Optimum dosages, toxicity, and therapeutic efficacy of the compositions of the present invention may vary depending on the relative potency of the administered composition and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Agents that exhibit large therapeutic indices are preferred. While agents that exhibit toxic side effects can be used, care should be taken to design a delivery system that targets such agents to the site of affected tissue to minimize potential damage to normal cells and, thereby, reduce side effects.

Optimal dosing schedules can be calculated from measurements of active ingredient accumulation in the body of a subject. In general, dosage is from about 1 ng to about 1,000 mg per kg of body weight and may be given once or more daily, weekly, monthly, or yearly. Persons of ordinary skill in the art can easily determine optimum dosages, dosing methodologies and repetition rates. One of skill in the art will be able to determine optimal dosing for administration of one or more RORγ inhibitors, such as SR2211 and/or XY011, to a human being following established protocols known in the art and the disclosure herein.

The data obtained from, for example, animal studies (e.g., rodents and monkeys) can be used to formulate a dosage range for use in humans. The dosage of compounds of the present invention lies preferably within a range of circulating concentrations that include the $ED_{50}$ with little or no toxicity. The dosage can vary within this range depending upon the dosage form employed and the route of administration. For any composition for use in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a chimeric protein, preferably a composition is from about 1 ng/kg to about 100 mg/kg for a typical subject.

A typical composition of the present invention for oral or intravenous administration can be about 0.1 to about 10 mg of active ingredient per patient per day; about 1 to about 100 mg per patient per day; about 25 to about 200 mg per patient per day; about 50 to about 500 mg per patient per day; about 100 to about 1000 mg per patient per day; or about 1000 to about 2000 mg per patient per day. Exemplary dosages include, but are not limited to, about 10 mg, 20 mg, 25 mg, 50 mg, 75 mg, 100 mg, 200 mg, 300 mg, 400 mg, 500 mg, 600 mg, 700 mg, 800 mg, 900 mg, 1,000 mg, 1,250 mg, 1,500 mg, 2,000 mg, 2,500 mg, 3,000 mg, or more of the active ingredient per patient per day. Methods for preparing administrable compositions will be known or apparent to those skilled in the art and are described in more detail in such publications as *Remington: The Science and Practice of Pharmacy*, 21' Ed., University of the Sciences in Philadelphia, Lippencott Williams & Wilkins (2005).

Exemplary doses of the compositions described herein include milligram or microgram amounts of the composition per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a composition depend upon the potency of the composition with respect to the desired effect to be achieved. When one or more of these compositions is to be administered to a mammal, a physician, veterinarian, or researcher may, for example, prescribe a relatively low dose at first, subsequently increasing the dose until an appropriate response is obtained. In addition, it is understood that the specific dose level for any particular mammal subject will depend upon a variety of factors including the activity of the specific composition employed, the age, body weight, general health, gender, and diet of the subject, the time of administration, the route of administration, the rate of excretion, any drug combination, and the degree of expression or activity to be modulated.

In some embodiments, a pharmaceutical composition or medicament of the present invention is administered, e.g., in a daily dose in the range from about 1 mg of compound per kg of subject weight (1 mg/kg) to about 1 g/kg. In another embodiment, the dose is a dose in the range of about 5 mg/kg to about 500 mg/kg. In yet another embodiment, the dose is about 10 mg/kg to about 250 mg/kg. In another embodiment, the dose is about 25 mg/kg to about 150 mg/kg. A preferred dose is about 2, 3, 4, 5, 6, 7, 8, 9, 10, 12, 15, 18, 20, 25, 30, 40, or 50 mg/kg. The daily dose can be administered once per day or divided into subdoses and administered in multiple doses, e.g., twice, three times, or four times per day. However, as will be appreciated by a skilled artisan, compositions described herein may be administered in different amounts and at different times. The skilled artisan will also appreciate that certain factors may influence the dosage and timing required to effectively treat a subject, including but not limited to the severity of the disease or malignant condition, previous treatments, the general health and/or age of the subject, and other diseases present. Moreover, treatment of a subject with a therapeutically effective amount of a composition can include a single treatment or, preferably, can include a series of treatments.

To achieve the desired therapeutic effect, compounds or agents described herein may be administered for multiple days at the therapeutically effective daily dose. Thus, therapeutically effective administration of compounds to treat prostate cancer in a subject may require periodic (e.g., daily) administration that continues for a period ranging from three days to two weeks or longer. Compositions set forth herein may be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the agents are not administered daily, so long as the administration is repeated frequently enough to maintain a therapeutically effective concentration of the agents in the subject. For example, one can administer the agents every other day, every third day, or, if higher dose ranges are employed and tolerated by the subject, once a week.

In some embodiments, the one or more RORγ inhibitors is orally administered. In some embodiments, the one or more RORγ inhibitors (e.g., SR2211 and/or XY011) is orally administered to a subject (e.g., an adult human) at a daily dose of approximately 100; 200; 300; 400; 500; 600; 700; 800; 900; 1,000; 1,250; 1,500; 1,750; 2,000; 2,500; 3,000; 3,500; 4,000; 4,500; 5,000; or more mg per day. In some embodiments, the one or more RORγ inhibitors (e.g., SR2211 and/or XY011) is orally administered to a subject (e.g., an adult human) at a daily dose of between 1,000 and 2,000 mg per day. In some embodiments, the one or more RORγ inhibitors (e.g., SR2211 and/or XY011) is orally administered to a subject (e.g., an adult human) at a daily dose of approximately 10, 15, 20, 25, 30, 35, 40, 50, 60, 70, 80, 90, 100, 125, 150, 175, 200, 225, 250, 300, 350, 400, 500, or more mg per day. In some embodiments, the one or more RORγ inhibitors (e.g., SR2211 and/or XY011) is orally administered to a subject (e.g., an adult human) at a daily dose of between 25 and 200 mg per day. In some embodiments, the one or more RORγ inhibitors (e.g., SR2211 and/or XY011) and an anticancer drug are orally co-administered. For example, the one or more RORγ inhibitors (e.g., SR2211 and/or XY011) can be co-administered at a daily oral dose of between 25 and 1000 mg per day with the anticancer drug at a daily oral dose of between 25 and 2000 mg per day.

In some embodiments, the methods comprise sequentially administering one or more RORγ inhibitors, such as SR2211 and/or XY011, followed by one or more anticancer drugs such as an anti-androgen drug (e.g., enzalutamide, abiraterone, bicalutamide), a chemotherapeutic agent such as a taxane (e.g., docetaxel) or tamoxifen, and combinations thereof. In some embodiments, the methods comprise sequentially administering one or more anticancer drugs followed by one or more RORγ inhibitors.

Following successful treatment, it may be desirable to have the subject undergo maintenance therapy to prevent the recurrence of the cancer.

Determination of an effective amount is well within the capability of those skilled in the art, especially in light of the detailed disclosure provided herein. Generally, an efficacious or effective amount of a composition is determined by first administering a low dose or small amount of the composition, and then incrementally increasing the administered dose or dosages, adding a second or third medication as needed, until a desired effect of is observed in the treated subject with minimal or no toxic side-effects.

Single or multiple administrations of the compositions are administered depending on the dosage and frequency as required and tolerated by the patient. In any event, the composition should provide a sufficient quantity of the compositions of this invention to effectively treat the patient. Generally, the dose is sufficient to treat or ameliorate symptoms or signs of disease without producing unacceptable toxicity to the patient.

F. Kits, Containers, Devices, and Systems

A wide variety of kits and systems can be prepared according to the present invention, depending upon the intended user of the kit and system and the particular needs of the user. In some embodiments, the present invention provides a kit that includes one or more RORγ inhibitors. In other aspects, the present invention provides a kit that includes one or more RORγ inhibitors and one or more anticancer drugs such as an anti-androgen drug (e.g., enzalutamide, abiraterone, and/or bicalutamide) and/or a chemotherapeutic agent (e.g., tamoxifen and/or a taxane such as docetaxel).

Some of the kits described herein can include a label describing a method of administering one or more RORγ inhibitors and/or one or more anticancer drugs. Some of the kits described herein can include a label describing a method of treating cancer in a subject with a cancer such as prostate cancer (e.g., CRPC), lung cancer, breast cancer, liver cancer, ovarian cancer, endometrial cancer, bladder cancer, colon cancer, lymphoma, or a glioma.

The compositions of the present invention, including but not limited to, compositions comprising one or more RORγ inhibitors and optionally one or more anticancer drugs may, if desired, be presented in a bottle, jar, vial, ampoule, tube, or other container-closure system approved by the Food and Drug Administration (FDA) or other regulatory body, which may provide one or more dosages containing the compounds. The package or dispenser may also be accompanied by a notice associated with the container in a form prescribed by a governmental agency regulating the manufacture, use, or sale of pharmaceuticals, the notice indicating approval by the agency. In certain aspects, the kit may include a formulation or composition as described herein, a container closure system including the formulation or a dosage unit form including the formulation, and a notice or instructions describing a method of use as described herein.

In some embodiments, the kit includes a container which is compartmentalized for holding the various elements of a formulation (e.g., the dry ingredients and the liquid ingredients) or composition, instructions for making the formulation or composition, and instructions for administering the formulation or composition for enhancing the immune response in a subject with a cancer.

In certain embodiments, the kit may include the pharmaceutical preparation(s) in dehydrated or dry form, with instructions for its rehydration (or reconstitution) and administration.

Kits with unit doses of the compounds described herein, e.g. in oral, rectal, transdermal, or injectable doses (e.g., for intramuscular, intravenous, or subcutaneous injection), are provided. In such kits, an informational package insert describing the use and attendant benefits of the composition for enhancing the immune response in a subject with a cancer such as prostate cancer (e.g., CRPC), lung cancer, breast cancer, liver cancer, ovarian cancer, endometrial cancer, bladder cancer, colon cancer, lymphoma, or a glioma may be included in addition to the containers containing the unit doses.

Some embodiments of the present invention provide packages that include one or more RORγ inhibitors and optionally one or more anticancer drugs such as an anti-androgen drug (e.g., enzalutamide, abiraterone, and/or bicalutamide) and/or a chemotherapeutic agent (e.g., tamoxifen and/or a taxane such as docetaxel).

IV. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1. Nuclear Receptor RORγ as a Novel Therapeutic Target for Cancer

Based on the concept that tumors have altered metabolisms and the fact that members of the nuclear receptor family proteins are key regulators of mammalian metabolism and are highly attractive therapeutic targets, we performed data mining of gene expressions in PCa tumors and found that the nuclear receptor RORγ gene is highly overexpressed in metastatic PCa tumors when compared to normal prostate or primary PCa tumors. This finding indicates that RORγ may play an important role in PCa development and progression. We thus performed the following experiments and obtained the following results that strongly support our conclusion that RORγ is a novel target for development of effective PCa therapeutics.

(1) Quantitative RT-PCR, Western blotting, and immunohistochemistry (IHC) assays were developed and used to specifically detect RORγ mRNA and protein and demonstrate clearly that RORγ is overexpressed in PCa cancer cells and a subgroup of PCa tumors. See, FIGS. 1A-1D.

(2) RNA interfering-mediated silencing/suppression of RORγ expression was developed using siRNAs and lentiviral vector-shRNAs to specifically block the human RORγ gene expression in different PCa cells.

(3) Suppression of RORγ expression and function by the siRNAs or the lenti-vector shRNAs resulted in potent inhibition of AR-positive PCa cell growth and survival in multiple cell lines, but not of AR-negative PCa cells. The suppression also induced marked cell death/apoptosis. The strong inhibition of cell growth was observed in metastatic CRPC models as well as in androgen-dependent PCa cells. Studies on RORγ so far are focused on its biological functions in control of circadian rhythm, metabolism and the differentiation of Th17 cells. A T cell-specific isoform of RORγ, called RORγt, has been studied as a therapeutic target for treatment of autoimmune diseases. So far, there has not been any report on the role of RORγ (or RORγt) in cancer cells. Therefore, the findings described above in (1) to (3) constitute the first evidence that the nuclear receptor RORγ plays a previously undescribed function in cancer and is a novel therapeutic target for cancer.

(4) Inhibition of RORγ function by treating the PCa cells with small molecule inhibitors (also known as inverse agonists) of RORγ including 8k (N-(3',4'-dimethoxyphenyl)-1-ethyl-2-oxo-1,2-dihydrobenzo[cd]indole-6-sulfonamide; also known as XY011 and E11), 7k ((E)-1-ethyl-2-oxo-N-(4'-(phenyldiazenyl)phenyl)-1,2-dihydrobenzo[cd]indole-6-sulfonamide), 6f (1-Ethyl-N-(isoquinolin-7'-yl)-2-oxo-1,2-dihydrobenzo[cd]indole-6-sulfonamide), SR2211, and SRI 555 also resulted in potent inhibition of AR-positive PCa cell growth and survival in the different cell line models and not in the AR-negative cells. See, FIGS. 2A-2F. Like the siRNAs, the small molecule inhibitor treatment elicited pronounced cell death, and the potent inhibitory activities were observed in multiple mCRPC cell models and in enzalutamide-resistant PCa cell models. In contrast, treating the same PCa cells with the RORα-specific, small molecule inhibitor SR3335 did not show any significant growth inhibition. RORα is a related member of the ROR sub-family.

(5) Treatment of immune-compromised nude mice with the small molecule inhibitors SR2211 and 8k (also known as XY011 and E11) strongly inhibited growth of xenograft tumors derived from one of AR-positive PCa cell line. See, FIGS. 3A-3D. In contrast, in the same experiment, treatment with enzalutamide (MDV3100) did not show any significant inhibitory effect on the same type of xenograft tumors. Therefore, the results indicate that RORγ inhibitors have the potential to be effective in treating enzalutamide-resistant prostate cancers.

The small molecule inhibitors SR2211 and 8k (also known as XY011 and E11) used in our study, among many other RORγ inhibitors such as TMP778 and GSK805, were identified based on their activity to inhibit RORγt function in the immune cells for potential use as therapeutics for treating the immune cell-mediated autoimmune diseases such as rheumatoid arthritis (RA), inflammatory bowel diseases (IBD), and multiple sclerosis (MS). Their activity in cancer cell proliferation and/or survival has not been reported for any type of cancer. Therefore, the findings described above in (4) to (5) constitute the first evidence that small molecule inhibitors targeting RORγ can be novel therapeutics for cancers.

(6) qRT-PCR and Western blotting analyses revealed that small molecule inhibitors such as SR2211 and siRNAs targeting RORγ strongly inhibited the expression of AR (e.g., both full-length and alternatively spliced variants such as ARV7) mRNA and protein expression. See, FIGS. 4A-4B.

(7) The above analysis also revealed that the RORγ inhibitors can effectively negate the induction of AR full-length and AR variant expression by enzalutamide in the PCa cells.

Figures 2B, 2C, 2D:
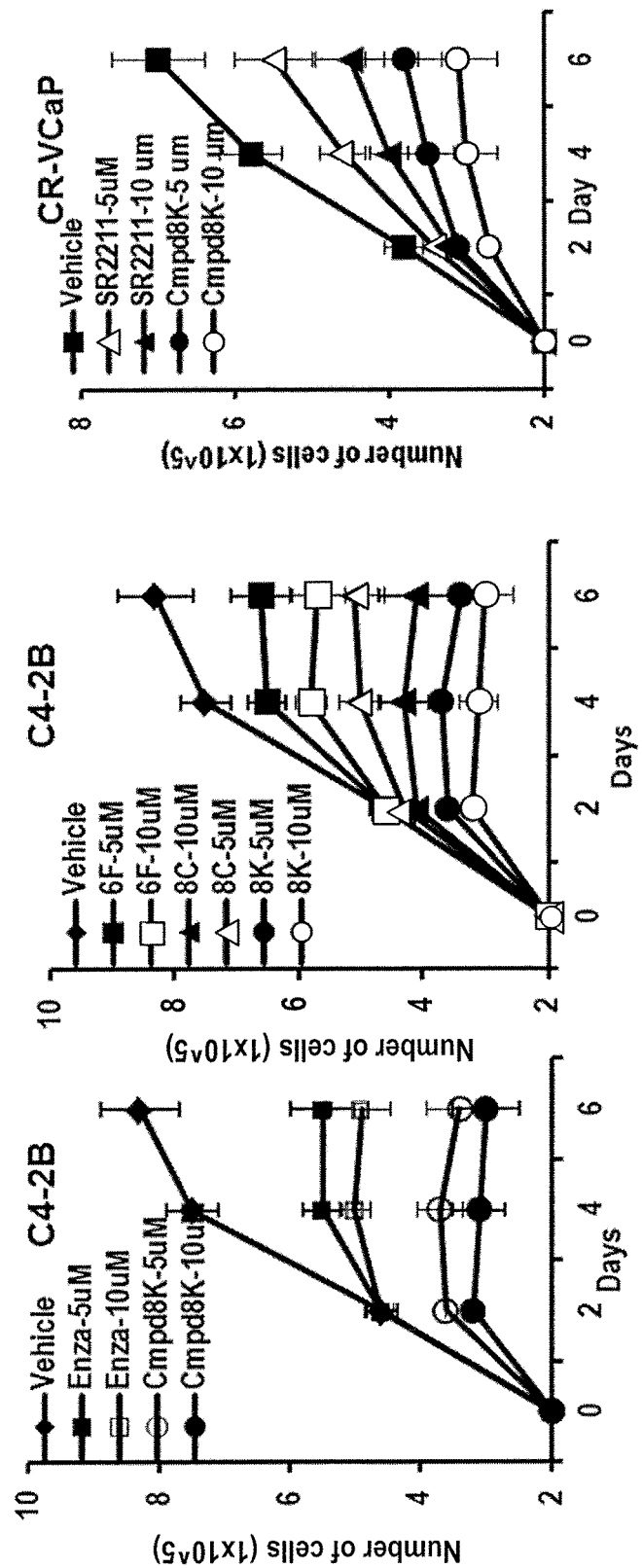
Figures 2E, 2F:
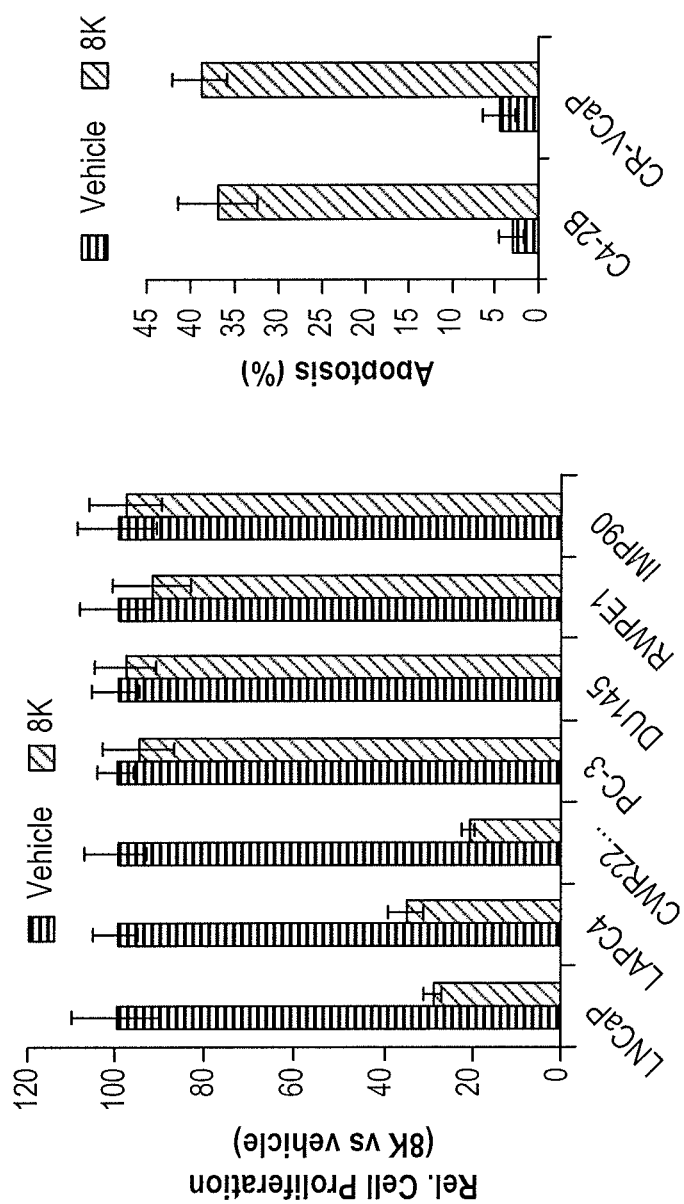
Figure 5:
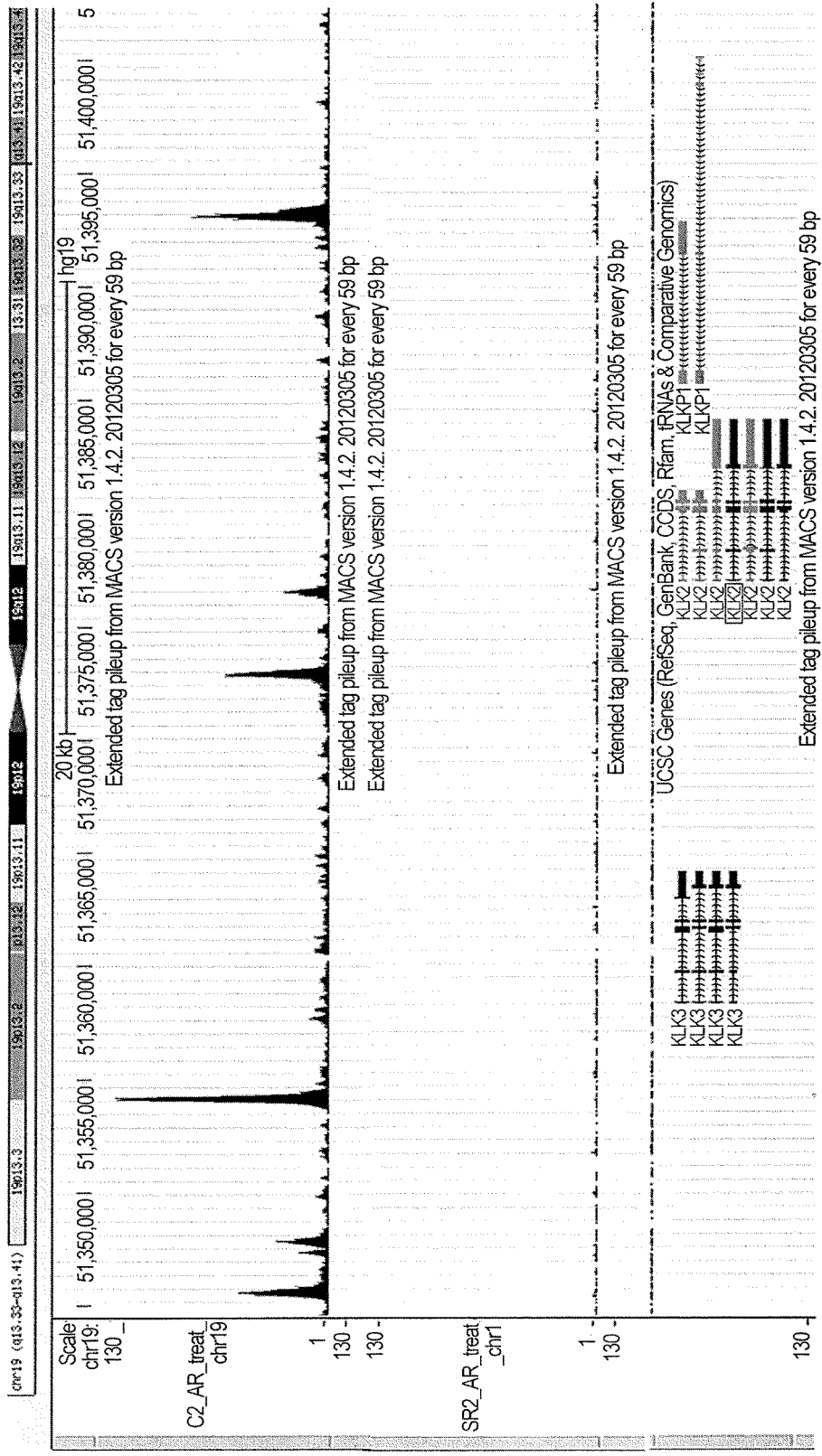
FIG. 5 shows that RORγ antagonists potently inhibit the genome-wide association of AR. Genome browser display of AR-binding on enhancers and/or promoters of the AR target genes KLK2 and KLK3.ChIP-seq was performed in C4-2B cells treated with either vehicle or SR2211 (5 μM) for 24 h.

(8) Gene expression profiling analysis revealed that the small molecule inhibitors of RORγ inhibited the expression of most of the well-defined AR target genes. See, FIG. 5.

(9) The gene expression profiling analysis also revealed that the RORγ inhibitors strongly suppressed the expression of key cell proliferation and survival genes, as well as genes that encode key enzymes of androgen synthesis.

(10) A specific ChIP assay was developed to detect RORγ binding to specific genomic DNA sequence in living cancer cells and detected a specific binding site in the human AR gene locus. Therefore, together with the findings in (6), (7), and (8), the results strongly support the conclusion that one major mechanism of action (MOA) by the RORγ inhibitors is their direct inhibition of RORγ function in activation of AR gene expression in the PCa cells and tumors.

Currently, small molecule therapeutics of PCa target either the AR, the so called anti-androgens which include enzalutamide, or the androgen biosynthesis enzymes which include abiraterone.

Advantage one: By targeting one protein target, namely RORγ, two most important PCa tumor-driving pathways are potently inhibited. One pathway is the AR gene/protein itself. Our findings indicate that RORγ directly activates the AR gene transcription in the same cancer cell and that the RORγ inhibitors strongly suppress the AR expression. The other is the tumor androgen biosynthesis pathway where multiple key androgen synthesis enzyme genes are inhibited by the RORγ inhibitors.

Advantage two: Targeting RORγ in the tumor cells prevents the development of resistance to currently advanced therapeutics such as enzalutamide and abiraterone. Both therapeutics are shown to induce tumor production of alternative spliced variant forms of AR that possess even higher potency than the full-length AR protein to drive PCa progression to more deadly forms. The AR variant induction is believed to be a major mechanism for resistance to enzalutamide and abiraterone. We found that RORγ inhibition can effectively negate enzalutamide induction of the AR variant proteins in the tumor cells.

Advantage three: Targeting RORγ in the tumor cells has the potential to be effective in treating cancers that have developed resistance to other therapeutics (e.g., enzalutamide-resistant prostate cancer).

Example 2. Therapeutic Targeting of the Nuclear Receptor RORγ-AR Axis for the Treatment of Cancer The following example illustrates how RORγ inhibitors can be used in the treatment of cancer. This example uses castration-resistant prostate cancer (CRPC) as a model system.

Abstract

Androgen receptor (AR) is overexpressed and hyperactivated in castration-resistant prostate cancer (CRPC). However, the determinants of AR overexpression are poorly defined. Here we identify RORγ, a master regulator of Th17 cells and therapeutic target of autoimmune diseases, as a key driver of AR aberrant expression. RORγ is overexpressed and amplified in metastatic tumors. Its overexpression confers CRPC cell growth. RORγ recruits coactivators SRC-1 and -3 to an AR-RORE to stimulate AR gene transcription. Its specific antagonists strongly suppress the expression of AR and its variant AR-V7. RORγ antagonists also markedly diminish genome-wide AR binding, H3K27ac marks and expression of the AR gene network. In vivo, the antagonists potently block tumor growth in multiple models and effectively sensitize CRPC tumors to enzalutamide, without overt toxicity. Together, the results establish RORγ as a previously unsuspected key player in CRPC by acting upstream of AR and a potential therapeutic target for advanced prostate cancers.

Introduction

Persistent or reactivated signaling by androgen receptor (AR), a member of the nuclear receptor (NR) superfamily, drives progression of prostate cancer to a deadly form of the disease, namely metastatic castration-resistant prostate cancer or mCRPC. Tumors in most mCRPC highly overexpress AR, either with or without its gene amplification or mutations[1]. However, little is known about key factors that up-regulate AR gene expression. Recently approved therapeutics such as androgen signaling inhibitor enzalutamide (ENZ) and androgen synthesis inhibitor abiraterone (ABI) benefit some patients. However, de novo and acquired resistance appears inevitable. In addition to aberrant levels of the full-length AR and intratumoral androgen synthesis, tumor cell production of alternatively spliced variants of AR such as AR-V7 that lack functional ligand binding domain (LBD) constitutes another major resistance mechanism[2,3]. Current therapeutics developments are largely focused on anti-androgens with increased potencies, although agents that can disrupt the functionally aberrant AR N-terminal domain or promote AR protein degradation are also been sought[4-10].

The RAR-related orphan receptors (RORs) are NRs with tissue endogenous ligands to be widely recognized. The three RORs, RORα, -β and -γ (with gene name RORA, RORB and RORC respectively) have distinct tissue expression patterns and likely play different physiological functions including metabolic homeostasis and circadian rhythms[11,12]. Interestingly, T cells express an isoform, RORγt (or RORc2 in human), which differs in the N-terminus due to T cell-specific promoter usage. RORγt plays a crucial role in Th17 cell development and autoimmune diseases. An increasing number of RORγ antagonists/inverse agonists are being developed with strong therapeutic potential for autoimmune and metabolic diseases[11,13]. Like other RORs, RORγ displays constitutive transactivation function through monomer binding toROREs at its genomic targets[14,15]. In mouse, RORγ is expressed in thymus, muscle, and testis. Its low mRNA levels are also detected in prostate and liver. RORγ global knockout mice are relatively healthy and fertile[16]. However, the expression and function of RORγ in human tumor cells are largely unexplored.

In this study, we found that RORγ is highly overexpressed in metastatic tumors of prostate cancer and functions as a key determinant of AR overexpression and aberrant signaling in CRPC cells and tumors. RORγ-selective antagonists strongly inhibit AR gene expression, its genome-wide binding and growth of xenograft tumors. Thus, our findings establish RORγ as a previously unsuspected key player and a novel therapeutic target for CRPCs.

Results

Figure 6A:
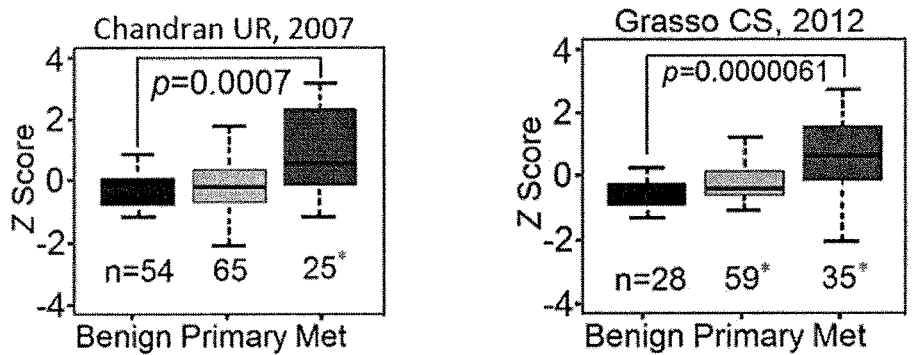
FIGS. 6A-6F show that RORγ overexpression associates with metastatic CRPC progression and is required for survival of prostate cancer cells.
Figure 6B:
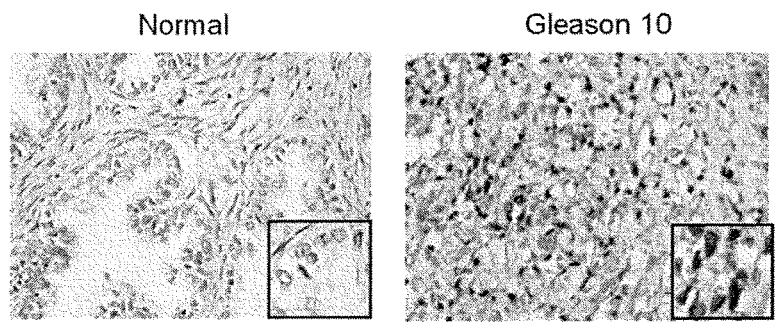
Figure 6C:
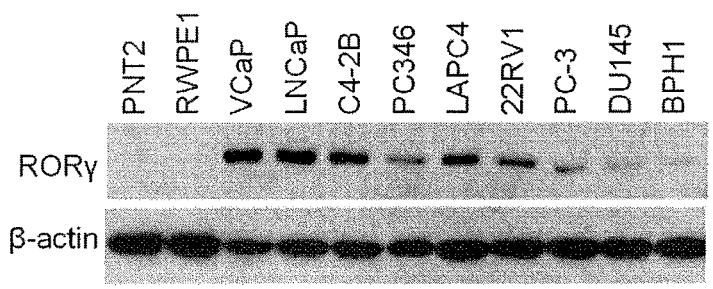
Figure 12A:
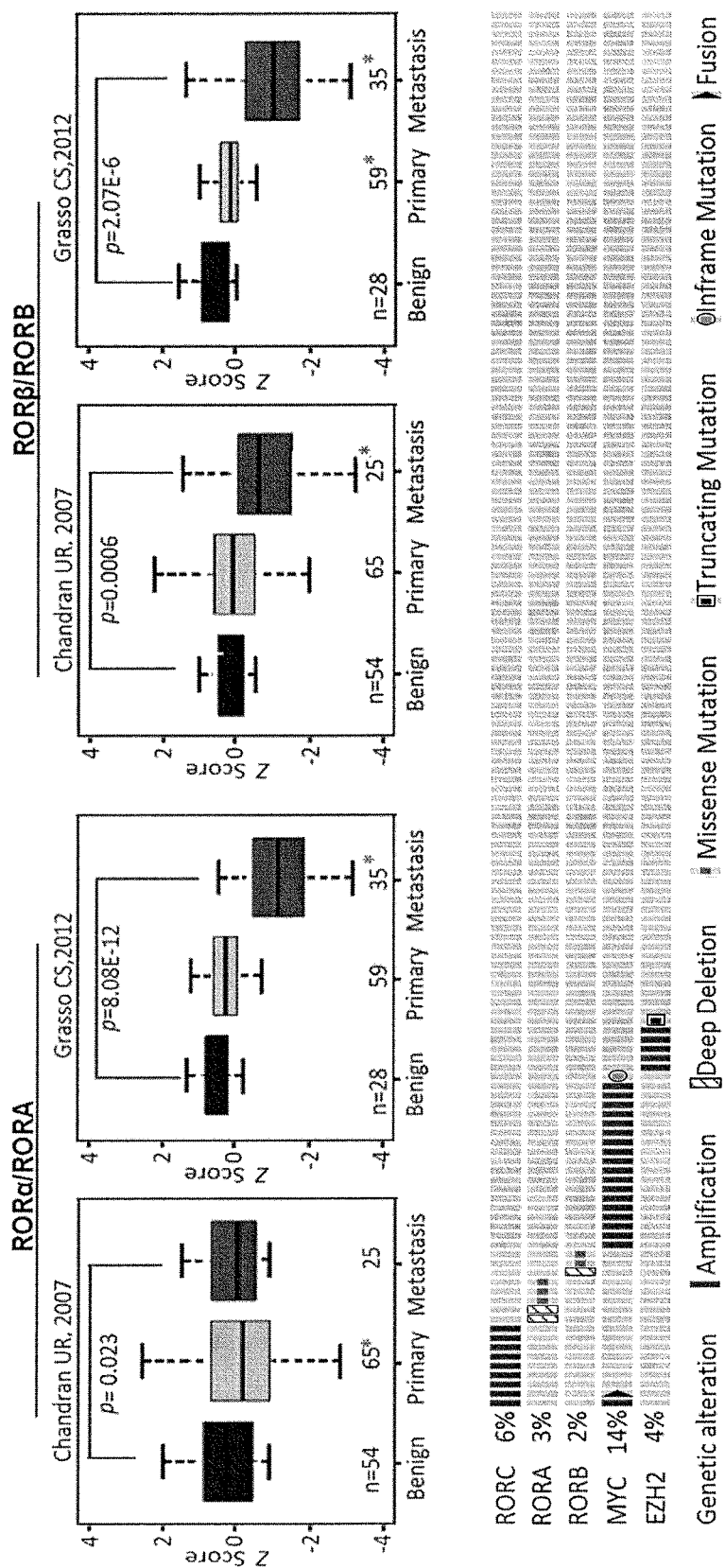

RORγ/RORC is Overexpressed and Amplified in Metastatic CRPCs and Required for Survival and Proliferation of CRPC Cells Nuclear receptors (NRs) are attractive therapeutic targets[17,18]. To assess the potential role of NSs in cancer progression, we queried several datasets of tumor gene expression profiling for NRs with altered expression and found that members of the ROR subfamily displayed distinct expression patterns. In two different datasets, the expression of RORα and RORβ decreased significantly in metastatic tumors when compared to benign prostate tissues or localized tumors. In contrast, the expression of RORγ showed a marked increase in metastatic tumors. Significantly, RORγ gene RORC is found amplified in 6% of metastic CRPC tumors in a recent study (FIG. 6A; FIG. 12A). Anti-RORγ IHC analysis of prostate specimens revealed that nuclear RORγ is overexpressed in over 50% of the tumors and high levels of RORγ protein are significantly associated with tumor metastasis (FIG. 6B). RORγ protein was readily seen in AR-positive cancer cell lines mostly derived from CRPC tumors (e.g., LNCaP, C4-2B, 22Rv1, VCaP, PC346C and LAPC4), but not in the non-malignant human prostate epithelial cells (RWPE1 and PNT-2) (FIG. 6C).

Figure 6D:
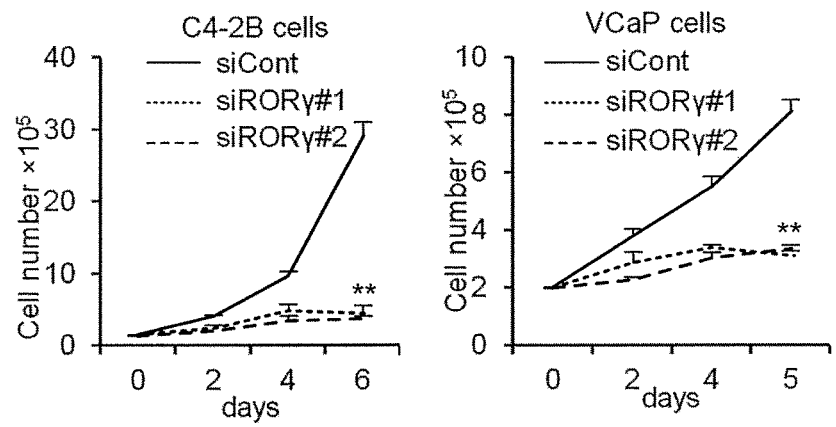
Figure 6E:
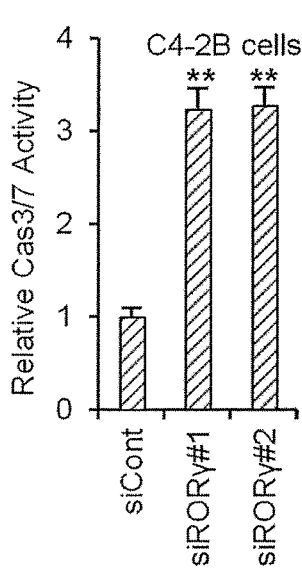
Figure 6F:
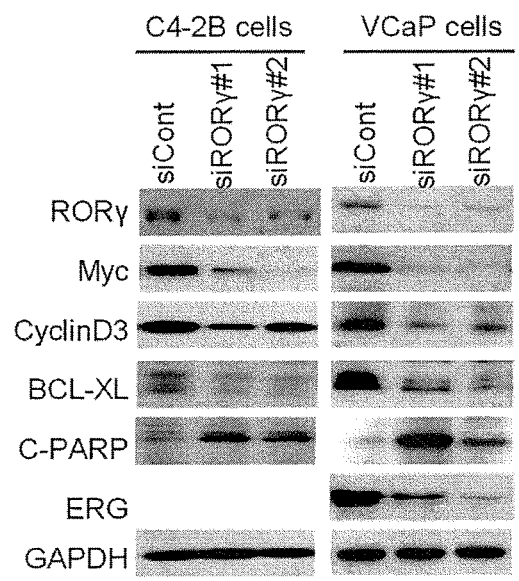

Next, we examined the function of RORγ in the cancer cells. Knockdown of RORγ by different RORC siRNAs markedly inhibited the growth of LNCaP and its CRPC derivative C4-2B cells. The strong growth inhibition was also observed in other androgen-sensitive and CRPC models such as VCaP and 22Rv1, but not in AR-negative PC-3 cells (FIG. 6D and FIG. 12B). In line with the growth inhibition, RORγ knockdown also resulted in marked apoptosis, demonstrated by the caspase activities and PARP1 cleavage, and strong inhibition of key proliferation and survival protein expression (e.g., cyclin-A, -E, -D3, -Cdc2, -Cdc6, and Bcl-xL), as well as the expression of other major drivers of prostate cancer such as Myc and ERG (FIGS. 6E, 6F; FIG. 12C). Consistent with its crucial role in proliferation and survival, ectopic expression of RORγ in androgen-sensitive LNCaP cells strongly promoted their growth in an androgen-deprived condition (FIG. 12D).

RORγ-Selective Antagonists Potently Inhibit Growth and Survival of CRPC Cells

Figure 7D:
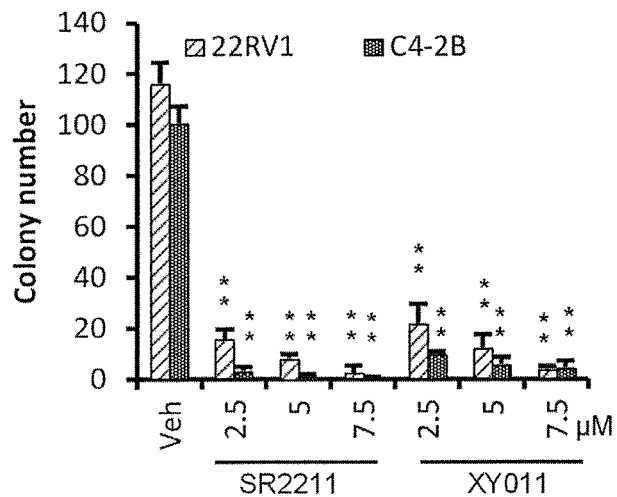
Figure 7E:
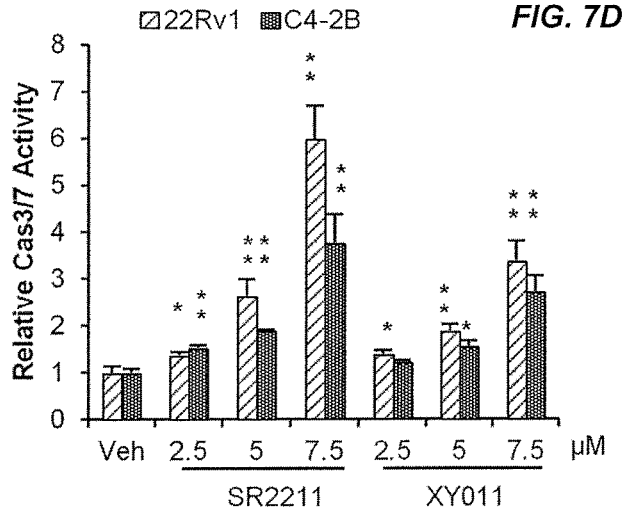
Figure 7F:
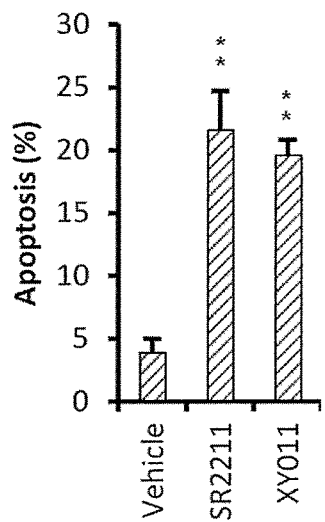
Figure 7G:
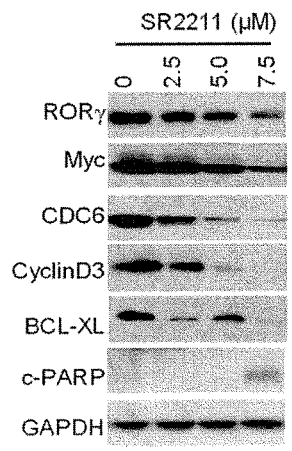
Figure 13A:
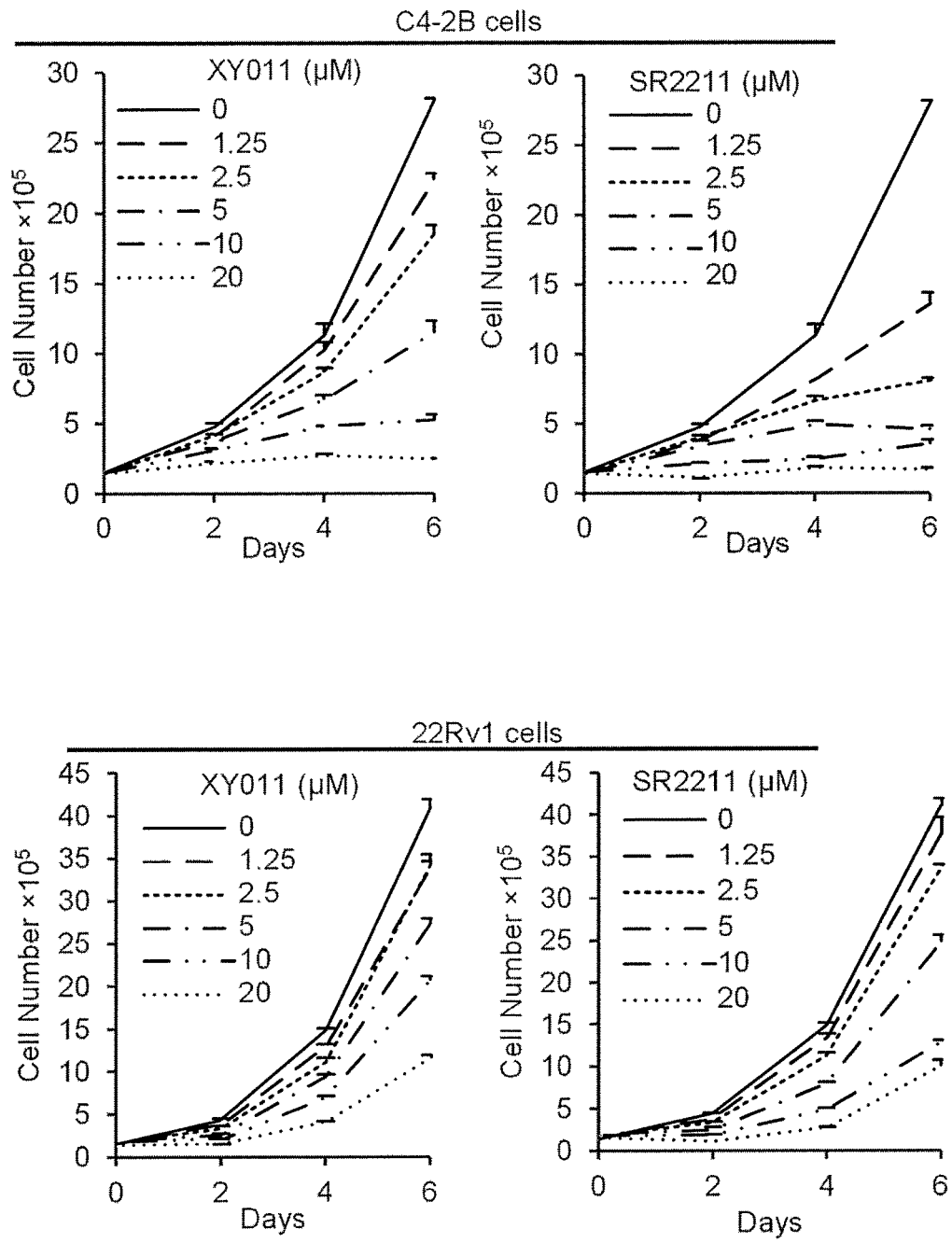
FIGS. 13A-13E show that RORγ antagonists potently inhibit growth and survival of CRPC cells.
Figure 13B:
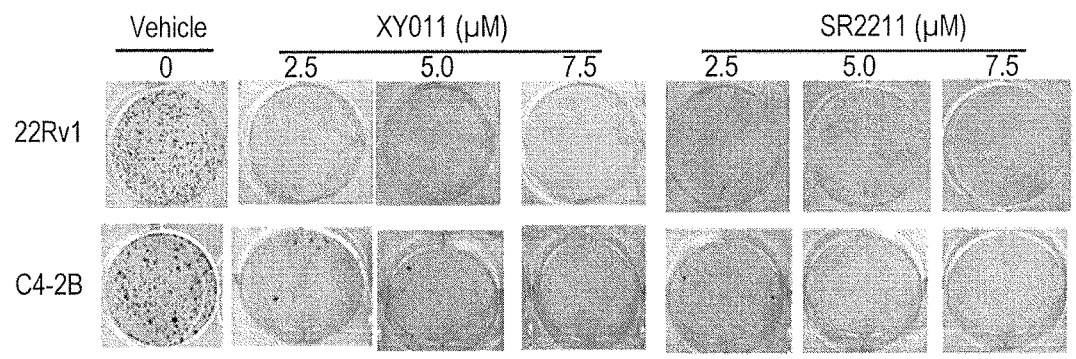
Figure 13C:
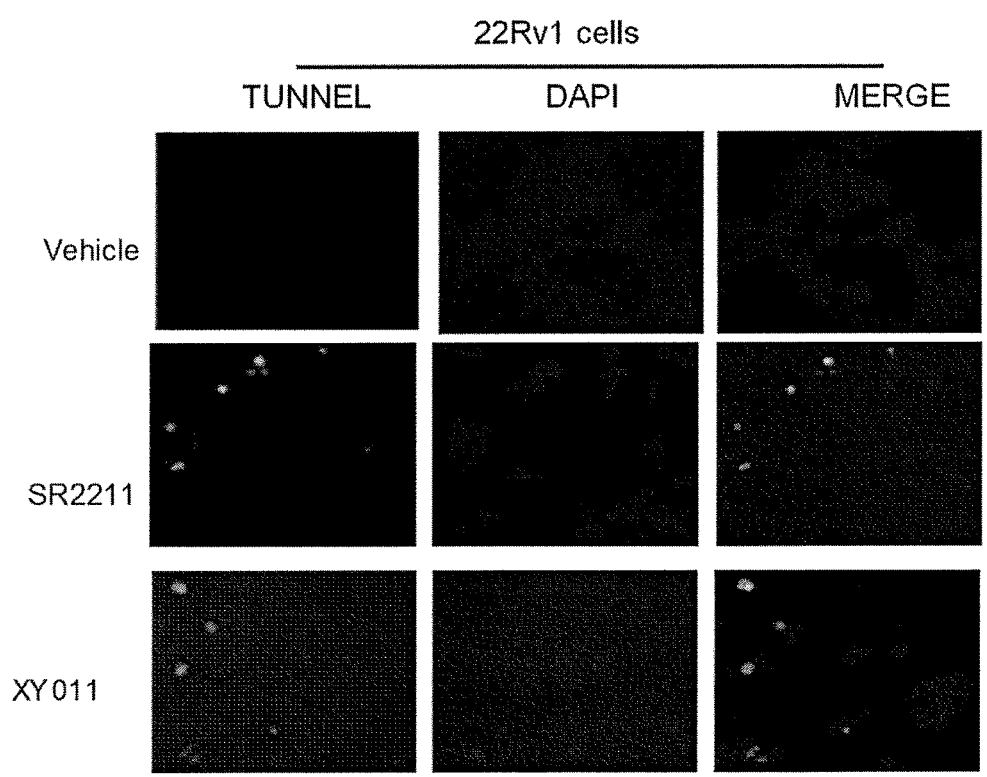
Figure 13D:
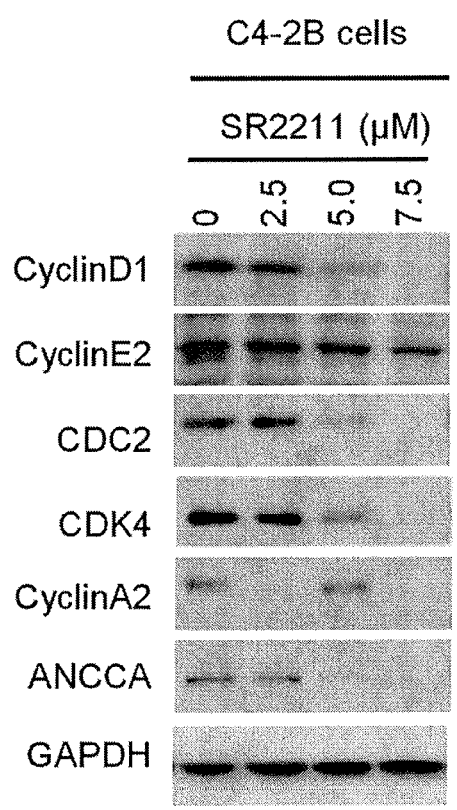
Figure 13E:
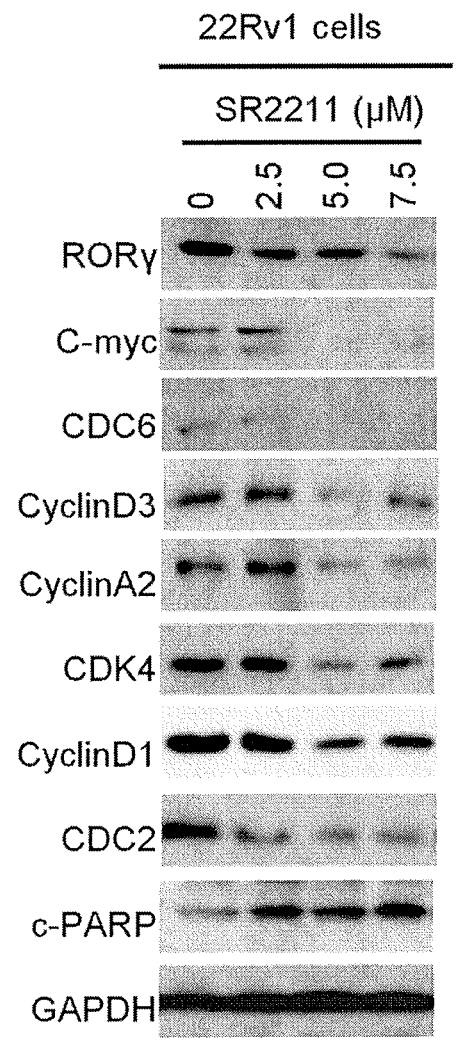

Recent studies identified several RORγ-specific antagonist ligands (e.g., SR2211 and GSK805, FIG. 7A)[19-23]. They have been evaluated for their therapeutic potential in suppression of Th17 cell-mediated autoimmune diseases models[22,24]. Given the crucial function of RORγ in prostate cancer cells, we examined whether its antagonists possess any growth-inhibitory effect. Strikingly, all of the RORγ antagonists tested displayed strong growth inhibition with much higher potencies than that of ENZ. For instance, SR2211 showed inhibitory potency at low μMs in LNCaP cells ($IC_{50}$ of 1.5 μM) while its precursors SR1555 displayed significant inhibitory effects with slightly lower potencies (FIGS. 7B, 7C; FIGS. 13A, 13B). Consistent with our data in FIG. 12A implying that RORα/RORA may play a different role in prostate cancer, a RORα-selective antagonist SR3335[25] did not display any significant effect. Moreover, strong growth inhibition by SR2211 was observed in other AR-positive PCa cell models including 22Rv1, VCaP, LNCaP, LAPC4 and PC346C (FIG. 7C and FIGS. 13A, 13B). No significant growth inhibition by the RORγ antagonists was seen in non-malignant human prostate cell RWPE1, normal human fibroblasts IMR90, or AR-negative PCa cells at the concentrations tested (FIG. 7C; FIG. 13B). Consistent with the cell death effect by RORγ gene knockdown, treatment of C4-2B and 22Rv1 cells with antagonist SR2211 elicited a pronounced inhibition of cell survival as shown by poor colony formation and marked apoptosis (FIGS. 7D-7F; FIGS. 13C, 13D). In line with the cellular effects, the antagonist strongly inhibited the expression of key proliferation and survival proteins, including Myc (FIG. 7G; FIG. 13E).

RORγ Antagonists Potently Inhibit AR Signaling

Figure 8A:
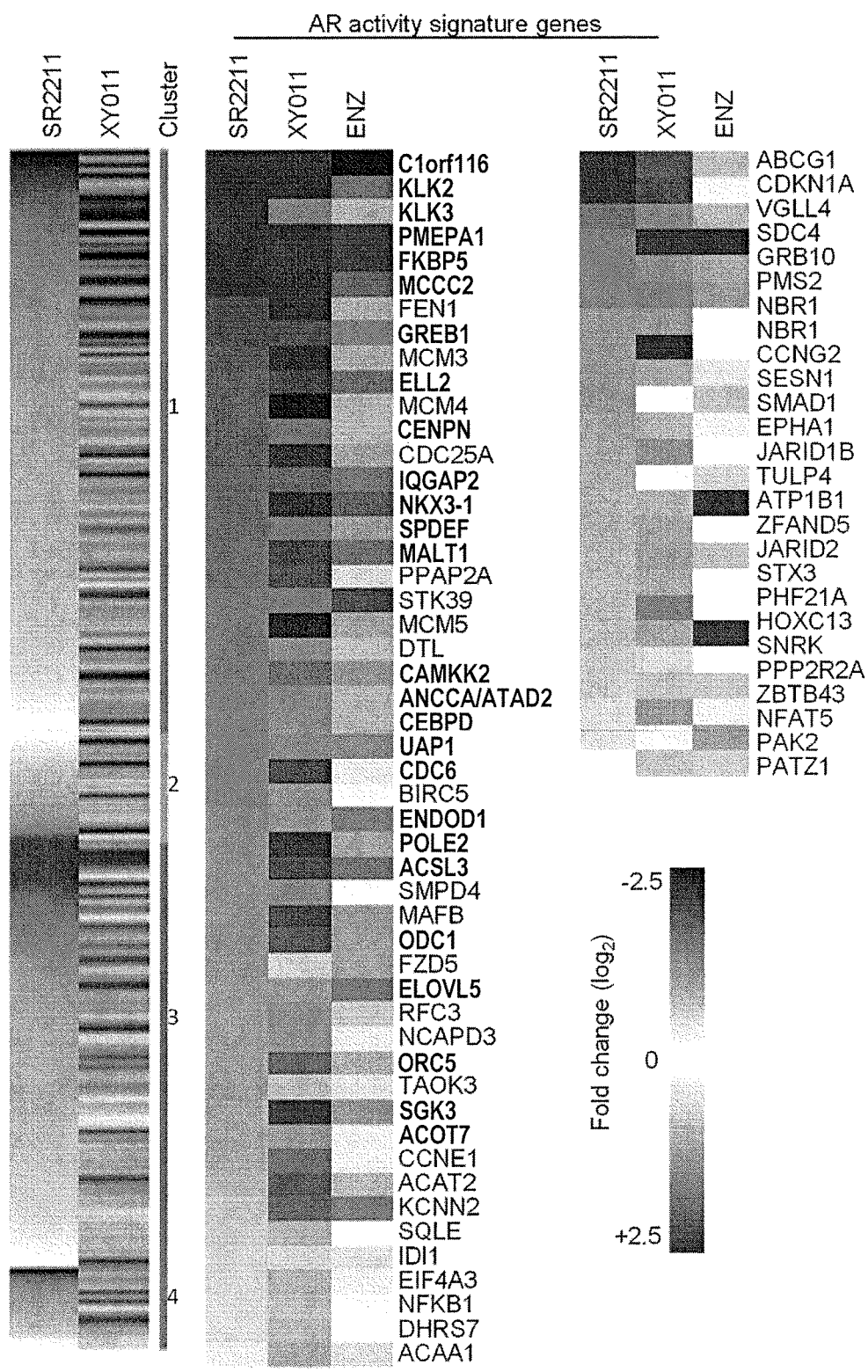
Figure 9A:
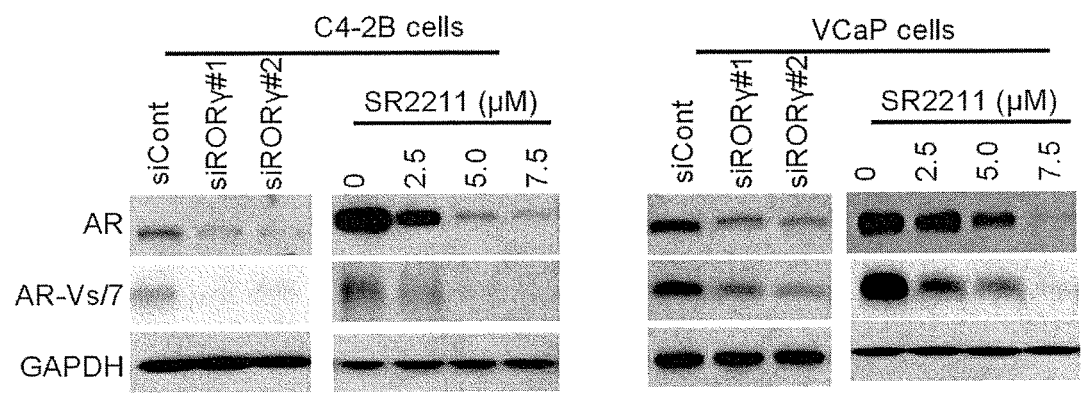
FIGS. 9A-9E show that RORγ inhibition strongly suppresses AR and its variant expression and eliminates AR genome binding.
Figure 9B:
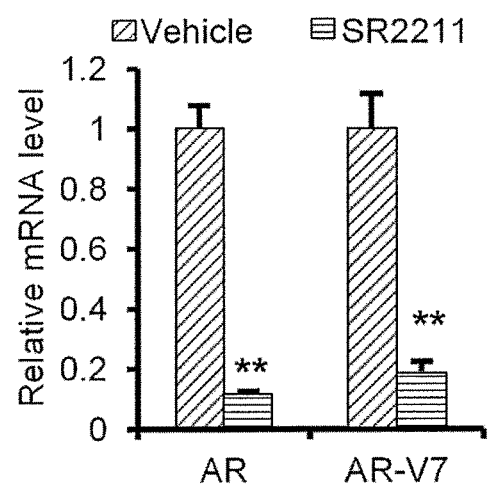
Figure 9C:
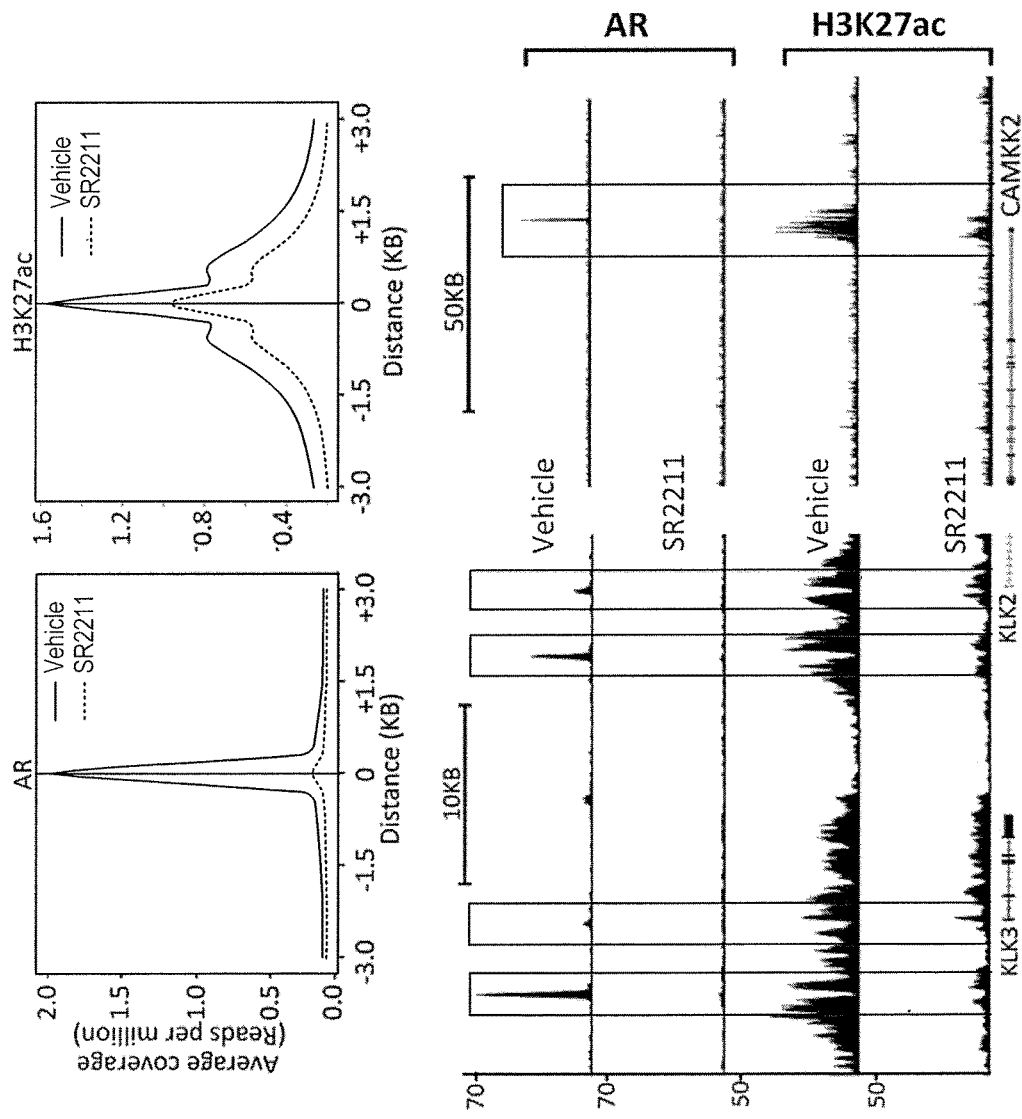
Figure 9D:
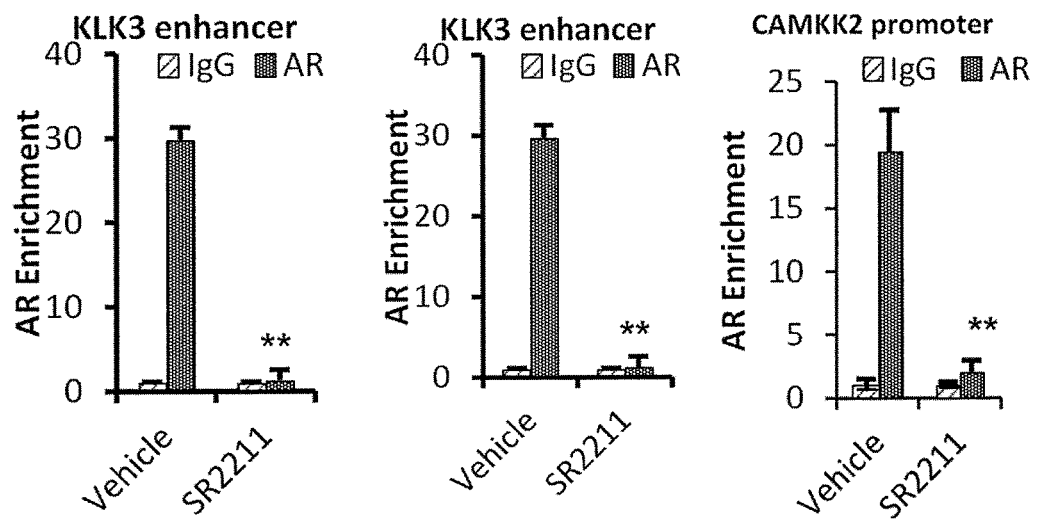
Figure 9E:
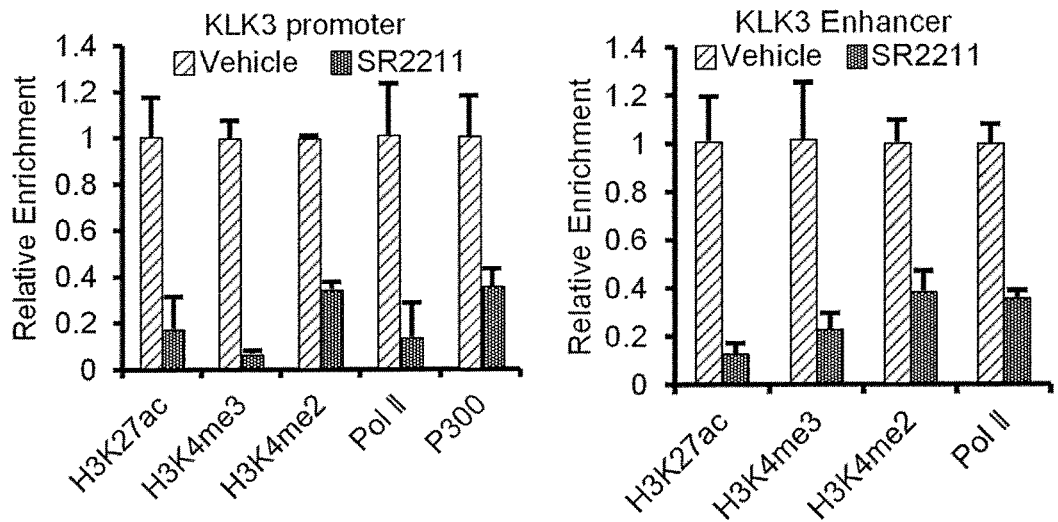
Figure 14A:
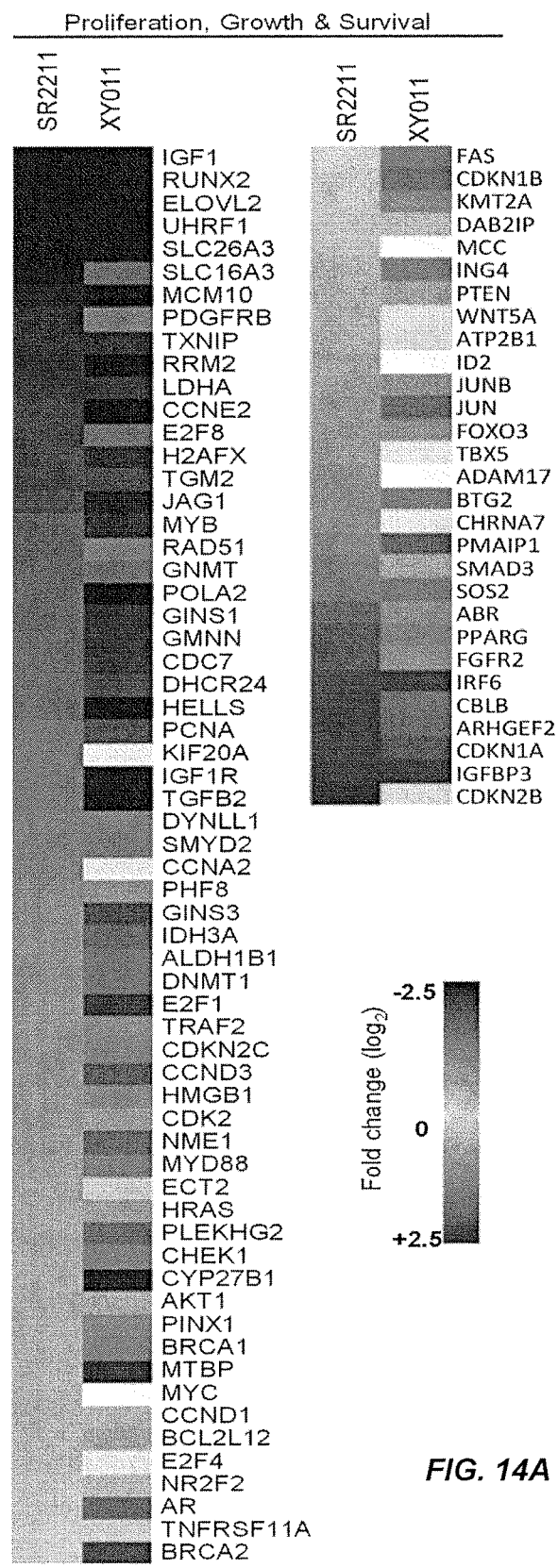
Figure 14C:
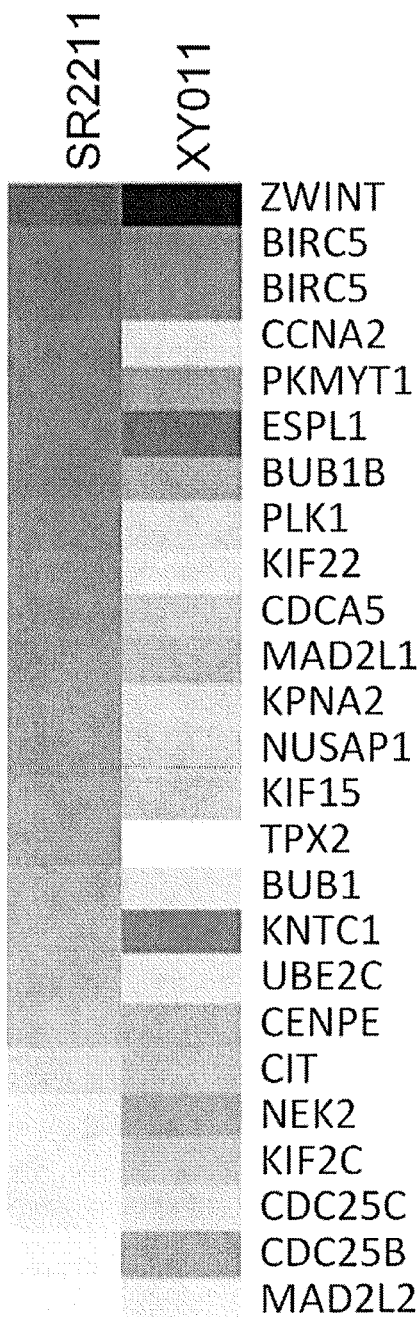
Figure 14D:
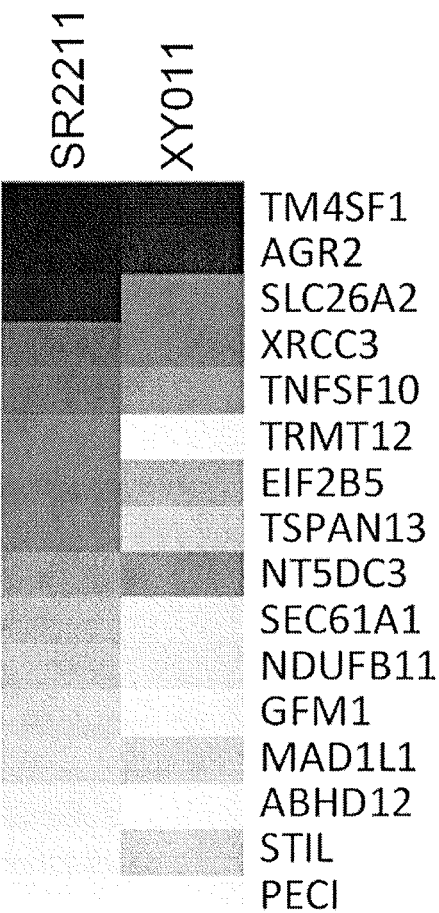

We next analyzed RNA-seq transcriptomes of cells treated with the two structurally distinct antagonists, SR2211 and XY011 (previously reported as compound 8k[21]), to identify gene programs affected by ROR inhibition. Clustering of genes with expression significantly altered by either antagonist (relative to vehicle) showed a high degree of concordance in expression change between the two RORγ inhibitors with over 75% of genes either decreased (cluster 1) or increased (cluster 3) by both antagonists (FIG. 8A). Notably, genes of an AR activity signature, which is of value in predicting clinical tumor response to androgen ablation therapy[26], constitute partly the two major clusters (cluster 1 and 3). Genes that are characterized as AR targets or androgen-induced genes were significantly inhibited by both antagonists. Conversely, the androgen-repressed genes were strongly induced by the antagonists (FIG. 8A). Importantly, genes linked to androgen-induced cancer cell proliferation and survival were also contained in cluster 1 and 3 (FIG. 14A). Moreover, the profile of the antagonists significantly overlapped with that of anti-androgen ENZ (41% for SR2211, 38% for XY011 for down-regulated genes) (FIG. 8A; FIG. 14B). Further examination by gene set enrichment analysis (GSEA) using an AR activity signature[26] revealed a highly robust disruption of AR gene programs by the RORγ inhibition (FIG. 8B). Significantly, the antagonists also strongly inhibited the expression of genes preferentially up-regulated by AR-V7[27], and most of the 16-AR target gene set recently identified in human CRPC tumors[28] (FIGS. 14C, 14D). qRT-PCR verified that some of the classic AR targets such as KLK3, KLK2, Nkx3.1, and FKBP5, and ones that are linked to CRPC such as CAMKK2[29], and ANCCA/ATAD2[30] were strongly inhibited by the antagonists and by RORγ knockdown (FIG. 8C; FIG. 14E).

Inhibition of RORγ Strongly Suppresses AR and its Variant Expression and Eliminates AR Genome Binding The prominent impact on AR-controlled gene programs by RORγ inhibition prompted us to investigate whether RORγ controls the expression and/or function of AR. Indeed, RORγ knockdown strongly suppressed the mRNA and protein expression of AR full-length and AR-Vs/7 in C4-2B and VCaP cells. Remarkably, the RORγ antagonists (SR2211 and XY011) also potently inhibited the expression of AR and AR-V7 in a dose-dependent manner (FIGS. 9A, 9B; FIGS. 15A, 15B). Similar dose-dependent inhibition was observed in other AR-positive cancer cells including 22Rv1, LAPC4 and PC346C (FIG. 15C). Conversely, RORγ overexpression significantly increased AR expression in LNCaP cells (FIG. 15D). Consistent with the results from cell models, in multiple data sets from clinical CRPC tumors, the expression of RORγ correlated strongly not only with AR expression but also with a CRPC AR-signature[28] (FIGS. 16A, 16B).

To assess the antagonist effect on AR function, we performed anti-AR ChIP-seq using C4-2B cells treated with 5 μM SR2211 for 24 hours, which caused a significant but incomplete suppression of AR expression (FIG. 17A). Strikingly, the treatment resulted in a dramatic inhibition of genome-wide AR binding to its target loci as well as a significant decrease of gene activation-associated histone mark H3K27ac (FIGS. 9C, 9D; FIG. 17B). AR binding at enhancers and/or promoters of its targets such as KLK2, KLK3, CAMKK2, NKX3.1, FKBP5, and ANCCA/ATAD2 were almost completely eliminated by the antagonist (FIG. 9C, right panel; FIG. 17C). In line with the loss of AR occupancy, transcriptional activation-linked histone marks including H3K27ac and H3K4me2/3 were significantly reduced at KLK3 promoter or enhancer. As expected, RNA polymerase II (Pol-II) recruitment at the target promoters was strongly affected (FIG. 9E; FIGS. 17D, 17E). Consistent with the antagonist effects, knockdown of RORγ showed similar inhibitory effects on AR binding and the associated histone marks (FIG. 17F). Interestingly, the overall genome-wide distributions of H3K4me2 and H3K4me3 marks as well as Pol-II peaks were not markedly affected by the antagonist (FIG. 17G), indicating that RORγ inhibition on H4K3me2/3 and Pol-II is target locus-specific.

The RORγ-selective antagonists (SR2211 and XY011) were identified based on the unique pocket structure of RORγ LBD. Nevertheless, to rule out the possibility that the antagonists act directly through AR, we performed a reporter gene assay. In a multimerized ARE-driven reporter that can be activated by synthetic androgen R1881 and repressed by anti-androgen ENZ, the RORγ antagonists, at up to 10 μM, did not display any effect on the androgen-AR activity (FIG. 18A). To provide further evidence, we performed an AR rescue experiment with a 5.8 kb KLK3 regulatory sequence-linked reporter that is sensitive to both increased AR and androgen stimulation. Results in FIG. 18B show that both the androgen-independent and androgen-stimulated activities of endogenous AR were strongly inhibited by the RORγ antagonist likely due to the suppression of AR expression. Strikingly, AR ectopic expression driven by CMV promoter effectively blocked the inhibition by the antagonists. In contrast, acting via a different mechanism, the anti-androgen ENZ was still effective in blocking of the ectopic AR activity. Together, our results strongly indicate that the RORγ antagonists, acting through RORγ, effectively suppress the aberrant AR expression and its genome function.

RORγ Directly Controls AR Gene Expression Through an Exonic RORE and Coactivators SRC-1 and SRC-3/ACTR The potent inhibition of AR expression by RORγ knockdown or antagonists led us to an examination whether RORγ directly controls AR gene transcription. RORγ binds DNA with specific sequence motifs AA/TNTAGGTCA (the classic RORE motif; SEQ ID NO:115) or CT/AG/AGGNCA (the variant RORE motif)[14, 31]. ChIP-qPCR of regions containing over 20 putative ROREs across the 250 kb AR locus demonstrated that a site in the first exon (2.3 kb downstream of AR TSS) displayed a strong RORγ binding (FIG. 10A). The site contains sequences matching the variant RORE motif. Significantly, when cells were treated with the RORγ antagonist, the ROR binding was strongly reduced, likely due to the inhibitory effect on RORγ expression (FIG. 7G; FIG. 10A).

Figure 10F:
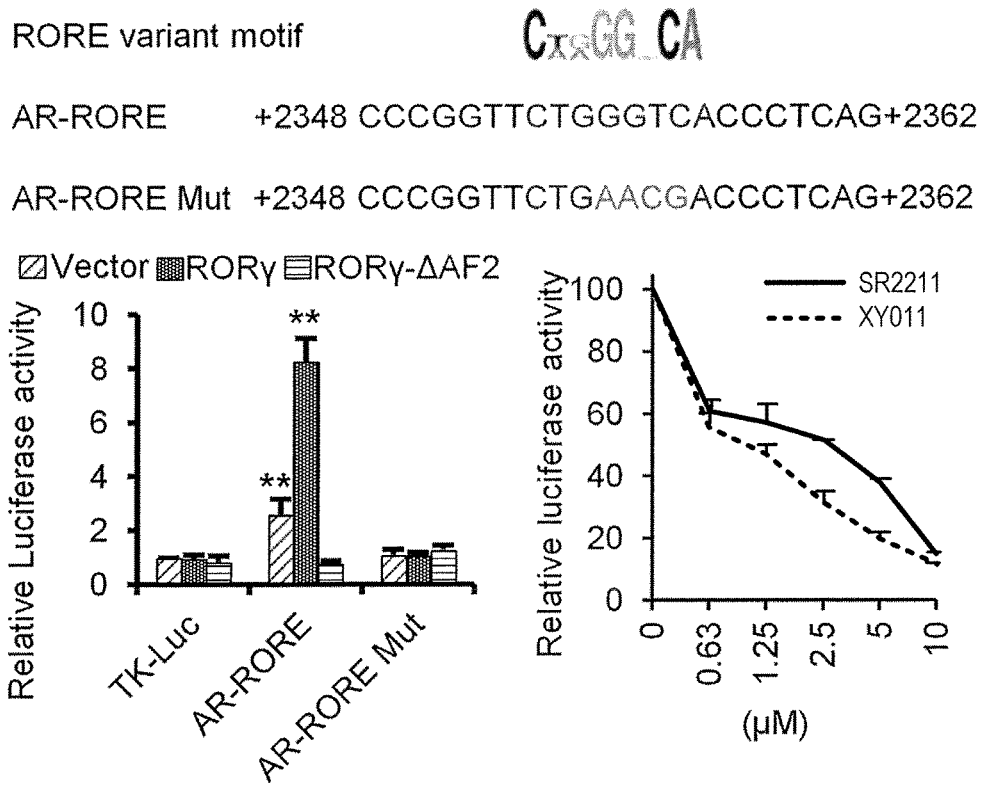

To examine the function of the putative RORE-containing site in mediating RORγ regulation of the AR gene, we used a lentiviral CRISPR-Cas9 editing system to first delete the site with two sets of sgRNAs in C4-2B cells (FIGS. 10B, 10C; FIG. 19A). Since the dependency of highly elevated AR for the cell proliferation and survival prevented us from expanding cell clones with editing-reduced AR, we analyzed populations of cells heterogeneous in the editing. We found that even deletion in about half of the cell populations resulted in a strong reduction of the total AR transcripts, which were detected by the upstream primers P1 and P2 (FIG. 10D). Next, we treated the lentivirus-infected cells with the RORγ antagonists and analyzed AR transcripts from the deleted or wild type alleles with primers P3 and P4. As expected, transcripts from the WT allele were strongly inhibited by the antagonists. In contrast, in the same samples, transcript levels from the deleted alleles were not altered by any of the antagonists (FIG. 10E; FIG. 19B), indicating that the site is required for RORγ antagonist inhibition of AR transcription. Moreover, as expected, the three sgRNAs, when used singularly, caused a "knock-out" effect on AR protein expression. Importantly, sgRNA#2, the only one that could be designed to cause indel type of alterations adjacent to the RORE sequence, displayed significant inhibition of AR mRNA expression while the other two showed no effect (FIG. 19C). Finally, we performed reporter gene assays with the RORE and found that it was highly responsive to RORγ-mediated transactivation. Mutations in the core RORE sequence or deletion of RORγ C-terminal, AF2 transactivation domain completely abrogated the AR-RORE-dependent activation. The RORγ antagonists suppressed the activation in a dose-dependent manner (FIG. 10F). Moreover, a tight correlation between RORγ inhibition, AR expression inhibition and anti-proliferation was observed (FIGS. 20A-20B), indicating that suppression of AR expression by the RORγ antagonists constitutes the major mechanism of their action in the cancer cells.

Figure 10G:
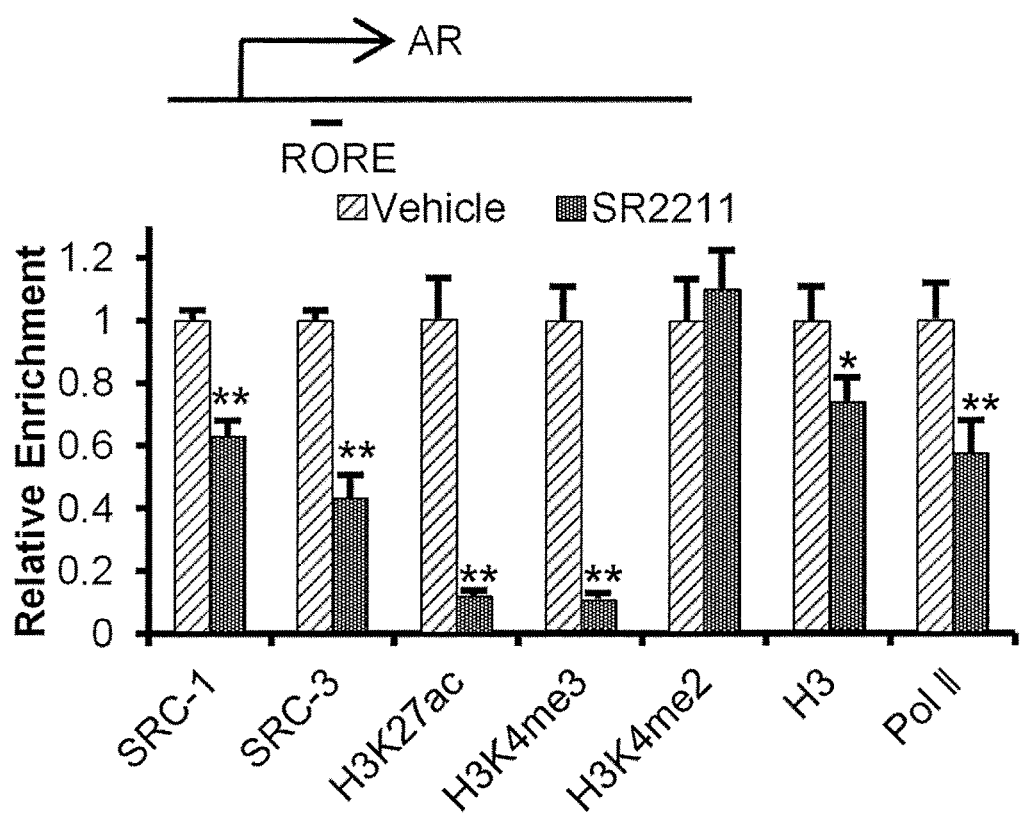

RORγ activates gene transcription through association with co-factors such as the p160/SRC/NCoA family members[32]. Indeed, SRC-1 and SRC-3/ACTR, but not SRC-2, were found to occupy the AR-RORE site. Furthermore, their binding was strongly reduced by the RORγ antagonists or knockdown (FIG. 10G; FIG. 21), indicating that the SRCs were recruited to the site via RORγ. Knockdown of SRC-1 and ACTR, but not SRC-2, individually or in combination, strongly decreased AR mRNA and protein expression. Treating cells with bufalin, a cardiac glycoside inhibitor that was recently shown to selectively degrade SRC-1 and ACTR in cancer cells[33], also resulted in a dose-dependent inhibition of AR expression (FIG. 21; FIGS. 22A, 22B). Next, we assessed the impact of RORγ inhibition on the local chromatin. Treatment with SR2211 strongly reduced the gene activating marks H3K4me3 and H3K27ac at the RORE site and AR promoter (FIG. 10G; FIG. 22C). Consistent with the strong reduction of AR transcripts, Pol-II occupancy at AR promoter and the RORE site was significantly inhibited by RORγ inhibition.

Antagonists of RORγ Potently Inhibit Tumor Growth and Sensitize CRPC Tumors to ENZ We next evaluated the antagonist effects on prostate cancer tumor growth. Given the disease heterogeneity, xenograft tumors with distinct features (e.g., C4-2B with mutated AR LBD, VCaP with amplified AR gene and AR-V7, and 22Rv1 with high levels of multiple AR variants, and AR-negative PC3) were used. In the three AR-positive tumor models including ENZ-resistant 22Rv1, we found that treating mice with 5 mg/kg, i.p., of SR2211 effectively stopped the tumor growth (FIGS. 11A, 11B; FIG. 23A). Strong tumor growth inhibition was also observed with the other antagonist XY011 as well as shRNA knockdown of RORγ in the models tested (FIG. 23B; FIG. 24). Moreover, in an orthotopic model, the antagonist was also very effective in blocking of tumor growth (FIGS. 25A-25C). In line with a lack of strong effect on the growth of PC3 cells in vitro as in FIG. 7C, no significant inhibitory effect by the antagonist was observed in PC3-derived xenograft tumors (FIGS. 26A-26C).

Figures 11C, 11D:
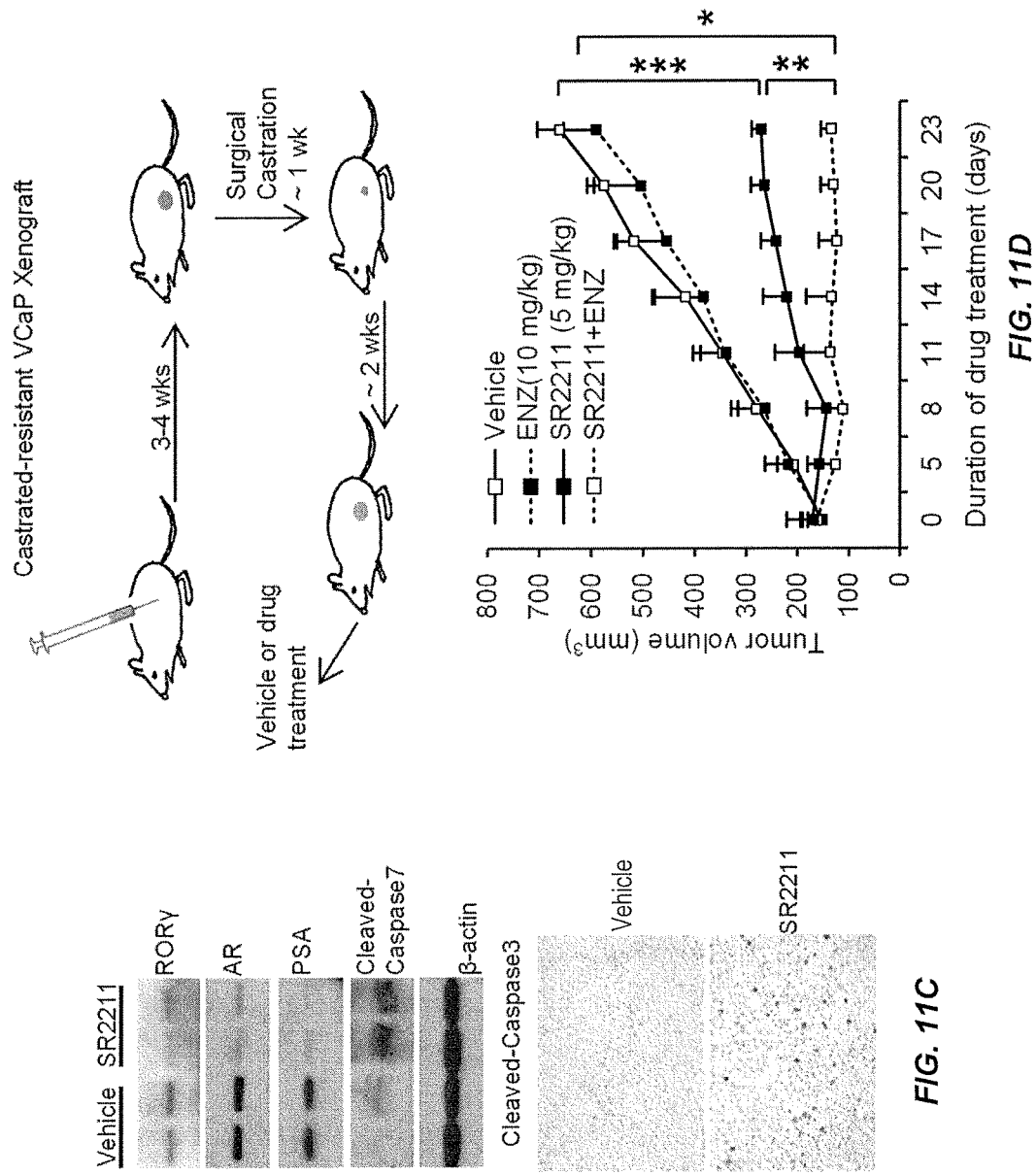

Notably, tumor AR and AR-V7 expression and AR targets were markedly inhibited whereas tumor cell apoptosis measured by cleaved caspase-3/7 was strongly induced (FIG. 11C). ChIP analysis with tumors showed that the antagonist treatment strongly blocked RORγ binding to the AR-RORE and AR binding to KLK3 as well as the H3K27ac enrichment (FIGS. 27A-27C). Moreover, in a VCaP-derived, castration-resistant model, the antagonist SR2211 alone, at 5 mg/kg, was very potent in inhibition of the CRPC tumor growth whereas ENZ alone, at 10 mg/kg, was only marginally effective. Co-administration of the two resulted in persistent reduction of the tumor size, indicating that the ROR antagonist can sensitize CRPC tumors to ENZ (FIG. 11D). As previously reported[34,35], VCaP xenograft tumors display micrometastasis. SR2211 treatment strongly inhibited the metastasis to femur bone and liver (FIG. 28A). Like ENZ, the RORγ antagonists were well tolerated, based on the weight of the animal whole body and vital organs, and their general behaviors (FIGS. 28B, 28C). Consistent with RORγ being an adipogenesis factor[36], the antagonist reduced the amount of the white adipose tissue. Thus, the antagonists can block CRPC tumor growth and effectively sensitize tumors to ENZ, without overt toxicity.

Interestingly, unlike ENZ, the antagonist did not display any discernable effect on the growth of androgen-responsive tissues such as mouse prostate and testis or AR expression in the tissue (FIGS. 29A-29C). Analysis of two non-malignant human prostate epithelial cells showed that the antagonist did not have any significant effect on the endogenous AR expression (FIG. 30A). To explore the underlying mechanism, we performed ChIP and found no detectable RORγ binding to the RORE-corresponding site in mouse prostate tissue and the two human cell lines (data not shown). Immunoblotting revealed very low level of RORγ expression in the human cells (FIG. 30A). Sequence comparison showed that the corresponding site of mouse AR gene lacks a functional RORE[14,15] (FIG. 30B). Together, our results indicate that the RORγ antagonists can inhibit AR expression in tumor cell-specific manner.

Discussion

The most common mechanism of CRPC development appears to be reactivated AR signaling mediated by high levels of AR and its variants in the tumors. Despite its pivotal roles, therapeutically actionable means to effectively suppress AR expression is still lacking. Our study here not only demonstrates that RORγ acts as a key determinant of AR gene expression but also provides a unique opportunity for effective therapeutic intervention of CRPC. We found that RORγ directly stimulates AR gene transcription by binding to an exonic RORE and partly through the NR coactivators SRC-1 and SRC-3. Although SRCs and other AR coactivators likely play important roles in prostate cancer[37-41], they have not been shown to be directly involved in AR gene overexpression. We demonstrate here that small molecule antagonists of RORγ potently disrupt RORγ and the SRC binding to the AR locus, reduce the local activating histone marks and effectively suppress AR expression in vitro and in vivo. A few transcription factors such as E2F1, LEF1 and NF-κB are shown to activate AR expression[42-45]. It is possible that RORγ acts in concert with them or other factors, through simultaneous interactions with SRCs and other coactivators[46].

The alternatively spliced variants of AR in tumors treated by anti-androgens and CYP17 inhibitors (e.g., ENZ and ABI) are linked to therapeutic resistance and metastasis[47]. Recently, agents targeting the AR NTD, an intrinsically unstructured/disordered domain, or enhancing degradation of the full-length AR protein are being sought[5-9]. Our study here offers a different, rational approach. We found that targeting RORγ with its selective antagonists effectively inhibits the expression of AR variants such as AR-V7 as well as AR full-length, at the gene transcriptional level, therefore mitigating or even eliminating the root cause of the problem, namely the highly elevated AR gene transcripts and proteins. The remarkable molecular effect of the antagonists is manifested in their potent inhibition of tumor growth, which is consistently observed in different AR-positive models including ones with AR gene amplification and/or high levels of AR variants, but not in the AR-negative one. Significantly, tumors that are resistant to ENZ are also very responsive to the antagonists (either alone or in combination with ENZ), indicating that RORγ targeting can have a broad clinical utility. The RORγ antagonists' effect on AR expression, instead of on AR LBD function, may also offer other therapeutic advantages over anti-androgens. Indeed, unlike anti-androgens that display clear suppression of the growth and function of normal androgen-responsive tissues such as testis and prostate, the RORγ antagonists do not show any significant impact on the size of the mouse tissues or AR expression in the tissues and in human non-malignant prostate cells. This tumor-specific effect of the antagonists is likely attributable to tumor cell addiction to highly elevated levels of AR and tumor cell-specific control of AR by RORγ.

The impact of RORγ antagonists on AR programs in the CRPC cells appears extensive, which includes AR targets that are up-regulated, down-regulated or persistently expressed in the CRPC tumors[28]. However, the overall impact on CRPC tumors is unlikely limited to AR and its programs. For instance, the strong suppression of Myc is unlikely to be a downstream effect of AR inhibition. Moreover, inflammatory tumor microenvironment is believed to promote CRPC and tumor metastasis through production of cytokines including IL-17[48] where RORγ in tumor cells or RORγt in leukocytes could play an important role. Therefore, targeting RORγ can stop tumor growth and metastasis possibly through blocking multiple pathways including aberrant AR signaling. As more potent and orally bioavailable RORγ antagonists are being developed and entering clinical trials for human autoimmune diseases, our findings here will likely have immediate implications in development of a new generation of prostate cancer therapeutics.

Materials and Methods

Cell Culture

LNCaP, C4-2B, 22Rv1, PC-3, and PC346C prostate cancer cells were cultured in RPMI1640, VCaP, HEK293T and human fibroblast IMR90 cells were in DMEM, LAPC-4 was in Iscove's MEM (all from Corning), and RWPE-1and PZ-HPV-7 were in Keratinocyte Serum Free Medium (K-SFM) (Invitrogen) with the supplements. All the culture media except for RWPE-1 and PZ-HPV-7 were supplemented with 10/o FBS (Hyclone) except indicated otherwise. For experiments, C4-2B cells were cultured in RPMI supplemented with 9% cds-FBS plus 1% regular FBS (to mimic the CRPC condition) unless indicated otherwise and 22Rv1 cells were cultured in RPMI supplemented with 10% cds-FBS. Cells were grown at 37° C. in 5% CO2 incubators. LNCaP, VCaP, 22Rv1, PC-3, 293T, IMR90, PZ-HPV-7 and RWPE-1 were from ATCC. C4-2B was from UroCor Inc. (Oklahoma City, Okla.). LAPC4 and PC346C were kindly provided respectively by Dr. Charles Sawyers (MSKCC, New York) or by Dr. Adrie van Bokhoven (University of Colorado). The prostate cancer cell lines were recently authenticated by ATCC using STR profiling. Cell lines were regularly tested being negative for *mycoplasma*.

Chemicals

Sources for chemicals are as follows: SR2211, Calbiochem and TOCRIS; SR1555 and SR3335, Cayman. Information on XY011, previously reported as compound 8k, was described before 21. Other chemicals are from Sigma unless indicated otherwise.

qRT-PCR and Immunoblotting Analysis

Total RNA was isolated from cells in 6-well or 10-cm plates or from xenograft tumors, and the cDNA was prepared, amplified and measured in the presence of SYBR as previously[49]. Briefly, the fluorescent values were collected and a melting curve analysis was performed. Fold difference was calculated as described previously[49]. The experiments were performed at least three times with data presented as mean values±s.d. Cell lysates were analyzed by immunoblotting with antibodies specifically recognizing RORγ, AR, AR-V7 and the indicated proteins. The PCR primers and all the antibodies used in this study are described in the Tables 3 and 4.

Analysis of ROR mRNA Expression, Genetic Alterations and Association with CRPC AR Signature in Clinical Tumors Publicly available prostate cancer expression data sets GSE6919, GSE35988, GSE6811 and GSE70768 from previous studies"-" were downloaded from GEO at http://www.ncbi.nlm.nih.gov/geo/. The datasets contain gene expression profiles of benign, primary, metastatic and/or CRPC tumor samples. Normalized probe set expression for RORs were compared between the different tissue/tumor groups by a two-tailed t test for significance. Computations were conducted in R statistical package (http://www.r-project.org/). For genetic alterations of ROR genes, data from a recent genomics study[54] at cBioPortal for Cancer Genomics (http://www.cbioportal.org) was interrogated and OncoPrint displays of gene alterations were presented. Expression correlation between RORγ and AR in tumors was assessed by computing the Pearson correlation coefficient (r) and a two-tailed t test for significance. For correlation between RORγ and the AR signature activity, the expression of the 150 CRPC AR-signature genes[28] is summarized as a single expression profile as previous reported[55] before applied to computation of the Pearson correlation statistics.

Immunohistochemistry (IHC) and Statistics Analysis

IHC was performed as previously described[49,56] with the following modifications. Antigen retrival for sections of tissue microarrays (TMA PR803b from Biomax. US) was performed in a pressure cooker. The slides were then incubated with anti-RORγ monoclonal antibody (AFKJS-9, eBioscience) at 1:50 dilutions overnight at 4° C., followed by incubations with biotinylated secondary antibody and the ABC reagents in the Vectastain Elite kit and counter-stained with hematoxylin. The TMA contained specimens from 70 cases of prostate cancer. The percentage of positive nuclear staining was scored as follows: 0%-<5%, score 0; 5%-<10%, score 1; 10%-50%, score 2; >50%, score 3. Differences and correlations in immunostaining among groups were analyzed with the $\chi^2$ test.

Cell Viability, Apoptosis and Growth Assays, and Colony Formation

For cell viability, cells were seeded in 96-well plates at 1500-2500 cells per well (optimum density for growth) in a total volume of 100 μl media. Serially diluted compounds in 100 μl of media were added to the cells 12 hours later. After 4 days of incubation, Cell-Titer GLO reagents (Promega) were added and luminescence was measured on GLOMAX microplate luminometer (Promega), according to the manufacturer's instructions. All experimental points were set up as sextuplicate as biological replication and the entire experiments were repeated three times. The data are presented as percentage of viable cells with vehicle treated cells set as 100. The estimated in vitro $IC_{50}$ values were calculated using GraphPad Prism 6 software.

For apoptosis, Terminal deoxynucleotidyl transferase-mediated dUTP nick end labeling (TUNEL) was performed by using in situ cell death detection kit (Roche) as previously described[56]. The results are expressed as a percentage of apoptotic cell number/total cell number. Caspase-3/7 activity was measured using a luminescent caspase-Glo 3/7 assay kit (Promega Corporation, Madison, USA) following the manufacturer's instructions. For cell growth, cells were seeded in 6-well plates at $2\times10^5$ per well and treated as indicated. Total viable cell numbers were counted using a Coulter cell counter. For colony formation, 800 cells were seeded in a well of 6-well plates and cultured for 14 days with the medium changed every 3 days. When the cell clone grew visible, the medium was removed and the cells were fixed with 10° % formalin for 10 minutes. Then the plates were washed with PBS for two times and the cell colonies were stained with 0.2% crystal violet (in 10% formalin) for 15 minutes. The numbers of cell colonies were counted after washed 5 times by PBS. The above assays were performed in triplicates and the entire experiments were repeated three times.

shRNA and Overexpression Lentivirus Production and siRNA Transfection

Lentiviral plasmids encoding shRNA targeting RORγ/RORC (TRCN0000033655 and TRCN0000033658) were purchased from Sigma. Non-targeting control shRNA were used as described[49]. For RORγ overexpression, human RORγ cDNA in pLX304 (DNASU) was amplified and cloned into a modified pLX304 vector with a V5 tag at the receptor N terminal. Lentiviral particles were produced in 293T cells after co-transfection of the above shRNA lentivirus vector, psPAX2 and pMD2.G in 10 cm dishes, as described[49]. siRNAs for gene knockdown were purchased from Dharmacon. The siRNA target sequences for RORγ and different SRCs are listed in Table 5. Transfections were performed with OptiMEM (Invitrogen) and Dharmafectin#1 (Dharmacon) following manufacturer's instruction.

Reporter Constructs and Reporter Gene Assays

Transient transfection and reporter gene assays were performed as previously described[49] with the following modifications. ARE reporter gene assays were performed by transfecting 22Rv1 cells with 5×ARE-tk-luc, pcDNA3.1-hAR and pCMV-β-gal for normalization. For transfection with constructs omitted for specific gene expression, corresponding empty vectors were used to ensure equal amount of total DNA used. Briefly, 22Rv1 cells seeded in 96-well plates in hormone-deprived medium supplemented with 10% cds-FBS (Hyclone) were transfected with lipofectamine 2000 (Life technology, Carlsbad, Calif., USA) and the indicated plasmid DNA. Cells were then treated at 12 hours after transfection with 3 nm R1881, indicated concentrations of RORγ antagonists or ENZ for another 24 hours before harvested for β-gal and luciferase assays. For RORE reporter gene assays, 4×AR-RORE-tk-luc was constructed by inserting four copies of the newly identified AR-RORE TTCTGGGTCA (SEQ ID NO: 1) into tk-luciferase reporter vector. AR-RORE mutant form (AR-RORE mut) contains sequences mutated from TTCTGGGTCA (SEQ ID NO: 1) to TTCTGAACGA (SEQ ID NO: 2). Cells (HEK293T) were co-transfected with CMX-RORγ or CMX-RORγΔH12 expression vector and the RORE-tk-luc reporter plasmid as indicated using Lipofectamine 2000 (Life technology, Carlsbad, Calif., USA). After 12 h incubation, cells were treated with vehicle or RORγ antagonists as indicated for another 24 hours. For Gal4-driven reporter assays, 293T cells were transfected with Gal4-RORγ LBD and pGL5-luc reporter. The luciferase and β-galactosidase were then analyzed with a Luciferase Assay Substrate (Promega) and Luminescent β-galactosidase Detection Kit II (Clontech). All transfections were performed in triplicate, and each experiment was repeated at least three times.

CRISPR/Cas9 sgRNA Design, Lentivirus Production and PCR-Based Assay to Detect Genomic Deletions sgRNAs were designed using the MIT CRISPR design software (http://crispr.mit.edu). Oligos corresponding to the sgRNAs were synthesized and cloned into lentiCRISPR v2 vectors following lentiCRISPRv2 and lentiGuide oligo cloning protocol (Addgene, plasmid#52961). sgRNA sequences are as follows: GFP: GGGCGAGGAGCTGTTCACCG (SEQ ID NO: 3); AR-RORE#1: CTGGCGAGCCTG-CATGGCGC (SEQ ID NO: 4); AR-RORE#2: GTGCAGCGGGACCCGGTTCT (SEQ ID NO: 5); AR-RORE#3: ACTCTCTTCACAGCCGAAGA (SEQ ID NO: 6). Lentiviral particles were produced in 293T cells as described above.

C4-2B cells were plated at $2\times10^5$ cells per well in 6-well plates. Sixteen hours later, one ml of virus-containing supernatant with 10 ng polybrene was added to the cells. After 4 to 6 hours, medium was changed to regular medium and cultured for another 72 hours. Genomic DNA was isolated from cells using the Pure link Genomic DNA kit (Life technology). PCR was performed using indicated primers flanking the sgRNA target sites. PCR products from deleted alleles were purified by running agarose gel and were ligated into plasmids using pGEM-T Easy Vector Systems (Promega). Plasmid DNA was purified from single bacterial colonies by mini-prep kit (Qiagen) and sequenced by GENEWIZ (Davis, Calif.) using Sanger sequencing method. Analysis of AR mRNA Expression in Cells Treated with CRISPR/Cas9-sgRNA Lentivirus Cells were infected with the CRISPR/Cas9 sgRNA lentiviruses as above and cultured for 2 days. RORγ antagonists or vehicle were then added and cells were cultured for another 2 days. Total RNA was extracted by TRIzol and reverse transcribed. Semi-quantitative RT-PCR was performed using the template cDNA generated and indicated primers. PCR products were separated on agarose gels. Quantification of the bands was performed as previously reported[57]. Band intensity was expressed as relative absorbance units and normalized to GAPDH.

RNA-Seq Data Analysis

C4-2B cells were treated with vehicle or the antagonists XY011 (5 μM) and SR2211 (5 μM) or ENZ (20 μM) for 48 hours before RNA extraction. RNA-seq libraries from 1 μg total RNA were prepared using Illumina Tru-Seq RNA Sample, according to the manufacturer's instructions. Libraries were validated with an Agilent Bioanalyzer (Agilent Technologies, Palo Alto, Calif.). Sequencing was performed on an Illumina HiSeq 2000 sequencer at BGI Tech (Hong Kong). The FASTQ-formatted sequence data were analyzed using a standard BWA-Bowtie-Cufflinks workflow[58-60]. In brief, sequence reads were mapped to the reference human genome assembly (February 2009, GRCh37/hg19) with BWA and Bowtie software. Subsequently, the Cufflinks package [61] was applied for transcript assembly, quantification of normalized gene and isoform expression in RPKM (Reads per kilobase per million mapped reads) or FPKM (fragments per kilobase of exon model per million mapped reads), and testing for differential expression (Cuffdiff). To avoid spurious fold levels due to low expression values, only those genes with expression RPKM or FPKM values>1 for either the vehicle/control cell, or the antagonist treated cells (but need not to be both), are included. The expression change of at least 1.5 fold up or down was clustered with K-mean clustering algorithm in Cluster software[62]. The cluster was displayed with TreeView. RNA-seq data have been deposited to NCBI-GEO with accession code GSE72483.

GSEA Analysis

GSEA was performed using the Java desktop software (http://www.broadinstitute.org/gsea) as described previously[63]. Genes were ranked according to the shrunken limma $\log_2$ fold changes and the GSEA tool was used in 'pre-ranked' mode with all default parameters. Previous reported AR activity signature genes[26] were used in the GSEA analysis.

ChIP-qPCR Analysis

ChIP-qPCR analysis was performed as described previously[49]. The antibodies used for ChIP assay are AR (Santa Cruz; sc-815); RNA Pol-II (Santa cruz; sc-899); H3K4me2 (Abcam ab32356); H3K4me3 (Abcam; ab8580); H3K27ac (Abcam; ab4729); H3 (Active Motif; #39163); p300 (Santa Cruz; sc-585); SRC-1 (Santa Cruz; sc-8995); SRC-3/ACTR[64], and IgG (Santa Cruz; sc-2027). PCR primers used in the ChIP assays were listed in the Supplementary table 2. ChIPs were performed with each experimental point in triplicate, and each experiment was repeated three times.

ChIP-Seq and Data Analysis

C4-2B cells were treated with vehicle or SR2211 (5 µM) for 24 hours before harvested for ChIP-seq. ChIP-seq experiments were performed as described[65]. Anti-AR ChIP-seq was repeated in two independent experiments. Antibodies used were against AR (Santa Cruz; sc-815); RNA Pol II (Santa cruz; sc-899); H3K4me2 (Abcam ab32356); H3K4me3 (Abcam; ab8580); H3 (acetyl K27) (Abcam; ab4729). Libraries were quantified with the Bioanalyzer 2100 (Agilent) and sequenced on the Illumina HiSeq 2000 Sequencer (BGI, Hong Kong). Sequencing tags were mapped against the *Homo sapiens* (Human) reference genome (hg19) using Bowtie 2[66]. Uniquely mapped tags were used for peak calling by MACS(2.1.0)[67] to identify regions of ChIP-Seq enrichment over background. A q value threshold of enrichment of $5 \times 10^{-2}$ was used for all data sets. Normalized genome-wide signal coverage tracks from raw read alignment files were built by MACS2, UCSC tools (http://hgdownload.cse.ucsc.edu/admin/exe/linux.x86_64/bedGraphToBigWig/bedClip) and bedTools (http://code.google.com/p/bedtools/). Visualization of ChIP-seq signal at enriched genomic regions (avgprof and heatmap) was achieved by using ngs.plot (https://github.com/shenlab-sinai/ngsplot). ChIP-seq data have been deposited to NCBI-GEO with accession code GSE72714.

Xenograft Tumor Models and Chemical Compound Treatments

Four-week-old male SCID C.B17 mice (for C4-2B and VCaP) or BALB/c nu/nu athymic mice (for 22Rv11 and PC-3) were purchased from Harlan Inc. For establishing tumors, $2 \times 10^6$ cells were suspended in total of 100 µL PBS/Matrigel (1:1) and implanted subcutaneously into the dorsal flank on both sides of the mice. Animal group size of six or more was estimated to have a high statistic power, based on power calculation (http://www.biomath.info/power/) and previous studies involving the same xenograft models[34,68]. When the tumor volume was approximately 80 mm³, the mice were randomized and then treated intraperitoneally (i.p.) with 100 µl of either vehicle or RORγ antagonists SR2211, XY011/8k (in a formulation of 15% Cremophor EL, Calbiochem, 82.5% PBS, and 2.5% DMSO) for five times per week. Tumor growth was monitored by calipers with volume calculated using the equation: ($\pi/6$ (length×width2)). Body weight during the course of the study was also monitored. At the end of the studies mice were killed and tumors were dissected and weighed. Additionally, prostate, seminal vesicle, testis, kidney, heart, lung, liver, epididymal fat pad and spleen were harvested and weighed. To assess the effect of combining RORγ antagonists and ENZ on the growth of castrated-resistant VCaP xenografts (CRPC-VCaP), first, SCID C.B17 mice were injected with VCaP cells as above to establish the tumors. Then, mice bearing tumors of approximately 180 mm³ were surgically castrated. They were then observed for tumor regression. Once tumors grew back to the pre-castration size, mice were randomized and treated with vehicle, 5 mg kg⁻¹ SR2211, 10 mg kg⁺¹ ENZ or a combination of 5 mg kg⁻¹ SR2211 and 10 mg kg⁻¹ ENZ. ENZ was given by oral gavage as previously described[68] and SR2211 was administered i.p as above. Mice were excluded from the study if bearing no tumor or tumor with size twice larger or smaller than the mean, at the time of randomization.

To assess the effect of RORγ antagonists on the growth of orthotopic prostate tumors, C4-2 cells suspended in Matrigel as above were injected orthotopically into SCID C.B17 mice. To monitor tumor growth, mice were bled and serum PSA levels were measured using PSA (human) ELISA kit (Abnova). When serum PSA were detectable, the mice were randomized into different groups for the treatment. To assess the effect of RORγ knock down on tumor growth, C4-2B cells infected with lentivirus encoding control shRNA or shRNA targeting RORγ were injected subcutaneously into both sides of the dorsal flank of mice. Tumor growth was monitored weekly by calipers. Tumor volumes were measured in a blinded fashion (to treatment groups). The procedures were approved by the Institutional Animal Care and Use Committee of University of California Davis.

Statistical Analysis

Cell culture-based experiments were performed three times or more with assay points triplicated or sextuplicated, as indicated. The data are presented as mean values±s.d. from three independent experiments. Statistics analysis was performed using two-tailed Student's t tests to compare means. $p<0.05$ was considered significant.

TABLE 3

Antibodies for immunoblotting

| Antibody | Vendor | Catalogue number | Dilution |
| --- | --- | --- | --- |
| ACTR | Upstate | 05-490 | 1:1000 |
| ANCCA | Homade | | 1:1000 |
| AR | NeoMarkers | MS-443-P0 | 1:1000 |
| AR-V7 | Precision antibody | AG10008 | 1:1000 |
| BCL-XL | Santa Cruz | sc-8392 | 1:500 |
| CDC2 | Santa Cruz | sc-54 | 1:500 |
| CDC6 | Santa Cruz | sc-9964 | 1:500 |
| CDK4 | Santa Cruz | sc-260 | 1:500 |
| cleaved-Caspase7 | Cell signaling | #9491 | 1:1000 |
| cleaved-PARP1 | Cell signaling | #9542 | 1:1000 |
| CyclinA2 | Cell signaling | #4656 | 1:1000 |
| CyclinD1 | NeoMarkers | RB-9041-P1 | 1:1000 |
| CyclinD3 | Santa Cruz | sc-182 | 1:500 |
| CyclinE2 | Santa Cruz | sc-9566 | 1:500 |
| GAPDH | Cell signaling | #2118 | 1:4000 |
| Myc | Santa Cruz | sc-764 | 1:500 |
| PSA | NeoMarkers | MS-260-P1 | 1:1000 |
| RORγ | Ebioscience | 14-6988-82 | 1:500 |
| SRC-1 | Santa Cruz | sc-8995 | 1:1000 |
| β-actin | Santa Cruz | sc-47778 | 1:2000 |

TABLE 4

Primers for qPCR and ChIP assay

| Primers for qPCR | | SEQ ID NO: |
|---|---|---|
| CAMKK2 qrt-F | TGAAGACCAGGCCCGTTTCTACTT | 7 |
| CAMKK2 qrt-R | TGGAAGGTTTGATGTCACGGTGGA | 8 |
| ATAD2/ANCCA qRT-F | CACCGAGTACTCCTGTGGCTTG | 9 |
| ATAD2/ANCCA qRT-R | TCTAGCTCGAGTCATTCGCAGAACAC | 10 |
| FKBP5 qRT-F1 | GGG AAG ATA GTG TCC TGG TTA G | 11 |
| FKBP5 qRT-R1 | GCA GTC TTG CAG CCT TAT TC | 12 |
| NKX3.1 qRT-F | CCA TAC CTG TAC TGC GTG GG | 13 |
| NKX3.1 qRT-R | TGC ACT GGG GGA ATG ACT TA | 14 |
| KLK3/PSA qRT-F1 | GGA AAT GAC CAG GCC AAG AC | 15 |
| KLK3/PSA qRT-R1 | CCA GCT TCT GCT CAG TGC TT | 16 |
| KLK2 qRT-F2 | CAACATCTGGAGGGGAAAGGG | 17 |
| KLK2 qRT-R2 | AGGCCAAGTGATGCCAGAAC | 18 |
| AR-FL-qRT-F | ACATCAAGGAACTCGATCGTATCATTGC | 19 |
| AR-FL-qRT-R | TTG GGC ACT GCA CAG AGA T | 20 |
| AR-V7-qRT-F | CCATCTTGTCGTCTTCGGAAATGTTATGAAGC | 21 |
| AR-V7-qRT-R | TTT GAA TGA GGC AAG TCA GCC TTT CT | 22 |
| β-Actin F | GAGAAAATCTGGCACCACACC | 23 |
| β-Actin R | ATACCCCTCGTAGATGGGCAC | 24 |

| Primers for ChIP assay | | SEQ ID NO: |
|---|---|---|
| PSA promoter-F1 | GCC AAG ACA TCT ATT TCA GGA GC | 25 |
| PSA promoter-R1 | CCC ACA CCC AGA GCT GTG AAG G | 26 |
| PSA promoter-F2 | TCC TGA GTG CTG GTG TCT AG | 27 |
| PSA promoter-R2 | AGC CCT ATA AAA CCT TCA TTC CCC | 28 |
| PSA enhancer-F1 | TGGGACAACTTGGAAACCTG | 29 |
| PSA enhancer-R1 | CCAGAGTAGGTCTGTTTTCAA | 30 |
| PSA enhancer-F2 | AGGACAGTCTCAACGTTCCACCAT | 31 |
| PSA enhancer-R2 | TGCCTTATTCTGGGTTTGGCAGTG | 32 |
| CAMKK2 promoter F1 | AGAACACTGTAGCTCACACAGGCA | 33 |
| CAMKK2 promoter R1 | GGGCACTTCCCAACCTTTCTTACT | 34 |
| CAMKK2 promoter F2 | AAAATGTGAAAGGCCAGGTG | 35 |
| CAMKK2 promoter R2 | AAAGCAGGGTTGCCAAACTA | 36 |
| AR chip -5.1 KB F | GGTTTGAAACCTCTGATGCAGG | 37 |
| AR chip -5.1 KB R | CTGTCCTCAATGTTGAAGCCATC | 38 |
| AR chip -3.2 KB F | GTG TAT ACC TAC CCT GTG ACT C | 39 |
| AR chip -3.2 KB R | CTG TAC CAC GCT TTG TTT ATC C | 40 |
| AR chip -2.5 KB F | GGC AGA TGT GTG AGA TAC TTA G | 41 |
| AR chip -2.5 KB R | CAG AGG TGT TCT CTC AGA TTA G | 42 |

TABLE 4-continued

Primers for qPCR and ChIP assay

| | | |
|---|---|---|
| AR chip -1.7 KB F | GTG TAG ACA CAT AGT TCT CCT G | 43 |
| AR chip -1.7 KB R | CCT TCC TTG AAT ATA CCT CAC C | 44 |
| AR chip -1 KB F | CCC AGA ATC AGA AGT CAA AGG A | 45 |
| AR chip -1 KB R | GTC CCA TAA GCC CTG TGT AAA G | 46 |
| AR chip -0.4 KB F | GCA GGT ATT CCT ATC GTC CTT T | 47 |
| AR chip -0.4 KB R | CTG AAT AGC TCC TGC TTT CCT A | 48 |
| AR chip +0.9 KB F | CTT CTT CTG CAC GAG ACT TTG A | 49 |
| AR chip +0.9 KB R | TCT TCC ACC TAC TTC CCT TAC C | 50 |
| AR chip +1.7 KB F | CCT GTT GAA CTC TTC TGA GCA | 51 |
| AR chip +1.7 KB R | CTG GAA CAG ATT CTG AAA GC | 52 |
| AR chip +2 KB F | TTC AAG GGA GGT TAC ACC AAA G | 53 |
| AR chip +2 KB R | CAG AGC CAG TGG AAA GTT GTA G | 54 |
| AR chip +2.3 KB F | TAC CCT GTC TCT CTA CAA GTC C | AR-RORE, 55 |
| AR chip +2.3 KB R | TAG TCC AGC GGG TTC TCC AG | AR-RORE, 56 |
| AR chip +2.8 KB F | GAG GGT GGA GTG AGG TTT TT | 57 |
| AR chip +2.8 KB R | CAA CTG CGG TGA GGA ATA AT | 58 |
| AR chip +3 KB F | ATT CCT CAC CGC AGT TG | 59 |
| AR chip +3 KB R | ATT TCG GAG AAG TCA CAG GT | 60 |
| AR chip +24 KB F | AAA CGA ATG CAG AGT GCT CCT | 61 |
| AR chip +24 KB R | GTC ACA GTC CAA ACC TTA CAA | 62 |
| AR chip +96 KB F | ATA GCA GCC ATA TCA GAT GGG | 63 |
| AR chip +96 KB R | TGT GAT TGA GCA TTT CCC CTG | 64 |
| AR chip +98 KB F1 | GGT GAC TAA TCC CAG ATC CTA | 65 |
| AR chip +98 KB R1 | TTA CCC AGC AAT GAT CAC AAG | 66 |
| AR chip +98 KB F2 | CTT GTG ATC ATT GCT GGG TA | 67 |
| AR chip +98 KB R2 | TGA TCT GTA CCA AAC AGC AC | 68 |
| AR chip +115 KB F | AGA TCA CTC TCG ACT AGC AAG | 69 |
| AR chip +115 KB R | GGC TTA TCT GCA GGA TCC ATT | 70 |
| AR chip +170 KB F | CCA GTT GAG TGC AAC TAA TCC | 71 |
| AR chip +170 KB R | GCG GCA CAT AGA AGT TCA GTA | 72 |
| AR chip +190 KB F | GCC TTT GGA GTC ATA GCT AAG | 73 |
| AR chip +190 KB R | GAC AAC TTG ATA TCC ACG TGC | 74 |
| AR chip +225 KB F | AGA TCA AGG GAA GCA ACA GTC | 75 |
| AR chip +225 KB R | TTA TGC AGC CTG CAG AAC CAT | 76 |

TABLE 5 siRNA sequences

| Gene | Sequence (SEQ ID NO) | Vendor and Cat. No |
|---|---|---|
| siRORγ#1 | CGAGGATGAGATTGCCCTCTA (77) | Dharmacon |
| siRORγ#2 | CACCTCACAAATTGAAGTGAT (78) | Dharmacon |
| siCont | CAGTCGCGTTTGCGACTGG (79) | Dharmacon |
| SRC-1 | CUAGCUGAGUUACUGUCUGCC (80) | |
| SRC-2 | CGAAGAGCAAACUCAUCCGUU (81) | |
| SRC-3 | GAUUACUGCAGAAGCCACUGG (82) | |
| SRC-1 smart pool siRNA | A-005196-17 GUAUUAGCUCACAAUUAGA (83)<br>A-005196-18 GGUGGAAAUACGAAUGUUC (84)<br>A-005196-17 CUAGCAGAUUAAAUAUACA (85)<br>A-005196-17 GGGUGGAUUAGAUGUAUUA (86) | Dharmacon, E-005196-00-0005 |
| SRC-2 smart pool siRNA | A-020159-13 GGACAAGGGUUGAAUAUGA (87)<br>A-020159-14 UAAUGAACCUCAACUUGUA (88)<br>A-020159-15 GCAAUAAUUUAAGUUGAGA (89)<br>A-020159-16 UUGCUAAGUAUUGAAUUUC (90) | Dharmacon, E-020159-00-0005 |
| SRC-3 smart pool siRNA | A-003759-18 CUCUGGGCUUUUAUUGCGA (91)<br>A-003759-18 CUGAUAUCUGCCAAUCUUA (92)<br>A-003759-18 GCAGCAGUAAUGAUGGAUC (93)<br>A-003759-18 CUACCAAGUUCAAAAUAUA (94) | Dharmacon, E-003759-00-0005 |

Example 3. Targeting of the Nuclear Receptor RORγ with Receptor-Specific. Small Molecule Inhibitors in Tumor Cells of Different Human Cancers The following example illustrates how a variety of different RORγ inhibitors can be used in the treatment of numerous different cancer types including prostate cancer, lung cancer, breast cancer, liver cancer, ovarian cancer, endometrial cancer, bladder cancer, colon cancer, lymphoma, and glioma.

Using a CellTiter-GLO assay, the viability of cells of different cancer types was measured after treatment with different concentrations of RORγ small molecule inhibitors for 4 days. FIGS. 31A-31C show that the RORγ inhibitors SR2211, GSK805, and GSK9b strongly inhibited the growth and survival of breast cancer cells having different major molecular features, with triple-negative breast cancer (TNBC) cells being more sensitive than ER-positive breast cancer cells. In particular, the RORγ inhibitors GSK805 and SR2211 displayed IC50 values ranging from approximately 1 µM to less than 10 µM in TNBC cells including MDA-MB468, MDA-MB231, BT20, SUM149, and HCC1937 (FIG. 31F). GSK805 and SR2211 also displayed relatively strong inhibition of HER2-positive cells, such as SKBR3 and HCC1954 (FIG. 31F). In addition, GSKS05 and SR2211 displayed significant inhibition of ER-positive cells, such as MCF-7 and T47D, with IC50 values greater than 10 µM (FIG. 31F). GSK9b showed an inhibition pattern similar to that of GSK805, although slightly less effective than GSK805. The RORγ inhibitor GNE3500 also displayed significant inhibition of the growth and survival of different breast cancer cells such as the HER2-positive HCC1954 cell line, the TNBC MDA-MB468 and MDA-MB231 cell lines, and the radiation-resistant MCF-7-C6 cell line (FIG. 31F).

FIGS. 31E and 31F show that different RORγ small molecule inhibitors were effective in potently inhibiting the growth and survival of human breast cancer cells that are resistant to different therapies including radiation (MCF-7-C6) and targeted therapies such as tamoxifen (MCF-7-TamR). FIG. 31D shows that RORγ inhibitors such as SR2211 and GSK805 were able to sensitize tamoxifen-resistant breast cancer cells to tamoxifen. In the case of the tamoxifen-resistant MCF-7-TamR cell line, tamoxifen (1 µM of 4(OH)-tamoxifen) alone did not show any inhibitory effect; in fact, it showed a slight stimulation. However, tamoxifen displayed a synergistic growth inhibitory effect on tamoxifen-resistant breast cancer cells when used in combination with RORγ inhibitors such as SR2211 and GSK805.

FIGS. 32A-32C show that the RORγ inhibitors SR2211 and GSK805 strongly inhibited the growth and survival of lung cancer cells with different molecular and histological features, including cells with an oncogenic mutant KRAS gene (e.g., A427, Calu1, A549, H23, and H358), cells with an oncogenic BRAF mutant gene (e.g., H1666), cells with an EGFR mutant gene (e.g., HCC827 and PC-9), and cells that are either sensitive (e.g. HCC827 and PC-9) or resistant (e.g. A427 and H1975) to the EGFR tyrosine kinase inhibitor Erlotinib. All those cells are derived from human tumors of non-small cell lung carcinoma (NSCLC). The RORγ inhibitors were also effective in the inhibition of cells derived from human tumors of small cell lung carcinoma (SCLC) such as H69 and H209.

FIG. 32D shows that RORγ inhibitors such as SR2211 strongly inhibited tumor growth of a xenograft lung tumor model. To demonstrate that RORγ-specific inhibitors can be effective in the inhibition of tumor growth, mice bearing xenograft tumors of the A549 human lung cancer cells were treated with either vehicle or 5 mg/kg/day of SR2211 (i.p.). After six weeks of treatment, treatment of the tumor-bearing mice with the RORγ inhibitor significantly inhibited tumor growth.

FIGS. 33A-33I show that the RORγ inhibitors SR2211, GSK805, and GSK9b displayed significant inhibition of the growth and survival of ovarian cancer cells (e.g., OVCAR420), bladder cancer cells (e.g., T24), endometrial cancer cells (e.g., ECC1), liver cancer cells (e.g., HepG2 and Hep3B), glioblastoma cells (e.g., T98G), diffuse large B cell lymphoma (DLBCL) (e.g., SUDHL4 and SUDHL6), colon cancer cells (e.g., HCT116), and docetaxel-resistant cells (e.g., C4-2B).

V. References

1. Ferraldeschi, R., Welti, J., Luo, J., Attard, G. & de Bono, J. S. Targeting the androgen receptor pathway in castration-resistant prostate cancer: progresses and prospects. *Oncogene* 34, 1745-1757 (2015).
2. Karantanos, T., et al. Understanding the mechanisms of androgen deprivation resistance in prostate cancer at the molecular level. *European urology* 67, 470-479 (2015).
3. Lu, J., Van der Steen, T. & Tindall, D. J. Are androgen receptor variants a substitute for the full-length receptor? *Nature reviews. Urology* 12, 137-144 (2015).
4. Mostaghel, E. A., Plymate, S. R. & Montgomery, B. Molecular pathways: targeting resistance in the androgen receptor for therapeutic benefit. *Clinical cancer research: an official journal of the American Association for Cancer Research* 20, 791-798 (2014).
5. Myung, J. K., et al. An androgen receptor N-terminal domain antagonist for treating prostate cancer. *The Journal of clinical investigation* 123, 2948-2960 (2013).
6. Lai, K. P., et al. New therapeutic approach to suppress castration-resistant prostate cancer using ASC-J9 via targeting androgen receptor in selective prostate cells. *The American journal of pathology* 182, 460-473 (2013).
7. Liu, C., et al. Niclosamide inhibits androgen receptor variants expression and overcomes enzalutamide resistance in castration-resistant prostate cancer. *Clinical cancer research: an official journal of the American Association for Cancer Research* 20, 3198-3210 (2014).
8. Yu, Z., et al. Galeterone prevents androgen receptor binding to chromatin and enhances degradation of mutant androgen receptor. *Clinical cancer research: an official journal of the American Association for Cancer Research* 20, 4075-4085 (2014).
9. Yamamoto, Y., et al. Generation 2.5 antisense oligonucleotides targeting the androgen receptor and its splice variants suppress enzalutamide-resistant prostate cancer cell growth. *Clinical cancer research: an official journal of the American Association for Cancer Research* 21, 1675-1687 (2015).
10. Malik, R., et al. Targeting the MLL complex in castration-resistant prostate cancer. *Nat Med* 21, 344-352 (2015).
11. Kojetin, D. J. & Burris, T. P. REV-ERB and ROR nuclear receptors as drug targets. *Nature reviews. Drug discovery* 13, 197-216 (2014).
12. Zhao, X., et al. Nuclear receptors rock around the clock. *EMBO reports* 15, 518-528 (2014).
13. Zhang, Y., Luo, X.-y., Wu, D.-h. & Xu, Y. ROR nuclear receptors: structures, related diseases, and drug discovery. *Acta Pharmacol Sin* 36, 71-87 (2015).
14. Takeda, Y., et al. Retinoic acid-related orphan receptor gamma (RORgamma): a novel participant in the diurnal regulation of hepatic gluconeogenesis and insulin sensitivity. *PLoS Genet* 10, e1004331 (2014).
15. Giguere, V., et al. Isoform-specific amino-terminal domains dictate DNA-binding properties of ROR alpha, a novel family of orphan hormone nuclear receptors. *Genes & development* 8, 538-553 (1994).
16. Sun, Z., et al. Requirement for RORgamma in thymocyte survival and lymphoid organ development. *Science* 288, 2369-2373 (2000).
17. Deblois, G. & Giguere, V. Oestrogen-related receptors in breast cancer: control of cellular metabolism and beyond. *Nature reviews. Cancer* 13, 27-36 (2013).
18. Flaveny, C. A., et al. Broad Anti-tumor Activity of a Small Molecule that Selectively Targets the Warburg Effect and Lipogenesis. *Cancer cell* 28, 42-56 (2015).
19. Solt, L. A., et al. Identification of a selective RORgamma ligand that suppresses T(H)17 cells and stimulates T regulatory cells. *ACS chemical biology* 7, 1515-1519 (2012).
20. Kumar, N., et al. Identification of SR2211: a potent synthetic RORgamma-selective modulator. *ACS chemical biology* 7, 672-677 (2012).
21. Zhang, Y., et al. Discovery of 2-oxo-1,2-dihydrobenzo[cd]indole-6-sulfonamide derivatives as new RORgamma inhibitors using virtual screening, synthesis and biological evaluation. *European journal of medicinal chemistry* 78, 431-441 (2014).
22. Xiao, S., et al. Small-molecule RORgammat antagonists inhibit T helper 17 cell transcriptional network by divergent mechanisms. *Immunity* 40, 477-489 (2014).
23. Wang, Y., et al. Discovery of novel N-(5-(arylcarbonyl)thiazol-2-yl)amides and N-(5-(arylcarbonyl)thiophen-2-yl)amides as potent RORgammat inhibitors. *Bioorganic & medicinal chemistry* 22, 692-702 (2014).
24. Chang, M. R., Lyda, B., Kamenecka, T. M. & Griffin, P. R. Pharmacologic repression of retinoic acid receptor-related orphan nuclear receptor gamma is therapeutic in the collagen-induced arthritis experimental model. *Arthritis Rheumatol* 66, 579-588 (2014).
25. Kumar, N., et al. Identification of SR3335 (ML-176): a synthetic RORalpha selective inverse agonist. *ACS chemical biology* 6, 218-222 (2011).
26. Mendiratta, P., et al. Genomic strategy for targeting therapy in castration-resistant prostate cancer. *J Clin Oncol* 27, 2022-2029 (2009).
27. Hu, R., et al. Distinct transcriptional programs mediated by the ligand-dependent full-length androgen receptor and its splice variants in castration-resistant prostate cancer. *Cancer research* 72, 3457-3462 (2012).
28. Sharma, N. L., et al. The androgen receptor induces a distinct transcriptional program in castration-resistant prostate cancer in man. *Cancer cell* 23, 35-47 (2013).
29. Frigo, D. E., et al. CaM kinase kinase beta-mediated activation of the growth regulatory kinase AMPK is required for androgen-dependent migration of prostate cancer cells. *Cancer research* 71, 528-537 (2011).
30. Zou, J. X., et al. Androgen-induced coactivator ANCCA mediates specific androgen receptor signaling in prostate cancer. *Cancer research* 69, 3339-3346 (2009).
31. Ciofani, M., et al. A validated regulatory network for Th17 cell specification. *Cell* 151, 289-303 (2012).
32. Rene, O., et al. Minor Structural Change to Tertiary Sulfonamide RORc Ligands Led to Opposite Mechanisms of Action. *ACS medicinal chemistry letters* 6, 276-281 (2015).
33. Wang, Y., et al. Bufalin is a potent small-molecule inhibitor of the steroid receptor coactivators SRC-3 and SRC-1. *Cancer research* 74, 1506-1517 (2014).
34. Asangani, I. A., et al. Therapeutic targeting of BET bromodomain proteins in castration-resistant prostate cancer. *Nature* 510, 278-282 (2014).
35. Lange, T., et al. Aberrant Presentation of HPA-Reactive Carbohydrates Implies Selectin-Independent Metastasis Formation in Human Prostate Cancer. Clinical *Cancer Research* 20, 1791-1802 (2014).

36. Meissburger, B., et al. Adipogenesis and insulin sensitivity in obesity are regulated by retinoid-related orphan receptor gamma. *EMBO molecular medicine* 3, 637-651 (2011).

37. Qin, J., et al. Androgen deprivation-induced NCoA2 promotes metastatic and castration-resistant prostate cancer. *The Journal of clinical investigation* 124, 5013-5026 (2014).

38. Zhong, J., et al. p300 acetyltransferase regulates androgen receptor degradation and PTEN-deficient prostate tumorigenesis. *Cancer research* 74, 1870-1880 (2014).

39. Agoulnik, I. U., et al. Androgens modulate expression of transcription intermediary factor 2, an androgen receptor coactivator whose expression level correlates with early biochemical recurrence in prostate cancer. *Cancer research* 66, 10594-10602 (2006).

40. Taylor, B. S., et al. Integrative genomic profiling of human prostate cancer. *Cancer cell* 18, 11-22 (2010).

41. Tien, J. C., et al. The steroid receptor coactivator-3 is required for the development of castration-resistant prostate cancer. *Cancer research* 73, 3997-4008 (2013).

42. Sharma, A., et al. The retinoblastoma tumor suppressor controls androgen signaling and human prostate cancer progression. *The Journal of clinical investigation* 120, 4478-4492 (2010).

43. Yang, L., et al. Induction of androgen receptor expression by phosphatidylinositol 3-kinase/Akt downstream substrate, FOXO3a, and their roles in apoptosis of LNCaP prostate cancer cells. *The Journal of biological chemistry* 280, 33558-33565 (2005).

44. Zhang, L., et al. NF-kappaB regulates androgen receptor expression and prostate cancer growth. *The American journal of pathology* 175, 489-499 (2009).

45. Li, Y., et al. LEF1 in androgen-independent prostate cancer: regulation of androgen receptor expression, prostate cancer growth, and invasion. *Cancer research* 69, 3332-3338 (2009).

46. Louie, M. C., Zou, J. X., Rabinovich, A. & Chen, H. W. ACTR/AIB1 functions as an E2F1 coactivator to promote breast cancer cell proliferation and antiestrogen resistance. *Molecular and cellular biology* 24, 5157-5171 (2004).

47. Antonarakis, E. S., et al. AR-V7 and resistance to enzalutamide and abiraterone in prostate cancer. *The New England journal of medicine* 371, 1028-1038 (2014).

48. Zhang, Q., et al. Interleukin-17 promotes formation and growth of prostate adenocarcinoma in mouse models. *Cancer research* 72, 2589-2599 (2012).

49. Yang, P., et al. Histone Methyltransferase NSD2/MMSET Mediates Constitutive NF-kappaB Signaling for Cancer Cell Proliferation, Survival, and Tumor Growth via a Feed-Forward Loop. *Molecular and cellular biology* 32, 3121-3131 (2012).

50. Chandran, U. R., et al. Gene expression profiles of prostate cancer reveal involvement of multiple molecular pathways in the metastatic process. *BMC cancer* 7, 64 (2007).

51. Grasso, C. S., et al. The mutational landscape of lethal castration-resistant prostate cancer. *Nature* 487, 239-243 (2012).

52. Tamura, K., et al. Molecular Features of Hormone-Refractory Prostate Cancer Cells by Genome-Wide Gene Expression Profiles. *Cancer research* 67, 5117-5125 (2007).

53. Ross-Adams, H., et al. Integration of copy number and transcriptomics provides risk stratification in prostate cancer: A discovery and validation cohort study. *EBioMedicine* 2, 1133-1144 (2015).

54. Robinson, D., et al. Integrative clinical genomics of advanced prostate cancer. *Cell* 161, 1215-1228 (2015).

55. Bild, A. H., et al. Oncogenic pathway signatures in human cancers as a guide to targeted therapies. *Nature* 439, 353-357 (2006).

56. Kalashnikova, E. V., et al. ANCCA/ATAD2 overexpression identifies breast cancer patients with poor prognosis, acting to drive proliferation and survival of triple-negative cells through control of B-Myb and EZH2. *Cancer research* 70, 9402-9412 (2010).

57. Wei, Q., et al. Reduced Expression of Mismatch Repair Genes Measured by Multiplex Reverse Transcription-Polymerase Chain Reaction in Human Gliomas. *Cancer research* 57, 1673-1677 (1997).

58. Li, H. & Durbin, R. Fast and accurate short read alignment with Burrows-Wheeler transform. Bioinformatics 25, 1754-1760 (2009).

59. Langmead, B., Trapnell, C., Pop, M. & Salzberg, S. L. Ultrafast and memory-efficient alignment of short DNA sequences to the human genome. *Genome biology* 10, R25-R25 (2009).

60. Trapnell, C., et al. Differential gene and transcript expression analysis of RNA-seq experiments with TopHat and Cufflinks. *Nat. Protocols* 7, 562-578 (2012).

61. Trapnell, C., et al. Transcript assembly and quantification by RNA-Seq reveals unannotated transcripts and isoform switching during cell differentiation. *Nat Biotech* 28, 511-515 (2010).

62. Eisen, M. B., Spellman, P. T., Brown, P. O. & Botstein, D. Cluster analysis and display of genome-wide expression patterns. *Proceedings of the National Academy of Sciences* 95, 14863-14868 (1998).

63. Subramanian, A., et al. Gene set enrichment analysis: a knowledge-based approach for interpreting genome-wide expression profiles. *Proceedings of the National Academy of Sciences of the United States of America* 102, 15545-15550 (2005).

64. Louie, M. C., et al. Androgen-induced recruitment of RNA polymerase II to a nuclear receptor-p160 coactivator complex. *Proceedings of the National Academy of Sciences of the United States of America* 100, 2226-2230 (2003).

65. Schmidt, D., et al. ChIP-seq: using high-throughput sequencing to discover protein-DNA interactions. *Methods* 48, 240-248 (2009).

66. Langmead, B. & Salzberg, S. L. Fast gapped-read alignment with Bowtie 2. *Nature methods* 9, 357-359 (2012).

67. Zhang, Y., et al. Model-based analysis of ChIP-Seq (MACS). *Genome biology* 9, R137 (2008).

68. Nguyen, H. G., et al. Targeting autophagy overcomes Enzalutamide resistance in castration-resistant prostate cancer cells and improves therapeutic response in a xenograft model. *Oncogene* 33, 4521-4530 (2014).

Although the forgoing invention has been described in some detail by way of illustration and example for clarity and understanding, it will be readily apparent to one of ordinary skill in the art in light of the teachings of this invention that certain variations, changes, modifications and substitutions of equivalents may be made thereto without necessarily departing from the spirit and scope of this invention. As a result, the embodiments described herein are subject to various modifications, changes and the like, with the scope of this invention being determined solely by reference to the claims appended hereto. Those of skill in the art will readily recognize a variety of non-critical parameters that could be changed, altered or modified to yield essentially similar results. It is also to be understood that the terminology used herein is for the purpose of describing particular embodiments only, and is not intended to be limiting, since the scope of the present invention will be limited only by the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method for treating a cancer in a subject in need thereof, the method comprising administering to the subject an effective amount of a retinoic acid receptor-related orphan receptor γ (RORγ) inhibitor,
wherein the cancer is selected from the group consisting of prostate cancer, breast cancer, lung cancer, ovarian cancer, bladder cancer, endometrial cancer, liver cancer, glioblastoma, B-cell lymphoma, and colon cancer,
wherein the cancer is resistant to an anticancer drug and
wherein the RORγ inhibitor selectively binds to RORγ and is selected from the group consisting of 2-Fluoro-4'-[[4-(4-pyridinylmethyl)-1-piperazinyl]methyl]-a,a-bis(trifluoromethyl) -[1,1'-biphenyl]-4-methanol (SR2211), N-(3,5-Dichloro-4-(2-(trifluoromethoxy)phenyl)phenyl) -2-(4-ethylsulfonylphenyl)acetamide (GSK805), analogs thereof, and combinations thereof.

2. The method of claim 1, wherein the anticancer drug is a chemotherapeutic agent, wherein the chemotherapeutic agent is tamoxifen, a taxane, an anthracenedione, or combinations thereof.

3. The method of claim 2, wherein the taxane is selected from the group consisting of paclitaxel, docetaxel, cabazitaxel, hongdoushan A, hongdoushan B, hongdoushan C, baccatin I, baccatin II, 10-deacetylbaccatin, and combinations thereof.

4. The method of claim 1, wherein the prostate cancer is a castration-resistant prostate cancer.

5. The method of claim 1, wherein the lung cancer is a non-small-cell lung cancer (NSCLC), K-Ras mutant lung cancer, BRAF mutant lung cancer, EGFR mutant lung cancer, tyrosine kinase inhibitor-resistant lung cancer, or small cell lung cancer (SCLC).

6. The method of claim 1, wherein the breast cancer is a triple-negative breast cancer (TNBC), tamoxifen-resistant breast cancer, radiation-resistant breast cancer, HER2-positive breast cancer, or ER-positive breast cancer.

7. The method of claim 1, wherein the subject is a human in need of cancer treatment.

8. The method of claim 1, wherein the method further comprises administering to the subject an effective amount of the anticancer drug.

9. The method of claim 8, wherein the RORγ inhibitor enhances the therapeutic effect of the anticancer drug.

10. The method of claim 9, wherein the RORγ inhibitor reverses or reduces cancer cell resistance to the anticancer drug and/or sensitizes cancer cells to the anticancer drug.

11. The method of claim 8, wherein the anticancer drug is a chemotherapeutic agent, wherein the chemotherapeutic agent is tamoxifen, a taxane, an anthracenedione, or combinations thereof.

12. The method of claim 11, wherein the taxane is selected from the group consisting of paclitaxel, docetaxel, cabazitaxel, hongdoushan A, hongdoushan B, hongdoushan C, baccatin I, baccatin II, 10-deacetylbaccatin, and combinations thereof.

13. The method of claim 8, wherein the subject is a human in need of cancer treatment.

14. The method of claim 1, wherein the anticancer drug is an endocrine therapy, wherein the endocrine therapy is selected from the group consisting of tamoxifen, raloxifene, an aromatase inhibitor, megestrol acetate, lasofoxifene, bazedoxifene, bazedoxifene/conjugated estrogens, and combinations thereof.

15. The method of claim 8, wherein the anticancer drug is an endocrine therapy, wherein the endocrine therapy is selected from the group consisting of tamoxifen, raloxifene, an aromatase inhibitor, megestrol acetate, lasofoxifene, bazedoxifene, bazedoxifene/conjugated estrogens, and combinations thereof.

16. The method of claim 1, wherein the RORγ inhibitor selectively binds to RORγ relative to RORα and/or RORβ.

17. The method of claim 8, wherein the RORγ inhibitor selectively binds to RORγ relative to RORα and/or RORβ.

18. The method of claim 1, wherein the RORγ inhibitor is SR2211.

19. The method of claim 1, wherein the RORγ inhibitor is GSK805.

* * * * *

```
                        SEQUENCE LISTING

<160> NUMBER OF SEQ ID NOS: 115

<210> SEQ ID NO 1
<211> LENGTH: 10
<212> TYPE: DNA
<213> ORGANISM: Artificial Sequence
<220> FEATURE:
<223> OTHER INFORMATION: Synthetic AR-RORE mutant form

<400> SEQUENCE: 1
ttctgggtca                                                                 10

<210> SEQ ID NO 2
<211> LENGTH: 10
<212> TYPE: DNA
<213> ORGANISM: Artificial Sequence
<220> FEATURE:
<223> OTHER INFORMATION: AR-RORE mutant form

<400> SEQUENCE: 2
ttctgaacga                                                                 10

<210> SEQ ID NO 3
<211> LENGTH: 20
<212> TYPE: DNA
<213> ORGANISM: Artificial Sequence
<220> FEATURE:
<223> OTHER INFORMATION: Synthetic sgRNA sequence GFP

<400> SEQUENCE: 3
gggcgaggag ctgttcaccg                                                      20

<210> SEQ ID NO 4
<211> LENGTH: 20
<212> TYPE: DNA
<213> ORGANISM: Artificial Sequence
<220> FEATURE:
<223> OTHER INFORMATION: Synthetic sgRNA sequence  AR-RORE#1

<400> SEQUENCE: 4
ctggcgagcc tgcatggcgc                                                      20

<210> SEQ ID NO 5
<211> LENGTH: 20
<212> TYPE: DNA
<213> ORGANISM: Artificial Sequence
<220> FEATURE:
<223> OTHER INFORMATION: Synthetic sgRNA sequence AR-RORE#2

<400> SEQUENCE: 5
gtgcagcggg acccggttct                                                      20

<210> SEQ ID NO 6
<211> LENGTH: 20
<212> TYPE: DNA
<213> ORGANISM: Artificial Sequence
<220> FEATURE:
<223> OTHER INFORMATION: Synthetic sgRNA sequence AR-RORE#3
```

-continued

```
<400> SEQUENCE: 6
actctcttca cagccgaaga                                               20

<210> SEQ ID NO 7
<211> LENGTH: 24
<212> TYPE: DNA
<213> ORGANISM: Artificial Sequence
<220> FEATURE:
<223> OTHER INFORMATION: Synthetic   qPCR Primer CAMKK2 qrt-F

<400> SEQUENCE: 7
tgaagaccag gcccgtttct actt                                          24

<210> SEQ ID NO 8
<211> LENGTH: 24
<212> TYPE: DNA
<213> ORGANISM: Artificial Sequence
<220> FEATURE:
<223> OTHER INFORMATION: Synthetic   qPCR Primer CAMKK2 qrt-R

<400> SEQUENCE: 8
tggaaggttt gatgtcacgg tgga                                          24

<210> SEQ ID NO 9
<211> LENGTH: 22
<212> TYPE: DNA
<213> ORGANISM: Artificial Sequence
<220> FEATURE:
<223> OTHER INFORMATION: Synthetic   qPCR Primer ATAD2/ANCCA qRT-F

<400> SEQUENCE: 9
caccgagtac tcctgtggct tg                                            22

<210> SEQ ID NO 10
<211> LENGTH: 26
<212> TYPE: DNA
<213> ORGANISM: Artificial Sequence
<220> FEATURE:
<223> OTHER INFORMATION: Synthetic   qPCR Primer ATAD2/ANCCA qRT-R

<400> SEQUENCE: 10
tctagctcga gtcattcgca gaacac                                        26

<210> SEQ ID NO 11
<211> LENGTH: 22
<212> TYPE: DNA
<213> ORGANISM: Artificial Sequence
<220> FEATURE:
<223> OTHER INFORMATION: Synthetic   qPCR Primer FKBP5 qRT-F1

<400> SEQUENCE: 11
gggaagatag tgtcctggtt ag                                            22

<210> SEQ ID NO 12
<211> LENGTH: 20
<212> TYPE: DNA
<213> ORGANISM: Artificial Sequence
<220> FEATURE:
<223> OTHER INFORMATION: Synthetic   qPCR Primer FKBP5 qRT-R1

<400> SEQUENCE: 12
gcagtcttgc agccttattc                                               20

<210> SEQ ID NO 13
```

```
<211> LENGTH: 20
<212> TYPE: DNA
<213> ORGANISM: Artificial Sequence
<220> FEATURE:
<223> OTHER INFORMATION: Synthetic  qPCR Primer NKX3.1 qRT-F

<400> SEQUENCE: 13
ccatacctgt actgcgtggg                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic  qPCR Primer NKX3.1 qRT-R

<400> SEQUENCE: 14
tgcactgggg gaatgactta                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic  qPCR Primer KLK3/PSA qRT-F1

<400> SEQUENCE: 15
ggaaatgacc aggccaagac                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic  qPCR Primer KLK3/PSA qRT-R1

<400> SEQUENCE: 16
ccagcttctg ctcagtgctt                                              20

<210> SEQ ID NO 17
<211> LENGTH: 21
<212> TYPE: DNA
<213> ORGANISM: Artificial Sequence
<220> FEATURE:
<223> OTHER INFORMATION: Synthetic  qPCR Primer KLK2 qRT-F2

<400> SEQUENCE: 17
caacatctgg aggggaaagg g                                            21

<210> SEQ ID NO 18
<211> LENGTH: 20
<212> TYPE: DNA
<213> ORGANISM: Artificial Sequence
<220> FEATURE:
<223> OTHER INFORMATION: Synthetic  qPCR Primer KLK2 qRT-R2

<400> SEQUENCE: 18
aggccaagtg atgccagaac                                              20

<210> SEQ ID NO 19
<211> LENGTH: 28
<212> TYPE: DNA
<213> ORGANISM: Artificial Sequence
<220> FEATURE:
<223> OTHER INFORMATION: Synthetic  qPCR Primer AR-FL-qRT-F

<400> SEQUENCE: 19
```

-continued acatcaagga actcgatcgt atcattgc					28

<210> SEQ ID NO 20
<211> LENGTH: 20
<212> TYPE: DNA
<213> ORGANISM: Artificial Sequence
<220> FEATURE:
<223> OTHER INFORMATION: Synthetic   qPCR Primer AR-FL-qRT-R

<400> SEQUENCE: 20
ttgggcactt gcacagagat					20

<210> SEQ ID NO 21
<211> LENGTH: 32
<212> TYPE: DNA
<213> ORGANISM: Artificial Sequence
<220> FEATURE:
<223> OTHER INFORMATION: Synthetic   qPCR Primer AR-V7-qRT-F

<400> SEQUENCE: 21
ccatcttgtc gtcttcggaa atgttatgaa gc					32

<210> SEQ ID NO 22
<211> LENGTH: 26
<212> TYPE: DNA
<213> ORGANISM: Artificial Sequence
<220> FEATURE:
<223> OTHER INFORMATION: Synthetic   qPCR Primer AR-V7-qRT-R

<400> SEQUENCE: 22
tttgaatgag gcaagtcagc ctttct					26

<210> SEQ ID NO 23
<211> LENGTH: 21
<212> TYPE: DNA
<213> ORGANISM: Artificial Sequence
<220> FEATURE:
<223> OTHER INFORMATION: Synthetic   qPCR Primer Beta-Actin F

<400> SEQUENCE: 23
gagaaaatct ggcaccacac c					21

<210> SEQ ID NO 24
<211> LENGTH: 21
<212> TYPE: DNA
<213> ORGANISM: Artificial Sequence
<220> FEATURE:
<223> OTHER INFORMATION: Synthetic   qPCR Primer Beta-Actin R

<400> SEQUENCE: 24
atacccctcg tagatgggca c					21

<210> SEQ ID NO 25
<211> LENGTH: 23
<212> TYPE: DNA
<213> ORGANISM: Artificial Sequence
<220> FEATURE:
<223> OTHER INFORMATION: Synthetic   ChIP assay Primer   PSA promoter-F1

<400> SEQUENCE: 25
gccaagacat ctatttcagg agc					23

<210> SEQ ID NO 26
<211> LENGTH: 23
<212> TYPE: DNA

```
<213> ORGANISM: Artificial Sequence
<220> FEATURE:
<223> OTHER INFORMATION: Synthetic  ChIP assay Primer  PSA promoter-R1

<400> SEQUENCE: 26
cccacaccca gagctgtgga agg                                              23

<210> SEQ ID NO 27
<211> LENGTH: 21
<212> TYPE: DNA
<213> ORGANISM: Artificial Sequence
<220> FEATURE:
<223> OTHER INFORMATION: Synthetic  ChIP assay Primer  PSA promoter-F2

<400> SEQUENCE: 27
tcctgagtgc tggtgtctta g                                                21

<210> SEQ ID NO 28
<211> LENGTH: 24
<212> TYPE: DNA
<213> ORGANISM: Artificial Sequence
<220> FEATURE:
<223> OTHER INFORMATION: Synthetic  ChIP assay Primer  PSA promoter-R2

<400> SEQUENCE: 28
agccctataa aaccttcatt cccc                                             24

<210> SEQ ID NO 29
<211> LENGTH: 20
<212> TYPE: DNA
<213> ORGANISM: Artificial Sequence
<220> FEATURE:
<223> OTHER INFORMATION: Synthetic  ChIP assay Primer  PSA enhancer-F1

<400> SEQUENCE: 29
tgggacaact tggaaacctg                                                  20

<210> SEQ ID NO 30
<211> LENGTH: 21
<212> TYPE: DNA
<213> ORGANISM: Artificial Sequence
<220> FEATURE:
<223> OTHER INFORMATION: Synthetic  ChIP assay Primer  PSA enhancer-R1

<400> SEQUENCE: 30
ccagagtagg tctgttttca a                                                21

<210> SEQ ID NO 31
<211> LENGTH: 24
<212> TYPE: DNA
<213> ORGANISM: Artificial Sequence
<220> FEATURE:
<223> OTHER INFORMATION: Synthetic  ChIP assay Primer  PSA enhancer-F2

<400> SEQUENCE: 31
aggacagtct caacgttcca ccat                                             24

<210> SEQ ID NO 32
<211> LENGTH: 24
<212> TYPE: DNA
<213> ORGANISM: Artificial Sequence
<220> FEATURE:
<223> OTHER INFORMATION: Synthetic  ChIP assay Primer  PSA enhancer-R2

<400> SEQUENCE: 32
tgccttattc tgggtttggc agtg                                             24
```

<210> SEQ ID NO 33
<211> LENGTH: 24
<212> TYPE: DNA
<213> ORGANISM: Artificial Sequence
<220> FEATURE:
<223> OTHER INFORMATION: Synthetic ChIP assay Primer CAMKK2 promoter
      F1

<400> SEQUENCE: 33
agaacactgt agctcacaca ggca                                          24

<210> SEQ ID NO 34
<211> LENGTH: 24
<212> TYPE: DNA
<213> ORGANISM: Artificial Sequence
<220> FEATURE:
<223> OTHER INFORMATION: Synthetic ChIP assay Primer CAMKK2 promoter
      R1

<400> SEQUENCE: 34
gggcacttcc caacctttct tact                                          24

<210> SEQ ID NO 35
<211> LENGTH: 20
<212> TYPE: DNA
<213> ORGANISM: Artificial Sequence
<220> FEATURE:
<223> OTHER INFORMATION: Synthetic ChIP assay Primer CAMKK2 promoter
      F2

<400> SEQUENCE: 35
aaaatgtgaa aggccaggtg                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic ChIP assay Primer CAMKK2 promoter
      R2

<400> SEQUENCE: 36
aaagcagggt tgccaaacta                                               20

<210> SEQ ID NO 37
<211> LENGTH: 22
<212> TYPE: DNA
<213> ORGANISM: Artificial Sequence
<220> FEATURE:
<223> OTHER INFORMATION: Synthetic ChIP assay Primer AR chip -5.1KB F

<400> SEQUENCE: 37
ggtttgaaac ctctgatgca gg                                            22

<210> SEQ ID NO 38
<211> LENGTH: 23
<212> TYPE: DNA
<213> ORGANISM: Artificial Sequence
<220> FEATURE:
<223> OTHER INFORMATION: Synthetic ChIP assay Primer AR chip -5.1KB R

<400> SEQUENCE: 38
ctgtcctcaa tgttgaagcc atc                                           23

<210> SEQ ID NO 39

```
<211> LENGTH: 22
<212> TYPE: DNA
<213> ORGANISM: Artificial Sequence
<220> FEATURE:
<223> OTHER INFORMATION: Synthetic  ChIP assay Primer  AR chip -3.2KB F

<400> SEQUENCE: 39
gtgtatacct accctgtgac tc                                              22

<210> SEQ ID NO 40
<211> LENGTH: 22
<212> TYPE: DNA
<213> ORGANISM: Artificial Sequence
<220> FEATURE:
<223> OTHER INFORMATION: Synthetic  ChIP assay Primer  AR chip -3.2KB R

<400> SEQUENCE: 40
ctgtaccacg ctttgtttat cc                                              22

<210> SEQ ID NO 41
<211> LENGTH: 22
<212> TYPE: DNA
<213> ORGANISM: Artificial Sequence
<220> FEATURE:
<223> OTHER INFORMATION: Synthetic  ChIP assay Primer  AR chip -2.5KB F

<400> SEQUENCE: 41
ggcagatgtg tgagatactt ag                                              22

<210> SEQ ID NO 42
<211> LENGTH: 22
<212> TYPE: DNA
<213> ORGANISM: Artificial Sequence
<220> FEATURE:
<223> OTHER INFORMATION: Synthetic  ChIP assay Primer  AR chip -2.5KB R

<400> SEQUENCE: 42
cagaggtgtt ctctcagatt ag                                              22

<210> SEQ ID NO 43
<211> LENGTH: 22
<212> TYPE: DNA
<213> ORGANISM: Artificial Sequence
<220> FEATURE:
<223> OTHER INFORMATION: Synthetic  ChIP assay Primer  AR chip -1.7KB F

<400> SEQUENCE: 43
gtgtagacac atagttctcc tg                                              22

<210> SEQ ID NO 44
<211> LENGTH: 22
<212> TYPE: DNA
<213> ORGANISM: Artificial Sequence
<220> FEATURE:
<223> OTHER INFORMATION: Synthetic  ChIP assay Primer  AR chip -1.7KB R

<400> SEQUENCE: 44
ccttccttga atatacctca cc                                              22

<210> SEQ ID NO 45
<211> LENGTH: 22
<212> TYPE: DNA
<213> ORGANISM: Artificial Sequence
<220> FEATURE:
<223> OTHER INFORMATION: Synthetic  ChIP assay Primer  AR chip -1KB F

<400> SEQUENCE: 45
```

```
cccagaatca gaagtcaaag ga                                              22

<210> SEQ ID NO 46
<211> LENGTH: 22
<212> TYPE: DNA
<213> ORGANISM: Artificial Sequence
<220> FEATURE:
<223> OTHER INFORMATION: Synthetic ChIP assay Primer AR chip -1KB R

<400> SEQUENCE: 46
gtcccataag ccctgtgtaa ag                                              22

<210> SEQ ID NO 47
<211> LENGTH: 22
<212> TYPE: DNA
<213> ORGANISM: Artificial Sequence
<220> FEATURE:
<223> OTHER INFORMATION: Synthetic ChIP assay Primer AR chip -0.4KB F

<400> SEQUENCE: 47
gcaggtattc ctatcgtcct tt                                              22

<210> SEQ ID NO 48
<211> LENGTH: 22
<212> TYPE: DNA
<213> ORGANISM: Artificial Sequence
<220> FEATURE:
<223> OTHER INFORMATION: Synthetic ChIP assay Primer AR chip -0.4KB R

<400> SEQUENCE: 48
ctgaatagct cctgctttcc ta                                              22

<210> SEQ ID NO 49
<211> LENGTH: 22
<212> TYPE: DNA
<213> ORGANISM: Artificial Sequence
<220> FEATURE:
<223> OTHER INFORMATION: Synthetic ChIP assay Primer AR chip +0.9KB F

<400> SEQUENCE: 49
cttcttctgc acgagacttt ga                                              22

<210> SEQ ID NO 50
<211> LENGTH: 22
<212> TYPE: DNA
<213> ORGANISM: Artificial Sequence
<220> FEATURE:
<223> OTHER INFORMATION: Synthetic ChIP assay Primer AR chip +0.9KB R

<400> SEQUENCE: 50
tcttccacct acttcccta cc                                               22

<210> SEQ ID NO 51
<211> LENGTH: 21
<212> TYPE: DNA
<213> ORGANISM: Artificial Sequence
<220> FEATURE:
<223> OTHER INFORMATION: Synthetic ChIP assay Primer AR chip +1.7KB F

<400> SEQUENCE: 51
cctgttgaac tcttctgagc a                                               21

<210> SEQ ID NO 52
<211> LENGTH: 21
<212> TYPE: DNA
```

<213> ORGANISM: Artificial Sequence
<220> FEATURE:
<223> OTHER INFORMATION: Synthetic ChIP assay Primer AR chip +1.7KB R

<400> SEQUENCE: 52
ctggaacaga ttctggaaag c                                      21

<210> SEQ ID NO 53
<211> LENGTH: 22
<212> TYPE: DNA
<213> ORGANISM: Artificial Sequence
<220> FEATURE:
<223> OTHER INFORMATION: Synthetic ChIP assay Primer AR chip +2KB F

<400> SEQUENCE: 53
ttcaagggag gttacaccaa ag                                     22

<210> SEQ ID NO 54
<211> LENGTH: 22
<212> TYPE: DNA
<213> ORGANISM: Artificial Sequence
<220> FEATURE:
<223> OTHER INFORMATION: Synthetic ChIP assay Primer AR chip +2KB R

<400> SEQUENCE: 54
cagagccagt ggaaagttgt ag                                     22

<210> SEQ ID NO 55
<211> LENGTH: 22
<212> TYPE: DNA
<213> ORGANISM: Artificial Sequence
<220> FEATURE:
<223> OTHER INFORMATION: Synthetic ChIP assay Primer AR chip +2.3KB F

<400> SEQUENCE: 55
taccctgtct ctctacaagt cc                                     22

<210> SEQ ID NO 56
<211> LENGTH: 20
<212> TYPE: DNA
<213> ORGANISM: Artificial Sequence
<220> FEATURE:
<223> OTHER INFORMATION: Synthetic ChIP assay Primer AR chip +2.3KB R

<400> SEQUENCE: 56
tagtccagcg ggttctccag                                        20

<210> SEQ ID NO 57
<211> LENGTH: 20
<212> TYPE: DNA
<213> ORGANISM: Artificial Sequence
<220> FEATURE:
<223> OTHER INFORMATION: Synthetic ChIP assay Primer AR chip +2.8KB F

<400> SEQUENCE: 57
gagggtggag tgaggttttt                                        20

<210> SEQ ID NO 58
<211> LENGTH: 20
<212> TYPE: DNA
<213> ORGANISM: Artificial Sequence
<220> FEATURE:
<223> OTHER INFORMATION: Synthetic ChIP assay Primer AR chip +2.8KB R

<400> SEQUENCE: 58
caactgcggt gaggaataat                                        20

<210> SEQ ID NO 59
<211> LENGTH: 17
<212> TYPE: DNA
<213> ORGANISM: Artificial Sequence
<220> FEATURE:
<223> OTHER INFORMATION: Synthetic  ChIP assay Primer  AR chip +3KB F

<400> SEQUENCE: 59
attcctcacc gcagttg                                                17

<210> SEQ ID NO 60
<211> LENGTH: 20
<212> TYPE: DNA
<213> ORGANISM: Artificial Sequence
<220> FEATURE:
<223> OTHER INFORMATION: Synthetic  ChIP assay Primer  AR chip +3KB R

<400> SEQUENCE: 60
atttcggaga agtcacaggt                                             20

<210> SEQ ID NO 61
<211> LENGTH: 21
<212> TYPE: DNA
<213> ORGANISM: Artificial Sequence
<220> FEATURE:
<223> OTHER INFORMATION: Synthetic  ChIP assay Primer  AR chip +24KB F

<400> SEQUENCE: 61
aaacgaatgc agagtgctcc t                                           21

<210> SEQ ID NO 62
<211> LENGTH: 21
<212> TYPE: DNA
<213> ORGANISM: Artificial Sequence
<220> FEATURE:
<223> OTHER INFORMATION: Synthetic  ChIP assay Primer  AR chip +24KB R

<400> SEQUENCE: 62
gtcacagtcc aaaccttaca a                                           21

<210> SEQ ID NO 63
<211> LENGTH: 21
<212> TYPE: DNA
<213> ORGANISM: Artificial Sequence
<220> FEATURE:
<223> OTHER INFORMATION: Synthetic  ChIP assay Primer  AR chip +96KB F

<400> SEQUENCE: 63
atagcagcca tatcagatgg g                                           21

<210> SEQ ID NO 64
<211> LENGTH: 21
<212> TYPE: DNA
<213> ORGANISM: Artificial Sequence
<220> FEATURE:
<223> OTHER INFORMATION: Synthetic  ChIP assay Primer  AR chip +96KB R

<400> SEQUENCE: 64
tgtgattgag catttcccct g                                           21

<210> SEQ ID NO 65
<211> LENGTH: 21
<212> TYPE: DNA
<213> ORGANISM: Artificial Sequence
<220> FEATURE:

```
<223> OTHER INFORMATION: Synthetic  ChIP assay Primer  AR chip +98KB F1

<400> SEQUENCE: 65
ggtgactaat cccagatcct a                                              21

<210> SEQ ID NO 66
<211> LENGTH: 21
<212> TYPE: DNA
<213> ORGANISM: Artificial Sequence
<220> FEATURE:
<223> OTHER INFORMATION: Synthetic  ChIP assay Primer  AR chip +98KB R1

<400> SEQUENCE: 66
ttacccagca atgatcacaa g                                              21

<210> SEQ ID NO 67
<211> LENGTH: 20
<212> TYPE: DNA
<213> ORGANISM: Artificial Sequence
<220> FEATURE:
<223> OTHER INFORMATION: Synthetic  ChIP assay Primer  AR chip +98KB F2

<400> SEQUENCE: 67
cttgtgatca ttgctgggta                                                20

<210> SEQ ID NO 68
<211> LENGTH: 20
<212> TYPE: DNA
<213> ORGANISM: Artificial Sequence
<220> FEATURE:
<223> OTHER INFORMATION: Synthetic  ChIP assay Primer  AR chip +98KB R2

<400> SEQUENCE: 68
tgatctgtac caaacagcac                                                20

<210> SEQ ID NO 69
<211> LENGTH: 21
<212> TYPE: DNA
<213> ORGANISM: Artificial Sequence
<220> FEATURE:
<223> OTHER INFORMATION: Synthetic  ChIP assay Primer  AR chip +115KB F

<400> SEQUENCE: 69
agatcactct cgactagcaa g                                              21

<210> SEQ ID NO 70
<211> LENGTH: 21
<212> TYPE: DNA
<213> ORGANISM: Artificial Sequence
<220> FEATURE:
<223> OTHER INFORMATION: Synthetic  ChIP assay Primer  AR chip +115KB R

<400> SEQUENCE: 70
ggcttatctg caggatccat t                                              21

<210> SEQ ID NO 71
<211> LENGTH: 21
<212> TYPE: DNA
<213> ORGANISM: Artificial Sequence
<220> FEATURE:
<223> OTHER INFORMATION: Synthetic  ChIP assay Primer  AR chip +170KB F

<400> SEQUENCE: 71
ccagttgagt gcaactaatc c                                              21
```

```
<210> SEQ ID NO 72
<211> LENGTH: 21
<212> TYPE: DNA
<213> ORGANISM: Artificial Sequence
<220> FEATURE:
<223> OTHER INFORMATION: Synthetic  ChIP assay Primer  AR chip +170KB R

<400> SEQUENCE: 72
gcggcacata gaagttcagt a                                              21

<210> SEQ ID NO 73
<211> LENGTH: 21
<212> TYPE: DNA
<213> ORGANISM: Artificial Sequence
<220> FEATURE:
<223> OTHER INFORMATION: Synthetic  ChIP assay Primer  AR chip +190KB F

<400> SEQUENCE: 73
gcctttggag tcatagctaa g                                              21

<210> SEQ ID NO 74
<211> LENGTH: 21
<212> TYPE: DNA
<213> ORGANISM: Artificial Sequence
<220> FEATURE:
<223> OTHER INFORMATION: Synthetic  ChIP assay Primer  AR chip +190KB R

<400> SEQUENCE: 74
gacaacttga tatccacgtg c                                              21

<210> SEQ ID NO 75
<211> LENGTH: 21
<212> TYPE: DNA
<213> ORGANISM: Artificial Sequence
<220> FEATURE:
<223> OTHER INFORMATION: Synthetic  ChIP assay Primer  AR chip +225KB F

<400> SEQUENCE: 75
agatcaaggg aagcaacagt c                                              21

<210> SEQ ID NO 76
<211> LENGTH: 21
<212> TYPE: DNA
<213> ORGANISM: Artificial Sequence
<220> FEATURE:
<223> OTHER INFORMATION: Synthetic  ChIP assay Primer  AR chip +225KB R

<400> SEQUENCE: 76
ttatgcagcc tgcagaacca t                                              21

<210> SEQ ID NO 77
<211> LENGTH: 21
<212> TYPE: DNA
<213> ORGANISM: Artificial Sequence
<220> FEATURE:
<223> OTHER INFORMATION: Synthetic  siRNA sequences siRORgamma#1

<400> SEQUENCE: 77
cgaggatgag attgccctct a                                              21

<210> SEQ ID NO 78
<211> LENGTH: 21
<212> TYPE: DNA
<213> ORGANISM: Artificial Sequence
<220> FEATURE:
<223> OTHER INFORMATION: Synthetic  siRNA sequences siRORgamma#2
```

```
<400> SEQUENCE: 78
cacctcacaa attgaagtga t                                              21

<210> SEQ ID NO 79
<211> LENGTH: 19
<212> TYPE: DNA
<213> ORGANISM: Artificial Sequence
<220> FEATURE:
<223> OTHER INFORMATION: Synthetic  siRNA sequences siCont

<400> SEQUENCE: 79
cagtcgcgtt tgcgactgg                                                 19

<210> SEQ ID NO 80
<211> LENGTH: 21
<212> TYPE: RNA
<213> ORGANISM: Artificial Sequence
<220> FEATURE:
<223> OTHER INFORMATION: Synthetic  siRNA sequences SRC-1

<400> SEQUENCE: 80
cuagcugagu uacugucugc c                                              21

<210> SEQ ID NO 81
<211> LENGTH: 21
<212> TYPE: RNA
<213> ORGANISM: Artificial Sequence
<220> FEATURE:
<223> OTHER INFORMATION: Synthetic  siRNA sequences SRC-2

<400> SEQUENCE: 81
cgaagagcaa acucauccgu u                                              21

<210> SEQ ID NO 82
<211> LENGTH: 21
<212> TYPE: RNA
<213> ORGANISM: Artificial Sequence
<220> FEATURE:
<223> OTHER INFORMATION: Synthetic  siRNA sequences SRC-3

<400> SEQUENCE: 82
gauuacugca gaagccacug g                                              21

<210> SEQ ID NO 83
<211> LENGTH: 19
<212> TYPE: RNA
<213> ORGANISM: Artificial Sequence
<220> FEATURE:
<223> OTHER INFORMATION: Synthetic  siRNA sequences SRC-1 smart pool
      siRNA A-005196-17

<400> SEQUENCE: 83
guauuagcuc acaauuaga                                                 19

<210> SEQ ID NO 84
<211> LENGTH: 19
<212> TYPE: RNA
<213> ORGANISM: Artificial Sequence
<220> FEATURE:
<223> OTHER INFORMATION: Synthetic  siRNA sequences SRC-1 smart pool
      siRNA A-005196-18

<400> SEQUENCE: 84
gguggaaaua cgaauguuc                                                 19
```

```
<210> SEQ ID NO 85
<211> LENGTH: 19
<212> TYPE: RNA
<213> ORGANISM: Artificial Sequence
<220> FEATURE:
<223> OTHER INFORMATION: Synthetic  siRNA sequences SRC-1 smart pool
      siRNA A-005196-17

<400> SEQUENCE: 85
cuagcagauu aaauauaca                                                    19

<210> SEQ ID NO 86
<211> LENGTH: 19
<212> TYPE: RNA
<213> ORGANISM: Artificial Sequence
<220> FEATURE:
<223> OTHER INFORMATION: Synthetic  siRNA sequences SRC-1 smart pool
      siRNA A-005196-17

<400> SEQUENCE: 86
ggguggauua gauguauua                                                    19

<210> SEQ ID NO 87
<211> LENGTH: 19
<212> TYPE: RNA
<213> ORGANISM: Artificial Sequence
<220> FEATURE:
<223> OTHER INFORMATION: Synthetic  siRNA sequences SRC-2 smart pool
      siRNA A-020159-13

<400> SEQUENCE: 87
ggacaagggu ugaauauga                                                    19

<210> SEQ ID NO 88
<211> LENGTH: 19
<212> TYPE: RNA
<213> ORGANISM: Artificial Sequence
<220> FEATURE:
<223> OTHER INFORMATION: Synthetic  siRNA sequences SRC-2 smart pool
      siRNA A-020159-14

<400> SEQUENCE: 88
uaaugaaccu caacuugua                                                    19

<210> SEQ ID NO 89
<211> LENGTH: 19
<212> TYPE: RNA
<213> ORGANISM: Artificial Sequence
<220> FEATURE:
<223> OTHER INFORMATION: Synthetic  siRNA sequences SRC-2 smart pool
      siRNA A-020159-15

<400> SEQUENCE: 89
gcaauaauuu aaguugaga                                                    19

<210> SEQ ID NO 90
<211> LENGTH: 19
<212> TYPE: RNA
<213> ORGANISM: Artificial Sequence
<220> FEATURE:
<223> OTHER INFORMATION: Synthetic  siRNA sequences SRC-2 smart pool
      siRNA A-020159-16

<400> SEQUENCE: 90
uugcuaagua uugaauuuc                                                    19

<210> SEQ ID NO 91
```

```
<211> LENGTH: 19
<212> TYPE: RNA
<213> ORGANISM: Artificial Sequence
<220> FEATURE:
<223> OTHER INFORMATION: Synthetic  siRNA sequences SRC-3 smart pool
      siRNA A-003759-18

<400> SEQUENCE: 91
cucugggcuu uuauugcga                                                  19

<210> SEQ ID NO 92
<211> LENGTH: 19
<212> TYPE: RNA
<213> ORGANISM: Artificial Sequence
<220> FEATURE:
<223> OTHER INFORMATION: Synthetic  siRNA sequences SRC-3 smart pool
      siRNA A-003759-18

<400> SEQUENCE: 92
cugauaucug ccaaucuua                                                  19

<210> SEQ ID NO 93
<211> LENGTH: 19
<212> TYPE: RNA
<213> ORGANISM: Artificial Sequence
<220> FEATURE:
<223> OTHER INFORMATION: Synthetic  siRNA sequences SRC-3 smart pool
      siRNA A-003759-18

<400> SEQUENCE: 93
gcagcaguaa ugauggauc                                                  19

<210> SEQ ID NO 94
<211> LENGTH: 19
<212> TYPE: RNA
<213> ORGANISM: Artificial Sequence
<220> FEATURE:
<223> OTHER INFORMATION: Synthetic  siRNA sequences SRC-3 smart pool
      siRNA A-003759-18

<400> SEQUENCE: 94
cuaccaaguu caaaauaua                                                  19

<210> SEQ ID NO 95
<211> LENGTH: 145
<212> TYPE: DNA
<213> ORGANISM: Artificial Sequence
<220> FEATURE:
<223> OTHER INFORMATION: Synthetic  portion of AR-RORE Region

<400> SEQUENCE: 95
agtgccgcta tggggacctg gcgagcctgc atggcgcggg tgcagcggga cccggttctg     60
ggtcaccctc agccgccgct tcctcatcct ggcacactct cttcacagcc gaagaaggcc    120
agttgtatgg accgtgtggt ggtgg                                          145

<210> SEQ ID NO 96
<211> LENGTH: 10
<212> TYPE: DNA
<213> ORGANISM: Artificial Sequence
<220> FEATURE:
<223> OTHER INFORMATION: Synthetic  portion of AR-RORE Region

<400> SEQUENCE: 96
tgcggtaagt                                                            10
```

```
<210> SEQ ID NO 97
<211> LENGTH: 16
<212> TYPE: DNA
<213> ORGANISM: Artificial Sequence
<220> FEATURE:
<223> OTHER INFORMATION: Synthetic  Genomic DNA

<400> SEQUENCE: 97
gacccggtag aaggcc                                                           16

<210> SEQ ID NO 98
<211> LENGTH: 16
<212> TYPE: DNA
<213> ORGANISM: Artificial Sequence
<220> FEATURE:
<223> OTHER INFORMATION: Synthetic  Genomic DNA

<400> SEQUENCE: 98
ctgcatggag aaggcc                                                           16

<210> SEQ ID NO 99
<211> LENGTH: 22
<212> TYPE: DNA
<213> ORGANISM: Artificial Sequence
<220> FEATURE:
<223> OTHER INFORMATION: Synthetic  AR-RORE

<400> SEQUENCE: 99
cccggttctg ggtcaccctc ag                                                    22

<210> SEQ ID NO 100
<211> LENGTH: 22
<212> TYPE: DNA
<213> ORGANISM: Artificial Sequence
<220> FEATURE:
<223> OTHER INFORMATION: Synthetic  AR-RORE mutation

<400> SEQUENCE: 100
cccggttctg aacgaccctc ag                                                    22

<210> SEQ ID NO 101
<211> LENGTH: 104
<212> TYPE: DNA
<213> ORGANISM: Artificial Sequence
<220> FEATURE:
<223> OTHER INFORMATION: Synthetic  AR-RORE

<400> SEQUENCE: 101
gcgggtgcag cgggacccgg ttctgggtca ccctcagccg ccgcttcctc atcctggcac           60
actctcttca cagccgaaga aggccagttg tatggaccgt gtgg                           104

<210> SEQ ID NO 102
<211> LENGTH: 47
<212> TYPE: DNA
<213> ORGANISM: Artificial Sequence
<220> FEATURE:
<223> OTHER INFORMATION: Synthetic  AR-RORE edited with CRISPR/Cas9

<400> SEQUENCE: 102
gcgggtgcag cgggacccgg tgaaggccag ttgtatggac cgtgtgg                         47

<210> SEQ ID NO 103
<211> LENGTH: 49
<212> TYPE: DNA
<213> ORGANISM: Artificial Sequence
<220> FEATURE:
```

<223> OTHER INFORMATION: Synthetic AR-RORE edited with CRISPR/Cas9

<400> SEQUENCE: 103
gcgggtgcag cgggacccgg taagaaggcc agttgtatgg accgtgtgg            49

<210> SEQ ID NO 104
<211> LENGTH: 48
<212> TYPE: DNA
<213> ORGANISM: Artificial Sequence
<220> FEATURE:
<223> OTHER INFORMATION: Synthetic AR-RORE edited with CRISPR/Cas9

<400> SEQUENCE: 104
gcgggtgcag cgggacccgg taaaagggcc gttgtatgga ccgtgtgg             48

<210> SEQ ID NO 105
<211> LENGTH: 48
<212> TYPE: DNA
<213> ORGANISM: Artificial Sequence
<220> FEATURE:
<223> OTHER INFORMATION: Synthetic AR-RORE edited with CRISPR/Cas9

<400> SEQUENCE: 105
gcgggtgcag cgggacccgg ttgaaggcca gttgtatgga ccgtgtgg             48

<210> SEQ ID NO 106
<211> LENGTH: 35
<212> TYPE: DNA
<213> ORGANISM: Artificial Sequence
<220> FEATURE:
<223> OTHER INFORMATION: Synthetic AR-RORE edited with CRISPR/Cas9

<400> SEQUENCE: 106
gcgggtgcag aaggccagtt gtatggaccg tgtgg                           35

<210> SEQ ID NO 107
<211> LENGTH: 38
<212> TYPE: DNA
<213> ORGANISM: Artificial Sequence
<220> FEATURE:
<223> OTHER INFORMATION: Synthetic AR-RORE edited with CRISPR/Cas9

<400> SEQUENCE: 107
gcgggtgcag cagtgtgcca gttgtatgga ccgtgtgg                        38

<210> SEQ ID NO 108
<211> LENGTH: 93
<212> TYPE: DNA
<213> ORGANISM: Homo sapiens

<400> SEQUENCE: 108
ggacctggcg agcctgcatg gcgcgggtgc agcgggaccc ggttctgggt caccctcagc    60
cgccgcttcc tcatcctggc acactctctt cac                                 93

<210> SEQ ID NO 109
<211> LENGTH: 93
<212> TYPE: DNA
<213> ORGANISM: Pan troglodytes

<400> SEQUENCE: 109
ggacctggcg agcctgcatg gcgcgggtgc agcgggaccc ggttctgggt caccctcagc    60
cgccgcttcc tcatcctggc acactctctt cac                                 93

```
<210> SEQ ID NO 110
<211> LENGTH: 93
<212> TYPE: DNA
<213> ORGANISM: Papio Anubis

<400> SEQUENCE: 110
ggacctggcg agcctgcatg gcgcgggtgc agcgggaccc ggctctgggt caccctcagc    60
ggccgcttcc tcatcctggc acactctctt cac                                 93

<210> SEQ ID NO 111
<211> LENGTH: 93
<212> TYPE: DNA
<213> ORGANISM: Macaca mulatta

<400> SEQUENCE: 111
ggacctggcg agcctgcatg gcgcgggtgc agcgggaccc ggctctgggt caccctcagc    60
ggccgcttcc tcatcctggc acactctctt cac                                 93

<210> SEQ ID NO 112
<211> LENGTH: 93
<212> TYPE: DNA
<213> ORGANISM: Mus musculus

<400> SEQUENCE: 112
ggacttggct agcctacatg gagggagtgt agccggaccc agcactggat cgcccccagc    60
caccgcctct tcttcctggc atactctctt cac                                 93

<210> SEQ ID NO 113
<211> LENGTH: 93
<212> TYPE: DNA
<213> ORGANISM: Rattus norvegicus

<400> SEQUENCE: 113
ggacttgggt agtctacatg gagggagtgt agccgggccc agcactggat cgcccccagc    60
caccacctct tcttcctggc atactctctt cac                                 93

<210> SEQ ID NO 114
<211> LENGTH: 93
<212> TYPE: DNA
<213> ORGANISM: Canis lupus

<400> SEQUENCE: 114
ggatctggcg agcctgcacg gagcgggtgc agcaggaccc agctcgggct caccttcggc    60
caccacctcc tcttcctggc acactctctt cac                                 93

<210> SEQ ID NO 115
<211> LENGTH: 10
<212> TYPE: DNA
<213> ORGANISM: Artificial Sequence
<220> FEATURE:
<223> OTHER INFORMATION: synthetic RORE motif
<220> FEATURE:
<221> NAME/KEY: misc_feature
<222> LOCATION: (3)..(3)
<223> OTHER INFORMATION: n = a, c, g, or t

<400> SEQUENCE: 115 awntaggtca                                                           10
```